US008506969B2

(12) United States Patent
Gottwein et al.

(10) Patent No.: US 8,506,969 B2
(45) Date of Patent: Aug. 13, 2013

(54) EFFICIENT CELL CULTURE SYSTEM FOR HEPATITIS C VIRUS GENOTYPE 7A

(75) Inventors: Judith M. Gottwein, Frederiksberg C (DK); Troels Kasper Hoyer Scheel, Copenhagen NV (DK); Tanja Bertelsen Jensen, Frederiksberg C (DK); Jens Bukh, Praesto (DK)

(73) Assignee: Hvidovre Hospital, Hvidovre (DK)

( * ) Notice: Subject to any disclaimer, the term of this patent is extended or adjusted under 35 U.S.C. 154(b) by 128 days.

(21) Appl. No.: 13/059,137

(22) PCT Filed: Jul. 31, 2009

(86) PCT No.: PCT/DK2009/050193
§ 371 (c)(1),
(2), (4) Date: Aug. 10, 2011

(87) PCT Pub. No.: WO2010/017819
PCT Pub. Date: Feb. 18, 2010

(65) Prior Publication Data
US 2011/0294195 A1 Dec. 1, 2011

(30) Foreign Application Priority Data
Aug. 15, 2008 (EP) ..................................... 08162472

(51) Int. Cl.
*A61K 39/12* (2006.01)
*A61K 39/29* (2006.01)
*C12Q 1/70* (2006.01)
*C12N 15/00* (2006.01)
*C12N 5/071* (2010.01)
*C12N 1/20* (2006.01)

(52) U.S. Cl.
USPC ................. 424/228.1; 424/202.1; 424/204.1; 424/205.1; 424/225.1; 435/5; 435/440; 435/455; 435/370; 435/252.3

(58) Field of Classification Search
None
See application file for complete search history.

(56) References Cited

U.S. PATENT DOCUMENTS

| 5,428,145 | A | 6/1995 | Okamoto et al. |
| 6,638,714 | B1 | 10/2003 | Linnen et al. |
| 7,674,612 | B2 | 3/2010 | Rice et al. |
| 7,935,676 | B2 | 5/2011 | Wakita et al. |
| 2007/0073039 | A1 | 3/2007 | Chisari |
| 2010/0093841 | A1 | 4/2010 | Gottwein et al. |
| 2010/0158948 | A1 | 6/2010 | Scheel et al. |
| 2010/0278865 | A1 | 11/2010 | Wakita et al. |
| 2010/0291545 | A1 | 11/2010 | Wakita et al. |
| 2011/0021611 | A1 | 1/2011 | Jensen et al. |
| 2011/0045020 | A1 | 2/2011 | Akazawa et al. |
| 2011/0059512 | A1 | 3/2011 | Gottwein et al. |
| 2011/0059513 | A1 | 3/2011 | Scheel et al. |
| 2011/0092688 | A1 | 4/2011 | Wakita et al. |
| 2011/0294195 | A1 | 12/2011 | Gottwein et al. |
| 2012/0003714 | A1 | 1/2012 | Hoelke et al. |
| 2012/0003719 | A1 | 1/2012 | Prento et al. |

FOREIGN PATENT DOCUMENTS

| EP | 1801209 A1 | 6/2007 |
| EP | 1930416 A1 | 6/2008 |
| WO | 9904008 A2 | 1/1999 |
| WO | 0121807 A1 | 3/2001 |
| WO | 02052015 A2 | 7/2002 |
| WO | 02059321 A2 | 8/2002 |
| WO | 2004/104198 A1 | 12/2004 |
| WO | 2005047463 A2 | 5/2005 |
| WO | 2005053516 A2 | 6/2005 |
| WO | 2006096459 A2 | 9/2006 |
| WO | 2007037429 A1 | 4/2007 |
| WO | 2007041487 A2 | 4/2007 |
| WO | 2007073039 A1 | 6/2007 |
| WO | 2008125117 A1 | 10/2008 |
| WO | 2008125119 A1 | 10/2008 |
| WO | 2008141651 A1 | 11/2008 |
| WO | 2009080052 A1 | 7/2009 |
| WO | 2009080053 A1 | 7/2009 |
| WO | 2011/118743 A1 | 9/2011 |

OTHER PUBLICATIONS

Gottwein et al., "Development and Characterization of Hepatitis C Virus Genotype 1-7 Cell Culture Systems: Role of CD81 and Scavenger Receptor Class B Type I and Effect of Antiviral Drugs", Hepatology, Oct. 2008, pp. 364-377, vol. 49, No. 2.
Gottwein et al., "Robust Hepatitis C Genotype 3a Cell Culture Releasing Adapted Intergenotypic 3a/2a (S52/JFH1) Viruses", Gastroenterology, Nov. 2007, pp. 1614-1626, vol. 133, No. 5, Elsevier, Philadelphia, PA.
International Search Report and Written Opinion for PCT/DK2009/050193 dated Oct. 30, 2009.

(Continued)

*Primary Examiner* — Louise Humphrey
(74) *Attorney, Agent, or Firm* — Thompson Coburn LLP; Charles P. Romano

(57) ABSTRACT

Genotype 7a has been identified recently, thus not much is known about the biology of this new, major HCV genotype. The present inventors developed hepatitis C virus 7a/2a intergenotypic recombinants in which the JFH1 structural genes (Core, E1 and E2), p7 and the complete NS2 were replaced by the corresponding genes of the genotype 7a strain QC69 and characterized them in Huh7.5 cells. Sequence analysis of 7a/JFH1 recombinants recovered after viral passage in Huh7.5 cells following 4 independent transfection experiments revealed adaptive mutations in Core, E2, NS2, NS5A and NS5B. In reverse genetic studies the importance of these mutations for improved growth kinetics was shown. Adapted 7a/JFH1 viruses showed growth kinetics, infectivity and RNA titers comparable to a previously developed 3a/JFH1 reference virus. Conclusion: The developed 7a/JFH1 viruses provide a robust in vitro tool for research in HCV genotype 7, including vaccine studies and functional analyses.

15 Claims, 3 Drawing Sheets

(56) References Cited

OTHER PUBLICATIONS

Figure 1A:
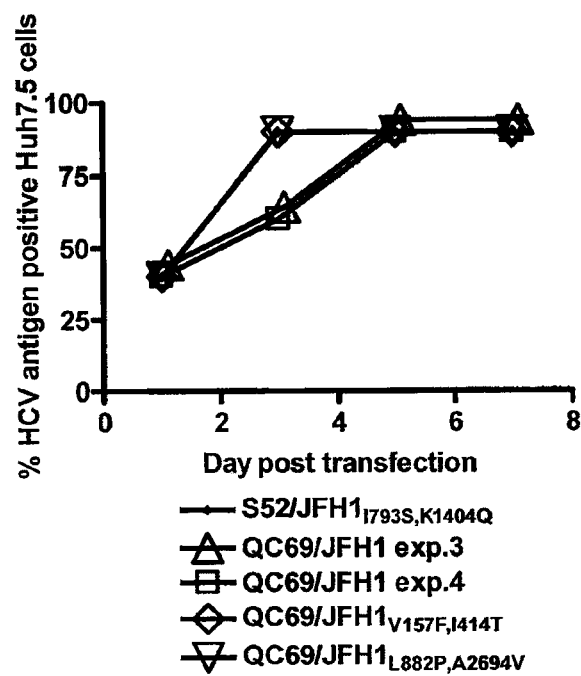

Lindenbach et al., "Complete Replication of Hepatitis C Virus in Cell Culture", Science, Jul. 2005, pp. 623-626, vol. 309, No. 5734, American Association for the Advancement of Science, Washington D.C.
Murphy, "Hepatitis C Virus Isolate QC69 Polyprotein Gene, Complete CDs", Database EMBL E.B.I. Hinxton U.K., Nov. 2007, XP002520134 Database Accession No. EF108306.
Scheel et al., "Development of JFH1-based Cell Culture Systems for Hepatitis C Virus Genotype 4a and Evidence for Cross-Genotype Neutralization", Proceedings of the National Academy of Sciences of USA, Jan. 2008, pp. 997-1002, vol. 105, No. 3, National Academy of Science, Washington D.C., US.
Simmonds et al., "Consensus Proposals for a Unified System of Nomenclature of Hepatitis C Virus Genotypes", Hepatology, Oct. 2005, pp. 962-973, vol. 42, No. 4.
Appel et al., "Mutational Analysis of Hepatitis C Virus Nonstructural Protein 5A: Potential Role of Differential Phosphorylation in RNA Replication and Identification of a Genetically Flexible Domain", Journal of Virology, Mar. 2005, pp. 3187-3194, vol. 79, No. 5.
Appel et al., "Essential Role of Domain III of Nonstructural Protein 5A for Hepatitis C Virus Infectious Particle Assembly", PLOS Pathogens, Mar. 2008, pp. 1-14, vol. 4, Issue 3.
Bukh et al., "Mutations That Permit Efficient Replication of Hepatitis C Virus RNA in Huh-7 Cells Prevent Productive Replication in Chimpanzees", Proc. Natl. Acad. Sci., Oct. 29, 2002, pp. 14416-14421, vol. 99, No. 22.
Chamberlain et al., "Complete Nucleotide Sequence of a Type 4 Hepatitis C Virus Variant, the Predominant Genotype in the Middle East", Journal of General Virology, 1997, pp. 1341-1347, vol. 78.
Forns et al., "Hepatitis C Virus Lacking the Hypervariable Region 1 of the Second Envelope Protein is Infectious and Causes Acute Resolving or Persistent Infection in Chimpanzees", Proceedings of the National Academy of Sciences of the United States of America, Nov. 21, 2000, pp. 13318-13323, vol. 97, No. 24.
Gottwein et al., "Monocistronic Hepatitis C Reporter Virus Recombinants of All Major Genotypes Expressing Enhanced Green Fluorescent Protein Tagged NS5A Protein", Journal of Hepatology, Apr. 2009, p. S33, vol. 50, No. sup1.
Hou et al., "A Recombinant Replication-Competent Hepatitis C Virus Expressing Azami-Green, a Bright Green-Emitting Fluorescent Protein, Suitable for Visualization of Infected Cells", Biochemical and Biophysical Research Communications, Sep. 9, 2008, pp. 7-11, vol. 377, No. 1.
Jensen et al., "Highly Efficient JFH1-Based Cell-Culture System for Hepatitis C Virus Genotype 5a: Failure of Homologous Neutralizing-Antibody Treatment to Control Infection", Journal of Infectious Diseases, Dec. 15, 2008, pp. 1756-1765, vol. 198.
Jensen, "Efficient Cell Culture System for Hepatitis C Virus Genotype 5a", Department of Infectious Diseases and Clinical Research Unit, Copenhagen University Hospital, Master Thesis, Mar. 2007, pp. 1-60.
Kim et al., "Monitoring the Antiviral Effect of Alpha Interferon on Individual Cells" Journal of Virology, Aug. 2007, pp. 8814-8820, vol. 81, No. 16.
Moradpour et al., "Insertion of Green Fluorescent Protein into Nonstructural Protein 5A Allows Direct Visualization of Functional Hepatitis C Virus Replication Complexes", Journal of Virology, Jul. 2004, pp. 7400-7409, vol. 78, No. 14.
Prentoe et al., "HCV Entry Related Studies", Booklet, 4th Smogen Summer Symposium on Virology, Aug. 2008, p. 23.
Schaller et al., "Analysis of Hepatitis C Virus Superinfection Exclusion by Using Novel Fluorochrome Gene-Tagged Viral Genomes", Journal of Virology, May 2007, pp. 4591-4603, vol. 81, No. 9.
Suzuki et al., "Novel Chimeric Hepatitis C Virus Genome Comprising Nucleic Acid Encoding Epitope Tag Peptide at Hypervariable Region 1 of E2 Protein, Useful as Vaccine for Preventing or Treating Hepatitis-C Viral Infection", Database WPI Week 200914, Thomson Scientific, AN 2009-E03534, Jan. 22, 2009.
International Preliminary Report on Patentability (Chapter II) for PCT/DK2008/050113 issued May 25, 2009.
"Written Description Training Materials", United States Patent and Trademark Office, Department of Commerce, Mar. 2008, pp. 1-84, Revision 1 (Part 1).
"Written Description Training Materials", United States Patent and Trademark Office, Department of Commerce, Mar. 2008, pp. 1-84, Revision 1 (part 2).
GenBank Accession No. AB047639.1, HCV JFH1 complete genomic RNA, Nov. 12, 2005.
GenBank Accession No. Y12083.1, HCV genotype 6a RNA for HCV polyprotein, Nov. 10, 2005.
Gottwein et al., "Cutting the Gordian Knot—Development and Biological Relevance of Hepatitis C Virus Cell Culture Systems", Advances in Virus Research, 2008, pp. 51-133, vol. 71, Chapter 2.
Gottwein et al., "Novel Chimeric Cell Culture System for Hepatitis C Genotypes 1A, 1B, 3A and 4A", Annual Meeting of the European Association for the Study of the Liver, Apr. 2007, pp. S30, vol. 46, No. Suppl.
Graham et al., "A Genotype 2b NS5B Polymerase with Novel Substitutions Supports Replication of a Chimeric HCV 1b: 2b Replicon Containing a Genotype 1b NS3-5A Background", Antiviral Research, Jan. 2006, pp. 24-30, vol. 69, No. 1, Elsevier Science BV., Amsterdam, NL.
Hui et al., "Interferon and Ribavirin Therapy for Chronic Hepatitis C Virus Genotype 6: A Comparison with Genotype 1", Article, Apr. 1, 2003, pp. 1071-1074, vol. 87.
International Preliminary Report on Patentability for PCT/DK2008/050333 dated Mar. 29, 2010.
International Search Report and Written Opinion of the International Searching Authority dated Nov. 3, 2009 for PCT Application No. PCT/DK2008/050332.
Kato et al., "Efficient Replication of the Genotype 2a Hepatitis C Virus Subgenomic Replicon", Gastroenterology, Dec. 2003, pp. 1808-1817, vol. 125, No. 6, Elsevier, Philadelphia, PA.
Kato et al., "Sequence Analysis of Hepatitis C Virus Isolated From a Fulminant Hepatitis Patient", Journal of Medical Virology, 2001, pp. 334-339, vol. 64.
Krieger et al., "Enhancement of Hepatitis C Virus RNA Replication by Cell Culture-Adaptive Mutations", Journal of Virology, May 2001, pp. 4614-4624, vol. 75, No. 10, The American Society for Microbiology, US.
Lohmann et al., "Mutation in Hepatitis C Virus RNAs Conferring Cell Culture Adaptation", Journal of Virology, Feb. 2001, pp. 1437-1449, vol. 75, No. 3, The American Society for Microbiology, US.
Murphy et al., "A New Genotype of Hepatitis C Virus Originating From Central Africa", Hepatology, Oct. 2007, p. 623A, vol. 64, No. 4.
Pietschmann et al., "Construction and Characterization of Infectious Intragenotypic and Intergenotypic Hepatitis C Virus Chimeras", Proceedings of the National Academy of Science of USA, May 9, 2006, pp. 7408-7413, vol. 103, No. 19, National Academy of Science, Washington D.C.
Sakai et al., "In Vivo Study of the HC-TN Strain of Hepatitis C Virus Recovered from a Patient with Fulminant Hepatitis: TNA Transcripts of a Molecular Clone (pHC-TN) are Infectious in Chimpanzees But Not in Huh7.5 Cells", Journal of Virology, Jul. 2007, pp. 7208-7219, vol. 81, No. 13, American Society for Microbiology.
Wakita et al., "Production of Infectious Hepatitis C Virus in Tissue Culture from a Cloned Viral Genome", Nature Medicine, Jul. 2005, pp. 791-796, vol. 11, No. 7, Nature Publishing Group, New York, NY.
Yanagi et al., "Transcripts of a Chimeric cDNA Clone of Hepatitis C Virus Genotype 1b Are Infectious in Vivo", Virology, 1998, pp. 161-172, vol. 244.
Yi et al., "Compensatory Mutations in E1, p7, NS2 and NS3 Enhance Yields of Cell Culture-Infectious Intergenotypic Chimeric Hepatitis C Virus", Journal of Virology, Jan. 2007, pp. 629-638, vol. 81, No. 2, The American Society for Microbiology, US.
Zhong et al., "Robust Hepatitis C Virus Infection in vitro", Proceedings of the National Academy of Sciences, 2005, pp. 9294-9299, vol. 102, No. 26.
Kaul et al., "Cell Culture Adaptation of Hepatitis C Virus and In Vivo Viability of an Adapted Variant", Journal of Virology, Dec. 2007, pp. 13168-13179, vol. 81, No. 23, The American Society for Microbiology, US.

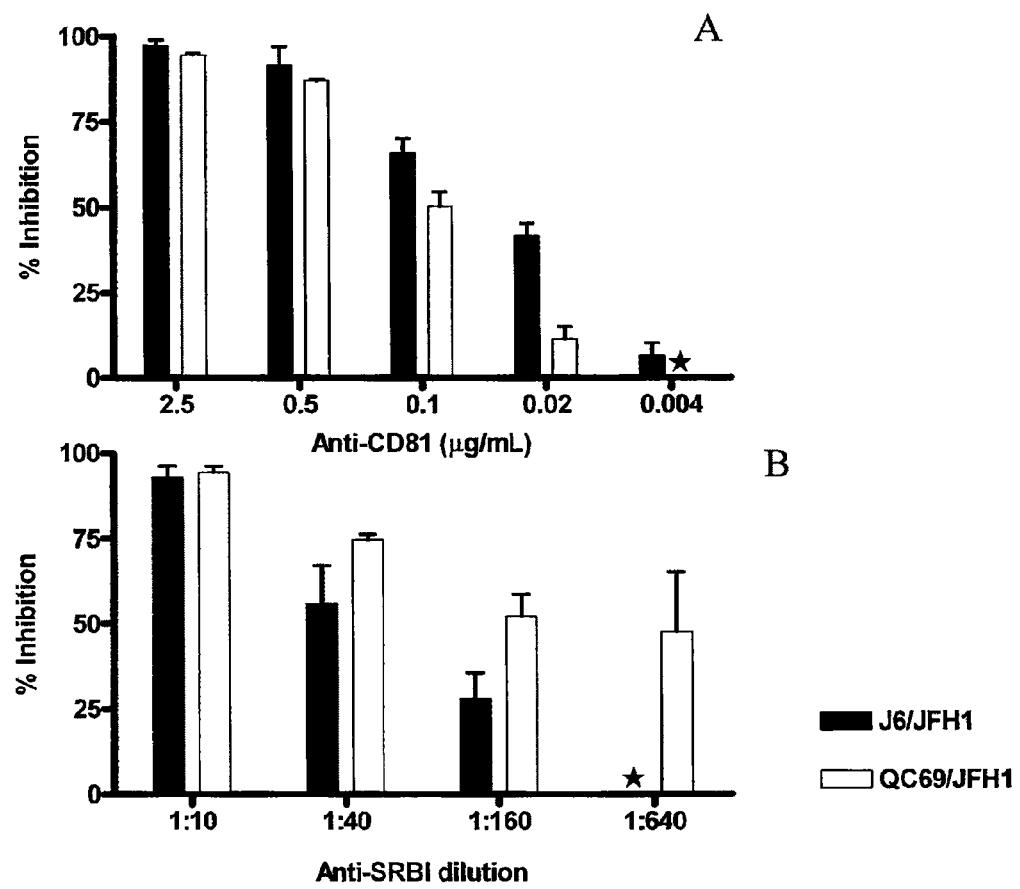
Fig. 2 A,B

SEQUENCE LISTING

<160> NUMBER OF SEQ ID NOS: 24

<210> SEQ ID NO 1
<211> LENGTH: 9678
<212> TYPE: DNA
<213> ORGANISM: Hepatitis C virus

<400> SEQUENCE: 1

```
acctgcccct aatagggcg acactccgcc atgaatcact ccctgtgag gaactactgt      60 cttcacgcag aaagcgccta gccatggcgt tagtatgagt gtcgtacagc ctccaggccc    120 cccctcccg ggagagccat agtggtctgc ggaaccggtg agtacaccgg aattgccggg    180
aagactgggt cctttcttgg ataaacccac tctatgcccg gccatttggg cgtgcccccg    240
caagactgct agccgagtag cgttgggttg cgaaaggcct tgtggtactg cctgataggg    300
tgcttgcgag tgccccggga ggtctcgtag accgtgcacc atgagcacga atcctaaacc    360
tcaaagatta accaaaagaa acaccgtccg tcgcccacag aacgttaagt tcccgggtgg    420
cgggcagatc gttggcggag tctacttgtt gccgcgcagg ggccctagat tgggtgtgcg    480
cggcactagg aagagttcgg agcgatcgca gcccagggga agacgccaac gtatcccaa    540 agctgcctct tcacagggta aagcctgggg caagcccggg tacccttggc ccctgtatgg    600
taacgagggc tgtggctggg cagggtggct cctgtccccc cgcggctctc gacctacttg    660 gggcccact gacccccggc accgctgcg aaacctcggt aaggtgatcg acaccatgac    720
ctgcgggttt gccgacctca tgggtacat ccctgtccta ggcgccccc taggggggcgt    780 tgccagggct ctggcacatg gtgttagagt tctggaggac ggggtcaact atgcaacagg    840
gaacttgcct ggttgctcct tttctatctt cttactagcc ctcctgtcat gtctaacagt    900
cccggcatcg gcttatgaag tccgcaactc cagtgggtgtc tatcatctca ccaatgactg    960
ccccaacgct agtatagtct atgaaacaga caacgccatc ctacacgagc ctgggtgcgt    1020
gccttgcgtt cgcgagggta atactagcag gtgttgggaa ccagtggccc ccactttggc    1080
ggtccgctat cgcggagcgc ttactgacga tttgcggacg catattgacc tagtggtggc    1140
gtcagctacc ctgtgctccg ccttgtacgt ggggacatt tgtggagcca tcttcattgc    1200
cagccaagct gttctctgga gcccgggg gggtcggata gtgcaagatt gcaattgttc    1260
gatctacccg ggccacgtca ccggccacag gatggcgtgg gacatgatgc agaactgggc    1320
gccggccttg tcaatggttg ccgcttacgc tgtgagagtg cccggtgtca tcattaccac    1380
tgtagcgggc ggccactggg gtgtgttatt tggcctcgct actttggta tggcgggaaa    1440 ctgggcaaag gtaatactca tcatgctact catgtccggc gtcgacgcgg aaaccatggc    1500 cgtcgggct agggccgctc acaccactgg cgcccttgtc agcctgctca tccagggcc    1560 cagtcagcgc ctgcagctga tcaacaccaa tgggtcatgg cacatcaacc ggaccgcttt    1620
gaactgcaat gactcttgc agacagggt catagcggcc ctcttctaca cataggtt    1680 caattctagt ggctgtcccg agaggatggc ttcttgtaaa cctctcagtg actttgacca    1740
```

```
ggggtggggc cgctgtggt acaattcaac agaaagacct tcggaccagc gaccctattg    1800
ctggcactac gcgccatcgc cgtgtggtat tgtgccggct aaggatgttt gcggtccggt    1860
ctactgcttt acaccaagcc cggttgtggt gggcaccacg gatcgccggg gggtgcccac    1920
gtatacttgg ggtgaaaatg agtctgatgt cttcctgctc aacagcacaa ggccgccgca    1980
aggcagttgg tttgggtgct catggatgaa cacaacgggg ttcacgaaga cctgcggagg    2040
tcctccgtgc aagatacgtc cccagggtgc ccagagtaac acctctctca cttgtcccac    2100
agactgcttc aggaaacatc cgcgtgccac atactccgct tgcggatctg gtccgtggtt    2160
gacacctaga tgcatggtcc attaccccta tagactgtgg cactacccgt gtacagtcaa    2220
cttcaccata cacaaagtca ggttatacat aggggggtgta gaacataggc tcgatgcagc    2280
gtgcaattgg acgcggggtg agcgatgcga cctggaggac cgagacaggg tggacatgtc    2340 cccctgctc cattccacta cggagctcgc aatacttccg tgttcctttg tgccgcttcc    2400
ggccttatct acgggactga tccacctgca ccaaaacatc gttgacgccc agtaccttta    2460 tggtcttct cccgctataa taagctgggc catcagatgg gagtgggtag tcctcgtttt    2520
cctactcctg gcggacgcgc ggatctgcgc ctgcctttgg atgatgatgc ttatggccca    2580
ggctgaagcc gctctggaga acttgatcca cctcaacgcg ccagccttg cgggaaccca    2640 tggtatctgg tggctccttt tagtcttttg tgcctcttgg catctacgag gcagggttgt    2700
ccctctggtg acgtatggga tatgcgggat gtggcccttc ttcctcatgt tgctgagcct    2760 cccccacga gcgtatgctc tggacaggga agtgagcgca gcgttgggaa cgggcatgct    2820
cgccatcatc ctattagtta ccttgggacc gcactacaag agacttctag cccttattct    2880
ctggtgggtc acatatttcc ttacaaggtg tgaagcagca ctccaaacgt gggtccctcc    2940
tctcaaccct cggggggca gggacggttt catcctgtgt gtgctgctgt gctatccagg    3000
ccttgtcttt gacatcacaa aatggttgct ggtcatgatg tgccctctct acctcctcca    3060
gttgtgtttg gtgaggactc catactttgt gagggcccag gccctcatca gagtgtgttc    3120
tctcttcaaa acgctagctg ggggacggta cgtgcaggcc gcgctgctca ctattggccg    3180
ctggaccggc acttatattt ataaccatct cgccccctg gaaacatggg ccgccggcgg    3240
cctacgggat ttggccgttg cagtcgagcc cgtgatattc tcccccatgg agaagaagat    3300
catagtttgg ggggcggaga ccactgcttg tggcgacatt ctttgtggcc tgcctgtctc    3360
agctcggctc ggcagggaag tcctgctagg gcccgcggat gactacaggt ccatgggatg    3420
gcaactcctg gctcccatca ctgcttatgc ccagcaaaca cgaggcctcc tgggcgccat    3480
agtggtgagt atgacgggc gtgacaggac agaacaggcc ggggaagtcc aaatcctgtc    3540
cacagtctct cagtccttcc tcggaacaac catctcgggg gttttgtgga ctgtttacca    3600
cggagctggc aacaagactc tagccggctt acggggtccg gtcacgcaga tgtactcgag    3660
tgctgagggg gacttggtag gctggcccag ccccccctggg accaagtctt tggagccgtg    3720
caagtgtgga gccgtcgacc tatatctggt cacgcggaac gctgatgtca tcccggctcg    3780
gagacgcggg gacaagcggg gagcattgct ctccccgaga cccatttcga ccttgaaggg    3840
gtcctcgggg gggccggtgc tctgccctag gggccacgtc gttgggctct tccgagcagc    3900
tgtgtgctct cggggcgtgg ccaaatccat cgatttcatc ccgttgaga cactcgacgt    3960 tgttacaagg tctcccactt tcagtgacaa cagcacgcca ccggctgtgc cccagaccta    4020
tcaggtcggg tacttgcatg ctccaactgg cagtggaaag agcaccaagg tccctgtcgc    4080
gtatgccgcc caggggtaca agtactagt gcttaacccc tcggtagctg ccaccctggg    4140
```

```
gtttggggcg tacctatcca aggcacatgg catcaatccc aacattagga ctggagtcag   4200
gaccgtgatg accggggagg ccatcacgta ctccacatat ggcaaatttc tcgccgatgg   4260
gggctgcgct agcggcgcct atgacatcat catatgcgat gaatgccacg ctgtggatgc   4320
tacctccatt ctcggcatcg aacggtcct  tgatcaagca gagacagccg gggtcagact   4380
aactgtgctg gctacggcca cacccccgg  gtcagtgaca accccccatc ccgatataga   4440
agaggtaggc ctcgggcggg agggtgagat ccccttctat ggagggcga ttcccctatc    4500 ctgcatcaag ggagggagac acctgatttt ctgccactca agaaaaagt gtgacgagct    4560 cgcggcggcc cttcggggca tgggcttgaa tgccgtggca tactatagag ggttggacgt   4620
ctccataata ccagctcagg agatgtggt ggtcgtcgcc accgacgccc tcatgacggg    4680
gtacactgga gactttgact ccgtgatcga ctgcaatgta gcggtcaccc aagctgtcga   4740
cttcagcctg gaccccacct tcactataac cacacagact gtcccacaag acgctgtctc   4800
acgcagtcag cgccgcgggc gcacaggtag aggaagacag ggcacttata ggtatgtttc   4860
cactggtgaa cgagcctcag gaatgtttga cagtgtagtg ctttgtgagt gctacgacgc   4920
aggggctgcg tggtacgatc tcacaccagc ggagaccacc gtcaggctta gagcgtattt   4980
caacacgccc ggcctacccg tgtgtcaaga ccatcttgaa ttttgggagg cagttttcac   5040
cggcctcaca cacatagacg cccacttcct ctcccaaaca aagcaagcgg gggagaactt   5100
cgcgtaccta gtagcctacc aagctacggt gtgcgccaga gccaaggccc ctccccgtc   5160 ctgggacgcg atgtgaagt gcctggcccg actcaagcct acgcttgcgg gccccacacc   5220
tctcctgtac cgtttgggcc ctattaccaa tgaggtcacc ctcacacacc ctgggacgaa   5280
gtacatcgcc acatgcatgc aagctgacct tgaggtcatg accagcacgt gggtcctagc   5340
tggaggagtc ctggcagccg tcgccgcata ttgcctggcg actggatgcg tttccatcat   5400
cggccgcttg cacgtcaacc agcgagtcgt cgttgcgccg gataaggagg tcctgtatga   5460
ggcttttgat gagatggagg aatgcgcctc tagggcggct ctcatcgaag agggggcagcg   5520 gatagccgag atgttgaagt ccaagatcca aggcttgctg cagcaggcct ctaagcaggc   5580
ccaggacata caacccgcta tgcaggcttc atggcccaaa gtggaacaat tttgggccag   5640
acacatgtgg aacttcatta gcggcatcca atacctcgca ggattgtcaa cactgccagg   5700
gaaccccgcg gtggcttcca tgatggcatt cagtgccgcc ctcaccagtc cgttgtcgac   5760
cagtaccacc atccttctca acatcatggg aggctggtta gcgtcccaga tcgcaccacc   5820
cgcgggggcc accggctttg tcgtcagtgg cctggtgggg ctgccgtgg gcagcatagg   5880 cctgggtaag gtgctggtgg acatcctggc aggatatggt gcgggcattt cggggccct    5940 cgtcgcattc aagatcatgt ctggcgagaa gccctctatg aagatgtca  tcaatctact   6000 gcctgggatc ctgtctccgg gagccctggt ggtgggggtc atctgcgcgg ccattctgcg   6060
ccgccacgtg ggaccggggg agggcgcggt ccaatggatg aacaggctta ttgcctttgc   6120
ttccagagga aaccacgtcg cccctactca ctacgtgacg gagtcggatg cgtcgcagcg   6180
tgtgacccaa ctacttggct ctcttactat aaccagccta ctcagaagac tccacaattg   6240
gataactgag gactgcccca tcccatgctc cggatcctgg ctccgcgacg tgtgggactg   6300
ggtttgcacc atcttgacag acttcaaaaa ttggctgacc tctaaattgt tccccaagct   6360
gcccggcctc cccttcatct cttgtcaaaa gggggtacaag ggtgtgtggg ccggcactgg   6420
catcatgacc acgcgctgcc cttgcggcgc caacatctct ggcaatgtcc gcctgggctc   6480
tatgaggatc acagggccta aaacctgcat gaacacctgg caggggacct ttcctatcaa   6540
```

```
ttgctacacg gagggccagt gcgcgccgaa acccccacg aactacaaga ccgccatctg   6600
gagggtggcg gcctcggagt acgcggaggt gacgcagcat gggtcgtact cctatgtaac   6660
aggactgacc actgacaatc tgaaaattcc ttgccaacta ccttctccag agttttctc    6720 ctgggtggac ggtgtgcaga tccataggtt tgcacccaca ccaaagccgt ttttccggga   6780
tgaggtctcg ttctgcgttg ggcttaattc ctatgctgtc gggtcccagc ttccctgtga   6840
acctgagccc gacgcagacg tattgaggtc catgctaaca gatccgcccc acatcacggc   6900
ggagactgcg gcgcggcgct tggcacgggg atcacctcca tctgaggcga gctcctcagt   6960
gagccagcta tcagcaccgt cgctgcgggc cacctgcacc acccacagca acacctatga   7020
cgtggacatg gtcgatgcca acctgctcat ggagggcggt gtggctcaga cagagcctga   7080
gtccagggtg cccgttctgg actttctcga gccaatggcc gaggaagaga gcgaccttga   7140
gccctcaata ccatcggagt gcatgctccc caggagcggg tttcacggg ccttaccggc    7200 ttgggcacgg cctgactaca acccgccgct cgtggaatcg tggaggaggc cagattacca   7260
accgcccacc gttgctggtt gtgctctccc cccccccaag aaggccccga cgcctccccc   7320
aaggagacgc cggacagtgg gtctgagcga gagcaccata tcagaagccc tccagcaact   7380
ggccatcaag acctttggcc agccccctc gagcggtgat gcaggctcgt ccacgggggc    7440
gggcgccgcc gaatccggcg gtccgacgtc ccctggtgag ccggccccct cagagacagg   7500
ttccgcctcc tctatgcccc ccctcgaggg ggagcctgga gatccggacc tggagtctga   7560
tcaggtagag cttcaacctc cccccagggg gggggggta gctcccggtt cgggctcggg    7620
gtcttggtct acttgctccg aggaggacga taccaccgtg tgctgctcca tgtcatactc   7680
ctggaccggg gctctaataa ctccctgtag ccccgaagag gaaagttgc caatcaaccc    7740 tttgagtaac tcgctgttgc gataccataa caaggtgtac tgtacaacat caaagagcgc   7800
ctcacagagg gctaaaaagg taacttttga caggacgcaa gtgctcgacg cccattatga   7860
ctcagtctta aaggacatca agctagcggc ttccaaggtc agcgcaaggc tcctcacctt   7920 ggaggaggc tgccagttga ctccacccca ttctgcaaga tccaagtatg gattcggggc    7980
caaggaggtc cgcagcttgt ccgggagggc cgttaaccac atcaagtccg tgtggaagga   8040
cctcctggaa gacccacaaa caccaattcc cacaaccatc atggccaaaa atgaggtgtt   8100
ctgcgtggac cccgccaagg ggggtaagaa accagctcgc ctcatcgttt accctgacct   8160
cggcgtccgg gtctgcgaga aaatggccct ctatgacatt acacaaaagc ttcctcaggc   8220
ggtaatggga gcttcctatg gcttccagta ctcccctgcc caacgggtgg agtatctctt   8280
gaaagcatgg gcgaaaaga aggacccccat gggttttcg tatgataccc gatgcttcga    8340
ctcaaccgtc actgagagag acatcaggac cgaggagtcc atataccagg cctgctccct   8400
gcccgaggag gcccgcactg ccatacactc gctgactgag agactttacg taggagggcc   8460
catgttcaac agcaagggtc aaacctgcgg ttacagacgt tgccgcgcca gcggggtgct   8520
aaccactagc atgggtaaca ccatcacatg ctatgtgaaa gccctagcgg cctgcaaggc   8580 tgcgggata gttgcgccca caatgctggt atgcggcgat gacctagtag tcatctcaga    8640
aagccagggg actgaggagg acgagcgaa cctgagagcc ttcacggagg ccatgaccag   8700
gtactctgcc cctcctggtg atcccccag accggaatat gacctggagc taataacatc    8760
ctgttcctca aatgtgtctg tggcgttggg cccgcggggc cgccgcagat actacctgac   8820
cagagaccca accactccac tcgccgggc tgcctgggaa acagttagac actccctat    8880 caattcatgg ctgggaaaca tcatccagta tgctccaacc atatgggttc gcatggtcct   8940
```

-continued

```
aatgacacac ttcttctcca ttctcatggt ccaagacacc ctggaccaga acctcaactt      9000
tgagatgtat ggatcagtat actccgtgaa tcctttggac cttccagcca taattgagag      9060
gttacacggg cttgacgcct tttctatgca cacatactct caccacgaac tgacgcgggt      9120
ggcttcagcc ctcagaaaac ttggggcgcc acccctcagg gtgtggaaga gtcgggctcg      9180
cgcagtcagg gcgtccctca tctcccgtgg agggaaagcg gccgtttgcg gccgatatct      9240
cttcaattgg gcggtgaaga ccaagctcaa actcactcca ttgccggagg cgcgcctact      9300
ggacttatcc agttggttca ccgtcggcgc cggcgggggc gacattttc acagcgtgtc       9360 gcgcgcccga ccccgctcat tactcttcgg cctactccta cttttcgtag gggtaggcct      9420
cttcctactc cccgctcggt agagcggcac acactaggta cactccatag ctaactgttc      9480
cttttttttt tttttttttt tttttttttt tttttttttt ttttctttt tttttttttc       9540 cctctttctt cccttctcat cttattctac tttctttctt ggtggctcca tcttagccct     9600
agtcacggct agctgtgaaa ggtccgtgag ccgcatgact gcagagagtg ccgtaactgg      9660
tctctctgca gatcatgt                                                    9678
```

<210> SEQ ID NO 2
<211> LENGTH: 3033
<212> TYPE: PRT
<213> ORGANISM: Hepatitis C virus

<400> SEQUENCE: 2

```
Met Ser Thr Asn Pro Lys Pro Gln Arg Leu Thr Lys Arg Asn Thr Val
  1               5                  10                  15

Arg Arg Pro Gln Asn Val Lys Phe Pro Gly Gly Gly Gln Ile Val Gly
             20                  25                  30

Gly Val Tyr Leu Leu Pro Arg Arg Gly Pro Arg Leu Gly Val Arg Gly
         35                  40                  45

Thr Arg Lys Ser Ser Glu Arg Ser Gln Pro Arg Gly Arg Arg Gln Arg
     50                  55                  60

Ile Pro Lys Ala Ala Ser Ser Gln Gly Lys Ala Trp Gly Lys Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Thr Trp Gly Pro Thr Asp Pro
            100                 105                 110

Arg His Arg Ser Arg Asn Leu Gly Lys Val Ile Asp Thr Met Thr Cys
        115                 120                 125

Gly Phe Ala Asp Leu Met Gly Tyr Ile Pro Val Leu Gly Ala Pro Leu
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Glu Val Arg Asn Ser Ser Gly Val Tyr His Leu Thr Asn Asp Cys Pro
        195                 200                 205

Asn Ala Ser Ile Val Tyr Glu Thr Asp Asn Ala Ile Leu His Glu Pro
    210                 215                 220

Gly Cys Val Pro Cys Val Arg Glu Gly Asn Thr Ser Arg Cys Trp Glu
225                 230                 235                 240
```

-continued

```
Pro Val Ala Pro Thr Leu Ala Val Arg Tyr Arg Gly Ala Leu Thr Asp
            245                 250                 255

Asp Leu Arg Thr His Ile Asp Leu Val Val Ala Ser Ala Thr Leu Cys
        260                 265                 270

Ser Ala Leu Tyr Val Gly Asp Ile Cys Gly Ala Ile Phe Ile Ala Ser
    275                 280                 285

Gln Ala Val Leu Trp Lys Pro Gly Gly Arg Ile Val Gln Asp Cys
290                 295                 300

Asn Cys Ser Ile Tyr Pro Gly His Val Thr Gly His Arg Met Ala Trp
305                 310                 315                 320

Asp Met Met Gln Asn Trp Ala Pro Ala Leu Ser Met Val Ala Ala Tyr
                325                 330                 335

Ala Val Arg Val Pro Gly Val Ile Ile Thr Thr Val Ala Gly Gly His
            340                 345                 350

Trp Gly Val Leu Phe Gly Leu Ala Tyr Phe Gly Met Ala Gly Asn Trp
        355                 360                 365

Ala Lys Val Ile Leu Ile Met Leu Leu Met Ser Gly Val Asp Ala Glu
    370                 375                 380

Thr Met Ala Val Gly Ala Arg Ala Ala His Thr Thr Gly Ala Leu Val
385                 390                 395                 400

Ser Leu Leu Asn Pro Gly Pro Ser Gln Arg Leu Gln Leu Ile Asn Thr
                405                 410                 415

Asn Gly Ser Trp His Ile Asn Arg Thr Ala Leu Asn Cys Asn Asp Ser
            420                 425                 430

Leu Gln Thr Gly Phe Ile Ala Ala Leu Phe Tyr Thr His Arg Phe Asn
        435                 440                 445

Ser Ser Gly Cys Pro Glu Arg Met Ala Ser Cys Lys Pro Leu Ser Asp
    450                 455                 460

Phe Asp Gln Gly Trp Gly Pro Leu Trp Tyr Asn Ser Thr Glu Arg Pro
465                 470                 475                 480

Ser Asp Gln Arg Pro Tyr Cys Trp His Tyr Ala Pro Ser Pro Cys Gly
                485                 490                 495

Ile Val Pro Ala Lys Asp Val Cys Gly Pro Val Tyr Cys Phe Thr Pro
            500                 505                 510

Ser Pro Val Val Gly Thr Thr Asp Arg Arg Gly Val Pro Thr Tyr
        515                 520                 525

Thr Trp Gly Glu Asn Glu Ser Asp Val Phe Leu Leu Asn Ser Thr Arg
    530                 535                 540

Pro Pro Gln Gly Ser Trp Phe Gly Cys Ser Trp Met Asn Thr Thr Gly
545                 550                 555                 560

Phe Thr Lys Thr Cys Gly Gly Pro Pro Cys Lys Ile Arg Pro Gln Gly
                565                 570                 575

Ala Gln Ser Asn Thr Ser Leu Thr Cys Pro Thr Asp Cys Phe Arg Lys
            580                 585                 590

His Pro Arg Ala Thr Tyr Ser Ala Cys Gly Ser Gly Pro Trp Leu Thr
        595                 600                 605

Pro Arg Cys Met Val His Tyr Pro Tyr Arg Leu Trp His Tyr Pro Cys
    610                 615                 620

Thr Val Asn Phe Thr Ile His Lys Val Arg Leu Tyr Ile Gly Gly Val
625                 630                 635                 640

Glu His Arg Leu Asp Ala Ala Cys Asn Trp Thr Arg Gly Glu Arg Cys
                645                 650                 655

Asp Leu Glu Asp Arg Asp Arg Val Asp Met Ser Pro Leu Leu His Ser
            660                 665                 670
```

Thr Thr Glu Leu Ala Ile Leu Pro Cys Ser Phe Val Pro Leu Pro Ala
                675                 680                 685

Leu Ser Thr Gly Leu Ile His Leu His Gln Asn Ile Val Asp Ala Gln
        690                 695                 700

Tyr Leu Tyr Gly Leu Ser Pro Ala Ile Ile Ser Trp Ala Ile Arg Trp
705                 710                 715                 720

Glu Trp Val Val Leu Val Phe Leu Leu Ala Asp Ala Arg Ile Cys
            725                 730                 735

Ala Cys Leu Trp Met Met Met Leu Met Ala Gln Ala Glu Ala Leu
                740                 745                 750

Glu Asn Leu Ile His Leu Asn Ala Ala Ser Leu Ala Gly Thr His Gly
            755                 760                 765

Ile Trp Trp Leu Leu Leu Val Phe Cys Ala Ser Trp His Leu Arg Gly
770                 775                 780

Arg Val Val Pro Leu Val Thr Tyr Gly Ile Cys Gly Met Trp Pro Phe
785                 790                 795                 800

Phe Leu Met Leu Leu Ser Leu Pro Pro Arg Ala Tyr Ala Leu Asp Arg
                805                 810                 815

Glu Val Ser Ala Ala Leu Gly Thr Gly Met Leu Ala Ile Ile Leu Leu
            820                 825                 830

Val Thr Leu Gly Pro His Tyr Lys Arg Leu Leu Ala Leu Ile Leu Trp
        835                 840                 845

Trp Val Thr Tyr Phe Leu Thr Arg Cys Glu Ala Ala Leu Gln Thr Trp
    850                 855                 860

Val Pro Pro Leu Asn Pro Arg Gly Gly Arg Asp Gly Phe Ile Leu Cys
865                 870                 875                 880

Val Leu Leu Cys Tyr Pro Gly Leu Val Phe Asp Ile Thr Lys Trp Leu
                885                 890                 895

Leu Val Met Met Cys Pro Leu Tyr Leu Leu Gln Leu Cys Leu Val Arg
            900                 905                 910

Thr Pro Tyr Phe Val Arg Ala Gln Ala Leu Ile Arg Val Cys Ser Leu
        915                 920                 925

Phe Lys Thr Leu Ala Gly Gly Arg Tyr Val Gln Ala Ala Leu Leu Thr
    930                 935                 940

Ile Gly Arg Trp Thr Gly Thr Tyr Ile Tyr Asn His Leu Ala Pro Leu
945                 950                 955                 960

Glu Thr Trp Ala Ala Gly Gly Leu Arg Asp Leu Ala Val Ala Val Glu
                965                 970                 975

Pro Val Ile Phe Ser Pro Met Glu Lys Lys Ile Ile Val Trp Gly Ala
            980                 985                 990

Glu Thr Thr Ala Cys Gly Asp Ile Leu Cys Gly Leu Pro Val Ser Ala
        995                 1000                1005

Arg Leu Gly Arg Glu Val Leu Leu Gly Pro Ala Asp Asp Tyr Arg
    1010                1015                1020

Ser Met Gly Trp Gln Leu Leu Ala Pro Ile Thr Ala Tyr Ala Gln
    1025                1030                1035

Gln Thr Arg Gly Leu Leu Gly Ala Ile Val Val Ser Met Thr Gly
    1040                1045                1050

Arg Asp Arg Thr Glu Gln Ala Gly Glu Val Gln Ile Leu Ser Thr
    1055                1060                1065

Val Ser Gln Ser Phe Leu Gly Thr Thr Ile Ser Gly Val Leu Trp
    1070                1075                1080

Thr Val Tyr His Gly Ala Gly Asn Lys Thr Leu Ala Gly Leu Arg

```
                1085                1090                1095
Gly Pro Val Thr Gln Met Tyr Ser Ser Ala Glu Gly Asp Leu Val
1100                1105                1110
Gly Trp Pro Ser Pro Pro Gly Thr Lys Ser Leu Glu Pro Cys Lys
1115                1120                1125
Cys Gly Ala Val Asp Leu Tyr Leu Val Thr Arg Asn Ala Asp Val
1130                1135                1140
Ile Pro Ala Arg Arg Gly Asp Lys Arg Gly Ala Leu Leu Ser
1145                1150                1155
Pro Arg Pro Ile Ser Thr Leu Lys Gly Ser Ser Gly Gly Pro Val
1160                1165                1170
Leu Cys Pro Arg Gly His Val Val Gly Leu Phe Arg Ala Ala Val
1175                1180                1185
Cys Ser Arg Gly Val Ala Lys Ser Ile Asp Phe Ile Pro Val Glu
1190                1195                1200
Thr Leu Asp Val Val Thr Arg Ser Pro Thr Phe Ser Asp Asn Ser
1205                1210                1215
Thr Pro Pro Ala Val Pro Gln Thr Tyr Gln Val Gly Tyr Leu His
1220                1225                1230
Ala Pro Thr Gly Ser Gly Lys Ser Thr Lys Val Pro Val Ala Tyr
1235                1240                1245
Ala Ala Gln Gly Tyr Lys Val Leu Val Leu Asn Pro Ser Val Ala
1250                1255                1260
Ala Thr Leu Gly Phe Gly Ala Tyr Leu Ser Lys Ala His Gly Ile
1265                1270                1275
Asn Pro Asn Ile Arg Thr Gly Val Arg Thr Val Met Thr Gly Glu
1280                1285                1290
Ala Ile Thr Tyr Ser Thr Tyr Gly Lys Phe Leu Ala Asp Gly Gly
1295                1300                1305
Cys Ala Ser Gly Ala Tyr Asp Ile Ile Ile Cys Asp Glu Cys His
1310                1315                1320
Ala Val Asp Ala Thr Ser Ile Leu Gly Ile Gly Thr Val Leu Asp
1325                1330                1335
Gln Ala Glu Thr Ala Gly Val Arg Leu Thr Val Leu Ala Thr Ala
1340                1345                1350
Thr Pro Pro Gly Ser Val Thr Thr Pro His Pro Asp Ile Glu Glu
1355                1360                1365
Val Gly Leu Gly Arg Glu Gly Glu Ile Pro Phe Tyr Gly Arg Ala
1370                1375                1380
Ile Pro Leu Ser Cys Ile Lys Gly Gly Arg His Leu Ile Phe Cys
1385                1390                1395
His Ser Lys Lys Lys Cys Asp Glu Leu Ala Ala Ala Leu Arg Gly
1400                1405                1410
Met Gly Leu Asn Ala Val Ala Tyr Tyr Arg Gly Leu Asp Val Ser
1415                1420                1425
Ile Ile Pro Ala Gln Gly Asp Val Val Val Val Ala Thr Asp Ala
1430                1435                1440
Leu Met Thr Gly Tyr Thr Gly Asp Phe Asp Ser Val Ile Asp Cys
1445                1450                1455
Asn Val Ala Val Thr Gln Ala Val Asp Phe Ser Leu Asp Pro Thr
1460                1465                1470
Phe Thr Ile Thr Thr Gln Thr Val Pro Gln Asp Ala Val Ser Arg
1475                1480                1485
```

```
Ser Gln Arg Arg Gly Arg Thr Gly Arg Gly Arg Gln Gly Thr Tyr
    1490                1495                1500

Arg Tyr Val Ser Thr Gly Glu Arg Ala Ser Gly Met Phe Asp Ser
1505                1510                1515

Val Val Leu Cys Glu Cys Tyr Asp Ala Gly Ala Ala Trp Tyr Asp
    1520                1525                1530

Leu Thr Pro Ala Glu Thr Thr Val Arg Leu Arg Ala Tyr Phe Asn
    1535                1540                1545

Thr Pro Gly Leu Pro Val Cys Gln Asp His Leu Glu Phe Trp Glu
    1550                1555                1560

Ala Val Phe Thr Gly Leu Thr His Ile Asp Ala His Phe Leu Ser
    1565                1570                1575

Gln Thr Lys Gln Ala Gly Glu Asn Phe Ala Tyr Leu Val Ala Tyr
    1580                1585                1590

Gln Ala Thr Val Cys Ala Arg Ala Lys Ala Pro Pro Pro Ser Trp
    1595                1600                1605

Asp Ala Met Trp Lys Cys Leu Ala Arg Leu Lys Pro Thr Leu Ala
    1610                1615                1620

Gly Pro Thr Pro Leu Leu Tyr Arg Leu Gly Pro Ile Thr Asn Glu
    1625                1630                1635

Val Thr Leu Thr His Pro Gly Thr Lys Tyr Ile Ala Thr Cys Met
    1640                1645                1650

Gln Ala Asp Leu Glu Val Met Thr Ser Thr Trp Val Leu Ala Gly
    1655                1660                1665

Gly Val Leu Ala Ala Val Ala Ala Tyr Cys Leu Ala Thr Gly Cys
    1670                1675                1680

Val Ser Ile Ile Gly Arg Leu His Val Asn Gln Arg Val Val Val
    1685                1690                1695

Ala Pro Asp Lys Glu Val Leu Tyr Glu Ala Phe Asp Glu Met Glu
    1700                1705                1710

Glu Cys Ala Ser Arg Ala Ala Leu Ile Glu Glu Gly Gln Arg Ile
    1715                1720                1725

Ala Glu Met Leu Lys Ser Lys Ile Gln Gly Leu Leu Gln Gln Ala
    1730                1735                1740

Ser Lys Gln Ala Gln Asp Ile Gln Pro Ala Met Gln Ala Ser Trp
    1745                1750                1755

Pro Lys Val Glu Gln Phe Trp Ala Arg His Met Trp Asn Phe Ile
    1760                1765                1770

Ser Gly Ile Gln Tyr Leu Ala Gly Leu Ser Thr Leu Pro Gly Asn
    1775                1780                1785

Pro Ala Val Ala Ser Met Met Ala Phe Ser Ala Ala Leu Thr Ser
    1790                1795                1800

Pro Leu Ser Thr Ser Thr Thr Ile Leu Leu Asn Ile Met Gly Gly
    1805                1810                1815

Trp Leu Ala Ser Gln Ile Ala Pro Pro Ala Gly Ala Thr Gly Phe
    1820                1825                1830

Val Val Ser Gly Leu Val Gly Ala Ala Val Gly Ser Ile Gly Leu
    1835                1840                1845

Gly Lys Val Leu Val Asp Ile Leu Ala Gly Tyr Gly Ala Gly Ile
    1850                1855                1860

Ser Gly Ala Leu Val Ala Phe Lys Ile Met Ser Gly Glu Lys Pro
    1865                1870                1875

Ser Met Glu Asp Val Ile Asn Leu Leu Pro Gly Ile Leu Ser Pro
    1880                1885                1890
```

```
Gly Ala Leu Val Val Gly Val Ile Cys Ala Ala Ile Leu Arg Arg
    1895                1900                1905

His Val Gly Pro Gly Glu Gly Ala Val Gln Trp Met Asn Arg Leu
    1910                1915                1920

Ile Ala Phe Ala Ser Arg Gly Asn His Val Ala Pro Thr His Tyr
    1925                1930                1935

Val Thr Glu Ser Asp Ala Ser Gln Arg Val Thr Gln Leu Leu Gly
    1940                1945                1950

Ser Leu Thr Ile Thr Ser Leu Leu Arg Arg Leu His Asn Trp Ile
    1955                1960                1965

Thr Glu Asp Cys Pro Ile Pro Cys Ser Gly Ser Trp Leu Arg Asp
    1970                1975                1980

Val Trp Asp Trp Val Cys Thr Ile Leu Thr Asp Phe Lys Asn Trp
    1985                1990                1995

Leu Thr Ser Lys Leu Phe Pro Lys Leu Pro Gly Leu Pro Phe Ile
    2000                2005                2010

Ser Cys Gln Lys Gly Tyr Lys Gly Val Trp Ala Gly Thr Gly Ile
    2015                2020                2025

Met Thr Thr Arg Cys Pro Cys Gly Ala Asn Ile Ser Gly Asn Val
    2030                2035                2040

Arg Leu Gly Ser Met Arg Ile Thr Gly Pro Lys Thr Cys Met Asn
    2045                2050                2055

Thr Trp Gln Gly Thr Phe Pro Ile Asn Cys Tyr Thr Glu Gly Gln
    2060                2065                2070

Cys Ala Pro Lys Pro Pro Thr Asn Tyr Lys Thr Ala Ile Trp Arg
    2075                2080                2085

Val Ala Ala Ser Glu Tyr Ala Glu Val Thr Gln His Gly Ser Tyr
    2090                2095                2100

Ser Tyr Val Thr Gly Leu Thr Thr Asp Asn Leu Lys Ile Pro Cys
    2105                2110                2115

Gln Leu Pro Ser Pro Glu Phe Phe Ser Trp Val Asp Gly Val Gln
    2120                2125                2130

Ile His Arg Phe Ala Pro Thr Pro Lys Pro Phe Phe Arg Asp Glu
    2135                2140                2145

Val Ser Phe Cys Val Gly Leu Asn Ser Tyr Ala Val Gly Ser Gln
    2150                2155                2160

Leu Pro Cys Glu Pro Glu Pro Asp Ala Asp Val Leu Arg Ser Met
    2165                2170                2175

Leu Thr Asp Pro Pro His Ile Thr Ala Glu Thr Ala Ala Arg Arg
    2180                2185                2190

Leu Ala Arg Gly Ser Pro Pro Ser Glu Ala Ser Ser Ser Val Ser
    2195                2200                2205

Gln Leu Ser Ala Pro Ser Leu Arg Ala Thr Cys Thr Thr His Ser
    2210                2215                2220

Asn Thr Tyr Asp Val Asp Met Val Asp Ala Asn Leu Leu Met Glu
    2225                2230                2235

Gly Gly Val Ala Gln Thr Glu Pro Glu Ser Arg Val Pro Val Leu
    2240                2245                2250

Asp Phe Leu Glu Pro Met Ala Glu Glu Ser Asp Leu Glu Pro
    2255                2260                2265

Ser Ile Pro Ser Glu Cys Met Leu Pro Arg Ser Gly Phe Pro Arg
    2270                2275                2280

Ala Leu Pro Ala Trp Ala Arg Pro Asp Tyr Asn Pro Pro Leu Val
```

```
                    2285                 2290                 2295

Glu Ser Trp Arg Arg Pro Asp Tyr Gln Pro Pro Thr Val Ala Gly
    2300                 2305                 2310

Cys Ala Leu Pro Pro Pro Lys Lys Ala Pro Thr Pro Pro Pro Arg
    2315                 2320                 2325

Arg Arg Arg Thr Val Gly Leu Ser Glu Ser Thr Ile Ser Glu Ala
    2330                 2335                 2340

Leu Gln Gln Leu Ala Ile Lys Thr Phe Gly Gln Pro Pro Ser Ser
    2345                 2350                 2355

Gly Asp Ala Gly Ser Ser Thr Gly Ala Gly Ala Ala Glu Ser Gly
    2360                 2365                 2370

Gly Pro Thr Ser Pro Gly Glu Pro Ala Pro Ser Glu Thr Gly Ser
    2375                 2380                 2385

Ala Ser Ser Met Pro Pro Leu Glu Gly Glu Pro Gly Asp Pro Asp
    2390                 2395                 2400

Leu Glu Ser Asp Gln Val Glu Leu Gln Pro Pro Gln Gly Gly
    2405                 2410                 2415

Gly Val Ala Pro Gly Ser Gly Ser Gly Ser Trp Ser Thr Cys Ser
    2420                 2425                 2430

Glu Glu Asp Asp Thr Thr Val Cys Cys Ser Met Ser Tyr Ser Trp
    2435                 2440                 2445

Thr Gly Ala Leu Ile Thr Pro Cys Ser Pro Glu Glu Glu Lys Leu
    2450                 2455                 2460

Pro Ile Asn Pro Leu Ser Asn Ser Leu Leu Arg Tyr His Asn Lys
    2465                 2470                 2475

Val Tyr Cys Thr Thr Ser Lys Ser Ala Ser Gln Arg Ala Lys Lys
    2480                 2485                 2490

Val Thr Phe Asp Arg Thr Gln Val Leu Asp Ala His Tyr Asp Ser
    2495                 2500                 2505

Val Leu Lys Asp Ile Lys Leu Ala Ala Ser Lys Val Ser Ala Arg
    2510                 2515                 2520

Leu Leu Thr Leu Glu Glu Ala Cys Gln Leu Thr Pro Pro His Ser
    2525                 2530                 2535

Ala Arg Ser Lys Tyr Gly Phe Gly Ala Lys Glu Val Arg Ser Leu
    2540                 2545                 2550

Ser Gly Arg Ala Val Asn His Ile Lys Ser Val Trp Lys Asp Leu
    2555                 2560                 2565

Leu Glu Asp Pro Gln Thr Pro Ile Pro Thr Thr Ile Met Ala Lys
    2570                 2575                 2580

Asn Glu Val Phe Cys Val Asp Pro Ala Lys Gly Gly Lys Lys Pro
    2585                 2590                 2595

Ala Arg Leu Ile Val Tyr Pro Asp Leu Gly Val Arg Val Cys Glu
    2600                 2605                 2610

Lys Met Ala Leu Tyr Asp Ile Thr Gln Lys Leu Pro Gln Ala Val
    2615                 2620                 2625

Met Gly Ala Ser Tyr Gly Phe Gln Tyr Ser Pro Ala Gln Arg Val
    2630                 2635                 2640

Glu Tyr Leu Leu Lys Ala Trp Ala Glu Lys Lys Asp Pro Met Gly
    2645                 2650                 2655

Phe Ser Tyr Asp Thr Arg Cys Phe Asp Ser Thr Val Thr Glu Arg
    2660                 2665                 2670

Asp Ile Arg Thr Glu Glu Ser Ile Tyr Gln Ala Cys Ser Leu Pro
    2675                 2680                 2685
```

-continued

| | | | | | | | | | | |
|---|---|---|---|---|---|---|---|---|---|---|
| Glu | Glu | Ala | Arg | Thr | Ala | Ile | His | Ser | Leu | Thr | Glu | Arg | Leu | Tyr |
| | 2690 | | | | 2695 | | | | 2700 | |

Val Gly Gly Pro Met Phe Asn Ser Lys Gly Gln Thr Cys Gly Tyr
　　2705　　　　　　　　2710　　　　　　　　2715

Arg Arg Cys Arg Ala Ser Gly Val Leu Thr Thr Ser Met Gly Asn
　　2720　　　　　　　　2725　　　　　　　　2730

Thr Ile Thr Cys Tyr Val Lys Ala Leu Ala Ala Cys Lys Ala Ala
　　2735　　　　　　　　2740　　　　　　　　2745

Gly Ile Val Ala Pro Thr Met Leu Val Cys Gly Asp Asp Leu Val
　　2750　　　　　　　　2755　　　　　　　　2760

Val Ile Ser Glu Ser Gln Gly Thr Glu Glu Asp Glu Arg Asn Leu
　　2765　　　　　　　　2770　　　　　　　　2775

Arg Ala Phe Thr Glu Ala Met Thr Arg Tyr Ser Ala Pro Pro Gly
　　2780　　　　　　　　2785　　　　　　　　2790

Asp Pro Pro Arg Pro Glu Tyr Asp Leu Glu Leu Ile Thr Ser Cys
　　2795　　　　　　　　2800　　　　　　　　2805

Ser Ser Asn Val Ser Val Ala Leu Gly Pro Arg Gly Arg Arg Arg
　　2810　　　　　　　　2815　　　　　　　　2820

Tyr Tyr Leu Thr Arg Asp Pro Thr Thr Pro Leu Ala Arg Ala Ala
　　2825　　　　　　　　2830　　　　　　　　2835

Trp Glu Thr Val Arg His Ser Pro Ile Asn Ser Trp Leu Gly Asn
　　2840　　　　　　　　2845　　　　　　　　2850

Ile Ile Gln Tyr Ala Pro Thr Ile Trp Val Arg Met Val Leu Met
　　2855　　　　　　　　2860　　　　　　　　2865

Thr His Phe Phe Ser Ile Leu Met Val Gln Asp Thr Leu Asp Gln
　　2870　　　　　　　　2875　　　　　　　　2880

Asn Leu Asn Phe Glu Met Tyr Gly Ser Val Tyr Ser Val Asn Pro
　　2885　　　　　　　　2890　　　　　　　　2895

Leu Asp Leu Pro Ala Ile Ile Glu Arg Leu His Gly Leu Asp Ala
　　2900　　　　　　　　2905　　　　　　　　2910

Phe Ser Met His Thr Tyr Ser His His Glu Leu Thr Arg Val Ala
　　2915　　　　　　　　2920　　　　　　　　2925

Ser Ala Leu Arg Lys Leu Gly Ala Pro Pro Leu Arg Val Trp Lys
　　2930　　　　　　　　2935　　　　　　　　2940

Ser Arg Ala Arg Ala Val Arg Ala Ser Leu Ile Ser Arg Gly Gly
　　2945　　　　　　　　2950　　　　　　　　2955

Lys Ala Ala Val Cys Gly Arg Tyr Leu Phe Asn Trp Ala Val Lys
　　2960　　　　　　　　2965　　　　　　　　2970

Thr Lys Leu Lys Leu Thr Pro Leu Pro Glu Ala Arg Leu Leu Asp
　　2975　　　　　　　　2980　　　　　　　　2985

Leu Ser Ser Trp Phe Thr Val Gly Ala Gly Gly Gly Asp Ile Phe
　　2990　　　　　　　　2995　　　　　　　　3000

His Ser Val Ser Arg Ala Arg Pro Arg Ser Leu Leu Phe Gly Leu
　　3005　　　　　　　　3010　　　　　　　　3015

Leu Leu Leu Phe Val Gly Val Gly Leu Phe Leu Leu Pro Ala Arg
　　3020　　　　　　　　3025　　　　　　　　3030

<210> SEQ ID NO 3
<211> LENGTH: 9678
<212> TYPE: DNA
<213> ORGANISM: Hepatitis C virus

<400> SEQUENCE: 3
acctgcccct aatagggggcg acactccgcc atgaatcact cccctgtgag gaactactgt        60
cttcacgcag aaagcgccta gccatggcgt tagtatgagt gtcgtacagc ctccaggccc       120

```
cccctcccg ggagagccat agtggtctgc ggaaccggtg agtacaccgg aattgccggg      180
aagactgggt cctttcttgg ataaacccac tctatgcccg gccatttggg cgtgcccccg      240
caagactgct agccgagtag cgttgggttg cgaaaggcct tgtggtactg cctgataggg      300
tgcttgcgag tgccccggga ggtctcgtag accgtgcacc atgagcacga atcctaaacc      360
tcaaagatta accaaaagaa acaccgtccg tcgcccacag aacgttaagt tcccgggtgg      420
cgggcagatc gttggcggag tctacttgtt gccgcgcagg ggccctagat tgggtgtgcg      480
cggcactagg aagagttcgg agcgatcgca gcccagggga agacgccaac gtatccccaa      540
agctgcctct tcacagggta aagcctgggg caagcccggg tacccttggc ccctgtatgg      600
taacgagggc tgtggctggg cagggtggct cctgtccccc cgcggctctc gacctacttg      660 gggcccccact gaccccggc accgctcgcg aaacctcggt aaggtgatcg acaccatgac      720
ctgcgggttt gccgacctca tggggtacat ccctgtccta ggcgccccc taggggggcgt      780 tgccagggct ctggcacatg gtgttagatt tctggaggac ggggtcaact atgcaacagg      840
gaacttgcct ggttgctcct tttctatctt cttactagcc ctcctgtcat gtctaacagt      900
cccggcatcg gcttatgaag tccgcaactc cagtgggggtc tatcatctca ccaatgactg      960
ccccaacgct agtatagtct atgaaacaga caacgccatc ctacacgagc tgggtgcgt      1020 gccttgcgtt cgcgagggta atactagcag gtgttgggaa ccagtggccc ccactttggc      1080
ggtccgctat cgcggagcgc ttactgacga tttgcggacg catattgacc tagtggtggc      1140
gtcagctacc ctgtgctccg ccttgtacgt gggggacatt tgtggagcca tcttcattgc      1200
cagccaagct gttctctgga agcccggggg gggtcggata gtgcaagatt gcaattgttc      1260
gatctacccg ggccacgtca ccggccacag gatggcgtgg gacatgatgc agaactgggc      1320
gccggccttg tcaatggttg ccgcttacgc tgtgagagtg cccggtgtca tcattaccac      1380
tgtagcgggc ggccactggg gtgtgttatt tggcctcgct tactttggta tggcgggaaa      1440
ctgggcaaag gtaatactca tcatgctact catgtccggc gtcgacgcgg aaaccatggc      1500
cgtcggggct agggccgctc acaccactgg cgcccttgtc agcctgctca atccagggcc      1560
cagtcagcgc ctgcagctga tcaacaccaa tgggtcatgg cacatcaacc ggaccgcttt      1620
gaactgcaat gactctttgc agacagggtt catagcggcc ctcttctaca cataggtt      1680 caattctagt ggctgtcccg agaggatggc ttcttgtaaa cctctcagtg actttgacca      1740 gggtgggc ccgctgtggt acaattcaac agaaagacct tcggaccagc gaccctattg      1800
ctggcactac gcgccatcgc cgtgtggtat tgtgccggct aaggatgttt gcggtccggt      1860
ctactgcttt acaccaagcc cggttgtggt gggcaccacg gatcgccggg gggtgcccac      1920
gtatacttgg ggtgaaaatg agtctgatgt cttcctgctc aacagcacaa ggccgccgca      1980
aggcagttgg tttgggtgct catggatgaa cacaacgggg ttcacgaaga cctgcggagg      2040
tcctccgtgc aagatacgtc cccagggtgc ccagagtaac acctctctca cttgtcccac      2100
agactgcttc aggaaacatc cgcgtgccac atactccgct tgcggatctg gtccgtggtt      2160
gacacctaga tgcatggtcc attaccccta tagactgtgg cactacccgt gtacagtcaa      2220
cttcaccata cacaaagtca ggttatacat aggggggtgta gaacataggc tcgatgcagc      2280
gtgcaattgg acgcggggtg agcgatgcga cctggaggac cgagacaggg tggacatgtc      2340 cccctgctc cattccacta cggagctcgc aatacttccg tgttcctttg tgccgcttcc      2400
ggccttatct acgggactga tccacctgca ccaaaacatc gttgacgccc agtaccctta      2460
tggtctttct cccgctataa taagctgggc catcagatgg gagtgggtag tcctcgtttt      2520
```

```
cctactcctg gcggacgcgc ggatctgcgc ctgcctttgg atgatgatgc ttatggccca    2580
ggctgaagcc gctctggaga acttgatcca cctcaacgcg gccagccttg cgggaaccca    2640
tggtatctgg tggctccttt tagtcttttg tgcctcttgg catctacgag gcagggttgt    2700
ccctctggtg acgtatggga tatgcgggat gtggcccttc ttcctcatgt tgctgagcct    2760
ccccccacga gcgtatgctc tggacaggga agtgagcgca gcgttgggaa cgggcatgct    2820
cgccatcatc ctattagtta ccttgggacc gcactacaag agacttctag cccttattct    2880
ctggtgggtc acatatttcc ttacaaggtg tgaagcagca ctccaaacgt gggtccctcc    2940
tctcaaccct cggggggca gggacggttt catcctgtgt gtgctgctgt gctatccagg    3000
ccttgtcttt gacatcacaa aatggttgct ggtcatgatg tgccctctct acctcctcca    3060
gttgtgtttg gtgaggactc catactttgt gagggcccag gccctcatca gagtgtgttc    3120
tctcttcaaa acgctagctg ggggacggta cgtgcaggcc gcgctgctca ctattggccg    3180
ctggaccggc acttatattt ataaccatct cgcccccctg gaaacatggg ccgccggcgg    3240
cctacgggat ttggccgttg cagtcgagcc cgtgatattc tcccccatgg agaagaagat    3300 catagttttgg ggggcggaga ccactgcttg tggcgacatt ctttgtggcc tgcctgtctc    3360
agctcggctc ggcagggaag tcctgctagg gcccgcggat gactacaggt ccatgggatg    3420
gcaactcctg gctcccatca ctgcttatgc ccagcaaaca cgaggcctcc tgggcgccat    3480
agtggtgagt atgacggggc gtgacaggac agaacaggcc ggggaagtcc aaatcctgtc    3540
cacagtctct cagtccttcc tcggaacaac catctcgggg gttttgtgga ctgtttacca    3600
cggagctggc aacaagactc tagccggctt acggggtccg gtcacgcaga tgtactcgag    3660
tgctgagggg gacttggtag gctggcccag ccccccctggg accaagtctt ggagccgtg    3720 caagtgtgga gccgtcgacc tatatctggt cacgcggaac gctgatgtca tcccggctcg    3780
gagacgcggg gacaagcggg gagcattgct ctccccgaga cccatttcga ccttgaaggg    3840
gtcctcgggg gggccggtgc tctgccctag gggccacgtc gttgggctct ccgagcagc    3900 tgtgtgctct cggggcgtgg ccaaatccat cgatttcatc cccgttgaga cactcgacgt    3960
tgttacaagg tctcccactt tcagtgacaa cagcacgcca ccggctgtgc cccagaccta    4020
tcaggtcgga tacttgcatg ctccaactgg cagtggaaag agcaccaagg tccctgtcgc    4080
gtatgccgcc cagggggtaca aagtactagt gcttaacccc tcggtagctg ccaccctggg    4140 gtttgggggcg tacctatcca aggcacatgg catcaatccc aacattagga ctggagtcag    4200
gaccgtgatg accggggagg ccatcacgta ctccacatat ggcaaatttc tcgccgatgg    4260
gggctgcgct agcggcgcct atgacatcat catatgcgat gaatgccacg ctgtggatgc    4320
tacctccatt ctcggcatcg gaacggtcct tgatcaagca gagacagccg gggtcagact    4380
aactgtgctg gctacggcca cacccccgg gtcagtgaca acccccatc ccgatataga    4440 agaggtaggc ctcgggcggg agggtgagat cccttctat ggagggcga ttcccctatc    4500 ctgcatcaag ggaggagac acctgatttt ctgccactca agaaaagt gtgacgagct    4560 cgcggcggcc cttcggggca tgggcttgaa tgccgtggca tactatagag ggttggacgt    4620
ctccataata ccagctcagg gagatgtggt ggtcgtcgcc accgacgccc tcatgacggg    4680
gtacactgga gactttgact ccgtgatcga ctgcaatgta gcggtcaccc aagctgtcga    4740
cttcagcctg gaccccacct tcactataac cacacagact gtcccacaag acgctgtctc    4800
acgcagtcag cgccgcgggc gcacaggtag aggaagacag gcacttata ggtatgtttc    4860 cactggtgaa cgagcctcag gaatgtttga cagtgtagtg cttgtgagt gctacgacgc    4920
```

-continued

```
aggggctgcg tggtacgatc tcacaccagc ggagaccacc gtcaggctta gagcgtattt    4980
caacacgccc ggcctacccg tgtgtcaaga ccatcttgaa ttttgggagg cagttttcac    5040
cggcctcaca cacatagacg cccacttcct ctcccaaaca aagcaagcgg gggagaactt    5100
cgcgtaccta gtagcctacc aagctacggt gtgcgccaga gccaaggccc ctccccgtc    5160
ctggacgcc atgtggaagt gcctggcccg actcaagcct acgcttgcgg gccccacacc     5220
tctcctgtac cgtttgggcc ctattaccaa tgaggtcacc ctcacacacc ctgggacgaa    5280
gtacatcgcc acatgcatgc aagctgacct tgaggtcatg accagcacgt gggtcctagc    5340
tggaggagtc ctggcagccg tcgccgcata ttgcctggcg actggatgcg tttccatcat    5400
cggccgcttg cacgtcaacc agcgagtcgt cgttgcgccg gataaggagg tcctgtatga    5460
ggcttttgat gagatggagg aatgcgcctc tagggcggct ctcatcgaag aggggcagcg    5520
gatagccgag atgttgaagt ccaagatcca aggcttgctg cagcaggcct ctaagcaggc    5580
ccaggacata caacccgcta tgcaggcttc atggcccaaa gtggaacaat tttgggccag    5640
acacatgtgg aacttcatta gcggcatcca atacctcgca ggattgtcaa cactgccagg    5700
gaaccccgcg gtggcttcca tgatggcatt cagtgccgcc ctcaccagtc cgttgtcgac    5760
cagtaccacc atccttctca acatcatggg aggctggtta gcgtcccaga tcgcaccacc    5820
cgcggggggc accggctttg tcgtcagtgg cctggtgggg gctgccgtgg gcagcatagg    5880
cctgggtaag gtgctggtgg acatcctggc aggatatggt gcgggcattt cgggggccct    5940
cgtcgcattc aagatcatgt ctggcgagaa gccctctatg gaagatgtca tcaatctact    6000
gcctgggatc ctgtctccgg gagccctggt ggtgggggtc atctgcgcgg ccattctgcg    6060
ccgccacgtg ggaccggggg agggcgcggt ccaatggatg aacaggctta ttgcctttgc    6120
ttccagagga aaccacgtcg cccctactca ctacgtgacg gagtcggatg cgtcgcagcg    6180
tgtgacccaa ctacttggct ctcttactat aaccagccta ctcagaagac tccacaattg    6240
gataactgag gactgcccca tcccatgctc cggatcctgg ctccgcgacg tgtgggactg    6300
ggtttgcacc atcttgacag acttcaaaaa ttggctgacc tctaaattgt tccccaagct    6360
gccccggcctc cccttcatct cttgtcaaaa ggggtacaag ggtgtgtggg ccggcactgg    6420
catcatgacc acgcgctgcc cttgcggcgc aacatctct ggcaatgtcc gcctgggctc     6480
tatgaggatc acagggccta aaacctgcat gaacacctgg cagggggacct ttcctatcaa    6540
ttgctcacg gagggccagt gcgcgccgaa acccccacg aactacaaga ccgccatctg      6600
gagggtggcg gcctcggagt acgcggaggt gacgcagcat gggtcgtact cctatgtaac    6660
aggactgacc actgacaatc tgaaaattcc ttgccaacta ccttctccag agttttctc     6720
ctgggtggac ggtgtgcaga tccataggtt tgcacccaca ccaaagccgt ttttccggga    6780
tgaggtctcg ttctgcgttg ggcttaattc ctatgctgtc gggtcccagc ttccctgtga    6840
acctgagccc gacgcagacg tattgaggtc catgctaaca gatccgcccc acatcacggc    6900
ggagactgcg gcgcggcgct tggcacgggg atcacctcca tctgaggcga gctcctcagt    6960
gagccagcta tcagcaccgt cgctgcgggc cacctgcacc acccacagca acacctatga    7020
cgtggacatg gtcgatgcca acctgctcat ggagggcggt gtggctcaga cagagcctga    7080
gtccagggtg cccgttctgg actttctcga gccaatggcc gaggaagaga gcgaccttga    7140
gccctcaata ccatcggagt gcatgctccc caggagcggg tttccacggg ccttaccggc    7200
ttgggcacgg cctgactaca acccgccgct cgtggaatcg tggaggaggc cagattacca    7260
accgccacc gttgctggtt gtgctctccc cccccccaag aaggcccga cgcctccccc      7320
```

```
aaggagacgc cggacagtgg gtctgagcga gagcaccata tcagaagccc tccagcaact    7380
ggccatcaag acctttggcc agcccccctc gagcggtgat gcaggctcgt ccacggggc    7440 gggcgccgcc gaatccggcg gtccgacgtc ccctggtgag ccggcccct cagagacagg    7500 ttccgcctcc tctatgcccc ccctcgaggg ggagcctgga gatccggacc tggagtctga    7560
tcaggtagag cttcaacctc ccccccaggg ggggggggta gctcccggtt cgggctcggg    7620
gtcttggtct acttgctccg aggaggacga taccaccgtg tgctgctcca tgtcatactc    7680
ctggaccggg gctctaataa ctccctgtag ccccgaagag gaaaagttgc caatcaaccc    7740
tttgagtaac tcgctgttgc gataccataa caaggtgtac tgtacaacat caaagagcgc    7800
ctcacagagg gctaaaaagg taacttttga caggacgcaa gtgctcgacg cccattatga    7860
ctcagtctta aaggacatca agctagcggc ttccaaggtc agcgcaaggc tcctcacctt    7920
ggaggaggcg tgccagttga ctccacccca ttctgcaaga tccaagtatg gattcggggc    7980
caaggaggtc cgcagcttgt ccgggagggc cgttaaccac atcaagtccg tgtggaagga    8040
cctcctggaa gacccacaaa caccaattcc cacaaccatc atggccaaaa atgaggtgtt    8100
ctgcgtggac cccgccaagg ggggtaagaa accagctcgc ctcatcgttt accctgacct    8160
cggcgtccgg gtctgcgaga aaatggccct ctatgacatt acacaaaagc ttcctcaggc    8220
ggtaatggga gcttcctatg gcttccagta ctcccctgcc caacgggtgg agtatctctt    8280
gaaagcatgg gcggaaaaga aggaccccat gggttttttcg tatgataccc gatgcttcga    8340
ctcaaccgtc actgagagag acatcaggac cgaggagtcc atataccagg cctgctccct    8400
gcccgaggag gcccgcactg ccatacactc gctgactgag agactttacg taggagggcc    8460
catgttcaac agcaagggtc aaacctgcgg ttacagacgt tgccgcgcca gcggggtgct    8520
aaccactagc atgggtaaca ccatcacatg ctatgtgaaa gccctagcgg cctgcaaggc    8580
tgcggggata gttgcgccca caatgctggt atgcggcgat gacctagtag tcatctcaga    8640
aagccagggg actgaggagg acgagcggaa cctgagagcc ttcacggagg ccatgaccag    8700
gtactctgcc cctcctggtg atccccccag accggaatat gacctggagc taataacatc    8760
ctgttcctca aatgtgtctg tggcgttggg cccgcggggc cgccgcagat actacctgac    8820
cagagaccca accactccac tcgcccgggc tgcctgggaa acagttagac actcccctat    8880
caattcatgg ctgggaaaca tcatccagta tgctccaacc atatgggttc gcatggtcct    8940
aatgacacac ttcttctcca ttctcatggt ccaagacacc ctggaccaga acctcaactt    9000
tgagatgtat ggatcagtat actccgtgaa tcctttggac cttccagcca taattgagag    9060
gttacacggg cttgacgcct tttctatgca cacatactct caccacgaac tgacgcgggt    9120
ggcttcagcc ctcagaaaac ttggggcgcc accccctcagg gtgtggaaga gtcgggctcg    9180
cgcagtcagg gcgtccctca tctcccgtgg agggaaagcg gccgtttgcg gccgatatct    9240
cttcaattgg gcggtgaaga ccaagctcaa actcactcca ttgccggagg cgcgcctact    9300
ggacttatcc agttggttca ccgtcggcgc cggcggggc gacattttc acagcgtgtc    9360 gcgcgcccga ccccgctcat tactcttcgg cctactccta cttttcgtag gggtaggcct    9420
cttcctactc cccgctcggt agagcggcac acactaggta cactccatag ctaactgttc    9480 ctttttttttt tttttttttt tttttttttt tttttttttt tttctttttt tttttttttc    9540
cctctttctt cccttctcat cttattctac tttctttctt ggtggctcca tcttagccct    9600
agtcacggct agctgtgaaa ggtccgtgag ccgcatgact gcagagagtg ccgtaactgg    9660
tctctctgca gatcatgt                                                   9678
```

<210> SEQ ID NO 4
<211> LENGTH: 3033
<212> TYPE: PRT
<213> ORGANISM: Hepatitis C virus

<400> SEQUENCE: 4

```
Met Ser Thr Asn Pro Lys Pro Gln Arg Leu Thr Lys Arg Asn Thr Val
1               5                   10                  15

Arg Arg Pro Gln Asn Val Lys Phe Pro Gly Gly Gly Gln Ile Val Gly
            20                  25                  30

Gly Val Tyr Leu Leu Pro Arg Arg Gly Pro Arg Leu Gly Val Arg Gly
        35                  40                  45

Thr Arg Lys Ser Ser Glu Arg Ser Gln Pro Arg Gly Arg Arg Gln Arg
    50                  55                  60

Ile Pro Lys Ala Ala Ser Ser Gln Gly Lys Ala Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Lys Val Ile Asp Thr Met Thr Cys
        115                 120                 125

Gly Phe Ala Asp Leu Met Gly Tyr Ile Pro Val Leu Gly Ala Pro Leu
    130                 135                 140

Gly Gly Val Ala Arg Ala Leu Ala His Gly Val Arg Phe Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Glu Val Arg Asn Ser Ser Gly Val Tyr His Leu Thr Asn Asp Cys Pro
        195                 200                 205

Asn Ala Ser Ile Val Tyr Glu Thr Asp Asn Ala Ile Leu His Glu Pro
    210                 215                 220

Gly Cys Val Pro Cys Val Arg Glu Gly Asn Thr Ser Arg Cys Trp Glu
225                 230                 235                 240

Pro Val Ala Pro Thr Leu Ala Val Arg Tyr Arg Gly Ala Leu Thr Asp
                245                 250                 255

Asp Leu Arg Thr His Ile Asp Leu Val Val Ala Ser Ala Thr Leu Cys
            260                 265                 270

Ser Ala Leu Tyr Val Gly Asp Ile Cys Gly Ala Ile Phe Ile Ala Ser
        275                 280                 285

Gln Ala Val Leu Trp Lys Pro Gly Gly Gly Arg Ile Val Gln Asp Cys
    290                 295                 300

Asn Cys Ser Ile Tyr Pro Gly His Val Thr Gly His Arg Met Ala Trp
305                 310                 315                 320

Asp Met Met Gln Asn Trp Ala Pro Ala Leu Ser Met Val Ala Ala Tyr
                325                 330                 335

Ala Val Arg Val Pro Gly Val Ile Ile Thr Thr Val Ala Gly Gly His
            340                 345                 350

Trp Gly Val Leu Phe Gly Leu Ala Tyr Phe Gly Met Ala Gly Asn Trp
        355                 360                 365

Ala Lys Val Ile Leu Ile Met Leu Leu Met Ser Gly Val Asp Ala Glu
    370                 375                 380
```

```
Thr Met Ala Val Gly Ala Arg Ala His Thr Thr Gly Ala Leu Val
385                 390                 395                 400

Ser Leu Leu Asn Pro Gly Pro Ser Gln Arg Leu Gln Leu Ile Asn Thr
            405                 410                 415

Asn Gly Ser Trp His Ile Asn Arg Thr Ala Leu Asn Cys Asn Asp Ser
                420                 425                 430

Leu Gln Thr Gly Phe Ile Ala Ala Leu Phe Tyr Thr His Arg Phe Asn
            435                 440                 445

Ser Ser Gly Cys Pro Glu Arg Met Ala Ser Cys Lys Pro Leu Ser Asp
450                 455                 460

Phe Asp Gln Gly Trp Gly Pro Leu Trp Tyr Asn Ser Thr Glu Arg Pro
465                 470                 475                 480

Ser Asp Gln Arg Pro Tyr Cys Trp His Tyr Ala Pro Ser Pro Cys Gly
            485                 490                 495

Ile Val Pro Ala Lys Asp Val Cys Gly Pro Val Tyr Cys Phe Thr Pro
            500                 505                 510

Ser Pro Val Val Gly Thr Thr Asp Arg Arg Gly Val Pro Thr Tyr
515                 520                 525

Thr Trp Gly Glu Asn Glu Ser Asp Val Phe Leu Leu Asn Ser Thr Arg
530                 535                 540

Pro Pro Gln Gly Ser Trp Phe Gly Cys Ser Trp Met Asn Thr Thr Gly
545                 550                 555                 560

Phe Thr Lys Thr Cys Gly Gly Pro Pro Cys Lys Ile Arg Pro Gln Gly
            565                 570                 575

Ala Gln Ser Asn Thr Ser Leu Thr Cys Pro Thr Asp Cys Phe Arg Lys
            580                 585                 590

His Pro Arg Ala Thr Tyr Ser Ala Cys Gly Ser Gly Pro Trp Leu Thr
            595                 600                 605

Pro Arg Cys Met Val His Tyr Pro Tyr Arg Leu Trp His Tyr Pro Cys
610                 615                 620

Thr Val Asn Phe Thr Ile His Lys Val Arg Leu Tyr Ile Gly Gly Val
625                 630                 635                 640

Glu His Arg Leu Asp Ala Ala Cys Asn Trp Thr Arg Gly Glu Arg Cys
                645                 650                 655

Asp Leu Glu Asp Arg Asp Arg Val Asp Met Ser Pro Leu Leu His Ser
                660                 665                 670

Thr Thr Glu Leu Ala Ile Leu Pro Cys Ser Phe Val Pro Leu Pro Ala
            675                 680                 685

Leu Ser Thr Gly Leu Ile His Leu His Gln Asn Ile Val Asp Ala Gln
690                 695                 700

Tyr Leu Tyr Gly Leu Ser Pro Ala Ile Ile Ser Trp Ala Ile Arg Trp
705                 710                 715                 720

Glu Trp Val Val Leu Val Phe Leu Leu Leu Ala Asp Ala Arg Ile Cys
            725                 730                 735

Ala Cys Leu Trp Met Met Met Leu Met Ala Gln Ala Glu Ala Ala Leu
            740                 745                 750

Glu Asn Leu Ile His Leu Asn Ala Ala Ser Leu Ala Gly Thr His Gly
            755                 760                 765

Ile Trp Trp Leu Leu Leu Val Phe Cys Ala Ser Trp His Leu Arg Gly
            770                 775                 780

Arg Val Val Pro Leu Val Thr Tyr Gly Ile Cys Gly Met Trp Pro Phe
785                 790                 795                 800

Phe Leu Met Leu Leu Ser Leu Pro Pro Arg Ala Tyr Ala Leu Asp Arg
```

-continued

```
                805                 810                 815
Glu Val Ser Ala Ala Leu Gly Thr Gly Met Leu Ala Ile Ile Leu Leu
                820                 825                 830

Val Thr Leu Gly Pro His Tyr Lys Arg Leu Leu Ala Leu Ile Leu Trp
            835                 840                 845

Trp Val Thr Tyr Phe Leu Thr Arg Cys Glu Ala Ala Leu Gln Thr Trp
850                 855                 860

Val Pro Pro Leu Asn Pro Arg Gly Gly Arg Asp Gly Phe Ile Leu Cys
865                 870                 875                 880

Val Leu Leu Cys Tyr Pro Gly Leu Val Phe Asp Ile Thr Lys Trp Leu
                885                 890                 895

Leu Val Met Met Cys Pro Leu Tyr Leu Gln Leu Cys Leu Val Arg
                900                 905                 910

Thr Pro Tyr Phe Val Arg Ala Gln Ala Leu Ile Arg Val Cys Ser Leu
            915                 920                 925

Phe Lys Thr Leu Ala Gly Gly Arg Tyr Val Gln Ala Ala Leu Leu Thr
        930                 935                 940

Ile Gly Arg Trp Thr Gly Thr Tyr Ile Tyr Asn His Leu Ala Pro Leu
945                 950                 955                 960

Glu Thr Trp Ala Ala Gly Gly Leu Arg Asp Leu Ala Val Ala Val Glu
                965                 970                 975

Pro Val Ile Phe Ser Pro Met Glu Lys Lys Ile Ile Val Trp Gly Ala
            980                 985                 990

Glu Thr Thr Ala Cys Gly Asp Ile Leu Cys Gly Leu Pro Val Ser Ala
            995                1000                1005

Arg Leu Gly Arg Glu Val Leu Leu Gly Pro Ala Asp Asp Tyr Arg
    1010                1015                1020

Ser Met Gly Trp Gln Leu Leu Ala Pro Ile Thr Ala Tyr Ala Gln
    1025                1030                1035

Gln Thr Arg Gly Leu Leu Gly Ala Ile Val Val Ser Met Thr Gly
    1040                1045                1050

Arg Asp Arg Thr Glu Gln Ala Gly Glu Val Gln Ile Leu Ser Thr
    1055                1060                1065

Val Ser Gln Ser Phe Leu Gly Thr Thr Ile Ser Gly Val Leu Trp
    1070                1075                1080

Thr Val Tyr His Gly Ala Gly Asn Lys Thr Leu Ala Gly Leu Arg
    1085                1090                1095

Gly Pro Val Thr Gln Met Tyr Ser Ser Ala Glu Gly Asp Leu Val
    1100                1105                1110

Gly Trp Pro Ser Pro Pro Gly Thr Lys Ser Leu Glu Pro Cys Lys
    1115                1120                1125

Cys Gly Ala Val Asp Leu Tyr Leu Val Thr Arg Asn Ala Asp Val
    1130                1135                1140

Ile Pro Ala Arg Arg Arg Gly Asp Lys Arg Gly Ala Leu Leu Ser
    1145                1150                1155

Pro Arg Pro Ile Ser Thr Leu Lys Gly Ser Ser Gly Gly Pro Val
    1160                1165                1170

Leu Cys Pro Arg Gly His Val Val Gly Leu Phe Arg Ala Ala Val
    1175                1180                1185

Cys Ser Arg Gly Val Ala Lys Ser Ile Asp Phe Ile Pro Val Glu
    1190                1195                1200

Thr Leu Asp Val Val Thr Arg Ser Pro Thr Phe Ser Asp Asn Ser
    1205                1210                1215
```

```
Thr Pro Pro Ala Val Pro Gln Thr Tyr Gln Val Gly Tyr Leu His
1220            1225                1230

Ala Pro Thr Gly Ser Gly Lys Ser Thr Lys Val Pro Val Ala Tyr
1235            1240                1245

Ala Ala Gln Gly Tyr Lys Val Leu Val Leu Asn Pro Ser Val Ala
1250            1255                1260

Ala Thr Leu Gly Phe Gly Ala Tyr Leu Ser Lys Ala His Gly Ile
1265            1270                1275

Asn Pro Asn Ile Arg Thr Gly Val Arg Thr Val Met Thr Gly Glu
1280            1285                1290

Ala Ile Thr Tyr Ser Thr Tyr Gly Lys Phe Leu Ala Asp Gly Gly
1295            1300                1305

Cys Ala Ser Gly Ala Tyr Asp Ile Ile Ile Cys Asp Glu Cys His
1310            1315                1320

Ala Val Asp Ala Thr Ser Ile Leu Gly Ile Gly Thr Val Leu Asp
1325            1330                1335

Gln Ala Glu Thr Ala Gly Val Arg Leu Thr Val Leu Ala Thr Ala
1340            1345                1350

Thr Pro Pro Gly Ser Val Thr Thr Pro His Pro Asp Ile Glu Glu
1355            1360                1365

Val Gly Leu Gly Arg Glu Gly Glu Ile Pro Phe Tyr Gly Arg Ala
1370            1375                1380

Ile Pro Leu Ser Cys Ile Lys Gly Gly Arg His Leu Ile Phe Cys
1385            1390                1395

His Ser Lys Lys Lys Cys Asp Glu Leu Ala Ala Ala Leu Arg Gly
1400            1405                1410

Met Gly Leu Asn Ala Val Ala Tyr Tyr Arg Gly Leu Asp Val Ser
1415            1420                1425

Ile Ile Pro Ala Gln Gly Asp Val Val Val Val Ala Thr Asp Ala
1430            1435                1440

Leu Met Thr Gly Tyr Thr Gly Asp Phe Asp Ser Val Ile Asp Cys
1445            1450                1455

Asn Val Ala Val Thr Gln Ala Val Asp Phe Ser Leu Asp Pro Thr
1460            1465                1470

Phe Thr Ile Thr Thr Gln Thr Val Pro Gln Asp Ala Val Ser Arg
1475            1480                1485

Ser Gln Arg Arg Gly Arg Thr Gly Arg Gly Arg Gln Gly Thr Tyr
1490            1495                1500

Arg Tyr Val Ser Thr Gly Glu Arg Ala Ser Gly Met Phe Asp Ser
1505            1510                1515

Val Val Leu Cys Glu Cys Tyr Asp Ala Gly Ala Ala Trp Tyr Asp
1520            1525                1530

Leu Thr Pro Ala Glu Thr Thr Val Arg Leu Arg Ala Tyr Phe Asn
1535            1540                1545

Thr Pro Gly Leu Pro Val Cys Gln Asp His Leu Glu Phe Trp Glu
1550            1555                1560

Ala Val Phe Thr Gly Leu Thr His Ile Asp Ala His Phe Leu Ser
1565            1570                1575

Gln Thr Lys Gln Ala Gly Glu Asn Phe Ala Tyr Leu Val Ala Tyr
1580            1585                1590

Gln Ala Thr Val Cys Ala Arg Ala Lys Ala Pro Pro Pro Ser Trp
1595            1600                1605

Asp Ala Met Trp Lys Cys Leu Ala Arg Leu Lys Pro Thr Leu Ala
1610            1615                1620
```

-continued

```
Gly Pro Thr Pro Leu Leu Tyr Arg Leu Gly Pro Ile Thr Asn Glu
    1625                1630                1635

Val Thr Leu Thr His Pro Gly Thr Lys Tyr Ile Ala Thr Cys Met
    1640                1645                1650

Gln Ala Asp Leu Glu Val Met Thr Ser Thr Trp Val Leu Ala Gly
    1655                1660                1665

Gly Val Leu Ala Ala Val Ala Ala Tyr Cys Leu Ala Thr Gly Cys
    1670                1675                1680

Val Ser Ile Ile Gly Arg Leu His Val Asn Gln Arg Val Val Val
    1685                1690                1695

Ala Pro Asp Lys Glu Val Leu Tyr Glu Ala Phe Asp Glu Met Glu
    1700                1705                1710

Glu Cys Ala Ser Arg Ala Ala Leu Ile Glu Glu Gly Gln Arg Ile
    1715                1720                1725

Ala Glu Met Leu Lys Ser Lys Ile Gln Gly Leu Leu Gln Gln Ala
    1730                1735                1740

Ser Lys Gln Ala Gln Asp Ile Gln Pro Ala Met Gln Ala Ser Trp
    1745                1750                1755

Pro Lys Val Glu Gln Phe Trp Ala Arg His Met Trp Asn Phe Ile
    1760                1765                1770

Ser Gly Ile Gln Tyr Leu Ala Gly Leu Ser Thr Leu Pro Gly Asn
    1775                1780                1785

Pro Ala Val Ala Ser Met Met Ala Phe Ser Ala Ala Leu Thr Ser
    1790                1795                1800

Pro Leu Ser Thr Ser Thr Thr Ile Leu Leu Asn Ile Met Gly Gly
    1805                1810                1815

Trp Leu Ala Ser Gln Ile Ala Pro Pro Ala Gly Ala Thr Gly Phe
    1820                1825                1830

Val Val Ser Gly Leu Val Gly Ala Ala Val Gly Ser Ile Gly Leu
    1835                1840                1845

Gly Lys Val Leu Val Asp Ile Leu Ala Gly Tyr Gly Ala Gly Ile
    1850                1855                1860

Ser Gly Ala Leu Val Ala Phe Lys Ile Met Ser Gly Glu Lys Pro
    1865                1870                1875

Ser Met Glu Asp Val Ile Asn Leu Leu Pro Gly Ile Leu Ser Pro
    1880                1885                1890

Gly Ala Leu Val Val Gly Val Ile Cys Ala Ala Ile Leu Arg Arg
    1895                1900                1905

His Val Gly Pro Gly Glu Gly Ala Val Gln Trp Met Asn Arg Leu
    1910                1915                1920

Ile Ala Phe Ala Ser Arg Gly Asn His Val Ala Pro Thr His Tyr
    1925                1930                1935

Val Thr Glu Ser Asp Ala Ser Gln Arg Val Thr Gln Leu Leu Gly
    1940                1945                1950

Ser Leu Thr Ile Thr Ser Leu Leu Arg Arg Leu His Asn Trp Ile
    1955                1960                1965

Thr Glu Asp Cys Pro Ile Pro Cys Ser Gly Ser Trp Leu Arg Asp
    1970                1975                1980

Val Trp Asp Trp Val Cys Thr Ile Leu Thr Asp Phe Lys Asn Trp
    1985                1990                1995

Leu Thr Ser Lys Leu Phe Pro Lys Leu Pro Gly Leu Pro Phe Ile
    2000                2005                2010

Ser Cys Gln Lys Gly Tyr Lys Gly Val Trp Ala Gly Thr Gly Ile
```

```
                2015                2020                2025
Met Thr Thr Arg Cys Pro Cys Gly Ala Asn Ile Ser Gly Asn Val
    2030                2035                2040

Arg Leu Gly Ser Met Arg Ile Thr Gly Pro Lys Thr Cys Met Asn
    2045                2050                2055

Thr Trp Gln Gly Thr Phe Pro Ile Asn Cys Tyr Thr Glu Gly Gln
    2060                2065                2070

Cys Ala Pro Lys Pro Pro Thr Asn Tyr Lys Thr Ala Ile Trp Arg
    2075                2080                2085

Val Ala Ala Ser Glu Tyr Ala Glu Val Thr Gln His Gly Ser Tyr
    2090                2095                2100

Ser Tyr Val Thr Gly Leu Thr Thr Asp Asn Leu Lys Ile Pro Cys
    2105                2110                2115

Gln Leu Pro Ser Pro Glu Phe Phe Ser Trp Val Asp Gly Val Gln
    2120                2125                2130

Ile His Arg Phe Ala Pro Thr Pro Lys Pro Phe Phe Arg Asp Glu
    2135                2140                2145

Val Ser Phe Cys Val Gly Leu Asn Ser Tyr Ala Val Gly Ser Gln
    2150                2155                2160

Leu Pro Cys Glu Pro Glu Pro Asp Ala Asp Val Leu Arg Ser Met
    2165                2170                2175

Leu Thr Asp Pro Pro His Ile Thr Ala Glu Thr Ala Ala Arg Arg
    2180                2185                2190

Leu Ala Arg Gly Ser Pro Pro Ser Glu Ala Ser Ser Val Ser
    2195                2200                2205

Gln Leu Ser Ala Pro Ser Leu Arg Ala Thr Cys Thr Thr His Ser
    2210                2215                2220

Asn Thr Tyr Asp Val Asp Met Val Asp Ala Asn Leu Leu Met Glu
    2225                2230                2235

Gly Gly Val Ala Gln Thr Glu Pro Glu Ser Arg Val Pro Val Leu
    2240                2245                2250

Asp Phe Leu Glu Pro Met Ala Glu Glu Glu Ser Asp Leu Glu Pro
    2255                2260                2265

Ser Ile Pro Ser Glu Cys Met Leu Pro Arg Ser Gly Phe Pro Arg
    2270                2275                2280

Ala Leu Pro Ala Trp Ala Arg Pro Asp Tyr Asn Pro Pro Leu Val
    2285                2290                2295

Glu Ser Trp Arg Arg Pro Asp Tyr Gln Pro Pro Thr Val Ala Gly
    2300                2305                2310

Cys Ala Leu Pro Pro Pro Lys Lys Ala Pro Thr Pro Pro Pro Arg
    2315                2320                2325

Arg Arg Arg Thr Val Gly Leu Ser Glu Ser Thr Ile Ser Glu Ala
    2330                2335                2340

Leu Gln Gln Leu Ala Ile Lys Thr Phe Gly Gln Pro Pro Ser Ser
    2345                2350                2355

Gly Asp Ala Gly Ser Ser Thr Gly Ala Gly Ala Ala Glu Ser Gly
    2360                2365                2370

Gly Pro Thr Ser Pro Gly Glu Pro Ala Pro Ser Glu Thr Gly Ser
    2375                2380                2385

Ala Ser Ser Met Pro Pro Leu Glu Gly Glu Pro Gly Asp Pro Asp
    2390                2395                2400

Leu Glu Ser Asp Gln Val Glu Leu Gln Pro Pro Gln Gly Gly
    2405                2410                2415
```

-continued

Gly Val Ala Pro Gly Ser Gly Ser Trp Ser Thr Cys Ser
2420            2425            2430

Glu Glu Asp Asp Thr Thr Val Cys Cys Ser Met Ser Tyr Ser Trp
2435            2440            2445

Thr Gly Ala Leu Ile Thr Pro Cys Ser Pro Glu Glu Lys Leu
2450            2455            2460

Pro Ile Asn Pro Leu Ser Asn Ser Leu Leu Arg Tyr His Asn Lys
2465            2470            2475

Val Tyr Cys Thr Thr Ser Lys Ser Ala Ser Gln Arg Ala Lys Lys
2480            2485            2490

Val Thr Phe Asp Arg Thr Gln Val Leu Asp Ala His Tyr Asp Ser
2495            2500            2505

Val Leu Lys Asp Ile Lys Leu Ala Ala Ser Lys Val Ser Ala Arg
2510            2515            2520

Leu Leu Thr Leu Glu Glu Ala Cys Gln Leu Thr Pro Pro His Ser
2525            2530            2535

Ala Arg Ser Lys Tyr Gly Phe Gly Ala Lys Glu Val Arg Ser Leu
2540            2545            2550

Ser Gly Arg Ala Val Asn His Ile Lys Ser Val Trp Lys Asp Leu
2555            2560            2565

Leu Glu Asp Pro Gln Thr Pro Ile Pro Thr Thr Ile Met Ala Lys
2570            2575            2580

Asn Glu Val Phe Cys Val Asp Pro Ala Lys Gly Gly Lys Lys Pro
2585            2590            2595

Ala Arg Leu Ile Val Tyr Pro Asp Leu Gly Val Arg Val Cys Glu
2600            2605            2610

Lys Met Ala Leu Tyr Asp Ile Thr Gln Lys Leu Pro Gln Ala Val
2615            2620            2625

Met Gly Ala Ser Tyr Gly Phe Gln Tyr Ser Pro Ala Gln Arg Val
2630            2635            2640

Glu Tyr Leu Leu Lys Ala Trp Ala Glu Lys Lys Asp Pro Met Gly
2645            2650            2655

Phe Ser Tyr Asp Thr Arg Cys Phe Asp Ser Thr Val Thr Glu Arg
2660            2665            2670

Asp Ile Arg Thr Glu Glu Ser Ile Tyr Gln Ala Cys Ser Leu Pro
2675            2680            2685

Glu Glu Ala Arg Thr Ala Ile His Ser Leu Thr Glu Arg Leu Tyr
2690            2695            2700

Val Gly Gly Pro Met Phe Asn Ser Lys Gly Gln Thr Cys Gly Tyr
2705            2710            2715

Arg Arg Cys Arg Ala Ser Gly Val Leu Thr Thr Ser Met Gly Asn
2720            2725            2730

Thr Ile Thr Cys Tyr Val Lys Ala Leu Ala Ala Cys Lys Ala Ala
2735            2740            2745

Gly Ile Val Ala Pro Thr Met Leu Val Cys Gly Asp Asp Leu Val
2750            2755            2760

Val Ile Ser Glu Ser Gln Gly Thr Glu Glu Asp Glu Arg Asn Leu
2765            2770            2775

Arg Ala Phe Thr Glu Ala Met Thr Arg Tyr Ser Ala Pro Pro Gly
2780            2785            2790

Asp Pro Pro Arg Pro Glu Tyr Asp Leu Glu Leu Ile Thr Ser Cys
2795            2800            2805

Ser Ser Asn Val Ser Val Ala Leu Gly Pro Arg Gly Arg Arg Arg
2810            2815            2820

Tyr Tyr Leu Thr Arg Asp Pro Thr Thr Pro Leu Ala Arg Ala Ala
2825                2830                2835

Trp Glu Thr Val Arg His Ser Pro Ile Asn Ser Trp Leu Gly Asn
    2840                2845                2850

Ile Ile Gln Tyr Ala Pro Thr Ile Trp Val Arg Met Val Leu Met
2855                2860                2865

Thr His Phe Phe Ser Ile Leu Met Val Gln Asp Thr Leu Asp Gln
2870                2875                2880

Asn Leu Asn Phe Glu Met Tyr Gly Ser Val Tyr Ser Val Asn Pro
2885                2890                2895

Leu Asp Leu Pro Ala Ile Ile Glu Arg Leu His Gly Leu Asp Ala
2900                2905                2910

Phe Ser Met His Thr Tyr Ser His His Glu Leu Thr Arg Val Ala
2915                2920                2925

Ser Ala Leu Arg Lys Leu Gly Ala Pro Pro Leu Arg Val Trp Lys
2930                2935                2940

Ser Arg Ala Arg Ala Val Arg Ala Ser Leu Ile Ser Arg Gly Gly
2945                2950                2955

Lys Ala Ala Val Cys Gly Arg Tyr Leu Phe Asn Trp Ala Val Lys
2960                2965                2970

Thr Lys Leu Lys Leu Thr Pro Leu Pro Glu Ala Arg Leu Leu Asp
2975                2980                2985

Leu Ser Ser Trp Phe Thr Val Gly Ala Gly Gly Gly Asp Ile Phe
2990                2995                3000

His Ser Val Ser Arg Ala Arg Pro Arg Ser Leu Leu Phe Gly Leu
3005                3010                3015

Leu Leu Leu Phe Val Gly Val Gly Leu Phe Leu Leu Pro Ala Arg
3020                3025                3030

<210> SEQ ID NO 5
<211> LENGTH: 9678
<212> TYPE: DNA
<213> ORGANISM: Hepatitis C virus

<400> SEQUENCE: 5
acctgcccct aatagggggcg acactccgcc atgaatcact cccctgtgag gaactactgt    60
cttcacgcag aaagcgccta gccatggcgt tagtatgagt gtcgtacagc ctccaggccc   120 cccctcccg ggagagccat agtggtctgc ggaaccggtg agtacaccgg aattgccggg   180
aagactgggt cctttcttgg ataaacccac tctatgcccg gccatttggg cgtgcccccg   240
caagactgct agccgagtag cgttgggttg cgaaaggcct tgtggtactg cctgataggg   300
tgcttgcgag tgccccggga ggtctcgtag accgtgcacc atgagcacga atcctaaacc   360
tcaaagatta accaaaagaa acaccgtccg tcgcccacag aacgttaagt tcccgggtgg   420
cgggcagatc gttggcggag tctacttgtt gccgcgcagg ggcccctagat gggtgtgcg   480 cggcactagg aagagttcgg agcgatcgca gcccagggga agacgccaac gtatccccaa   540
agctgcctct tcacagggta aagcctgggg caagcccggg tacccttggc cctgtatgg   600 taacgagggc tgtggctggg cagggtggct cctgtccccc gcggctctc gacctacttg   660 gggccccact gaccccggc accgtcgcg aaacctcggt aaggtgatcg acaccatgac   720 ctgcggggttt gccgacctca tgggtacat ccctgtccta ggcgcccccc taggggggcgt   780 tgccagggct ctggcacatg gtgttagagt tctggaggac ggggtcaact atgcaacagg   840
gaacttgcct ggttgctcct tttctatctt cttactagcc ctcctgtcat gtctaacagt   900

```
cccggcatcg gcttatgaag tccgcaactc cagtggggtc tatcatctca ccaatgactg    960
ccccaacgct agtatagtct atgaaacaga caacgccatc ctacacgagc ctgggtgcgt   1020
gccttgcgtt cgcgagggta atactagcag gtgttgggaa ccagtggccc ccactttggc   1080
ggtccgctat cgcggagcgc ttactgacga tttgcggacg catattgacc tagtggtggc   1140
gtcagctacc ctgtgctccg ccttgtacgt gggggacatt tgtggagcca tcttcattgc   1200
cagccaagct gttctctgga agcccggggg gggtcggata gtgcaagatt gcaattgttc   1260
gatctacccg ggccacgtca ccggccacag gatggcgtgg gacatgatgc agaactgggc   1320
gccggccttg tcaatggttg ccgcttacgc tgtgagagtg cccggtgtca tcattaccac   1380
tgtagcgggc ggccactggg gtgtgttatt tggcctcgct tactttggta tggcgggaaa   1440
ctgggcaaag gtaatactca tcatgctact catgtccggc gtcgacgcgg aaaccatggc   1500
cgtcggggct agggccgctc acaccactgg cgcccttgtc agcctgctca atccagggcc   1560
cagtcagcgc ctgcagctga ccaacaccaa tgggtcatgg cacatcaacc ggaccgcttt   1620
gaactgcaat gactctttgc agacagggtt catagcggcc ctcttctaca cacataggtt   1680
caattctagt ggctgtcccg agaggatggc ttccttgtaaa cctctcagtg actttgacca   1740
ggggtggggc ccgctgtggt acaattcaac agaaagacct tcggaccagc gaccctattg   1800
ctggcactac gcgccatcgc cgtgtggtat tgtgccggct aaggatgttt gcggtccggt   1860
ctactgcttt acaccaagcc cggttgtggt gggcaccacg gatcgccggg gggtgcccac   1920
gtatacttgg ggtgaaaatg agtctgatgt cttcctgctc aacagcacaa ggccgccgca   1980
aggcagttgg tttgggtgct catggatgaa cacaacgggg ttcacgaaga cctgcggagg   2040
tcctccgtgc aagatacgtc cccagggtgc ccagagtaac acctctctca cttgtcccac   2100
agactgcttc aggaaacatc cgcgtgccac atactccgct tgcggatctg gtccgtggtt   2160
gacacctaga tgcatggtcc attacccta tagactgtgg cactacccgt gtacagtcaa   2220
cttcaccata cacaaagtca ggttatacat aggggggtgta gaacataggc tcgatgcagc   2280
gtgcaattgg acgcggggtg agcgatgcga cctggaggac cgagacaggg tggacatgtc   2340 cccctgctc cattccacta cggagctcgc aatacttccg tgttcctttg tgccgcttcc   2400
ggccttatct acgggactga tccacctgca ccaaaacatc gttgacgccc agtaccctta   2460
tggtcttcct cccgctataa taagctgggc catcagatgg gagtggggtag tcctcgtttt   2520 cctactcctg gcgacgcgc ggatctgcgc ctgcctttgg atgatgatgc ttatggccca   2580
ggctgaagcc gctctggaga acttgatcca cctcaacgcg gccagccttg cgggaaccca   2640
tggtatctgg tggctccttt tagtcttttg tgcctcttgg catctacgag gcagggttgt   2700
ccctctggtg acgtatggga tatgcgggat gtggccctc ttcctcatgt tgctgagcct   2760
ccccccacga gcgtatgctc tggacaggga agtgagcgca gcgttgggaa cgggcatgct   2820
cgccatcatc ctattagtta ccttgggacc gcactacaag agacttctag cccttattct   2880
ctggtgggtc acatatttcc ttacaaggtg tgaagcagca ctccaaacgt gggtccctcc   2940 tctcaacccct cggggggca gggacggttt catcctgtgt gtgctgctgt gctatccagg   3000
ccttgtcttt gacatcacaa aatggttgct ggtcatgatg tgccctctct acctcctcca   3060
gttgtgtttg gtgaggactc catactttgt gagggcccag gccctcatca gagtgtgttc   3120
tctcttcaaa acgctagctg ggggacggta cgtgcaggcc gcgctgctca ctattggccg   3180
ctggaccggc acttatattt ataaccatct cgcccccctg gaaacatggg ccgccggcgg   3240
cctacgggat ttggccgttg cagtcgagcc cgtgatattc tcccccatgg agaagaagat   3300
```

```
catagtttgg ggggcggaga ccactgcttg tggcgacatt ctttgtggcc tgcctgtctc   3360
agctcggctc ggcagggaag tcctgctagg gcccgcggat gactacaggt ccatgggatg   3420
gcaactcctg gctcccatca ctgcttatgc ccagcaaaca cgaggcctcc tgggcgccat   3480
agtggtgagt atgacggggc gtgacaggac agaacaggcc ggggaagtcc aaatcctgtc   3540
cacagtctct cagtccttcc tcggaacaac catctcgggg gttttgtgga ctgtttacca   3600
cggagctggc aacaagactc tagccggctt acggggtccg gtcacgcaga tgtactcgag   3660
tgctgagggg gacttggtag gctggcccag cccccctggg accaagtctt ggagccgtg   3720 caagtgtgga gccgtcgacc tatatctggt cacgcggaac gctgatgtca tcccggctcg   3780
gagacgcggg gacaagcggg gagcattgct ctccccgaga cccatttcga ccttgaaggg   3840
gtcctcgggg gggccggtgc tctgccctag ggccacgtc gtttgggctct tccgagcagc   3900 tgtgtgctct cggggcgtgg ccaaatccat cgatttcatc cccgttgaga cactcgacgt   3960
tgttacaagg tctcccactt tcagtgacaa cagcacgcca ccggctgtgc cccagaccta   4020
tcaggtcggg tacttgcatg ctccaactgg cagtggaaag agcaccaagg tccctgtcgc   4080
gtatgccgcc caggggtaca aagtactagt gcttaacccc tcggtagctg ccaccctggg   4140
gtttggggcg tacctatcca aggcacatgg catcaatccc aacattagga ctggagtcag   4200
gaccgtgatg accggggagg ccatcacgta ctccacatat ggcaaatttc tcgccgatgg   4260
gggctgcgct agcggcgcct atgacatcat catatgcgat gaatgccacg ctgtggatgc   4320
tacctccatt ctcggcatcg gaacggtcct tgatcaagca gagacagccg gggtcagact   4380
aactgtgctg gctacggcca cacccccgg gtcagtgaca accccccatc ccgatataga   4440
agaggtaggc ctcgggcggg aggtgagat ccccttctat gggagggcga ttcccctatc   4500
ctgcatcaag ggagggagac acctgatttt ctgccactca agaaaaagt gtgacgagct   4560 cgcggcggcc cttcggggca tgggcttgaa tgccgtggca tactatagag ggttggacgt   4620
ctccataata ccagctcagg gagatgtggt ggtcgtcgcc accgacgccc tcatgacggg   4680
gtacactgga gactttgact ccgtgatcga ctgcaatgta gcggtcaccc aagctgtcga   4740
cttcagcctg gaccccacct tcactataac cacacagact gtcccacaag acgctgtctc   4800
acgcagtcag cgccgcgggc gcacaggtag aggaagacag ggcacttata ggtatgtttc   4860
cactggtgaa cgagcctcag gaatgtttga cagtgtagtg ctttgtgagt gctacgacgc   4920
aggggctgcg tggtacgatc tcacaccagc ggagaccacc gtcaggctta gagcgtattt   4980
caacacgccc ggcctacccg tgtgtcaaga ccatcttgaa ttttgggagg cagttttcac   5040
cggcctcaca cacatagacg cccacttcct ctcccaaaca aagcaagcgg gggagaactt   5100
cgcgtaccta gtagcctacc aagctacggt gtgcgccaga gccaaggccc ctccccgtc   5160 ctggacgcc atgtggaagt gcctggcccg actcaagcct acgcttgcgg ccccacacc   5220 tctcctgtac cgtttgggcc ctattaccaa tgaggtcacc ctcacacacc ctgggacgaa   5280
gtacatcgcc acatgcatgc aagctgacct tgaggtcatg accagcacgt gggtcctagc   5340
tggaggagtc ctggcagccg tcgccgcata ttgcctggcg actggatgcg tttccatcat   5400
cggccgcttg cacgtcaacc agcgagtcgt cgttgcgccg gataaggagg tcctgtatga   5460
ggcttttgat gagatggagg aatgcgcctc tagggcggct ctcatcgaag aggggcagcg   5520
gatagccgag atgttgaagt ccaagatcca aggcttgctg cagcaggcct ctaagcaggc   5580
ccaggacata caacccgcta tgcaggcttc atggcccaaa gtggaacaat tgggccag   5640 acacatgtgg aacttcatta gcggcatcca atacctcgca ggattgtcaa cactgccagg   5700
```

```
gaaccccgcg gtggcttcca tgatggcatt cagtgccgcc ctcaccagtc cgttgtcgac    5760
cagtaccacc atccttctca acatcatggg aggctggtta gcgtcccaga tcgcaccacc    5820
cgcgggggcc accggctttg tcgtcagtgg cctggtgggg gctgccgtgg gcagcatagg    5880
cctgggtaag gtgctggtgg acatcctggc aggatatggt gcgggcattt cgggggccct    5940
cgtcgcattc aagatcatgt ctggcgagaa gccctctatg gaagatgtca tcaatctact    6000
gcctgggatc ctgtctccgg gagccctggt ggtgggggtc atctgcgcgg ccattctgcg    6060
ccgccacgtg ggaccggggg agggcgcggt ccaatggatg aacaggctta ttgccttttgc   6120 ttccagagga aaccacgtcg cccctactca ctacgtgacg gagtcggatg cgtcgcagcg    6180
tgtgacccaa ctacttggct ctcttactat aaccagccta ctcagaagac tccacaattg    6240
gataactgag gactgcccca tcccatgctc cggatcctgg ctccgcgacg tgtgggactg    6300
ggtttgcacc atcttgacag acttcaaaaa ttggctgacc tctaaattgt tccccaagct    6360 gccccggcctc cccttcatct cttgtcaaaa ggggtacaag ggtgtgtggg ccggcactgg   6420
catcatgacc acgcgctgcc cttgcggcgc caacatctct ggcaatgtcc gcctgggctc    6480
tatgaggatc acagggccta aaacctgcat gaacacctgg caggggacct ttcctatcaa    6540
ttgctacacg gagggccagt gcgcgccgaa accccccacg aactacaaga ccgccatctg    6600
gagggtggcg gcctcggagt acgcggaggt gacgcagcat gggtcgtact cctatgtaac    6660
aggactgacc actgacaatc tgaaaattcc ttgccaacta ccttctccag agttttctc    6720 ctgggtggac ggtgtgcaga tccataggtt tgcacccaca ccaaagccgt ttttccggga    6780
tgaggtctcg ttctgcgttg gcttaattc ctatgctgtc gggtcccagc ttccctgtga    6840
acctgagccc gacgcagacg tattgaggtc catgctaaca gatccgcccc acatcacggc    6900
ggagactgcg gcgcggcgct tggcacgggg atcacctcca tctgaggcga gctcctcagt    6960
gagccagcta tcagcaccgt cgctgcgggc cacctgcacc acccacagca acacctatga    7020
cgtggacatg gtcgatgcca acctgctcat ggagggcggt gtggctcaga cagagcctga    7080
gtccagggtg cccgttctgg actttctcga gccaatggcc gaggaagaga gcgaccttga    7140
gccctcaata ccatcggagt gcatgctccc caggagcggg tttccacggg ccttaccggc    7200
ttgggcacgg cctgactaca acccgccgct cgtggaatcg tggaggaggc cagattacca    7260 accgccacc gttgctggtt gtgctctccc cccccccaag aaggcccga cgcctccccc     7320 aaggagacgc cggacagtgg gtctgagcga gagcaccata tcagaagccc tccagcaact    7380
ggccatcaag acctttggcc agccccctc gagcggtgat gcaggctcgt ccacgggggc     7440
gggcgccgcc gaatccggcg gtccgacgtc cctggtgag ccggcccct cagagacagg      7500 ttccgcctcc tctatgcccc ccctcgaggg ggagcctgga gatccggacc tggagtctga    7560
tcaggtagag cttcaacctc cccccaggg gggggggta gctccggtt cgggctcggg      7620 gtcttggtct acttgctccg aggaggacga taccaccgtg tgctgctcca tgtcatactc    7680
ctggaccggg gctctaataa ctccctgtag ccccgaagag gaaaagttgc aatcaacccc    7740
tttgagtaac tcgctgttgc gataccataa caaggtgtac tgtacaacat caaagagcgc    7800
ctcacagagg gctaaaaagg taacttttga caggacgcaa gtgctcgacg cccattatga    7860
ctcagtctta aaggacatca agctagcggc ttccaaggtc agcgcaaggc tcctcacctt    7920
ggaggaggcg tgccagttga ctccaccca ttctgcaaga tccaagtatg gattcggggc    7980
caaggaggtc gcgcagcttg tccgggaggc cgttaaccac atcaagtccg tgtggaagga    8040
cctcctggaa gacccacaaa caccaattcc cacaaccatc atggccaaaa atgaggtgtt    8100
```

```
ctgcgtggac cccgccaagg ggggtaagaa accagctcgc ctcatcgttt accctgacct   8160
cggcgtccgg gtctgcgaga aaatggccct ctatgacatt acacaaaagc ttcctcaggc   8220
ggtaatggga gcttcctatg gcttccagta ctcccctgcc caacgggtgg agtatctctt   8280
gaaagcatgg gcggaaaaga aggaccccat gggttttttcg tatgataccc gatgcttcga   8340
ctcaaccgtc actgagagag acatcaggac cgaggagtcc atataccagg cctgctccct   8400
gcccgaggag gcccgcactg ccatacactc gctgactgag agactttacg taggagggcc   8460
catgttcaac agcaagggtc aaacctgcgg ttacagacgt tgccgcgcca gcggggtgct   8520
aaccactagc atgggtaaca ccatcacatg ctatgtgaaa gccctagcgg cctgcaaggc   8580
tgcggggata gttgcgccca caatgctggt atgcggcgat gacctagtag tcatctcaga   8640
aagccagggg actgaggagg acgagcggaa cctgagagcc ttcacggagg ccatgaccag   8700
gtactctgcc cctcctggtg atccccccag accggaatat gacctggagc taataacatc   8760
ctgttcctca aatgtgtctg tggcgttggg cccgcggggc cgccgcagat actacctgac   8820
cagagaccca accactccac tcgcccgggc tgcctgggaa acagttagac actcccctat   8880
caattcatgc ctgggaaaca tcatccagta tgctccaacc atatgggttc gcatggtcct   8940
aatgacacac ttcttctcca ttctcatggt ccaagacacc ctggaccaga acctcaactt   9000
tgagatgtat ggatcagtat actccgtgaa tcctttggac cttccagcca taattgagag   9060
gttacacggg cttgacgcct tttctatgca cacatactct caccacgaac tgacgcgggt   9120
ggcttcagcc ctcagaaaac ttggggcgcc acccctcagg gtgtggaaga gtcgggctcg   9180
cgcagtcagg gcgtccctca tctcccgtgg agggaaagcg gccgtttgcg gccgatatct   9240
cttcaattgg gcggtgaaga ccaagctcaa actcactcca ttgccggagg cgcgcctact   9300
ggacttatcc agttggttca ccgtcggcgc cggcggggc gacattttc acagcgtgtc   9360 gcgcgcccga ccccgctcat tactcttcgg cctactccta cttttcgtag ggtaggcct   9420 cttcctactc cccgctcggt agagcggcac acactaggta cactccatag ctaactgttc   9480
cttttttttt tttttttttt tttttttttt tttttttttt tttctttttt ttttttttc   9540 cctctttctt cccttctcat cttattctac tttctttctt ggtggctcca tcttagccct   9600
agtcacggct agctgtgaaa ggtccgtgag ccgcatgact gcagagagtg ccgtaactgg   9660
tctctctgca gatcatgt                                                9678
```

<210> SEQ ID NO 6
<211> LENGTH: 3033
<212> TYPE: PRT
<213> ORGANISM: Hepatitis C virus

<400> SEQUENCE: 6

```
Met Ser Thr Asn Pro Lys Pro Gln Arg Leu Thr Lys Arg Asn Thr Val
1               5                   10                  15

Arg Arg Pro Gln Asn Val Lys Phe Pro Gly Gly Gly Gln Ile Val Gly
                20                  25                  30

Gly Val Tyr Leu Leu Pro Arg Arg Gly Pro Arg Leu Gly Val Arg Gly
            35                  40                  45

Thr Arg Lys Ser Ser Glu Arg Ser Gln Pro Arg Gly Arg Arg Gln Arg
        50                  55                  60

Ile Pro Lys Ala Ala Ser Ser Gln Gly Lys Ala Trp Gly Lys Pro Gly
65                  70                  75                  80

Tyr Pro Trp Pro Leu Tyr Gly Asn Glu Gly Cys Gly Trp Ala Gly Trp
                85                  90                  95
```

```
Leu Leu Ser Pro Arg Gly Ser Arg Pro Thr Trp Gly Pro Thr Asp Pro
            100                 105                 110

Arg His Arg Ser Arg Asn Leu Gly Lys Val Ile Asp Thr Met Thr Cys
        115                 120                 125

Gly Phe Ala Asp Leu Met Gly Tyr Ile Pro Val Leu Gly Ala Pro Leu
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
                180                 185                 190

Glu Val Arg Asn Ser Ser Gly Val Tyr His Leu Thr Asn Asp Cys Pro
            195                 200                 205

Asn Ala Ser Ile Val Tyr Glu Thr Asp Asn Ala Ile Leu His Glu Pro
    210                 215                 220

Gly Cys Val Pro Cys Val Arg Glu Gly Asn Thr Ser Arg Cys Trp Glu
225                 230                 235                 240

Pro Val Ala Pro Thr Leu Ala Val Arg Tyr Arg Gly Ala Leu Thr Asp
                245                 250                 255

Asp Leu Arg Thr His Ile Asp Leu Val Val Ala Ser Ala Thr Leu Cys
            260                 265                 270

Ser Ala Leu Tyr Val Gly Asp Ile Cys Gly Ala Ile Phe Ile Ala Ser
    275                 280                 285

Gln Ala Val Leu Trp Lys Pro Gly Gly Arg Ile Val Gln Asp Cys
290                 295                 300

Asn Cys Ser Ile Tyr Pro Gly His Val Thr Gly His Arg Met Ala Trp
305                 310                 315                 320

Asp Met Met Gln Asn Trp Ala Pro Ala Leu Ser Met Val Ala Ala Tyr
                325                 330                 335

Ala Val Arg Val Pro Gly Val Ile Ile Thr Thr Val Ala Gly Gly His
            340                 345                 350

Trp Gly Val Leu Phe Gly Leu Ala Tyr Phe Gly Met Ala Gly Asn Trp
    355                 360                 365

Ala Lys Val Ile Leu Ile Met Leu Leu Met Ser Gly Val Asp Ala Glu
            370                 375                 380

Thr Met Ala Val Gly Ala Arg Ala Ala His Thr Thr Gly Ala Leu Val
385                 390                 395                 400

Ser Leu Leu Asn Pro Gly Pro Ser Gln Arg Leu Gln Leu Thr Asn Thr
                405                 410                 415

Asn Gly Ser Trp His Ile Asn Arg Thr Ala Leu Asn Cys Asn Asp Ser
            420                 425                 430

Leu Gln Thr Gly Phe Ile Ala Ala Leu Phe Tyr Thr His Arg Phe Asn
    435                 440                 445

Ser Ser Gly Cys Pro Glu Arg Met Ala Ser Cys Lys Pro Leu Ser Asp
450                 455                 460

Phe Asp Gln Gly Trp Gly Pro Leu Trp Tyr Asn Ser Thr Glu Arg Pro
465                 470                 475                 480

Ser Asp Gln Arg Pro Tyr Cys Trp His Tyr Ala Pro Ser Pro Cys Gly
                485                 490                 495

Ile Val Pro Ala Lys Asp Val Cys Gly Pro Val Tyr Cys Phe Thr Pro
            500                 505                 510

Ser Pro Val Val Val Gly Thr Thr Asp Arg Arg Gly Val Pro Thr Tyr
```

```
                515                 520                 525
Thr Trp Gly Glu Asn Glu Ser Asp Val Phe Leu Leu Asn Ser Thr Arg
530                 535                 540

Pro Pro Gln Gly Ser Trp Phe Gly Cys Ser Trp Met Asn Thr Thr Gly
545                 550                 555                 560

Phe Thr Lys Thr Cys Gly Gly Pro Cys Lys Ile Arg Pro Gln Gly
                    565                 570                 575

Ala Gln Ser Asn Thr Ser Leu Thr Cys Pro Thr Asp Cys Phe Arg Lys
                580                 585                 590

His Pro Arg Ala Thr Tyr Ser Ala Cys Gly Ser Gly Pro Trp Leu Thr
                595                 600                 605

Pro Arg Cys Met Val His Tyr Pro Tyr Arg Leu Trp His Tyr Pro Cys
610                 615                 620

Thr Val Asn Phe Thr Ile His Lys Val Arg Leu Tyr Ile Gly Gly Val
625                 630                 635                 640

Glu His Arg Leu Asp Ala Ala Cys Asn Trp Thr Arg Gly Glu Arg Cys
                645                 650                 655

Asp Leu Glu Asp Arg Asp Arg Val Asp Met Ser Pro Leu Leu His Ser
                660                 665                 670

Thr Thr Glu Leu Ala Ile Leu Pro Cys Ser Phe Val Pro Leu Pro Ala
                675                 680                 685

Leu Ser Thr Gly Leu Ile His Leu His Gln Asn Ile Val Asp Ala Gln
690                 695                 700

Tyr Leu Tyr Gly Leu Ser Pro Ala Ile Ile Ser Trp Ala Ile Arg Trp
705                 710                 715                 720

Glu Trp Val Val Leu Val Phe Leu Leu Leu Ala Asp Ala Arg Ile Cys
                725                 730                 735

Ala Cys Leu Trp Met Met Met Leu Met Ala Gln Ala Glu Ala Ala Leu
                740                 745                 750

Glu Asn Leu Ile His Leu Asn Ala Ala Ser Leu Ala Gly Thr His Gly
                755                 760                 765

Ile Trp Trp Leu Leu Leu Val Phe Cys Ala Ser Trp His Leu Arg Gly
770                 775                 780

Arg Val Val Pro Leu Val Thr Tyr Gly Ile Cys Gly Met Trp Pro Phe
785                 790                 795                 800

Phe Leu Met Leu Leu Ser Leu Pro Pro Arg Ala Tyr Ala Leu Asp Arg
                805                 810                 815

Glu Val Ser Ala Ala Leu Gly Thr Gly Met Leu Ala Ile Ile Leu Leu
                820                 825                 830

Val Thr Leu Gly Pro His Tyr Lys Arg Leu Leu Ala Leu Ile Leu Trp
                835                 840                 845

Trp Val Thr Tyr Phe Leu Thr Arg Cys Glu Ala Ala Leu Gln Thr Trp
850                 855                 860

Val Pro Pro Leu Asn Pro Arg Gly Gly Arg Asp Gly Phe Ile Leu Cys
865                 870                 875                 880

Val Leu Leu Cys Tyr Pro Gly Leu Val Phe Asp Ile Thr Lys Trp Leu
                885                 890                 895

Leu Val Met Met Cys Pro Leu Tyr Leu Leu Gln Leu Cys Leu Val Arg
                900                 905                 910

Thr Pro Tyr Phe Val Arg Ala Gln Ala Leu Ile Arg Val Cys Ser Leu
                915                 920                 925

Phe Lys Thr Leu Ala Gly Gly Arg Tyr Val Gln Ala Ala Leu Leu Thr
930                 935                 940
```

```
Ile Gly Arg Trp Thr Gly Thr Tyr Ile Tyr Asn His Leu Ala Pro Leu
945                 950                 955                 960

Glu Thr Trp Ala Ala Gly Gly Leu Arg Asp Leu Ala Val Ala Val Glu
                965                 970                 975

Pro Val Ile Phe Ser Pro Met Glu Lys Lys Ile Ile Val Trp Gly Ala
            980                 985                 990

Glu Thr Thr Ala Cys Gly Asp Ile Leu Cys Gly Leu Pro Val Ser Ala
        995                 1000                1005

Arg Leu Gly Arg Glu Val Leu Leu Gly Pro Ala Asp Asp Tyr Arg
    1010                1015                1020

Ser Met Gly Trp Gln Leu Leu Ala Pro Ile Thr Ala Tyr Ala Gln
    1025                1030                1035

Gln Thr Arg Gly Leu Leu Gly Ala Ile Val Val Ser Met Thr Gly
    1040                1045                1050

Arg Asp Arg Thr Glu Gln Ala Gly Glu Val Gln Ile Leu Ser Thr
    1055                1060                1065

Val Ser Gln Ser Phe Leu Gly Thr Thr Ile Ser Gly Val Leu Trp
    1070                1075                1080

Thr Val Tyr His Gly Ala Gly Asn Lys Thr Leu Ala Gly Leu Arg
    1085                1090                1095

Gly Pro Val Thr Gln Met Tyr Ser Ser Ala Glu Gly Asp Leu Val
    1100                1105                1110

Gly Trp Pro Ser Pro Pro Gly Thr Lys Ser Leu Glu Pro Cys Lys
    1115                1120                1125

Cys Gly Ala Val Asp Leu Tyr Leu Val Thr Arg Asn Ala Asp Val
    1130                1135                1140

Ile Pro Ala Arg Arg Arg Gly Asp Lys Arg Gly Ala Leu Leu Ser
    1145                1150                1155

Pro Arg Pro Ile Ser Thr Leu Lys Gly Ser Ser Gly Gly Pro Val
    1160                1165                1170

Leu Cys Pro Arg Gly His Val Val Gly Leu Phe Arg Ala Ala Val
    1175                1180                1185

Cys Ser Arg Gly Val Ala Lys Ser Ile Asp Phe Ile Pro Val Glu
    1190                1195                1200

Thr Leu Asp Val Val Thr Arg Ser Pro Thr Phe Ser Asp Asn Ser
    1205                1210                1215

Thr Pro Pro Ala Val Pro Gln Thr Tyr Gln Val Gly Tyr Leu His
    1220                1225                1230

Ala Pro Thr Gly Ser Gly Lys Ser Thr Lys Val Pro Val Ala Tyr
    1235                1240                1245

Ala Ala Gln Gly Tyr Lys Val Leu Val Leu Asn Pro Ser Val Ala
    1250                1255                1260

Ala Thr Leu Gly Phe Gly Ala Tyr Leu Ser Lys Ala His Gly Ile
    1265                1270                1275

Asn Pro Asn Ile Arg Thr Gly Val Arg Thr Val Met Thr Gly Glu
    1280                1285                1290

Ala Ile Thr Tyr Ser Thr Tyr Gly Lys Phe Leu Ala Asp Gly Gly
    1295                1300                1305

Cys Ala Ser Gly Ala Tyr Asp Ile Ile Ile Cys Asp Glu Cys His
    1310                1315                1320

Ala Val Asp Ala Thr Ser Ile Leu Gly Ile Gly Thr Val Leu Asp
    1325                1330                1335

Gln Ala Glu Thr Ala Gly Val Arg Leu Thr Val Leu Ala Thr Ala
    1340                1345                1350
```

```
Thr Pro Pro Gly Ser Val Thr Pro His Pro Asp Ile Glu Glu
    1355                1360            1365

Val Gly Leu Gly Arg Glu Gly Glu Ile Pro Phe Tyr Gly Arg Ala
    1370                1375            1380

Ile Pro Leu Ser Cys Ile Lys Gly Gly Arg His Leu Ile Phe Cys
    1385                1390            1395

His Ser Lys Lys Lys Cys Asp Glu Leu Ala Ala Ala Leu Arg Gly
    1400                1405            1410

Met Gly Leu Asn Ala Val Ala Tyr Tyr Arg Gly Leu Asp Val Ser
    1415                1420            1425

Ile Ile Pro Ala Gln Gly Asp Val Val Val Ala Thr Asp Ala
    1430                1435            1440

Leu Met Thr Gly Tyr Thr Gly Asp Phe Asp Ser Val Ile Asp Cys
    1445                1450            1455

Asn Val Ala Val Thr Gln Ala Val Asp Phe Ser Leu Asp Pro Thr
    1460                1465            1470

Phe Thr Ile Thr Thr Gln Thr Val Pro Gln Asp Ala Val Ser Arg
    1475                1480            1485

Ser Gln Arg Arg Gly Arg Thr Gly Arg Gly Arg Gln Gly Thr Tyr
    1490                1495            1500

Arg Tyr Val Ser Thr Gly Glu Arg Ala Ser Gly Met Phe Asp Ser
    1505                1510            1515

Val Val Leu Cys Glu Cys Tyr Asp Ala Gly Ala Ala Trp Tyr Asp
    1520                1525            1530

Leu Thr Pro Ala Glu Thr Thr Val Arg Leu Arg Ala Tyr Phe Asn
    1535                1540            1545

Thr Pro Gly Leu Pro Val Cys Gln Asp His Leu Glu Phe Trp Glu
    1550                1555            1560

Ala Val Phe Thr Gly Leu Thr His Ile Asp Ala His Phe Leu Ser
    1565                1570            1575

Gln Thr Lys Gln Ala Gly Glu Asn Phe Ala Tyr Leu Val Ala Tyr
    1580                1585            1590

Gln Ala Thr Val Cys Ala Arg Ala Lys Ala Pro Pro Pro Ser Trp
    1595                1600            1605

Asp Ala Met Trp Lys Cys Leu Ala Arg Leu Lys Pro Thr Leu Ala
    1610                1615            1620

Gly Pro Thr Pro Leu Leu Tyr Arg Leu Gly Pro Ile Thr Asn Glu
    1625                1630            1635

Val Thr Leu Thr His Pro Gly Thr Lys Tyr Ile Ala Thr Cys Met
    1640                1645            1650

Gln Ala Asp Leu Glu Val Met Thr Ser Thr Trp Val Leu Ala Gly
    1655                1660            1665

Gly Val Leu Ala Ala Val Ala Ala Tyr Cys Leu Ala Thr Gly Cys
    1670                1675            1680

Val Ser Ile Ile Gly Arg Leu His Val Asn Gln Arg Val Val Val
    1685                1690            1695

Ala Pro Asp Lys Glu Val Leu Tyr Glu Ala Phe Asp Glu Met Glu
    1700                1705            1710

Glu Cys Ala Ser Arg Ala Ala Leu Ile Glu Glu Gly Gln Arg Ile
    1715                1720            1725

Ala Glu Met Leu Lys Ser Lys Ile Gln Gly Leu Leu Gln Gln Ala
    1730                1735            1740

Ser Lys Gln Ala Gln Asp Ile Gln Pro Ala Met Gln Ala Ser Trp
```

-continued

```
            1745                1750                1755

Pro Lys Val Glu Gln Phe Trp Ala Arg His Met Trp Asn Phe Ile
    1760                1765                1770

Ser Gly Ile Gln Tyr Leu Ala Gly Leu Ser Thr Leu Pro Gly Asn
    1775                1780                1785

Pro Ala Val Ala Ser Met Met Ala Phe Ser Ala Ala Leu Thr Ser
    1790                1795                1800

Pro Leu Ser Thr Ser Thr Thr Ile Leu Leu Asn Ile Met Gly Gly
    1805                1810                1815

Trp Leu Ala Ser Gln Ile Ala Pro Pro Ala Gly Ala Thr Gly Phe
    1820                1825                1830

Val Val Ser Gly Leu Val Gly Ala Ala Val Gly Ser Ile Gly Leu
    1835                1840                1845

Gly Lys Val Leu Val Asp Ile Leu Ala Gly Tyr Gly Ala Gly Ile
    1850                1855                1860

Ser Gly Ala Leu Val Ala Phe Lys Ile Met Ser Gly Glu Lys Pro
    1865                1870                1875

Ser Met Glu Asp Val Ile Asn Leu Leu Pro Gly Ile Leu Ser Pro
    1880                1885                1890

Gly Ala Leu Val Val Gly Val Ile Cys Ala Ala Ile Leu Arg Arg
    1895                1900                1905

His Val Gly Pro Gly Glu Gly Ala Val Gln Trp Met Asn Arg Leu
    1910                1915                1920

Ile Ala Phe Ala Ser Arg Gly Asn His Val Ala Pro Thr His Tyr
    1925                1930                1935

Val Thr Glu Ser Asp Ala Ser Gln Arg Val Thr Gln Leu Leu Gly
    1940                1945                1950

Ser Leu Thr Ile Thr Ser Leu Leu Arg Arg Leu His Asn Trp Ile
    1955                1960                1965

Thr Glu Asp Cys Pro Ile Pro Cys Ser Gly Ser Trp Leu Arg Asp
    1970                1975                1980

Val Trp Asp Trp Val Cys Thr Ile Leu Thr Asp Phe Lys Asn Trp
    1985                1990                1995

Leu Thr Ser Lys Leu Phe Pro Lys Leu Pro Gly Leu Pro Phe Ile
    2000                2005                2010

Ser Cys Gln Lys Gly Tyr Lys Gly Val Trp Ala Gly Thr Gly Ile
    2015                2020                2025

Met Thr Thr Arg Cys Pro Cys Gly Ala Asn Ile Ser Gly Asn Val
    2030                2035                2040

Arg Leu Gly Ser Met Arg Ile Thr Gly Pro Lys Thr Cys Met Asn
    2045                2050                2055

Thr Trp Gln Gly Thr Phe Pro Ile Asn Cys Tyr Thr Glu Gly Gln
    2060                2065                2070

Cys Ala Pro Lys Pro Pro Thr Asn Tyr Lys Thr Ala Ile Trp Arg
    2075                2080                2085

Val Ala Ala Ser Glu Tyr Ala Glu Val Thr Gln His Gly Ser Tyr
    2090                2095                2100

Ser Tyr Val Thr Gly Leu Thr Thr Asp Asn Leu Lys Ile Pro Cys
    2105                2110                2115

Gln Leu Pro Ser Pro Glu Phe Phe Ser Trp Val Asp Gly Val Gln
    2120                2125                2130

Ile His Arg Phe Ala Pro Thr Pro Lys Pro Phe Phe Arg Asp Glu
    2135                2140                2145
```

| | | | | | | | | | | |
|---|---|---|---|---|---|---|---|---|---|---|
| Val | Ser | Phe | Cys | Val | Gly | Leu | Asn | Ser | Tyr | Ala | Val | Gly | Ser | Gln |
| | 2150 | | | | 2155 | | | | 2160 | |
| Leu | Pro | Cys | Glu | Pro | Glu | Pro | Asp | Ala | Asp | Val | Leu | Arg | Ser | Met |
| | 2165 | | | | 2170 | | | | 2175 | |
| Leu | Thr | Asp | Pro | Pro | His | Ile | Thr | Ala | Glu | Thr | Ala | Ala | Arg | Arg |
| | 2180 | | | | 2185 | | | | 2190 | |
| Leu | Ala | Arg | Gly | Ser | Pro | Pro | Ser | Glu | Ala | Ser | Ser | Ser | Val | Ser |
| | 2195 | | | | 2200 | | | | 2205 | |
| Gln | Leu | Ser | Ala | Pro | Ser | Leu | Arg | Ala | Thr | Cys | Thr | Thr | His | Ser |
| | 2210 | | | | 2215 | | | | 2220 | |
| Asn | Thr | Tyr | Asp | Val | Asp | Met | Val | Asp | Ala | Asn | Leu | Leu | Met | Glu |
| | 2225 | | | | 2230 | | | | 2235 | |
| Gly | Gly | Val | Ala | Gln | Thr | Glu | Pro | Glu | Ser | Arg | Val | Pro | Val | Leu |
| | 2240 | | | | 2245 | | | | 2250 | |
| Asp | Phe | Leu | Glu | Pro | Met | Ala | Glu | Glu | Glu | Ser | Asp | Leu | Glu | Pro |
| | 2255 | | | | 2260 | | | | 2265 | |
| Ser | Ile | Pro | Ser | Glu | Cys | Met | Leu | Pro | Arg | Ser | Gly | Phe | Pro | Arg |
| | 2270 | | | | 2275 | | | | 2280 | |
| Ala | Leu | Pro | Ala | Trp | Ala | Arg | Pro | Asp | Tyr | Asn | Pro | Pro | Leu | Val |
| | 2285 | | | | 2290 | | | | 2295 | |
| Glu | Ser | Trp | Arg | Arg | Pro | Asp | Tyr | Gln | Pro | Pro | Thr | Val | Ala | Gly |
| | 2300 | | | | 2305 | | | | 2310 | |
| Cys | Ala | Leu | Pro | Pro | Pro | Lys | Lys | Ala | Pro | Thr | Pro | Pro | Pro | Arg |
| | 2315 | | | | 2320 | | | | 2325 | |
| Arg | Arg | Arg | Thr | Val | Gly | Leu | Ser | Glu | Ser | Thr | Ile | Ser | Glu | Ala |
| | 2330 | | | | 2335 | | | | 2340 | |
| Leu | Gln | Gln | Leu | Ala | Ile | Lys | Thr | Phe | Gly | Gln | Pro | Pro | Ser | Ser |
| | 2345 | | | | 2350 | | | | 2355 | |
| Gly | Asp | Ala | Gly | Ser | Ser | Thr | Gly | Ala | Gly | Ala | Ala | Glu | Ser | Gly |
| | 2360 | | | | 2365 | | | | 2370 | |
| Gly | Pro | Thr | Ser | Pro | Gly | Glu | Pro | Ala | Pro | Ser | Glu | Thr | Gly | Ser |
| | 2375 | | | | 2380 | | | | 2385 | |
| Ala | Ser | Ser | Met | Pro | Pro | Leu | Glu | Gly | Glu | Pro | Gly | Asp | Pro | Asp |
| | 2390 | | | | 2395 | | | | 2400 | |
| Leu | Glu | Ser | Asp | Gln | Val | Glu | Leu | Gln | Pro | Pro | Gln | Gly | Gly | Gly |
| | 2405 | | | | 2410 | | | | 2415 | |
| Gly | Val | Ala | Pro | Gly | Ser | Gly | Ser | Gly | Ser | Trp | Ser | Thr | Cys | Ser |
| | 2420 | | | | 2425 | | | | 2430 | |
| Glu | Glu | Asp | Asp | Thr | Thr | Val | Cys | Cys | Ser | Met | Ser | Tyr | Ser | Trp |
| | 2435 | | | | 2440 | | | | 2445 | |
| Thr | Gly | Ala | Leu | Ile | Thr | Pro | Cys | Ser | Pro | Glu | Glu | Glu | Lys | Leu |
| | 2450 | | | | 2455 | | | | 2460 | |
| Pro | Ile | Asn | Pro | Leu | Ser | Asn | Ser | Leu | Leu | Arg | Tyr | His | Asn | Lys |
| | 2465 | | | | 2470 | | | | 2475 | |
| Val | Tyr | Cys | Thr | Thr | Ser | Lys | Ser | Ala | Ser | Gln | Arg | Ala | Lys | Lys |
| | 2480 | | | | 2485 | | | | 2490 | |
| Val | Thr | Phe | Asp | Arg | Thr | Gln | Val | Leu | Asp | Ala | His | Tyr | Asp | Ser |
| | 2495 | | | | 2500 | | | | 2505 | |
| Val | Leu | Lys | Asp | Ile | Lys | Leu | Ala | Ala | Ser | Lys | Val | Ser | Ala | Arg |
| | 2510 | | | | 2515 | | | | 2520 | |
| Leu | Leu | Thr | Leu | Glu | Glu | Ala | Cys | Gln | Leu | Thr | Pro | Pro | His | Ser |
| | 2525 | | | | 2530 | | | | 2535 | |
| Ala | Arg | Ser | Lys | Tyr | Gly | Phe | Gly | Ala | Lys | Glu | Val | Arg | Ser | Leu |
| | 2540 | | | | 2545 | | | | 2550 | |

-continued

```
Ser Gly Arg Ala Val Asn His Ile Lys Ser Val Trp Lys Asp Leu
    2555                2560                2565
Leu Glu Asp Pro Gln Thr Pro Ile Pro Thr Thr Ile Met Ala Lys
    2570                2575                2580
Asn Glu Val Phe Cys Val Asp Pro Ala Lys Gly Gly Lys Lys Pro
    2585                2590                2595
Ala Arg Leu Ile Val Tyr Pro Asp Leu Gly Val Arg Val Cys Glu
    2600                2605                2610
Lys Met Ala Leu Tyr Asp Ile Thr Gln Lys Leu Pro Gln Ala Val
    2615                2620                2625
Met Gly Ala Ser Tyr Gly Phe Gln Tyr Ser Pro Ala Gln Arg Val
    2630                2635                2640
Glu Tyr Leu Leu Lys Ala Trp Ala Glu Lys Lys Asp Pro Met Gly
    2645                2650                2655
Phe Ser Tyr Asp Thr Arg Cys Phe Asp Ser Thr Val Thr Glu Arg
    2660                2665                2670
Asp Ile Arg Thr Glu Glu Ser Ile Tyr Gln Ala Cys Ser Leu Pro
    2675                2680                2685
Glu Glu Ala Arg Thr Ala Ile His Ser Leu Thr Glu Arg Leu Tyr
    2690                2695                2700
Val Gly Gly Pro Met Phe Asn Ser Lys Gly Gln Thr Cys Gly Tyr
    2705                2710                2715
Arg Arg Cys Arg Ala Ser Gly Val Leu Thr Thr Ser Met Gly Asn
    2720                2725                2730
Thr Ile Thr Cys Tyr Val Lys Ala Leu Ala Ala Cys Lys Ala Ala
    2735                2740                2745
Gly Ile Val Ala Pro Thr Met Leu Val Cys Gly Asp Asp Leu Val
    2750                2755                2760
Val Ile Ser Glu Ser Gln Gly Thr Glu Glu Asp Glu Arg Asn Leu
    2765                2770                2775
Arg Ala Phe Thr Glu Ala Met Thr Arg Tyr Ser Ala Pro Pro Gly
    2780                2785                2790
Asp Pro Pro Arg Pro Glu Tyr Asp Leu Glu Leu Ile Thr Ser Cys
    2795                2800                2805
Ser Ser Asn Val Ser Val Ala Leu Gly Pro Arg Gly Arg Arg Arg
    2810                2815                2820
Tyr Tyr Leu Thr Arg Asp Pro Thr Thr Pro Leu Ala Arg Ala Ala
    2825                2830                2835
Trp Glu Thr Val Arg His Ser Pro Ile Asn Ser Trp Leu Gly Asn
    2840                2845                2850
Ile Ile Gln Tyr Ala Pro Thr Ile Trp Val Arg Met Val Leu Met
    2855                2860                2865
Thr His Phe Phe Ser Ile Leu Met Val Gln Asp Thr Leu Asp Gln
    2870                2875                2880
Asn Leu Asn Phe Glu Met Tyr Gly Ser Val Tyr Ser Val Asn Pro
    2885                2890                2895
Leu Asp Leu Pro Ala Ile Ile Glu Arg Leu His Gly Leu Asp Ala
    2900                2905                2910
Phe Ser Met His Thr Tyr Ser His His Glu Leu Thr Arg Val Ala
    2915                2920                2925
Ser Ala Leu Arg Lys Leu Gly Ala Pro Pro Leu Arg Val Trp Lys
    2930                2935                2940
Ser Arg Ala Arg Ala Val Arg Ala Ser Leu Ile Ser Arg Gly Gly
```

```
                  2945                2950                2955
Lys  Ala  Ala  Val  Cys  Gly  Arg  Tyr  Leu  Phe  Asn  Trp  Ala  Val  Lys
              2960                2965                2970

Thr  Lys  Leu  Lys  Leu  Thr  Pro  Leu  Pro  Glu  Ala  Arg  Leu  Leu  Asp
              2975                2980                2985

Leu  Ser  Ser  Trp  Phe  Thr  Val  Gly  Ala  Gly  Gly  Asp  Ile  Phe
              2990                2995                3000

His  Ser  Val  Ser  Arg  Ala  Arg  Pro  Arg  Ser  Leu  Leu  Phe  Gly  Leu
              3005                3010                3015

Leu  Leu  Leu  Phe  Val  Gly  Val  Gly  Leu  Phe  Leu  Leu  Pro  Ala  Arg
              3020                3025                3030

<210> SEQ ID NO 7
<211> LENGTH: 9678
<212> TYPE: DNA
<213> ORGANISM: Hepatitis C virus

<400> SEQUENCE: 7
acctgcccct aatagggggcg acactccgcc atgaatcact ccctgtgag gaactactgt     60 cttcacgcag aaagcgccta gccatggcgt tagtatgagt gtcgtacagc ctccaggccc    120 cccctcccg ggagagccat agtggtctgc ggaaccggtg agtacaccgg aattgccggg    180
aagactgggt cctttcttgg ataaacccac tctatgcccg ccatttgggg cgtgccccccg    240 caagactgct agccgagtag cgttgggttg cgaaaggcct tgtggtactg cctgataggg    300
tgcttgcgag tgccccggga ggtctcgtag accgtgcacc atgagcacga atcctaaacc    360
tcaaagatta accaaaagaa acaccgtccg tcgcccacag aacgttaagt tcccgggtgg    420
cgggcagatc gttggcggag tctacttgtt gccgcgcagg ggccctagat tgggtgtgcg    480
cggcactagg aagagttcgg agcgatcgca gcccagggga agacgccaac gtatccccaa    540
agctgcctct tcacagggta aagcctgggg caagcccggg tacccttggc ccctgtatgg    600
taacgagggc tgtggctggg cagggtggct cctgtccccc cgcggctctc gacctacttg    660
gggccccact gaccccccggc accgctcgcg aaacctcggt aaggtgatcg acaccatgac    720 ctgcggggttt gccgacctca tgggtacat ccctgtccta ggcgccccccc taggggggcgt    780 tgccagggct ctggcacatg gtgttagagt tctggaggac ggggtcaact atgcaacagg    840
gaacttgcct ggttgctcct tttctatctt cttactagcc ctcctgtcat gtctaacagt    900
cccggcatcg gcttatgaag tccgcaactc cagtgggggtc tatcatctca ccaatgactg    960
ccccaacgct agtatagtct atgaaacaga caacgccatc ctacacgagc ctgggtgcgt   1020
gccttgcgtt cgcgagggta atactagcag gtgttgggaa ccagtggccc ccactttggc   1080
ggtccgctat cgcggagcgc ttactgacga tttgcggacg catattgacc tagtggtggc   1140
gtcagctacc ctgtgctccg ccttgtacgt gggggacatt tgtggagcca tcttcattgc   1200
cagccaagct gttctctgga agcccggggg gggtcggata gtgcaagatt gcaattgttc   1260
gatctacccg ggccacgtca ccggccacag gatggcgtgg gacatgatgc agaactgggc   1320
gccggccttg tcaatggttg ccgcttacgc tgtgagagtg cccggtgtca tcattaccac   1380
tgtagcgggc ggccactggg gtgtgttatt tggcctcgct tactttggta tggcgggaaa   1440
ctgggcaaag gtaatactca tcatgctact catgtccggc gtcgacgcgg aaaccatggc   1500
cgtcggggct agggccgctc acaccactgg cgcccttgtc agcctgctca atccagggcc   1560
cagtcagcgc ctgcagctga tcaacaccaa tgggtcatgg cacatcaacc ggaccgcttt   1620
gaactgcaat gactctttgc agacagggtt catagcggcc ctcttctaca cacataggtt   1680
```

```
caattctagt ggctgtcccg agaggatggc ttcttgtaaa cctctcagtg actttgacca      1740 gggtggggc ccgctgtggt acaattcaac agaaagacct tcggaccagc gaccctattg      1800
ctggcactac gcgccatcgc cgtgtggtat tgtgccggct aaggatgttt gcggtccggt      1860
ctactgcttt acaccaagcc cggttgtggt gggcaccacg gatcgccggg gggtgcccac      1920
gtatacttgg ggtgaaaatg agtctgatgt cttcctgctc aacagcacaa ggccgccgca      1980
aggcagttgg tttgggtgct catggatgaa cacaacgggg ttcacgaaga cctgcggagg      2040
tcctccgtgc aagatacgtc cccagggtgc ccagagtaac acctctctca cttgtcccac      2100
agactgcttc aggaaacatc cgcgtgccac atactccgct tgcggatctg gtccgtggtt      2160
gacacctaga tgcatggtcc attcccccta tagactgtgg cactaccegt gtacagtcaa      2220 cttcaccata cacaaagtca ggttatacat aggggggtgta aacataggc tcgatgcagc      2280 gtgcaattgg acgcggggtg agcgatgcga cctggaggac cgagacaggg tggacatgtc      2340 cccctgctc cattccacta cggagctcgc aatacttccg tgttcctttg tgccgcttcc      2400
ggccttatct acgggactga tccacctgca ccaaaacatc gttgacgccc agtaccttta      2460 tggtcttct cccgctataa taagctgggc catcagatgg gagtgggtag tcctcgtttt      2520
cctactcctg gcggacgcgc ggatctgcgc ctgcctttgg atgatgatgc ttatggccca      2580
ggctgaagcc gctctggaga acttgatcca cctcaacgcg ccagccttg cgggaaccca      2640 tggtatctgg tggctccttt tagtcttttg tgcctcttgg catctacgag gcagggttgt      2700
ccctctggtg acgtatggga tatgcgggat gtggcccttc ttcctcatgt tgctgagcct      2760 cccccacga gcgtatgctc tggacaggga agtgagcgca gcgttgggaa cgggcatgct      2820
cgccatcatc ctattagtta ccttgggacc gcactacaag agacttctag cccttattct      2880
ctggtgggtc acatatttcc ttacaaggtg tgaagcagca ctccaaacgt gggtccctcc      2940
tctcaaccct cgggggggca gggacggttt catcctgtgt gtgccgctgt gctatccagg      3000
ccttgtcttt gacatcacaa aatggttgct ggtcatgatg tgccctctct acctcctcca      3060
gttgtgtttg gtgaggactc catactttgt gagggcccag gccctcatca gagtgtgttc      3120
tctcttcaaa acgctagctg ggggacggta cgtgcaggcc gcgctgctca ctattggccg      3180
ctggaccggc acttatattt ataaccatct cgccccctg gaaacatggg ccgccggcgg      3240
cctacgggat ttggccgttg cagtcgagcc cgtgatattc tcccccatgg agaagaagat      3300
catagtttgg ggggcggaga ccactgcttg tggcgacatt cttttgtggcc tgcctgtctc      3360 agctcggctc ggcagggaag tcctgctagg gcccgcggat gactacaggt ccatgggatg      3420
gcaactcctg gctcccatca ctgcttatgc ccagcaaaca cgaggcctcc tgggcgccat      3480
agtggtgagt atgacgggc gtgacaggac agaacaggcc ggggaagtcc aaatcctgtc      3540
cacagtctct cagtccttcc tcggaacaac catctcgggg gttttgtgga ctgtttacca      3600
cggagctggc aacaagactc tagccggctt acggggtccg gtcacgcaga tgtactcgag      3660
tgctgagggg gacttggtag gctggccag ccccctggg accaagtctt tggagccgtg      3720
caagtgtgga gccgtcgacc tatatctggt cacgcgcaac gctgatgtca tcccggctcg      3780
gagacgcggg gacaagcggg gagcattgct ctccccgaga cccatttcga ccttgaaggg      3840
gtcctcgggg gggccggtgc tctgccctag gggcacgtc gttgggctct tccgagcagc      3900
tgtgtgctct cggggcgtgg ccaaatccat cgatttcatc ccgttgaga cactcgacgt      3960 tgttacaagg tctcccactt tcagtgacaa cagcacgcca ccggctgtgc cccagaccta      4020
tcaggtcggg tacttgcatg ctccaactgg cagtggaaag agcaccaagg tccctgtcgc      4080
```

```
gtatgccgcc caggggtaca aagtactagt gcttaacccc tcggtagctg ccaccctggg    4140
gtttggggcg tacctatcca aggcacatgg catcaatccc aacattagga ctggagtcag    4200
gaccgtgatg accggggagg ccatcacgta ctccacatat ggcaaatttc tcgccgatgg    4260
gggctgcgct agcggcgcct atgacatcat catatgcgat gaatgccacg ctgtggatgc    4320
tacctccatt ctcggcatcg aacggtcct tgatcaagca gagacagccg ggtcagact     4380 aactgtgctg gctacggcca caccccccgg gtcagtgaca accccccatc ccgatataga    4440
agaggtaggc ctcgggcggg agggtgagat ccccttctat ggagggcga ttccctatc     4500 ctgcatcaag ggagggagac acctgatttt ctgccactca aagaaaaagt gtgacgagct    4560 ccgcggcggcc cttcgggca tgggcttgaa tgccgtggca tactatagag ggttggacgt    4620
ctccataata ccagctcagg gagatgtggt ggtcgtcgcc accgacgccc tcatgacggg    4680
gtacactgga gactttgact ccgtgatcga ctgcaatgta gcggtcaccc aagctgtcga    4740
cttcagcctg gaccccacct tcactataac cacacagact gtcccacaag acgctgtctc    4800
acgcagtcag cgccgcgggc gcacaggtag aggaagacag ggcacttata ggtatgtttc    4860
cactggtgaa cgagcctcag gaatgtttga cagtgtagtg ctttgtgagt gctacgacgc    4920
aggggctgcg tggtacgatc tcacaccagc ggagaccacc gtcaggctta gagcgtattt    4980
caacacgccc ggcctacccg tgtgtcaaga ccatcttgaa ttttgggagg cagttttcac    5040
cggcctcaca cacatagacg cccacttcct ctcccaaaca aagcaagcgg gggagaactt    5100
cgcgtaccta gtagcctacc aagctacggt gtgcgccaga gccaaggccc ctcccccgtc    5160
ctgggacgcc atgtggaagt gcctggcccg actcaagcct acgcttgcgg gccccacacc    5220
tctcctgtac cgtttgggcc ctattaccaa tgaggtcacc ctcacacacc ctgggacgaa    5280
gtacatcgcc acatgcatgc aagctgacct tgaggtcatg accagcacgt gggtcctagc    5340
tggaggagtc ctggcagccg tcgccgcata ttgcctggcg actggatgcg tttccatcat    5400
cggccgcttg cacgtcaacc agcgagtcgt cgttgcgccg gataaggagg tcctgtatga    5460
ggcttttgat gagatggagg aatgcgcctc tagggcggct ctcatcgaag aggggcagcg    5520
gatagccgag atgttgaagt ccaagatcca aggcttgctg cagcaggcct ctaagcaggc    5580
ccaggacata caacccgcta tgcaggcttc atggccaaaa gtggaacaat tttgggccag    5640
acacatgtgg aacttcatta gcggcatcca atacctcgca ggattgtcaa cactgccagg    5700
gaaccccgcg gtggcttcca tgatggcatt cagtgccgcc ctcaccagtc cgttgtcgac    5760
cagtaccacc atccttctca acatcatggg aggctggtta gcgtcccaga tcgcaccacc    5820
cgcgggggcc accggctttg tcgtcagtgg cctggtgggg gctgccgtgg cagcatagg    5880 cctgggtaag gtgctggtgg acatcctggc aggatatggt gcgggcattt cggggccct     5940 cgtcgcattc aagatcatgt ctggcgagaa gccctctatg gaagatgtca tcaatctact    6000
gcctgggatc ctgtctccgg gagccctggt ggtgggggtc atctgcgcgg ccattctgcg    6060
ccgccacgtg ggaccggggg agggcgcggt ccaatggatg aacaggctta ttgcctttgc    6120
ttccagagga aaccacgtcg cccctactca ctacgtgacg gagtcggatg cgtcgcagcg    6180
tgtgacccaa ctacttggct ctcttactat aaccagccta ctcagaagac tccacaattg    6240
gataactgag gactgcccca tcccatgctc cggatcctgg ctccgcgacg tgtgggactg    6300
ggtttgcacc atcttgacag acttcaaaaa ttggctgacc tctaaattgt tccccaagct    6360
gcccggcctc cccttcatct cttgtcaaaa ggggtacaag ggtgtgtggg ccggcactgg    6420
catcatgacc acgcgctgcc cttgcggcgc caacatctct ggcaatgtcc gcctgggctc    6480
```

```
tatgaggatc acagggccta aaacctgcat gaacacctgg caggggacct ttcctatcaa   6540
ttgctacacg gagggccagt gcgcgccgaa accccccacg aactacaaga ccgccatctg   6600
gagggtggcg gcctcggagt acgcggaggt gacgcagcat gggtcgtact cctatgtaac   6660
aggactgacc actgacaatc tgaaaattcc ttgccaacta ccttctccag agttttctc    6720 ctgggtggac ggtgtgcaga tccataggtt tgcacccaca ccaaagccgt ttttccggga   6780
tgaggtctcg ttctgcgttg ggcttaattc ctatgctgtc gggtcccagc ttccctgtga   6840
acctgagccc gacgcagacg tattgaggtc catgctaaca gatccgcccc acatcacggc   6900
ggagactgcg gcgcggcgct tggcacgggg atcacctcca tctgaggcga gctcctcagt   6960
gagccagcta tcagcaccgt cgctgcgggc cacctgcacc acccacagca acacctatga   7020
cgtggacatg gtcgatgcca acctgctcat ggagggcggt gtggctcaga cagagcctga   7080
gtccagggtg cccgttctgg actttctcga gccaatggcc gaggaagaga gcgaccttga   7140
gccctcaata ccatcggagt gcatgctccc caggagcggg tttccacggg ccttaccggc   7200
ttgggcacgg cctgactaca acccgccgct cgtggaatcg tggaggaggc cagattacca   7260 accgccacc gttgctggtt gtgctctccc ccccccaag aaggcccga cgcctccccc     7320 aaggagacgc cggacagtgg gtctgagcga gagcaccata tcagaagccc tccagcaact   7380
ggccatcaag acctttggcc agccccctc gagcggtgat gcaggctcgt ccacgggggc    7440
gggcgccgcc gaatccggcg gtccgacgtc ccctggtgag ccggcccct cagagacagg   7500 ttccgcctcc tctatgcccc ccctcgaggg ggagcctgga gatccggacc tggagtctga   7560
tcaggtagag cttcaacctc cccccaggg ggggggggta gctcccggtt cgggctcggg    7620
gtcttggtct acttgctccg aggaggacga taccaccgtg tgctgctcca tgtcatactc   7680
ctggaccggg gctctaataa ctccctgtag ccccgaagag gaaaagttgc caatcaaccc   7740
tttgagtaac tcgctgttgc gataccataa caaggtgtac tgtacaacat caagagcgc    7800 ctcacagagg gctaaaaagg taacttttga caggacgcaa gtgctcgacg cccattatga   7860
ctcagtctta aaggacatca agctagcggc ttccaaggtc agcgcaaggc tcctcacctt   7920
ggaggaggcg tgccagttga ctccacccca ttctgcaaga tccaagtatg gattcggggc   7980
caaggaggtc cgcagcttgt ccgggagggc cgttaaccac atcaagtccg tgtgaagga    8040 cctcctggaa gacccacaaa caccaattcc cacaaccatc atggccaaaa atgaggtgtt   8100
ctgcgtggac cccgccaagg ggggtaagaa accagctcgc ctcatcgttt accctgacct   8160
cggcgtccgg gtctgcgaga aaatggccct ctatgacatt acacaaaagc ttcctcaggc   8220
ggtaatggga gcttcctatg gcttccagta ctcccctgcc caacgggtgg agtatctctt   8280
gaaagcatgg gcggaaaaga aggaccccat gggttttcg tatgataccc gatgcttcga    8340
ctcaaccgtc actgagagag acatcaggac cgaggagtcc atataccagg cctgctccct   8400
gcccgaggag gcccgcactg ccatacactc gctgactgag agactttacg taggagggcc   8460
catgttcaac agcaagggtc aaacctgcgg ttacagacgt tgccgcgcca gcggggtgct   8520
aaccactagc atgggtaaca ccatcacatg ctatgtgaaa gccctagcgg cctgcaaggc   8580
tgcggggata gttgcgccca caatgctggt atgcggcgat gacctagtag tcatctcaga   8640
aagccagggg actgaggagg acgagcggaa cctgagagcc ttcacggagg ccatgaccag   8700
gtactctgcc cctcctggtg atccccccag accggaatat gacctggagc taataacatc   8760
ctgttcctca aatgtgtctg tggcgttggg cccgcggggc cgccgcagat actacctgac   8820
cagagaccca accactccac tcgcccgggc tgcctgggaa acagttagac actcccctat   8880
```

-continued

```
caattcatgg ctgggaaaca tcatccagta tgctccaacc atatgggttc gcatggtcct    8940
aatgacacac ttcttctcca ttctcatggt ccaagacacc ctggaccaga acctcaactt    9000
tgagatgtat ggatcagtat actccgtgaa tcctttggac cttccagcca taattgagag    9060
gttacacggg cttgacgcct tttctatgca cacatactct caccacgaac tgacgcgggt    9120
ggcttcagcc ctcagaaaac ttggggcgcc acccctcagg gtgtggaaga gtcgggctcg    9180
cgcagtcagg gcgtccctca tctcccgtgg agggaaagcg gccgtttgcg gccgatatct    9240
cttcaattgg gcggtgaaga ccaagctcaa actcactcca ttgccggagg cgcgcctact    9300
ggacttatcc agttggttca ccgtcggcgc cggcggggc  gacatttttc acagcgtgtc    9360
gcgcgcccga ccccgctcat tactcttcgg cctactccta cttttcgtag gggtaggcct    9420
cttcctactc cccgctcggt agagcggcac acactaggta cactccatag ctaactgttc    9480
cttttttttt tttttttttt tttttttttt tttttttttt ttttcttttt ttttttttc    9540 cctctttctt cccttctcat cttattctac tttctttctt ggtggctcca tcttagcccc    9600
agtcacggct agctgtgaaa ggtccgtgag ccgcatgact gcagagagtg ccgtaactgg    9660
tctctctgca gatcatgt                                                  9678
```

<210> SEQ ID NO 8
<211> LENGTH: 3033
<212> TYPE: PRT
<213> ORGANISM: Hepatitis C virus

<400> SEQUENCE: 8

```
Met Ser Thr Asn Pro Lys Pro Gln Arg Leu Thr Lys Arg Asn Thr Val
1               5                   10                  15

Arg Arg Pro Gln Asn Val Lys Phe Pro Gly Gly Gly Gln Ile Val Gly
            20                  25                  30

Gly Val Tyr Leu Leu Pro Arg Arg Gly Pro Arg Leu Gly Val Arg Gly
        35                  40                  45

Thr Arg Lys Ser Ser Glu Arg Ser Gln Pro Arg Gly Arg Arg Gln Arg
    50                  55                  60

Ile Pro Lys Ala Ala Ser Ser Gln Gly Lys Ala Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Lys Val Ile Asp Thr Met Thr Cys
        115                 120                 125

Gly Phe Ala Asp Leu Met Gly Tyr Ile Pro Val Leu Gly Ala Pro Leu
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Glu Val Arg Asn Ser Ser Gly Val Tyr His Leu Thr Asn Asp Cys Pro
        195                 200                 205

Asn Ala Ser Ile Val Tyr Glu Thr Asp Asn Ala Ile Leu His Glu Pro
    210                 215                 220

Gly Cys Val Pro Cys Val Arg Glu Gly Asn Thr Ser Arg Cys Trp Glu
```

```
                225                 230                 235                 240
Pro Val Ala Pro Thr Leu Ala Val Arg Tyr Arg Gly Ala Leu Thr Asp
                    245                 250                 255

Asp Leu Arg Thr His Ile Asp Leu Val Val Ala Ser Ala Thr Leu Cys
                    260                 265                 270

Ser Ala Leu Tyr Val Gly Asp Ile Cys Gly Ala Ile Phe Ile Ala Ser
                    275                 280                 285

Gln Ala Val Leu Trp Lys Pro Gly Gly Arg Ile Val Gln Asp Cys
                    290                 295                 300

Asn Cys Ser Ile Tyr Pro Gly His Val Thr Gly His Arg Met Ala Trp
305                 310                 315                 320

Asp Met Met Gln Asn Trp Ala Pro Ala Leu Ser Met Val Ala Ala Tyr
                    325                 330                 335

Ala Val Arg Val Pro Gly Val Ile Ile Thr Thr Val Ala Gly Gly His
                    340                 345                 350

Trp Gly Val Leu Phe Gly Leu Ala Tyr Phe Gly Met Ala Gly Asn Trp
                    355                 360                 365

Ala Lys Val Ile Leu Ile Met Leu Leu Met Ser Gly Val Asp Ala Glu
                    370                 375                 380

Thr Met Ala Val Gly Ala Arg Ala Ala His Thr Thr Gly Ala Leu Val
385                 390                 395                 400

Ser Leu Leu Asn Pro Gly Pro Ser Gln Arg Leu Gln Leu Ile Asn Thr
                    405                 410                 415

Asn Gly Ser Trp His Ile Asn Arg Thr Ala Leu Asn Cys Asn Asp Ser
                    420                 425                 430

Leu Gln Thr Gly Phe Ile Ala Ala Leu Phe Tyr Thr His Arg Phe Asn
                    435                 440                 445

Ser Ser Gly Cys Pro Glu Arg Met Ala Ser Cys Lys Pro Leu Ser Asp
450                 455                 460

Phe Asp Gln Gly Trp Gly Pro Leu Trp Tyr Asn Ser Thr Glu Arg Pro
465                 470                 475                 480

Ser Asp Gln Arg Pro Tyr Cys Trp His Tyr Ala Pro Ser Pro Cys Gly
                    485                 490                 495

Ile Val Pro Ala Lys Asp Val Cys Gly Pro Val Tyr Cys Phe Thr Pro
                    500                 505                 510

Ser Pro Val Val Gly Thr Thr Asp Arg Arg Gly Val Pro Thr Tyr
                    515                 520                 525

Thr Trp Gly Glu Asn Glu Ser Asp Val Phe Leu Leu Asn Ser Thr Arg
                    530                 535                 540

Pro Pro Gln Gly Ser Trp Phe Gly Cys Ser Trp Met Asn Thr Thr Gly
545                 550                 555                 560

Phe Thr Lys Thr Cys Gly Gly Pro Pro Cys Lys Ile Arg Pro Gln Gly
                    565                 570                 575

Ala Gln Ser Asn Thr Ser Leu Thr Cys Pro Thr Asp Cys Phe Arg Lys
                    580                 585                 590

His Pro Arg Ala Thr Tyr Ser Ala Cys Gly Ser Gly Pro Trp Leu Thr
                    595                 600                 605

Pro Arg Cys Met Val His Tyr Pro Tyr Arg Leu Trp His Tyr Pro Cys
                    610                 615                 620

Thr Val Asn Phe Thr Ile His Lys Val Arg Leu Tyr Ile Gly Gly Val
625                 630                 635                 640

Glu His Arg Leu Asp Ala Ala Cys Asn Trp Thr Arg Gly Glu Arg Cys
                    645                 650                 655
```

```
Asp Leu Glu Asp Arg Asp Arg Val Asp Met Ser Pro Leu Leu His Ser
            660                 665                 670

Thr Thr Glu Leu Ala Ile Leu Pro Cys Ser Phe Val Pro Leu Pro Ala
            675                 680                 685

Leu Ser Thr Gly Leu Ile His Leu His Gln Asn Ile Val Asp Ala Gln
        690                 695                 700

Tyr Leu Tyr Gly Leu Ser Pro Ala Ile Ile Ser Trp Ala Ile Arg Trp
705                 710                 715                 720

Glu Trp Val Val Leu Val Phe Leu Leu Leu Ala Asp Ala Arg Ile Cys
                725                 730                 735

Ala Cys Leu Trp Met Met Met Leu Met Ala Gln Ala Glu Ala Ala Leu
                740                 745                 750

Glu Asn Leu Ile His Leu Asn Ala Ala Ser Leu Ala Gly Thr His Gly
        755                 760                 765

Ile Trp Trp Leu Leu Leu Val Phe Cys Ala Ser Trp His Leu Arg Gly
770                 775                 780

Arg Val Val Pro Leu Val Thr Tyr Gly Ile Cys Gly Met Trp Pro Phe
785                 790                 795                 800

Phe Leu Met Leu Leu Ser Leu Pro Pro Arg Ala Tyr Ala Leu Asp Arg
                805                 810                 815

Glu Val Ser Ala Ala Leu Gly Thr Gly Met Leu Ala Ile Ile Leu Leu
                820                 825                 830

Val Thr Leu Gly Pro His Tyr Lys Arg Leu Leu Ala Leu Ile Leu Trp
        835                 840                 845

Trp Val Thr Tyr Phe Leu Thr Arg Cys Glu Ala Ala Leu Gln Thr Trp
        850                 855                 860

Val Pro Pro Leu Asn Pro Arg Gly Gly Arg Asp Gly Phe Ile Leu Cys
865                 870                 875                 880

Val Pro Leu Cys Tyr Pro Gly Leu Val Phe Asp Ile Thr Lys Trp Leu
                885                 890                 895

Leu Val Met Met Cys Pro Leu Tyr Leu Gln Leu Cys Leu Val Arg
                900                 905                 910

Thr Pro Tyr Phe Val Arg Ala Gln Ala Leu Ile Arg Val Cys Ser Leu
                915                 920                 925

Phe Lys Thr Leu Ala Gly Gly Arg Tyr Val Gln Ala Ala Leu Leu Thr
        930                 935                 940

Ile Gly Arg Trp Thr Gly Thr Tyr Ile Tyr Asn His Leu Ala Pro Leu
945                 950                 955                 960

Glu Thr Trp Ala Ala Gly Gly Leu Arg Asp Leu Ala Val Ala Val Glu
                965                 970                 975

Pro Val Ile Phe Ser Pro Met Glu Lys Lys Ile Ile Val Trp Gly Ala
                980                 985                 990

Glu Thr Thr Ala Cys Gly Asp Ile Leu Cys Gly Leu Pro Val Ser Ala
            995                1000                1005

Arg Leu Gly Arg Glu Val Leu Leu Gly Pro Ala Asp Asp Tyr Arg
        1010                1015                1020

Ser Met Gly Trp Gln Leu Leu Ala Pro Ile Thr Ala Tyr Ala Gln
        1025                1030                1035

Gln Thr Arg Gly Leu Leu Gly Ala Ile Val Val Ser Met Thr Gly
        1040                1045                1050

Arg Asp Arg Thr Glu Gln Ala Gly Glu Val Gln Ile Leu Ser Thr
        1055                1060                1065

Val Ser Gln Ser Phe Leu Gly Thr Thr Ile Ser Gly Val Leu Trp
        1070                1075                1080
```

```
Thr Val Tyr His Gly Ala Gly Asn Lys Thr Leu Ala Gly Leu Arg
1085                1090                1095

Gly Pro Val Thr Gln Met Tyr Ser Ser Ala Glu Gly Asp Leu Val
1100                1105                1110

Gly Trp Pro Ser Pro Pro Gly Thr Lys Ser Leu Glu Pro Cys Lys
1115                1120                1125

Cys Gly Ala Val Asp Leu Tyr Leu Val Thr Arg Asn Ala Asp Val
1130                1135                1140

Ile Pro Ala Arg Arg Gly Asp Lys Arg Gly Ala Leu Leu Ser
1145                1150                1155

Pro Arg Pro Ile Ser Thr Leu Lys Gly Ser Ser Gly Gly Pro Val
1160                1165                1170

Leu Cys Pro Arg Gly His Val Val Gly Leu Phe Arg Ala Ala Val
1175                1180                1185

Cys Ser Arg Gly Val Ala Lys Ser Ile Asp Phe Ile Pro Val Glu
1190                1195                1200

Thr Leu Asp Val Val Thr Arg Ser Pro Thr Phe Ser Asp Asn Ser
1205                1210                1215

Thr Pro Pro Ala Val Pro Gln Thr Tyr Gln Val Gly Tyr Leu His
1220                1225                1230

Ala Pro Thr Gly Ser Gly Lys Ser Thr Lys Val Pro Val Ala Tyr
1235                1240                1245

Ala Ala Gln Gly Tyr Lys Val Leu Val Leu Asn Pro Ser Val Ala
1250                1255                1260

Ala Thr Leu Gly Phe Gly Ala Tyr Leu Ser Lys Ala His Gly Ile
1265                1270                1275

Asn Pro Asn Ile Arg Thr Gly Val Arg Thr Val Met Thr Gly Glu
1280                1285                1290

Ala Ile Thr Tyr Ser Thr Tyr Gly Lys Phe Leu Ala Asp Gly Gly
1295                1300                1305

Cys Ala Ser Gly Ala Tyr Asp Ile Ile Cys Asp Glu Cys His
1310                1315                1320

Ala Val Asp Ala Thr Ser Ile Leu Gly Ile Gly Thr Val Leu Asp
1325                1330                1335

Gln Ala Glu Thr Ala Gly Val Arg Leu Thr Val Leu Ala Thr Ala
1340                1345                1350

Thr Pro Pro Gly Ser Val Thr Thr Pro His Pro Asp Ile Glu Glu
1355                1360                1365

Val Gly Leu Gly Arg Glu Gly Glu Ile Pro Phe Tyr Gly Arg Ala
1370                1375                1380

Ile Pro Leu Ser Cys Ile Lys Gly Gly Arg His Leu Ile Phe Cys
1385                1390                1395

His Ser Lys Lys Lys Cys Asp Glu Leu Ala Ala Ala Leu Arg Gly
1400                1405                1410

Met Gly Leu Asn Ala Val Ala Tyr Tyr Arg Gly Leu Asp Val Ser
1415                1420                1425

Ile Ile Pro Ala Gln Gly Asp Val Val Val Val Ala Thr Asp Ala
1430                1435                1440

Leu Met Thr Gly Tyr Thr Gly Asp Phe Asp Ser Val Ile Asp Cys
1445                1450                1455

Asn Val Ala Val Thr Gln Ala Val Asp Phe Ser Leu Asp Pro Thr
1460                1465                1470

Phe Thr Ile Thr Thr Gln Thr Val Pro Gln Asp Ala Val Ser Arg
```

```
                1475                1480                1485

Ser Gln Arg Arg Gly Arg Thr Gly Arg Gly Arg Gln Gly Thr Tyr
    1490                1495                1500

Arg Tyr Val Ser Thr Gly Glu Arg Ala Ser Gly Met Phe Asp Ser
    1505                1510                1515

Val Val Leu Cys Glu Cys Tyr Asp Ala Gly Ala Ala Trp Tyr Asp
    1520                1525                1530

Leu Thr Pro Ala Glu Thr Thr Val Arg Leu Arg Ala Tyr Phe Asn
    1535                1540                1545

Thr Pro Gly Leu Pro Val Cys Gln Asp His Leu Glu Phe Trp Glu
    1550                1555                1560

Ala Val Phe Thr Gly Leu Thr His Ile Asp Ala His Phe Leu Ser
    1565                1570                1575

Gln Thr Lys Gln Ala Gly Glu Asn Phe Ala Tyr Leu Val Ala Tyr
    1580                1585                1590

Gln Ala Thr Val Cys Ala Arg Ala Lys Ala Pro Pro Pro Ser Trp
    1595                1600                1605

Asp Ala Met Trp Lys Cys Leu Ala Arg Leu Lys Pro Thr Leu Ala
    1610                1615                1620

Gly Pro Thr Pro Leu Leu Tyr Arg Leu Gly Pro Ile Thr Asn Glu
    1625                1630                1635

Val Thr Leu Thr His Pro Gly Thr Lys Tyr Ile Ala Thr Cys Met
    1640                1645                1650

Gln Ala Asp Leu Glu Val Met Thr Ser Thr Trp Val Leu Ala Gly
    1655                1660                1665

Gly Val Leu Ala Ala Val Ala Ala Tyr Cys Leu Ala Thr Gly Cys
    1670                1675                1680

Val Ser Ile Ile Gly Arg Leu His Val Asn Gln Arg Val Val Val
    1685                1690                1695

Ala Pro Asp Lys Glu Val Leu Tyr Glu Ala Phe Asp Glu Met Glu
    1700                1705                1710

Glu Cys Ala Ser Arg Ala Ala Leu Ile Glu Glu Gly Gln Arg Ile
    1715                1720                1725

Ala Glu Met Leu Lys Ser Lys Ile Gln Gly Leu Leu Gln Gln Ala
    1730                1735                1740

Ser Lys Gln Ala Gln Asp Ile Gln Pro Ala Met Gln Ala Ser Trp
    1745                1750                1755

Pro Lys Val Glu Gln Phe Trp Ala Arg His Met Trp Asn Phe Ile
    1760                1765                1770

Ser Gly Ile Gln Tyr Leu Ala Gly Leu Ser Thr Leu Pro Gly Asn
    1775                1780                1785

Pro Ala Val Ala Ser Met Met Ala Phe Ser Ala Ala Leu Thr Ser
    1790                1795                1800

Pro Leu Ser Thr Ser Thr Thr Ile Leu Leu Asn Ile Met Gly Gly
    1805                1810                1815

Trp Leu Ala Ser Gln Ile Ala Pro Pro Ala Gly Ala Thr Gly Phe
    1820                1825                1830

Val Val Ser Gly Leu Val Gly Ala Ala Val Gly Ser Ile Gly Leu
    1835                1840                1845

Gly Lys Val Leu Val Asp Ile Leu Ala Gly Tyr Gly Ala Gly Ile
    1850                1855                1860

Ser Gly Ala Leu Val Ala Phe Lys Ile Met Ser Gly Glu Lys Pro
    1865                1870                1875
```

-continued

| | | | | | | | | | | | |
|---|---|---|---|---|---|---|---|---|---|---|---|
| Ser | Met | Glu | Asp | Val | Ile | Asn | Leu | Leu | Pro | Gly | Ile | Leu | Ser | Pro |
| | 1880 | | | | 1885 | | | | | 1890 | |

Ser Met Glu Asp Val Ile Asn Leu Leu Pro Gly Ile Leu Ser Pro
    1880                1885                 1890

Gly Ala Leu Val Val Gly Val Ile Cys Ala Ala Ile Leu Arg Arg
    1895                1900                 1905

His Val Gly Pro Gly Glu Gly Ala Val Gln Trp Met Asn Arg Leu
    1910                1915                 1920

Ile Ala Phe Ala Ser Arg Gly Asn His Val Ala Pro Thr His Tyr
    1925                1930                 1935

Val Thr Glu Ser Asp Ala Ser Gln Arg Val Thr Gln Leu Leu Gly
    1940                1945                 1950

Ser Leu Thr Ile Thr Ser Leu Leu Arg Arg Leu His Asn Trp Ile
    1955                1960                 1965

Thr Glu Asp Cys Pro Ile Pro Cys Ser Gly Ser Trp Leu Arg Asp
    1970                1975                 1980

Val Trp Asp Trp Val Cys Thr Ile Leu Thr Asp Phe Lys Asn Trp
    1985                1990                 1995

Leu Thr Ser Lys Leu Phe Pro Lys Leu Pro Gly Leu Pro Phe Ile
    2000                2005                 2010

Ser Cys Gln Lys Gly Tyr Lys Gly Val Trp Ala Gly Thr Gly Ile
    2015                2020                 2025

Met Thr Thr Arg Cys Pro Cys Gly Ala Asn Ile Ser Gly Asn Val
    2030                2035                 2040

Arg Leu Gly Ser Met Arg Ile Thr Gly Pro Lys Thr Cys Met Asn
    2045                2050                 2055

Thr Trp Gln Gly Thr Phe Pro Ile Asn Cys Tyr Thr Glu Gly Gln
    2060                2065                 2070

Cys Ala Pro Lys Pro Pro Thr Asn Tyr Lys Thr Ala Ile Trp Arg
    2075                2080                 2085

Val Ala Ala Ser Glu Tyr Ala Glu Val Thr Gln His Gly Ser Tyr
    2090                2095                 2100

Ser Tyr Val Thr Gly Leu Thr Thr Asp Asn Leu Lys Ile Pro Cys
    2105                2110                 2115

Gln Leu Pro Ser Pro Glu Phe Phe Ser Trp Val Asp Gly Val Gln
    2120                2125                 2130

Ile His Arg Phe Ala Pro Thr Pro Lys Pro Phe Phe Arg Asp Glu
    2135                2140                 2145

Val Ser Phe Cys Val Gly Leu Asn Ser Tyr Ala Val Gly Ser Gln
    2150                2155                 2160

Leu Pro Cys Glu Pro Glu Pro Asp Ala Asp Val Leu Arg Ser Met
    2165                2170                 2175

Leu Thr Asp Pro Pro His Ile Thr Ala Glu Thr Ala Ala Arg Arg
    2180                2185                 2190

Leu Ala Arg Gly Ser Pro Pro Ser Glu Ala Ser Ser Ser Val Ser
    2195                2200                 2205

Gln Leu Ser Ala Pro Ser Leu Arg Ala Thr Cys Thr Thr His Ser
    2210                2215                 2220

Asn Thr Tyr Asp Val Asp Met Val Asp Ala Asn Leu Leu Met Glu
    2225                2230                 2235

Gly Gly Val Ala Gln Thr Glu Pro Glu Ser Arg Val Pro Val Leu
    2240                2245                 2250

Asp Phe Leu Glu Pro Met Ala Glu Glu Ser Asp Leu Glu Pro
    2255                2260                 2265

Ser Ile Pro Ser Glu Cys Met Leu Pro Arg Ser Gly Phe Pro Arg
    2270                2275                 2280

-continued

Ala Leu Pro Ala Trp Ala Arg Pro Asp Tyr Asn Pro Pro Leu Val
2285                2290                2295

Glu Ser Trp Arg Arg Pro Asp Tyr Gln Pro Pro Thr Val Ala Gly
2300                2305                2310

Cys Ala Leu Pro Pro Pro Lys Lys Ala Pro Thr Pro Pro Pro Arg
2315                2320                2325

Arg Arg Arg Thr Val Gly Leu Ser Glu Ser Thr Ile Ser Glu Ala
2330                2335                2340

Leu Gln Gln Leu Ala Ile Lys Thr Phe Gly Gln Pro Pro Ser Ser
2345                2350                2355

Gly Asp Ala Gly Ser Ser Thr Gly Ala Gly Ala Ala Glu Ser Gly
2360                2365                2370

Gly Pro Thr Ser Pro Gly Glu Pro Ala Pro Ser Glu Thr Gly Ser
2375                2380                2385

Ala Ser Ser Met Pro Pro Leu Glu Gly Glu Pro Gly Asp Pro Asp
2390                2395                2400

Leu Glu Ser Asp Gln Val Glu Leu Gln Pro Pro Gln Gly Gly
2405                2410                2415

Gly Val Ala Pro Gly Ser Gly Ser Gly Ser Trp Ser Thr Cys Ser
2420                2425                2430

Glu Glu Asp Asp Thr Thr Val Cys Cys Ser Met Ser Tyr Ser Trp
2435                2440                2445

Thr Gly Ala Leu Ile Thr Pro Cys Ser Pro Glu Glu Glu Lys Leu
2450                2455                2460

Pro Ile Asn Pro Leu Ser Asn Ser Leu Leu Arg Tyr His Asn Lys
2465                2470                2475

Val Tyr Cys Thr Thr Ser Lys Ser Ala Ser Gln Arg Ala Lys Lys
2480                2485                2490

Val Thr Phe Asp Arg Thr Gln Val Leu Asp Ala His Tyr Asp Ser
2495                2500                2505

Val Leu Lys Asp Ile Lys Leu Ala Ala Ser Lys Val Ser Ala Arg
2510                2515                2520

Leu Leu Thr Leu Glu Glu Ala Cys Gln Leu Thr Pro Pro His Ser
2525                2530                2535

Ala Arg Ser Lys Tyr Gly Phe Gly Ala Lys Glu Val Arg Ser Leu
2540                2545                2550

Ser Gly Arg Ala Val Asn His Ile Lys Ser Val Trp Lys Asp Leu
2555                2560                2565

Leu Glu Asp Pro Gln Thr Pro Ile Pro Thr Thr Ile Met Ala Lys
2570                2575                2580

Asn Glu Val Phe Cys Val Asp Pro Ala Lys Gly Gly Lys Lys Pro
2585                2590                2595

Ala Arg Leu Ile Val Tyr Pro Asp Leu Gly Val Arg Val Cys Glu
2600                2605                2610

Lys Met Ala Leu Tyr Asp Ile Thr Gln Lys Leu Pro Gln Ala Val
2615                2620                2625

Met Gly Ala Ser Tyr Gly Phe Gln Tyr Ser Pro Ala Gln Arg Val
2630                2635                2640

Glu Tyr Leu Leu Lys Ala Trp Ala Glu Lys Lys Asp Pro Met Gly
2645                2650                2655

Phe Ser Tyr Asp Thr Arg Cys Phe Asp Ser Thr Val Thr Glu Arg
2660                2665                2670

Asp Ile Arg Thr Glu Glu Ser Ile Tyr Gln Ala Cys Ser Leu Pro

|  |  |  | 2675 |  |  |  |  | 2680 |  |  |  |  | 2685 |  |

Glu Glu Ala Arg Thr Ala Ile His Ser Leu Thr Glu Arg Leu Tyr
2690                2695                2700

Val Gly Gly Pro Met Phe Asn Ser Lys Gly Gln Thr Cys Gly Tyr
2705                2710                2715

Arg Arg Cys Arg Ala Ser Gly Val Leu Thr Thr Ser Met Gly Asn
2720                2725                2730

Thr Ile Thr Cys Tyr Val Lys Ala Leu Ala Ala Cys Lys Ala Ala
2735                2740                2745

Gly Ile Val Ala Pro Thr Met Leu Val Cys Gly Asp Asp Leu Val
2750                2755                2760

Val Ile Ser Glu Ser Gln Gly Thr Glu Glu Asp Glu Arg Asn Leu
2765                2770                2775

Arg Ala Phe Thr Glu Ala Met Thr Arg Tyr Ser Ala Pro Pro Gly
2780                2785                2790

Asp Pro Pro Arg Pro Glu Tyr Asp Leu Glu Leu Ile Thr Ser Cys
2795                2800                2805

Ser Ser Asn Val Ser Val Ala Leu Gly Pro Arg Gly Arg Arg Arg
2810                2815                2820

Tyr Tyr Leu Thr Arg Asp Pro Thr Thr Pro Leu Ala Arg Ala Ala
2825                2830                2835

Trp Glu Thr Val Arg His Ser Pro Ile Asn Ser Trp Leu Gly Asn
2840                2845                2850

Ile Ile Gln Tyr Ala Pro Thr Ile Trp Val Arg Met Val Leu Met
2855                2860                2865

Thr His Phe Phe Ser Ile Leu Met Val Gln Asp Thr Leu Asp Gln
2870                2875                2880

Asn Leu Asn Phe Glu Met Tyr Gly Ser Val Tyr Ser Val Asn Pro
2885                2890                2895

Leu Asp Leu Pro Ala Ile Ile Glu Arg Leu His Gly Leu Asp Ala
2900                2905                2910

Phe Ser Met His Thr Tyr Ser His His Glu Leu Thr Arg Val Ala
2915                2920                2925

Ser Ala Leu Arg Lys Leu Gly Ala Pro Pro Leu Arg Val Trp Lys
2930                2935                2940

Ser Arg Ala Arg Ala Val Arg Ala Ser Leu Ile Ser Arg Gly Gly
2945                2950                2955

Lys Ala Ala Val Cys Gly Arg Tyr Leu Phe Asn Trp Ala Val Lys
2960                2965                2970

Thr Lys Leu Lys Leu Thr Pro Leu Pro Glu Ala Arg Leu Leu Asp
2975                2980                2985

Leu Ser Ser Trp Phe Thr Val Gly Ala Gly Gly Asp Ile Phe
2990                2995                3000

His Ser Val Ser Arg Ala Arg Pro Arg Ser Leu Leu Phe Gly Leu
3005                3010                3015

Leu Leu Leu Phe Val Gly Val Gly Leu Phe Leu Leu Pro Ala Arg
3020                3025                3030

<210> SEQ ID NO 9
<211> LENGTH: 9678
<212> TYPE: DNA
<213> ORGANISM: Hepatitis C virus

<400> SEQUENCE: 9
acctgcccct aatagggggcg acactccgcc atgaatcact cccctgtgag gaactactgt    60

```
cttcacgcag aaagcgccta gccatggcgt tagtatgagt gtcgtacagc ctccaggccc    120
ccccctcccg ggagagccat agtggtctgc ggaaccggtg agtacaccgg aattgccggg    180
aagactgggt cctttcttgg ataaacccac tctatgcccg ccatttgggc gtgcccccg     240 caagactgct agccgagtag cgttgggttg cgaaaggcct tgtggtactg cctgataggg    300
tgcttgcgag tgcccgggga ggtctcgtag accgtgcacc atgagcacga atcctaaacc    360
tcaaagatta accaaaagaa acaccgtccg tcgcccacag aacgttaagt tcccgggtgg    420
cgggcagatc gttggcggag tctacttgtt gccgcgcagg ggccctagat tgggtgtgcg    480
cggcactagg aagagttcgg agcgatcgca gcccagggga agacgccaac gtatcccaa     540 agctgcctct tcacagggta aagcctgggg caagcccggg tacccttggc ccctgtatgg    600
taacgagggc tgtggctggg cagggtggct cctgtccccc cgcggctctc gacctacttg    660
gggccccact gaccccggc accgctcgcg aaacctcggt aaggtgatcg acaccatgac     720
ctgcgggttt gccgacctca tggggtacat ccctgtccta ggcgcccccc taggggcgt     780 tgccagggct ctggcacatg gtgttagagt tctggaggac ggggtcaact atgcaacagg    840
gaacttgcct ggttgctcct tttctatctt cttactagcc ctcctgtcat gtctaacagt    900
cccggcatcg gcttatgaag tccgcaactc cagtggggtc tatcatctca ccaatgactg    960
ccccaacgct agtatagtct atgaaacaga caacgccatc ctacgcgagc ctgggtgcgt   1020
gccttgcgtt cgcgagggta atactagcag gtgttgggaa ccagtggccc ccactttggc   1080
ggtccgctat cgcggagcgc ttactgacga tttgcggacg catattgacc tagtggtggc   1140
gtcagctacc ctgtgctccg ccttgtacgt gggggacatt tgtggagcca tcttcattgc   1200
cagccaagct gttctctgga agcccgggg gggtcggata tgcaagatt gcaattgttc     1260 gatctacccg ggccacgtca ccggccacag gatggcgtgg gacatgatgc agaactgggc   1320
gccggccttg tcaatggttg ccgcttacgc tgtgagagtg cccggtgtca tcattaccac   1380
tgtagcgggc ggccactggg gtgtgttatt tggcctcgct tactttggta tggcgggaaa   1440
ctgggcaaag gtaatactca tcatgctact catgtccggc gtcgacgcgg aaaccatggc   1500
cgtcggggct agggccgctc acaccactgg cgcccttgtc agcctgctca atccagggcc   1560
cagtcagcgc ctgcagctga tcaacaccaa tgggtcatgg cacatcaacc ggaccgcttt   1620
gaactgcaat gactctttgc agacagggtt catagcggcc ctcttctaca cacataggtt   1680
caattctagt ggctgtcccg agaggatggc ttcttgtaaa cctctcagtg actttgacca   1740 gggtgggc ccgctgtggt acaattcaac agaaagacct tcggaccagc gaccctattg     1800
ctggcactac gcgccatcgc cgtgtggtat tgtgccggct aaggatgttt gcggtccggt   1860
ctactgcttt acaccaagcc cggttgtggt gggcaccacg gatcgccggg gggtgccac    1920 gtatacttgg ggtgaaaatg agtctgatgt cttcctgctc aacagcacaa ggccgccgca   1980
aggcagttgg tttgggtgct catggatgaa cacaacgggg ttcacgaaga cctgcggagg   2040
tcctccgtgc aagatacgtc cccagggtgc ccagagtaac acctctctca cttgtcccac   2100
agactgcttc aggaaacatc cgcgtgccac atactccgct tgcggatctg gtccgtggtt   2160
gacacctaga tgcatggtcc attacccctc tagactgtgg cactaccgt gtacagtcaa    2220 cttcaccata cacaaagtca ggttatacat aggggtgta gaacataggc tcgatgcagc    2280
gtgcaattgg acgcgggtg agcgatgcga cctggaggac cgagacaggg tggacatgtc   2340 cccccctgctc cattccacta cggagctcgc aatacttccg tgttcctttg tgccgcttcc   2400
ggccttatct acgggactga tccacctgca ccaaaacatc gttgacgccc agtaccttta   2460
```

```
tggtctttct cccgctataa taagctgggc catcagatgg gagtgggtag tcctcgtttt   2520
cctactcctg gcggacgcgc ggatctgcgc ctgcctttgg atgatgatgc ttatggccca   2580
ggctgaagcc gctctggaga acttgatcca cctcaacgcg ccagccttg  cgggaaccca   2640 tggtatctgg tggctccttt tagtcttttg tgcctcttgg catctacgag gcagggttgt   2700
ccctctggtg acgtatggga tatgcgggat gtggcccttc ttcctcatgt tgctgagcct   2760
ccccccacga gcgtatgctc tggacaggga agtgagcgca gcgttgggaa cgggcatgct   2820
cgccatcatc ctattagtta ccttgggacc gcactacaag agacttctag cccttattct   2880
ctggtgggtc acatatttcc ttacaaggtg tgaagcagca ctccaaacgt gggtccctcc   2940
tctcaaccct cggggggca gggacggttt catcctgtgt gtgctgctgt gctatccagg   3000
ccttgtcttt gacatcacaa aatggttgct ggtcatgatg tgccctctct acctcctcca   3060
gttgtgtttg gtgaggactc catactttgt gagggcccag gccctcatca gagtgtgttc   3120
tctcttcaaa acgctagctg ggggacggta cgtgcaggcc gcgctgctca ctattggccg   3180
ctggaccggc acttatattt ataaccatct cgccccctg gaaacatggg ccgccggcgg   3240
cctacgggat ttggccgttg cagtcgagcc cgtgatattc tcccccatgg agaagaagat   3300
catagtttgg ggggcggaga ccactgcttg tggcgacatt ctttgtggcc tgcctgtctc   3360
agctcggctc ggcagggaag tcctgctagg gcccgcggat gactacaggt ccatgggatg   3420
gcaactcctg gctcccatca ctgcttatgc ccagcaaaca cgaggcctcc tgggcgccat   3480
agtggtgagt atgacggggc gtgacaggac agaacaggcc ggggaagtcc aaatcctgtc   3540
cacagtctct cagtccttcc tcggaacaac catctcgggg gttttgtgga ctgtttacca   3600 cggagctgg  aacaagactc tagccggctt acggggtccg gtcacgcaga tgtactcgag   3660
tgctgagggg gacttggtag gctggcccag ccccctggg  accaagtctt tggagccgtg   3720
caagtgtgga gccgtcgacc tatatctggt cacgcggaac gctgatgtca tcccggctcg   3780
gagacgcggg gacaagcggg gagcattgct ctccccgaga cccatttcga ccttgaaggg   3840
gtcctcgggg gggccggtgc tctgccctag gggccacgtc gttgggctct tccgagcagc   3900
tgtgtgctct cggggcgtgg ccaaatccat cgatttcatc cccgttgaga cactcgacgt   3960
tgttacaagg tctcccactt tcagtgacaa cagcacgcca ccggctgtgc cccagaccta   4020
tcaggtcggg tacttgcatg ctccaactgg cagtggaaag agcaccaagg tccctgtcgc   4080
gtatgccgcc cagggtaca  aagtactagt gcttaacccc tcggtagctg ccaccctggg   4140
gtttggggcg tacctatcca aggcacatgg catcaatccc aacattagga ctggagtcag   4200
gaccgtgatg accggggagg ccatcacgta ctccacatat ggcaaatttc tcgccgatgg   4260
gggctgcgct agcggcgcct atgacatcat catatgcgat gaatgccacg ctgtggatgc   4320
tacctccatt ctcggcatcg gaacggtcct tgatcaagca gagacagccg gggtcagact   4380
aactgtgctg gctacggcca caccccccgg gtcagtgaca accccccatc ccgatataga   4440
agaggtaggc ctcgggcggg agggtgagat ccccttctat ggagggcga ttccccctatc   4500 ctgcatcaag ggagggagac acctgatttt ctgccactca aagaaaaagt gtgacgagct   4560
cgcggcggcc cttcgcggca tgggcttgaa tgccgtggca tactatagag gttggacgt    4620 ctccataata ccagctcagg gagatgtggt ggtcgtcgcc accgacgccc tcatgacggg   4680
gtacactgga gactttgact ccgtgatcga ctgcaatgta gcggtcaccc aagctgtcga   4740
cttcagcctg gaccccacct tcactataac cacacagact gtcccacaag acgctgtctc   4800
acgcagtcag cgccgcgggc gcacaggtag aggaagacag ggcacttata ggtatgtttc   4860
```

```
cactggtgaa cgagcctcag gaatgtttga cagtgtagtg ctttgtgagt gctacgacgc   4920
aggggctgcg tggtacgatc tcacaccagc ggagaccacc gtcaggctta gagcgtattt   4980
caacacgccc ggcctacccg tgtgtcaaga ccatcttgaa ttttgggagg cagttttcac   5040
cggcctcaca cacatagacg cccacttcct ctcccaaaca aagcaagcgg gggagaactt   5100
cgcgtaccta gtagcctacc aagctacggt gtgcgccaga gccaaggccc ctccccgtc    5160 ctgggacgcc atgtggaagt gcctggcccg actcaagcct acgcttgcgg ccccacacc    5220 tctcctgtac cgtttgggcc ctattaccaa tgaggtcacc ctcacacacc ctgggacgaa   5280
gtacatcgcc acatgcatgc aagctgacct tgaggtcatg accagcacgt gggtcctagc   5340
tggaggagtc ctggcagccg tcgccgcata ttgcctggcg actggatgcg tttccatcat   5400
cggccgcttg cacgtcaacc agcgagtcgt cgttgcgccg gataaggagg tcctgtatga   5460
ggcttttgat gagatggagg aatgcgcctc tagggcggct ctcatcgaag aggggcagcg   5520
gatagccgag atgttgaagt ccaagatcca aggcttgctg cagcaggcct ctaagcaggc   5580
ccaggacata aacccgcta tgcaggcttc atggcccaaa gtggaacaat tttgggccag    5640
acacatgtgg aacttcatta gcggcatcca ataccctcgca ggattgtcaa cactgccagg   5700 gaacccgcg gtggcttcca tgatggcatt cagtgccgcc ctcaccagtc gttgtcgac    5760 cagtaccacc atccttctca acatcatggg aggctggtta gcgtcccaga tcgcaccacc   5820
cgcgggggcc accggctttg tcgtcagtgg cctggtgggg gctgccgtgg gcagcatagg   5880
cctgggtaag gtgctggtgg acatcctggc aggatatggt gcgggcattt cggggggcct  5940
cgtcgcattc aagatcatgt ctggcgagaa gccctctatg aagatgtca tcaatctact    6000 gcctgggatc ctgtctccgg gagccctggt ggtgggggtc atctgcgcgg ccattctgcg   6060
ccgccacgtg gaccgggggg agggcgcggt ccaatggatg aacaggctta ttgcctttgc   6120
ttccagagga aaccacgtcg cccctactca ctacgtgacg gagtcggatg cgtcgcagcg   6180
tgtgacccaa ctacttggct ctcttactat aaccagccta ctcagaagac tccacaattg   6240
gataactgag gactgcccca tcccatgctc cggatcctgg ctccgcgacg tgtgggactg   6300
ggtttgcacc atcttgacag acttcaaaaa ttggctgacc tctaaattgt tccccaagct   6360 gccccggcctc cccttcatct cttgtcaaaa ggggtacaag ggtgtgtggg ccggcactgg   6420
catcatgacc acgcgctgcc cttgcggcgc caacatctct ggcaatgtcc gcctgggctc   6480
tatgaggatc acagggccta aaacctgcat gaacacctgg caggggacct ttcctatcaa   6540
ttgctacacg gagggccagt gcgcgccgaa accccccacg aactacaaga ccgccatctg   6600
gagggtggcg gcctcggagt acgcggaggt gacgcagcat gggtcgtact cctatgtaac   6660
aggactgacc actgacaatc tgaaaattcc ttgccaacta ccttctccag agttttctc    6720 ctgggtggac ggtgtgcaga tccataggtt gcacccaca ccaaagccgt ttttccggga    6780
tgaggtctcg ttctgcgttg gcttaattc ctatgctgtc gggtcccagc ttccctgtga    6840
acctgagccc gacgcagacg tattgaggtc catgctaaca gatccgcccc acatcacggc   6900
ggagactgcg gcgcggcgct tggcacgggg atcacctcca tctgaggcga gctcctcagt   6960
gagccagcta tcagcaccgt cgctgcgggc cacctgcacc acccacagca cacctatga    7020 cgtggacatg gtcgatgcca acctgctcat ggagggcggt gtggctcaga cagagcctga   7080
gtccagggtg cccgttctgg actttctcga gccaatggcc gaggaagaga gcgaccttga   7140
gccctcaata ccatcggagt gcatgctccc caggagcggg tttccacggg ccttaccggc   7200
ttgggcacgg cctgactaca acccgccgct cgtggaatcg tggaggaggc cagattacca   7260
```

```
accgcccacc gttgctggtt gtgctctccc ccccccaag aaggcccga cgcctccccc    7320 aaggagacgc cggacagtgg gtctgagcga gagcaccata tcagaagccc tccagcaact    7380
ggccatcaag acctttggcc agcccccctc gagcggtgat gcaggctcgt ccacgggggc    7440
gggcgccgcc gaatccggcg gtccgacgtc ccctggtgag ccggccccct cagagacagg    7500
ttccgcctcc tctatgcccc ccctcgaggg ggagcctgga gatccggacc tggagtctga    7560
tcaggtagag cttcaacctc cccccaggg gggggggta gctcccggtt cgggctcggg    7620
gtcttggtct acttgctccg aggaggacga taccaccgtg tgctgctcca tgtcatactc    7680
ctggaccggg gctctaataa ctccctgtag ccccgaagag gaaaagttgc caatcaaccc    7740
tttgagtaac tcgctgttgc gataccataa caaggtgtac tgtacaacat caaagagcgc    7800
ctcacagagg gctaaaaagg taacttttga caggacgcaa gtgctcgacg cccattatga    7860
ctcagtctta aaggacatca agctagcggc ttccaaggtc agcgcaaggc tcctcacctt    7920
ggaggaggcg tgccagttga ctccacccca ttctgcaaga tccaagtatg gattcggggc    7980
caaggaggtc cgcagcttgt cgggagggc cgttaaccac atcaagtccg tgtggaagga    8040
cctcctggaa gacccacaaa caccaattcc cacaaccatc atggccaaaa atgaggtgtt    8100
ctgcgtggac cccgccaagg ggggtaagaa accagctcgc ctcatcgttt accctgacct    8160
cggcgtccgg gtctgcgaga aaatggccct ctatgacatt acacaaaagc ttcctcaggc    8220
ggtaatggga gcttcctatg gcttccagta ctcccctgcc caacgggtgg agtatctctt    8280
gaaagcatgg gcgaaaaga aggacccat gggttttcg tatgataccc gatgcttcga    8340
ctcaaccgtc actgagagag acatcaggac cgaggagtcc atataccagg cctgctccct    8400
gcccgaggag gcccgcactg tcatacactc gctgactgag agactttacg taggagggcc    8460
catgttcaac agcaagggtc aaacctgcgg ttacagacgt tgccgcgcca gcggggtgct    8520
aaccactagc atgggtaaca ccatcacatg ctatgtgaaa gccctagcgg cctgcaaggc    8580
tgcggggata gttgcgccca caatgctggt atgcggcgat gacctagtag tcatctcaga    8640
aagccagggg actgaggagg acgagcggaa cctgagagcc ttcacggagg ccatgaccag    8700
gtactctgcc cctcctggtg atcccccag accggaatat gacctggagc taataacatc    8760
ctgttcctca aatgtgtctg tggcgttggg cccgcgggc cgccgcagat actacctgac    8820
cagagaccca accactccac tcgcccgggc tgcctgggaa acagttagac actcccctat    8880
caattcatgg ctgggaaaca tcatccagta tgctccaacc atatgggttc gcatggtcct    8940
aatgacacac ttcttctcca ttctcatggt ccaagacacc ctggaccaga acctcaactt    9000
tgagatgtat ggatcagtat actccgtgaa tcctttggac cttccagcca taattgagag    9060
gttacacggg cttgacgcct tttctatgca cacatactct caccacgaac tgacgcgggt    9120
ggcttcagcc ctcagaaaac ttgggggcgcc acccctcagg gtgtggaaga gtcgggctcg    9180
cgcagtcagg gcgtccctca tctcccgtgg agggaaagcg gccgtttgcg gccgatatct    9240
cttcaattgg gcggtgaaga ccaagctcaa actcactcca ttgccggagg gcgcgcctact    9300 ggacttatcc agttggttca ccgtcggcgc cggcggggc gacatttttc acagcgtgtc    9360
gcgcgcccga ccccgctcat tactcttcgg cctactccta cttttcgtag gggtaggcct    9420
cttcctactc cccgctcggt agagcggcac acactaggta cactccatag ctaactgttc    9480 ctttttttt ttttttttttt tttttttttt tttttttttt tttcttttt ttttttttttc    9540 cctctttctt cccttctcat cttattctac tttcttctt ggtggctcca tcttagccct    9600
agtcacggct agctgtgaaa ggtccgtgag ccgcatgact gcagagagtg ccgtaactgg    9660
```
tctctctgca gatcatgt                                                9678

<210> SEQ ID NO 10
<211> LENGTH: 3033
<212> TYPE: PRT
<213> ORGANISM: Hepatitis C virus

<400> SEQUENCE: 10

```
Met Ser Thr Asn Pro Lys Pro Gln Arg Leu Thr Lys Arg Asn Thr Val
1               5                   10                  15

Arg Arg Pro Gln Asn Val Lys Phe Pro Gly Gly Gly Gln Ile Val Gly
            20                  25                  30

Gly Val Tyr Leu Leu Pro Arg Arg Gly Pro Arg Leu Gly Val Arg Gly
        35                  40                  45

Thr Arg Lys Ser Ser Glu Arg Ser Gln Pro Arg Gly Arg Arg Gln Arg
    50                  55                  60

Ile Pro Lys Ala Ala Ser Ser Gln Gly Lys Ala Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Lys Val Ile Asp Thr Met Thr Cys
        115                 120                 125

Gly Phe Ala Asp Leu Met Gly Tyr Ile Pro Val Leu Gly Ala Pro Leu
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Glu Val Arg Asn Ser Ser Gly Val Tyr His Leu Thr Asn Asp Cys Pro
        195                 200                 205

Asn Ala Ser Ile Val Tyr Glu Thr Asp Asn Ala Ile Leu His Glu Pro
    210                 215                 220

Gly Cys Val Pro Cys Val Arg Glu Gly Asn Thr Ser Arg Cys Trp Glu
225                 230                 235                 240

Pro Val Ala Pro Thr Leu Ala Val Arg Tyr Arg Gly Ala Leu Thr Asp
                245                 250                 255

Asp Leu Arg Thr His Ile Asp Leu Val Val Ala Ser Ala Thr Leu Cys
            260                 265                 270

Ser Ala Leu Tyr Val Gly Asp Ile Cys Gly Ala Ile Phe Ile Ala Ser
        275                 280                 285

Gln Ala Val Leu Trp Lys Pro Gly Gly Gly Arg Ile Val Gln Asp Cys
    290                 295                 300

Asn Cys Ser Ile Tyr Pro Gly His Val Thr Gly His Arg Met Ala Trp
305                 310                 315                 320

Asp Met Met Gln Asn Trp Ala Pro Ala Leu Ser Met Val Ala Ala Tyr
                325                 330                 335

Ala Val Arg Val Pro Gly Val Ile Ile Thr Thr Val Ala Gly Gly His
            340                 345                 350

Trp Gly Val Leu Phe Gly Leu Ala Tyr Phe Gly Met Ala Gly Asn Trp
        355                 360                 365
```

-continued

```
Ala Lys Val Ile Leu Ile Met Leu Leu Met Ser Gly Val Asp Ala Glu
        370                 375                 380

Thr Met Ala Val Gly Ala Arg Ala His Thr Gly Ala Leu Val
385                 390                 395                 400

Ser Leu Leu Asn Pro Gly Pro Ser Gln Arg Leu Gln Leu Ile Asn Thr
                405                 410                 415

Asn Gly Ser Trp His Ile Asn Arg Thr Ala Leu Asn Cys Asn Asp Ser
            420                 425                 430

Leu Gln Thr Gly Phe Ile Ala Ala Leu Phe Tyr Thr His Arg Phe Asn
        435                 440                 445

Ser Ser Gly Cys Pro Glu Arg Met Ala Ser Cys Lys Pro Leu Ser Asp
    450                 455                 460

Phe Asp Gln Gly Trp Gly Pro Leu Trp Tyr Asn Ser Thr Glu Arg Pro
465                 470                 475                 480

Ser Asp Gln Arg Pro Tyr Cys Trp His Tyr Ala Pro Ser Pro Cys Gly
                485                 490                 495

Ile Val Pro Ala Lys Asp Val Cys Gly Pro Val Tyr Cys Phe Thr Pro
            500                 505                 510

Ser Pro Val Val Gly Thr Thr Asp Arg Arg Gly Val Pro Thr Tyr
        515                 520                 525

Thr Trp Gly Glu Asn Glu Ser Asp Val Phe Leu Leu Asn Ser Thr Arg
    530                 535                 540

Pro Pro Gln Gly Ser Trp Phe Gly Cys Ser Trp Met Asn Thr Thr Gly
545                 550                 555                 560

Phe Thr Lys Thr Cys Gly Gly Pro Pro Cys Lys Ile Arg Pro Gln Gly
                565                 570                 575

Ala Gln Ser Asn Thr Ser Leu Thr Cys Pro Thr Asp Cys Phe Arg Lys
            580                 585                 590

His Pro Arg Ala Thr Tyr Ser Ala Cys Gly Ser Gly Pro Trp Leu Thr
        595                 600                 605

Pro Arg Cys Met Val His Tyr Pro Tyr Arg Leu Trp His Tyr Pro Cys
    610                 615                 620

Thr Val Asn Phe Thr Ile His Lys Val Arg Leu Tyr Ile Gly Gly Val
625                 630                 635                 640

Glu His Arg Leu Asp Ala Ala Cys Asn Trp Thr Arg Gly Glu Arg Cys
                645                 650                 655

Asp Leu Glu Asp Arg Asp Arg Val Asp Met Ser Pro Leu Leu His Ser
            660                 665                 670

Thr Thr Glu Leu Ala Ile Leu Pro Cys Ser Phe Val Pro Leu Pro Ala
        675                 680                 685

Leu Ser Thr Gly Leu Ile His Leu His Gln Asn Ile Val Asp Ala Gln
    690                 695                 700

Tyr Leu Tyr Gly Leu Ser Pro Ala Ile Ile Ser Trp Ala Ile Arg Trp
705                 710                 715                 720

Glu Trp Val Val Leu Val Phe Leu Leu Leu Ala Asp Ala Arg Ile Cys
                725                 730                 735

Ala Cys Leu Trp Met Met Met Leu Met Ala Gln Ala Glu Ala Ala Leu
            740                 745                 750

Glu Asn Leu Ile His Leu Asn Ala Ala Ser Leu Ala Gly Thr His Gly
        755                 760                 765

Ile Trp Trp Leu Leu Leu Val Phe Cys Ala Ser Trp His Leu Arg Gly
    770                 775                 780

Arg Val Val Pro Leu Val Thr Tyr Gly Ile Cys Gly Met Trp Pro Phe
785                 790                 795                 800
```

```
Phe Leu Met Leu Leu Ser Leu Pro Pro Arg Ala Tyr Ala Leu Asp Arg
                805                 810                 815

Glu Val Ser Ala Ala Leu Gly Thr Gly Met Leu Ala Ile Ile Leu Leu
            820                 825                 830

Val Thr Leu Gly Pro His Tyr Lys Arg Leu Leu Ala Leu Ile Leu Trp
        835                 840                 845

Trp Val Thr Tyr Phe Leu Thr Arg Cys Glu Ala Ala Leu Gln Thr Trp
    850                 855                 860

Val Pro Pro Leu Asn Pro Arg Gly Gly Arg Asp Gly Phe Ile Leu Cys
865                 870                 875                 880

Val Leu Leu Cys Tyr Pro Gly Leu Val Phe Asp Ile Thr Lys Trp Leu
                885                 890                 895

Leu Val Met Met Cys Pro Leu Tyr Leu Leu Gln Leu Cys Leu Val Arg
            900                 905                 910

Thr Pro Tyr Phe Val Arg Ala Gln Ala Leu Ile Arg Val Cys Ser Leu
        915                 920                 925

Phe Lys Thr Leu Ala Gly Gly Arg Tyr Val Gln Ala Ala Leu Leu Thr
    930                 935                 940

Ile Gly Arg Trp Thr Gly Thr Tyr Ile Tyr Asn His Leu Ala Pro Leu
945                 950                 955                 960

Glu Thr Trp Ala Ala Gly Gly Leu Arg Asp Leu Ala Val Ala Val Glu
                965                 970                 975

Pro Val Ile Phe Ser Pro Met Glu Lys Lys Ile Ile Val Trp Gly Ala
            980                 985                 990

Glu Thr Thr Ala Cys Gly Asp Ile Leu Cys Gly Leu Pro Val Ser Ala
        995                 1000                1005

Arg Leu Gly Arg Glu Val Leu Leu Gly Pro Ala Asp Asp Tyr Arg
    1010                1015                1020

Ser Met Gly Trp Gln Leu Leu Ala Pro Ile Thr Ala Tyr Ala Gln
    1025                1030                1035

Gln Thr Arg Gly Leu Leu Gly Ala Ile Val Val Ser Met Thr Gly
    1040                1045                1050

Arg Asp Arg Thr Glu Gln Ala Gly Glu Val Gln Ile Leu Ser Thr
    1055                1060                1065

Val Ser Gln Ser Phe Leu Gly Thr Thr Ile Ser Gly Val Leu Trp
    1070                1075                1080

Thr Val Tyr His Gly Ala Gly Asn Lys Thr Leu Ala Gly Leu Arg
    1085                1090                1095

Gly Pro Val Thr Gln Met Tyr Ser Ser Ala Glu Gly Asp Leu Val
    1100                1105                1110

Gly Trp Pro Ser Pro Pro Gly Thr Lys Ser Leu Glu Pro Cys Lys
    1115                1120                1125

Cys Gly Ala Val Asp Leu Tyr Leu Val Thr Arg Asn Ala Asp Val
    1130                1135                1140

Ile Pro Ala Arg Arg Arg Gly Asp Lys Arg Gly Ala Leu Leu Ser
    1145                1150                1155

Pro Arg Pro Ile Ser Thr Leu Lys Gly Ser Ser Gly Gly Pro Val
    1160                1165                1170

Leu Cys Pro Arg Gly His Val Val Gly Leu Phe Arg Ala Ala Val
    1175                1180                1185

Cys Ser Arg Gly Val Ala Lys Ser Ile Asp Phe Ile Pro Val Glu
    1190                1195                1200

Thr Leu Asp Val Val Thr Arg Ser Pro Thr Phe Ser Asp Asn Ser
```

|      |     |     |     |     |     |     |     |     |     |     |     |     |     |     |
|------|-----|-----|-----|-----|-----|-----|-----|-----|-----|-----|-----|-----|-----|-----|
|      |     |     |     |     | 1205|     |     |     |     | 1210|     |     |     | 1215|
| Thr  | Pro | Pro | Ala | Val | Pro | Gln | Thr | Tyr | Gln | Val | Gly | Tyr | Leu | His |
| 1220 |     |     |     |     | 1225|     |     |     |     | 1230|     |     |     |     |
| Ala  | Pro | Thr | Gly | Ser | Gly | Lys | Ser | Thr | Lys | Val | Pro | Val | Ala | Tyr |
| 1235 |     |     |     |     | 1240|     |     |     |     | 1245|     |     |     |     |
| Ala  | Ala | Gln | Gly | Tyr | Lys | Val | Leu | Val | Leu | Asn | Pro | Ser | Val | Ala |
| 1250 |     |     |     |     | 1255|     |     |     |     | 1260|     |     |     |     |
| Ala  | Thr | Leu | Gly | Phe | Gly | Ala | Tyr | Leu | Ser | Lys | Ala | His | Gly | Ile |
| 1265 |     |     |     |     | 1270|     |     |     |     | 1275|     |     |     |     |
| Asn  | Pro | Asn | Ile | Arg | Thr | Gly | Val | Arg | Thr | Val | Met | Thr | Gly | Glu |
| 1280 |     |     |     |     | 1285|     |     |     |     | 1290|     |     |     |     |
| Ala  | Ile | Thr | Tyr | Ser | Thr | Tyr | Gly | Lys | Phe | Leu | Ala | Asp | Gly | Gly |
| 1295 |     |     |     |     | 1300|     |     |     |     | 1305|     |     |     |     |
| Cys  | Ala | Ser | Gly | Ala | Tyr | Asp | Ile | Ile | Ile | Cys | Asp | Glu | Cys | His |
| 1310 |     |     |     |     | 1315|     |     |     |     | 1320|     |     |     |     |
| Ala  | Val | Asp | Ala | Thr | Ser | Ile | Leu | Gly | Ile | Gly | Thr | Val | Leu | Asp |
| 1325 |     |     |     |     | 1330|     |     |     |     | 1335|     |     |     |     |
| Gln  | Ala | Glu | Thr | Ala | Gly | Val | Arg | Leu | Thr | Val | Leu | Ala | Thr | Ala |
| 1340 |     |     |     |     | 1345|     |     |     |     | 1350|     |     |     |     |
| Thr  | Pro | Pro | Gly | Ser | Val | Thr | Thr | Pro | His | Pro | Asp | Ile | Glu | Glu |
| 1355 |     |     |     |     | 1360|     |     |     |     | 1365|     |     |     |     |
| Val  | Gly | Leu | Gly | Arg | Glu | Gly | Glu | Ile | Pro | Phe | Tyr | Gly | Arg | Ala |
| 1370 |     |     |     |     | 1375|     |     |     |     | 1380|     |     |     |     |
| Ile  | Pro | Leu | Ser | Cys | Ile | Lys | Gly | Gly | Arg | His | Leu | Ile | Phe | Cys |
| 1385 |     |     |     |     | 1390|     |     |     |     | 1395|     |     |     |     |
| His  | Ser | Lys | Lys | Lys | Cys | Asp | Glu | Leu | Ala | Ala | Ala | Leu | Arg | Gly |
| 1400 |     |     |     |     | 1405|     |     |     |     | 1410|     |     |     |     |
| Met  | Gly | Leu | Asn | Ala | Val | Ala | Tyr | Tyr | Arg | Gly | Leu | Asp | Val | Ser |
| 1415 |     |     |     |     | 1420|     |     |     |     | 1425|     |     |     |     |
| Ile  | Ile | Pro | Ala | Gln | Gly | Asp | Val | Val | Val | Val | Ala | Thr | Asp | Ala |
| 1430 |     |     |     |     | 1435|     |     |     |     | 1440|     |     |     |     |
| Leu  | Met | Thr | Gly | Tyr | Thr | Gly | Asp | Phe | Asp | Ser | Val | Ile | Asp | Cys |
| 1445 |     |     |     |     | 1450|     |     |     |     | 1455|     |     |     |     |
| Asn  | Val | Ala | Val | Thr | Gln | Ala | Val | Asp | Phe | Ser | Leu | Asp | Pro | Thr |
| 1460 |     |     |     |     | 1465|     |     |     |     | 1470|     |     |     |     |
| Phe  | Thr | Ile | Thr | Thr | Gln | Thr | Val | Pro | Gln | Asp | Ala | Val | Ser | Arg |
| 1475 |     |     |     |     | 1480|     |     |     |     | 1485|     |     |     |     |
| Ser  | Gln | Arg | Arg | Gly | Arg | Thr | Gly | Arg | Gly | Arg | Gln | Gly | Thr | Tyr |
| 1490 |     |     |     |     | 1495|     |     |     |     | 1500|     |     |     |     |
| Arg  | Tyr | Val | Ser | Thr | Gly | Glu | Arg | Ala | Ser | Gly | Met | Phe | Asp | Ser |
| 1505 |     |     |     |     | 1510|     |     |     |     | 1515|     |     |     |     |
| Val  | Val | Leu | Cys | Glu | Cys | Tyr | Asp | Ala | Gly | Ala | Ala | Trp | Tyr | Asp |
| 1520 |     |     |     |     | 1525|     |     |     |     | 1530|     |     |     |     |
| Leu  | Thr | Pro | Ala | Glu | Thr | Thr | Val | Arg | Leu | Arg | Ala | Tyr | Phe | Asn |
| 1535 |     |     |     |     | 1540|     |     |     |     | 1545|     |     |     |     |
| Thr  | Pro | Gly | Leu | Pro | Val | Cys | Gln | Asp | His | Leu | Glu | Phe | Trp | Glu |
| 1550 |     |     |     |     | 1555|     |     |     |     | 1560|     |     |     |     |
| Ala  | Val | Phe | Thr | Gly | Leu | Thr | His | Ile | Asp | Ala | His | Phe | Leu | Ser |
| 1565 |     |     |     |     | 1570|     |     |     |     | 1575|     |     |     |     |
| Gln  | Thr | Lys | Gln | Ala | Gly | Glu | Asn | Phe | Ala | Tyr | Leu | Val | Ala | Tyr |
| 1580 |     |     |     |     | 1585|     |     |     |     | 1590|     |     |     |     |
| Gln  | Ala | Thr | Val | Cys | Ala | Arg | Ala | Lys | Ala | Pro | Pro | Pro | Ser | Trp |
| 1595 |     |     |     |     | 1600|     |     |     |     | 1605|     |     |     |     |

```
Asp Ala Met Trp Lys Cys Leu Ala Arg Leu Lys Pro Thr Leu Ala
1610                1615                1620

Gly Pro Thr Pro Leu Leu Tyr Arg Leu Gly Pro Ile Thr Asn Glu
1625                1630                1635

Val Thr Leu Thr His Pro Gly Thr Lys Tyr Ile Ala Thr Cys Met
1640                1645                1650

Gln Ala Asp Leu Glu Val Met Thr Ser Thr Trp Val Leu Ala Gly
1655                1660                1665

Gly Val Leu Ala Ala Val Ala Ala Tyr Cys Leu Ala Thr Gly Cys
1670                1675                1680

Val Ser Ile Ile Gly Arg Leu His Val Asn Gln Arg Val Val Val
1685                1690                1695

Ala Pro Asp Lys Glu Val Leu Tyr Glu Ala Phe Asp Glu Met Glu
1700                1705                1710

Glu Cys Ala Ser Arg Ala Ala Leu Ile Glu Glu Gly Gln Arg Ile
1715                1720                1725

Ala Glu Met Leu Lys Ser Lys Ile Gln Gly Leu Leu Gln Gln Ala
1730                1735                1740

Ser Lys Gln Ala Gln Asp Ile Gln Pro Ala Met Gln Ala Ser Trp
1745                1750                1755

Pro Lys Val Glu Gln Phe Trp Ala Arg His Met Trp Asn Phe Ile
1760                1765                1770

Ser Gly Ile Gln Tyr Leu Ala Gly Leu Ser Thr Leu Pro Gly Asn
1775                1780                1785

Pro Ala Val Ala Ser Met Met Ala Phe Ser Ala Ala Leu Thr Ser
1790                1795                1800

Pro Leu Ser Thr Ser Thr Thr Ile Leu Leu Asn Ile Met Gly Gly
1805                1810                1815

Trp Leu Ala Ser Gln Ile Ala Pro Pro Ala Gly Ala Thr Gly Phe
1820                1825                1830

Val Val Ser Gly Leu Val Gly Ala Ala Val Gly Ser Ile Gly Leu
1835                1840                1845

Gly Lys Val Leu Val Asp Ile Leu Ala Gly Tyr Gly Ala Gly Ile
1850                1855                1860

Ser Gly Ala Leu Val Ala Phe Lys Ile Met Ser Gly Glu Lys Pro
1865                1870                1875

Ser Met Glu Asp Val Ile Asn Leu Leu Pro Gly Ile Leu Ser Pro
1880                1885                1890

Gly Ala Leu Val Val Gly Val Ile Cys Ala Ala Ile Leu Arg Arg
1895                1900                1905

His Val Gly Pro Gly Glu Gly Ala Val Gln Trp Met Asn Arg Leu
1910                1915                1920

Ile Ala Phe Ala Ser Arg Gly Asn His Val Ala Pro Thr His Tyr
1925                1930                1935

Val Thr Glu Ser Asp Ala Ser Gln Arg Val Thr Gln Leu Leu Gly
1940                1945                1950

Ser Leu Thr Ile Thr Ser Leu Leu Arg Arg Leu His Asn Trp Ile
1955                1960                1965

Thr Glu Asp Cys Pro Ile Pro Cys Ser Gly Ser Trp Leu Arg Asp
1970                1975                1980

Val Trp Asp Trp Val Cys Thr Ile Leu Thr Asp Phe Lys Asn Trp
1985                1990                1995

Leu Thr Ser Lys Leu Phe Pro Lys Leu Pro Gly Leu Pro Phe Ile
2000                2005                2010
```

```
Ser Cys Gln Lys Gly Tyr Lys Gly Val Trp Ala Gly Thr Gly Ile
    2015                2020                2025

Met Thr Thr Arg Cys Pro Cys Gly Ala Asn Ile Ser Gly Asn Val
    2030                2035                2040

Arg Leu Gly Ser Met Arg Ile Thr Gly Pro Lys Thr Cys Met Asn
    2045                2050                2055

Thr Trp Gln Gly Thr Phe Pro Ile Asn Cys Tyr Thr Glu Gly Gln
    2060                2065                2070

Cys Ala Pro Lys Pro Pro Thr Asn Tyr Lys Thr Ala Ile Trp Arg
    2075                2080                2085

Val Ala Ala Ser Glu Tyr Ala Glu Val Thr Gln His Gly Ser Tyr
    2090                2095                2100

Ser Tyr Val Thr Gly Leu Thr Thr Asp Asn Leu Lys Ile Pro Cys
    2105                2110                2115

Gln Leu Pro Ser Pro Glu Phe Phe Ser Trp Val Asp Gly Val Gln
    2120                2125                2130

Ile His Arg Phe Ala Pro Thr Pro Lys Pro Phe Phe Arg Asp Glu
    2135                2140                2145

Val Ser Phe Cys Val Gly Leu Asn Ser Tyr Ala Val Gly Ser Gln
    2150                2155                2160

Leu Pro Cys Glu Pro Glu Pro Asp Ala Asp Val Leu Arg Ser Met
    2165                2170                2175

Leu Thr Asp Pro Pro His Ile Thr Ala Glu Thr Ala Ala Arg Arg
    2180                2185                2190

Leu Ala Arg Gly Ser Pro Pro Ser Glu Ala Ser Ser Ser Val Ser
    2195                2200                2205

Gln Leu Ser Ala Pro Ser Leu Arg Ala Thr Cys Thr Thr His Ser
    2210                2215                2220

Asn Thr Tyr Asp Val Asp Met Val Asp Ala Asn Leu Leu Met Glu
    2225                2230                2235

Gly Gly Val Ala Gln Thr Glu Pro Glu Ser Arg Val Pro Val Leu
    2240                2245                2250

Asp Phe Leu Glu Pro Met Ala Glu Glu Glu Ser Asp Leu Glu Pro
    2255                2260                2265

Ser Ile Pro Ser Glu Cys Met Leu Pro Arg Ser Gly Phe Pro Arg
    2270                2275                2280

Ala Leu Pro Ala Trp Ala Arg Pro Asp Tyr Asn Pro Pro Leu Val
    2285                2290                2295

Glu Ser Trp Arg Arg Pro Asp Tyr Gln Pro Pro Thr Val Ala Gly
    2300                2305                2310

Cys Ala Leu Pro Pro Pro Lys Lys Ala Pro Thr Pro Pro Pro Arg
    2315                2320                2325

Arg Arg Arg Thr Val Gly Leu Ser Glu Ser Thr Ile Ser Glu Ala
    2330                2335                2340

Leu Gln Gln Leu Ala Ile Lys Thr Phe Gly Gln Pro Pro Ser Ser
    2345                2350                2355

Gly Asp Ala Gly Ser Ser Thr Gly Ala Gly Ala Ala Glu Ser Gly
    2360                2365                2370

Gly Pro Thr Ser Pro Gly Glu Pro Ala Pro Ser Glu Thr Gly Ser
    2375                2380                2385

Ala Ser Ser Met Pro Pro Leu Glu Gly Glu Pro Gly Asp Pro Asp
    2390                2395                2400

Leu Glu Ser Asp Gln Val Glu Leu Gln Pro Pro Pro Gln Gly Gly
```

-continued

```
            2405                2410                2415

Gly Val Ala Pro Gly Ser Gly Ser Gly Ser Trp Ser Thr Cys Ser
    2420                2425                2430

Glu Glu Asp Asp Thr Thr Val Cys Cys Ser Met Ser Tyr Ser Trp
    2435                2440                2445

Thr Gly Ala Leu Ile Thr Pro Cys Ser Pro Glu Glu Glu Lys Leu
    2450                2455                2460

Pro Ile Asn Pro Leu Ser Asn Ser Leu Leu Arg Tyr His Asn Lys
    2465                2470                2475

Val Tyr Cys Thr Thr Ser Lys Ser Ala Ser Gln Arg Ala Lys Lys
    2480                2485                2490

Val Thr Phe Asp Arg Thr Gln Val Leu Asp Ala His Tyr Asp Ser
    2495                2500                2505

Val Leu Lys Asp Ile Lys Leu Ala Ala Ser Lys Val Ser Ala Arg
    2510                2515                2520

Leu Leu Thr Leu Glu Glu Ala Cys Gln Leu Thr Pro Pro His Ser
    2525                2530                2535

Ala Arg Ser Lys Tyr Gly Phe Gly Ala Lys Glu Val Arg Ser Leu
    2540                2545                2550

Ser Gly Arg Ala Val Asn His Ile Lys Ser Val Trp Lys Asp Leu
    2555                2560                2565

Leu Glu Asp Pro Gln Thr Pro Ile Pro Thr Thr Ile Met Ala Lys
    2570                2575                2580

Asn Glu Val Phe Cys Val Asp Pro Ala Lys Gly Gly Lys Lys Pro
    2585                2590                2595

Ala Arg Leu Ile Val Tyr Pro Asp Leu Gly Val Arg Val Cys Glu
    2600                2605                2610

Lys Met Ala Leu Tyr Asp Ile Thr Gln Lys Leu Pro Gln Ala Val
    2615                2620                2625

Met Gly Ala Ser Tyr Gly Phe Gln Tyr Ser Pro Ala Gln Arg Val
    2630                2635                2640

Glu Tyr Leu Leu Lys Ala Trp Ala Glu Lys Lys Asp Pro Met Gly
    2645                2650                2655

Phe Ser Tyr Asp Thr Arg Cys Phe Asp Ser Thr Val Thr Glu Arg
    2660                2665                2670

Asp Ile Arg Thr Glu Glu Ser Ile Tyr Gln Ala Cys Ser Leu Pro
    2675                2680                2685

Glu Glu Ala Arg Thr Val Ile His Ser Leu Thr Glu Arg Leu Tyr
    2690                2695                2700

Val Gly Gly Pro Met Phe Asn Ser Lys Gly Gln Thr Cys Gly Tyr
    2705                2710                2715

Arg Arg Cys Arg Ala Ser Gly Val Leu Thr Thr Ser Met Gly Asn
    2720                2725                2730

Thr Ile Thr Cys Tyr Val Lys Ala Leu Ala Ala Cys Lys Ala Ala
    2735                2740                2745

Gly Ile Val Ala Pro Thr Met Leu Val Cys Gly Asp Asp Leu Val
    2750                2755                2760

Val Ile Ser Glu Ser Gln Gly Thr Glu Glu Asp Glu Arg Asn Leu
    2765                2770                2775

Arg Ala Phe Thr Glu Ala Met Thr Arg Tyr Ser Ala Pro Pro Gly
    2780                2785                2790

Asp Pro Pro Arg Pro Glu Tyr Asp Leu Glu Leu Ile Thr Ser Cys
    2795                2800                2805
```

```
Ser Ser Asn Val Ser Val Ala Leu Gly Pro Arg Gly Arg Arg Arg
    2810            2815                2820

Tyr Tyr Leu Thr Arg Asp Pro Thr Thr Pro Leu Ala Arg Ala Ala
    2825            2830                2835

Trp Glu Thr Val Arg His Ser Pro Ile Asn Ser Trp Leu Gly Asn
    2840            2845                2850

Ile Ile Gln Tyr Ala Pro Thr Ile Trp Val Arg Met Val Leu Met
    2855            2860                2865

Thr His Phe Phe Ser Ile Leu Met Val Gln Asp Thr Leu Asp Gln
    2870            2875                2880

Asn Leu Asn Phe Glu Met Tyr Gly Ser Val Tyr Ser Val Asn Pro
    2885            2890                2895

Leu Asp Leu Pro Ala Ile Ile Glu Arg Leu His Gly Leu Asp Ala
    2900            2905                2910

Phe Ser Met His Thr Tyr Ser His His Glu Leu Thr Arg Val Ala
    2915            2920                2925

Ser Ala Leu Arg Lys Leu Gly Ala Pro Pro Leu Arg Val Trp Lys
    2930            2935                2940

Ser Arg Ala Arg Ala Val Arg Ala Ser Leu Ile Ser Arg Gly Gly
    2945            2950                2955

Lys Ala Ala Val Cys Gly Arg Tyr Leu Phe Asn Trp Ala Val Lys
    2960            2965                2970

Thr Lys Leu Lys Leu Thr Pro Leu Pro Glu Ala Arg Leu Leu Asp
    2975            2980                2985

Leu Ser Ser Trp Phe Thr Val Gly Ala Gly Gly Gly Asp Ile Phe
    2990            2995                3000

His Ser Val Ser Arg Ala Arg Pro Arg Ser Leu Leu Phe Gly Leu
    3005            3010                3015

Leu Leu Leu Phe Val Gly Val Gly Leu Phe Leu Leu Pro Ala Arg
    3020            3025                3030
```

<210> SEQ ID NO 11
<211> LENGTH: 40
<212> TYPE: DNA
<213> ORGANISM: Artificial Sequence
<220> FEATURE:
<223> OTHER INFORMATION: OligoDNA primer

<400> SEQUENCE: 11
gtagcgttgg gttgcgaaag gccttgtggt actgcctgat    40

<210> SEQ ID NO 12
<211> LENGTH: 24
<212> TYPE: DNA
<213> ORGANISM: Artificial Sequence
<220> FEATURE:
<223> OTHER INFORMATION: OligoDNA primer

<400> SEQUENCE: 12
gacggccatg gtttccgcgt cgac    24

<210> SEQ ID NO 13
<211> LENGTH: 25
<212> TYPE: DNA
<213> ORGANISM: Artificial Sequence
<220> FEATURE:
<223> OTHER INFORMATION: OligoDNA primer

<400> SEQUENCE: 13
ccacaggatg gcgtgggaca tgatg    25

<210> SEQ ID NO 14
<211> LENGTH: 21
<212> TYPE: DNA
<213> ORGANISM: Artificial Sequence
<220> FEATURE:
<223> OTHER INFORMATION: OligoDNA primer

<400> SEQUENCE: 14
cccgcgtcca attgcacgct g                                              21

<210> SEQ ID NO 15
<211> LENGTH: 24
<212> TYPE: DNA
<213> ORGANISM: Artificial Sequence
<220> FEATURE:
<223> OTHER INFORMATION: OligoDNA primer

<400> SEQUENCE: 15
cggggttcac gaagacctgc ggag                                           24

<210> SEQ ID NO 16
<211> LENGTH: 22
<212> TYPE: DNA
<213> ORGANISM: Artificial Sequence
<220> FEATURE:
<223> OTHER INFORMATION: OligoDNA primer

<400> SEQUENCE: 16 cccccccgagg gttgagagga gg                                             22

<210> SEQ ID NO 17
<211> LENGTH: 21
<212> TYPE: DNA
<213> ORGANISM: Artificial Sequence
<220> FEATURE:
<223> OTHER INFORMATION: OligoDNA primer

<400> SEQUENCE: 17
cctcaacgcg gccagccttg c                                              21

<210> SEQ ID NO 18
<211> LENGTH: 22
<212> TYPE: DNA
<213> ORGANISM: Artificial Sequence
<220> FEATURE:
<223> OTHER INFORMATION: OligoDNA primer

<400> SEQUENCE: 18
cccgcgtctc cgagccggga tg                                             22

<210> SEQ ID NO 19
<211> LENGTH: 22
<212> TYPE: DNA
<213> ORGANISM: Artificial Sequence
<220> FEATURE:
<223> OTHER INFORMATION: OligoDNA primer

<400> SEQUENCE: 19
gtcctgctag ggcccgcgga tg                                             22

<210> SEQ ID NO 20
<211> LENGTH: 26
<212> TYPE: DNA
<213> ORGANISM: Artificial Sequence
<220> FEATURE:
<223> OTHER INFORMATION: oligoDNA primer

```
<400> SEQUENCE: 20
cgcccgaggc ctacctcttc tatatc                                          26

<210> SEQ ID NO 21
<211> LENGTH: 3013
<212> TYPE: PRT
<213> ORGANISM: Hepatitis C virus

<400> SEQUENCE: 21

Met Ser Thr Asn Pro Lys Pro Gln Arg Leu Thr Lys Arg Asn Thr Val
1               5                   10                  15

Arg Arg Pro Gln Asn Val Lys Phe Pro Gly Gly Gly Gln Ile Val Gly
            20                  25                  30

Gly Val Tyr Leu Leu Pro Arg Arg Gly Pro Arg Leu Gly Val Arg Gly
        35                  40                  45

Thr Arg Lys Ser Ser Glu Arg Ser Gln Pro Arg Gly Arg Arg Gln Arg
    50                  55                  60

Ile Pro Lys Ala Ala Ser Ser Gln Gly Lys Ala Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Lys Val Ile Asp Thr Met Thr Cys
        115                 120                 125

Gly Phe Ala Asp Leu Met Gly Tyr Ile Pro Val Leu Gly Ala Pro Leu
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Glu Val Arg Asn Ser Ser Gly Val Tyr His Leu Thr Asn Asp Cys Pro
        195                 200                 205

Asn Ala Ser Ile Val Tyr Glu Thr Asp Asn Ala Ile Leu His Glu Pro
    210                 215                 220

Gly Cys Val Pro Cys Val Arg Glu Gly Asn Thr Ser Arg Cys Trp Glu
225                 230                 235                 240

Pro Val Ala Pro Thr Leu Ala Val Arg Tyr Arg Gly Ala Leu Thr Asp
                245                 250                 255

Asp Leu Arg Thr His Ile Asp Leu Val Val Ala Ser Ala Thr Leu Cys
            260                 265                 270

Ser Ala Leu Tyr Val Gly Asp Ile Cys Gly Ala Ile Phe Ile Ala Ser
        275                 280                 285

Gln Ala Val Leu Trp Lys Pro Gly Gly Gly Arg Ile Val Gln Asp Cys
    290                 295                 300

Asn Cys Ser Ile Tyr Pro Gly His Val Thr Gly His Arg Met Ala Trp
305                 310                 315                 320

Asp Met Met Gln Asn Trp Ala Pro Ala Leu Ser Met Val Ala Ala Tyr
                325                 330                 335

Ala Val Arg Val Pro Gly Val Ile Ile Thr Thr Val Ala Gly Gly His
            340                 345                 350

Trp Gly Val Leu Phe Gly Leu Ala Tyr Phe Gly Met Ala Gly Asn Trp
```

```
              355                 360                 365
Ala Lys Val Ile Leu Ile Met Leu Leu Met Ser Gly Val Asp Ala Glu
        370                 375                 380

Thr Met Ala Val Gly Ala Arg Ala Ala His Thr Thr Gly Ala Leu Val
385                 390                 395                 400

Ser Leu Leu Asn Pro Gly Pro Ser Gln Arg Leu Gln Leu Ile Asn Thr
                405                 410                 415

Asn Gly Ser Trp His Ile Asn Arg Thr Ala Leu Asn Cys Asn Asp Ser
                420                 425                 430

Leu Gln Thr Gly Phe Ile Ala Ala Leu Phe Tyr Thr His Arg Phe Asn
            435                 440                 445

Ser Ser Gly Cys Pro Glu Arg Met Ala Ser Cys Lys Pro Leu Ser Asp
        450                 455                 460

Phe Asp Gln Gly Trp Gly Pro Leu Trp Tyr Asn Ser Thr Glu Arg Pro
465                 470                 475                 480

Ser Asp Gln Arg Pro Tyr Cys Trp His Tyr Ala Pro Ser Pro Cys Gly
                485                 490                 495

Ile Val Pro Ala Lys Asp Val Cys Gly Pro Val Tyr Cys Phe Thr Pro
                500                 505                 510

Ser Pro Val Val Gly Thr Thr Asp Arg Arg Gly Val Pro Thr Tyr
            515                 520                 525

Thr Trp Gly Glu Asn Glu Ser Asp Val Phe Leu Leu Asn Ser Thr Arg
            530                 535                 540

Pro Pro Gln Gly Ser Trp Phe Gly Cys Ser Trp Met Asn Thr Thr Gly
545                 550                 555                 560

Phe Thr Lys Thr Cys Gly Gly Pro Pro Cys Lys Ile Arg Pro Gln Gly
                565                 570                 575

Ala Gln Ser Asn Thr Ser Leu Thr Cys Pro Thr Asp Cys Phe Arg Lys
                580                 585                 590

His Pro Arg Ala Thr Tyr Ser Ala Cys Gly Ser Gly Pro Trp Leu Thr
            595                 600                 605

Pro Arg Cys Met Val His Tyr Pro Tyr Arg Leu Trp His Tyr Pro Cys
610                 615                 620

Thr Val Asn Phe Thr Ile His Lys Val Arg Leu Tyr Ile Gly Gly Val
625                 630                 635                 640

Glu His Arg Leu Asp Ala Ala Cys Asn Trp Thr Arg Gly Glu Arg Cys
                645                 650                 655

Asp Leu Glu Asp Arg Asp Arg Val Asp Met Ser Pro Leu Leu His Ser
                660                 665                 670

Thr Thr Glu Leu Ala Ile Leu Pro Cys Ser Phe Val Pro Leu Pro Ala
            675                 680                 685

Leu Ser Thr Gly Leu Ile His Leu His Gln Asn Ile Val Asp Ala Gln
690                 695                 700

Tyr Leu Tyr Gly Leu Ser Pro Ala Ile Ile Ser Trp Ala Ile Arg Trp
705                 710                 715                 720

Glu Trp Val Val Leu Val Phe Leu Leu Leu Ala Asp Ala Arg Ile Cys
                725                 730                 735

Ala Cys Leu Trp Met Met Met Leu Met Ala Gln Ala Glu Ala Ala Leu
            740                 745                 750

Glu Asn Leu Ile His Leu Asn Ala Ala Ser Leu Ala Gly Thr His Gly
            755                 760                 765

Ile Trp Trp Leu Leu Leu Val Phe Cys Ala Ser Trp His Leu Arg Gly
        770                 775                 780
```

-continued

```
Arg Val Val Pro Leu Val Thr Tyr Gly Ile Cys Gly Met Trp Pro Phe
785                 790                 795                 800

Phe Leu Met Leu Leu Ser Leu Pro Pro Arg Ala Tyr Ala Leu Asp Arg
                805                 810                 815

Glu Val Ser Ala Ala Leu Gly Thr Gly Met Leu Ala Ile Ile Leu Leu
            820                 825                 830

Val Thr Leu Gly Pro His Tyr Lys Arg Leu Leu Ala Leu Ile Leu Trp
        835                 840                 845

Trp Val Thr Tyr Phe Leu Thr Arg Cys Glu Ala Ala Leu Gln Thr Trp
850                 855                 860

Val Pro Pro Leu Asn Pro Arg Gly Gly Arg Asp Gly Phe Ile Leu Cys
865                 870                 875                 880

Val Leu Leu Cys Tyr Pro Gly Leu Val Phe Asp Ile Thr Lys Trp Leu
                885                 890                 895

Leu Val Met Met Cys Pro Leu Tyr Leu Gln Leu Cys Leu Val Arg
                900                 905                 910

Thr Pro Tyr Phe Val Arg Ala Gln Ala Leu Ile Arg Val Cys Ser Leu
            915                 920                 925

Phe Lys Thr Leu Ala Gly Gly Arg Tyr Val Gln Ala Ala Leu Leu Thr
        930                 935                 940

Ile Gly Arg Trp Thr Gly Thr Tyr Ile Tyr Asn His Leu Ala Pro Leu
945                 950                 955                 960

Glu Thr Trp Ala Ala Gly Gly Leu Arg Asp Leu Ala Val Ala Val Glu
                965                 970                 975

Pro Val Ile Phe Ser Pro Met Glu Lys Lys Ile Ile Val Trp Gly Ala
            980                 985                 990

Glu Thr Thr Ala Cys Gly Asp Ile Leu Cys Gly Leu Pro Val Ser Ala
        995                 1000                1005

Arg Leu Gly Arg Glu Val Leu Leu Gly Pro Ala Asp Asp Tyr Arg
    1010                1015                1020

Ser Met Gly Trp Gln Leu Leu Ala Pro Ile Ser Ala Tyr Ala Gln
    1025                1030                1035

Gln Thr Arg Gly Leu Ile Ser Thr Leu Val Val Ser Leu Thr Gly
    1040                1045                1050

Arg Asp Lys Asn Glu Thr Ala Gly Glu Val Gln Val Leu Ser Thr
    1055                1060                1065

Ser Thr Gln Thr Phe Leu Gly Thr Asn Val Gly Val Met Trp
    1070                1075                1080

Gly Pro Tyr His Gly Ala Gly Thr Arg Thr Val Ala Gly Arg Gly
    1085                1090                1095

Gly Pro Val Leu Gln Met Tyr Thr Ser Val Ser Asp Asp Leu Val
    1100                1105                1110

Gly Trp Pro Ala Pro Pro Gly Ser Lys Ser Leu Glu Pro Cys Ser
    1115                1120                1125

Cys Gly Ser Ala Asp Leu Tyr Leu Val Thr Arg Asn Ala Asp Val
    1130                1135                1140

Leu Pro Leu Arg Arg Lys Gly Asp Gly Thr Ala Ser Leu Leu Ser
    1145                1150                1155

Pro Arg Pro Val Ser Ser Leu Lys Gly Ser Ser Gly Gly Pro Val
    1160                1165                1170

Leu Cys Pro Gln Ser His Cys Val Gly Ile Phe Arg Ala Ala Val
    1175                1180                1185

Cys Thr Arg Gly Val Ala Lys Ala Val Gln Phe Val Pro Ile Glu
    1190                1195                1200
```

```
Lys Met Gln Val Ala Gln Arg Ser Pro Ser Phe Ser Asp Asn Ser
    1205            1210                1215
Thr Pro Pro Ala Val Pro Ser Thr Tyr Gln Val Gly Tyr Leu His
    1220            1225                1230
Ala Pro Thr Gly Ser Gly Lys Ser Thr Lys Val Pro Ala Ala Tyr
    1235            1240                1245
Ala Ser Gln Gly Tyr Lys Val Leu Val Leu Asn Pro Ser Val Ala
    1250            1255                1260
Ala Thr Leu Gly Phe Gly Ala Tyr Met Ser Lys Ala Tyr Gly Ile
    1265            1270                1275
Asp Pro Ser Val Arg Thr Gly Ala Arg Thr Val Thr Thr Gly Ala
    1280            1285                1290
Pro Ile Thr Tyr Ser Thr Tyr Gly Lys Phe Leu Ala Asp Gly Gly
    1295            1300                1305
Cys Ser Gly Gly Ala Tyr Asp Ile Ile Ile Cys Asp Glu Cys His
    1310            1315                1320
Ala Ile Asp Ala Thr Thr Val Val Gly Ile Gly Thr Val Leu Asp
    1325            1330                1335
Gln Ala Glu Thr Ser Gly Val Arg Leu Val Val Leu Ala Thr Ala
    1340            1345                1350
Thr Pro Pro Gly Ser Val Thr Val Pro His Pro Asn Ile Glu Glu
    1355            1360                1365
Val Ala Leu Gly Asn Asp Gly Glu Ile Pro Phe Tyr Gly Lys Ala
    1370            1375                1380
Ile Pro Leu Gln His Ile Lys Gly Gly Arg His Leu Ile Phe Cys
    1385            1390                1395
His Ser Lys Lys Lys Cys Asp Glu Leu Ala Gly Lys Leu Thr Ser
    1400            1405                1410
Leu Gly Leu Thr Ala Val Ala Tyr Tyr Arg Gly Leu Asp Val Ser
    1415            1420                1425
Val Ile Pro Thr Ser Gly Asp Val Val Val Val Ala Thr Asp Ala
    1430            1435                1440
Leu Met Thr Gly Phe Thr Gly Asp Phe Asp Ser Val Ile Asp Cys
    1445            1450                1455
Asn Val Ala Val Thr Gln Thr Val Asp Phe Ser Leu Asp Pro Thr
    1460            1465                1470
Phe Thr Ile Glu Thr Thr Thr Val Pro Gln Asp Ser Val Ser Arg
    1475            1480                1485
Ser Gln Arg Arg Gly Arg Thr Gly Arg Gly Arg Leu Gly Ile Tyr
    1490            1495                1500
Arg Tyr Val Ser Ser Gly Glu Arg Pro Ser Gly Met Phe Asp Thr
    1505            1510                1515
Ser Val Leu Cys Glu Cys Tyr Asp Leu Gly Cys Ser Trp Tyr Glu
    1520            1525                1530
Leu Thr Pro Ser Glu Thr Thr Thr Arg Leu Arg Ala Tyr Leu Asn
    1535            1540                1545
Cys Pro Gly Leu Pro Val Cys Gln Asp His Leu Glu Phe Trp Glu
    1550            1555                1560
Gly Val Phe Thr Gly Leu Thr His Ile Asp Ala His Phe Leu Ser
    1565            1570                1575
Gln Thr Lys Gln Glu Gly Gln Asn Tyr Ala Tyr Leu Thr Ala Tyr
    1580            1585                1590
Gln Ala Thr Val Cys Ala Arg Ala Lys Ala Pro Pro Pro Ser Trp
```

-continued

```
                1595                1600                1605

Asp Val Gln Trp Lys Cys Leu Gln Arg Leu Lys Pro Leu Leu Val
1610                1615                1620

Gly Pro Thr Pro Leu Leu Tyr Arg Leu Gly Ser Val Thr Asn Glu
1625                1630                1635

Val Thr Phe Thr His Pro Ile Thr Lys Tyr Ile Ala Thr Cys Met
1640                1645                1650

Ala Ala Asp Leu Glu Val Thr Thr Ser Thr Trp Val Ile Val Gly
1655                1660                1665

Gly Val Leu Ala Ala Val Ala Ala Tyr Cys Met Ser Thr Gly Ser
1670                1675                1680

Val Val Val Val Gly Arg Val Val Leu Gly Ser Asn Val Val Thr
1685                1690                1695

Ala Pro Asp Arg Glu Val Leu Tyr Gln His Phe Asp Glu Met Glu
1700                1705                1710

Glu Cys Ser Lys Ala Pro Glu Leu Leu Lys His Ala Gln Thr Ile
1715                1720                1725

Gly Gly Met Phe Lys Asp Lys Ala Leu Ala Val Leu Asp Thr Leu
1730                1735                1740

Lys Pro Ala Ala Gln Ala Ala Val Pro Ile Val Glu Thr Asn Phe
1745                1750                1755

Gln Lys Val Glu Lys Leu Trp Asn Gln His Met Trp Asn Phe Ile
1760                1765                1770

Ser Gly Ile Gln Tyr Leu Ala Gly Leu Ser Thr Leu Pro Gly Asn
1775                1780                1785

Pro Thr Val Ala Ser Leu Met Ala Phe Thr Ala Ser Val Thr Ser
1790                1795                1800

Pro Leu Ala Thr Ser Thr Thr Leu Leu Val Asn Ile Leu Gly Gly
1805                1810                1815

Trp Phe Ala Ser Gln Leu Ala Pro Pro Ser Ala Ala Thr Thr Phe
1820                1825                1830

Val Val Ser Gly Leu Ala Gly Ala Ala Val Gly Ser Val Gly Leu
1835                1840                1845

Gly Lys Val Leu Val Asp Val Leu Ala Gly Tyr Gly Ala Gly Ile
1850                1855                1860

Ala Gly Ala Leu Val Ala Phe Lys Ile Met Ser Gly Glu Val Pro
1865                1870                1875

Ser Thr Glu Asp Leu Ala Asn Leu Leu Pro Ala Ile Leu Ser Pro
1880                1885                1890

Gly Ala Leu Val Val Gly Val Val Cys Ala Ala Ile Ile Lys Arg
1895                1900                1905

His Thr Gly Thr Ser Glu Gly Val Thr Gln Trp Met Asn Arg Leu
1910                1915                1920

Ile Ala Phe Ala Ser Arg Gly Asn His Val Ser Pro Thr His Tyr
1925                1930                1935

Ile Gln Asp Asp Asp Ala Ser Lys Arg Val Met Gly Ile Leu Ser
1940                1945                1950

Ser Leu Thr Ile Thr Ser Leu Ile Lys Arg Val Leu Ala Trp Ala
1955                1960                1965

Gln Thr Asp Tyr Ser Ala Pro Cys Ala Gly Ser Trp Leu Arg Glu
1970                1975                1980

Val Trp Asp Trp Val Cys Met Val Leu Ser Asp Phe Ala Ser Trp
1985                1990                1995
```

-continued

```
Leu Lys Ala Lys Val Leu Pro Ser Leu Pro Gly Ile Pro Phe Leu
2000             2005             2010

Ser Cys Gln Lys Gly Tyr Lys Gly Glu Trp Arg Asn Asp Gly Ile
2015             2020             2025

Met Asn Thr Lys Cys Pro Cys Gly Ala Leu Ile Ala Gly His Val
2030             2035             2040

Lys Asn Gly Ser Met Arg Ile Val Gly Pro Lys Thr Cys Arg Asn
2045             2050             2055

Thr Trp Trp Gly Thr Phe Pro Ile Asn Ser His Thr Thr Gly Pro
2060             2065             2070

Ser Ser Pro Val Pro Ser His Cys Tyr Gln Arg Ala Leu Trp Arg
2075             2080             2085

Val Ser Ala Thr Glu Tyr Val Glu Ile Leu Arg His Asn Asp Gln
2090             2095             2100

His Tyr Val Val Gly Val Thr Ala Glu Asp Leu Lys Cys Pro Cys
2105             2110             2115

Gln Val Pro Ser Pro Glu Phe Phe Ser Phe Val Asp Gly Val Arg
2120             2125             2130

Ile His Arg Phe Ala Pro Glu Pro Lys Pro Met Ile Arg Glu Glu
2135             2140             2145

Ala Ala Phe Val Val Gly Leu His Ser Tyr Val Val Gly Ser Gln
2150             2155             2160

Leu Pro Cys Glu Pro Glu Pro Asp Val Gln Thr Val Ser Gln Leu
2165             2170             2175

Leu Thr Asp Pro Ser His Ile Thr Ala Glu Thr Ala Ala Arg Arg
2180             2185             2190

Leu Arg Arg Gly Ser Pro Pro Ser Asn Ala Ser Ser Ser Ala Ser
2195             2200             2205

Gln Leu Ser Ala Pro Ser Leu Lys Ala Thr His Thr Thr Leu Pro
2210             2215             2220

Gln His Pro Asp Ala Glu Leu Ile Glu Ala Asn Leu Met Trp Glu
2225             2230             2235

His Lys Val Gly Ala Ile Arg Arg Met Glu Thr Asp Thr Lys Val
2240             2245             2250

Ile Ile Leu Asp Ser Phe Asp Ser Ala Ser Ser Val Glu Asp Asp
2255             2260             2265

Met Glu Pro Ser Thr Ala Ala Glu Cys Leu Arg Thr Arg Lys Val
2270             2275             2280

Phe Pro Pro Ala Met Pro Ile Trp Ala Arg Pro Asp Tyr Asn Pro
2285             2290             2295

Pro Val Val Glu Asn Trp Lys Asp Pro Glu Tyr Ala Pro Pro Gln
2300             2305             2310

Val Ser Gly Cys Ala Leu Pro Pro Ala Gln Thr Pro Pro Val Pro
2315             2320             2325

Pro Pro Arg Arg Lys Arg Ala Val Ile Gln Leu Thr Glu Ser Ala
2330             2335             2340

Val Ser Thr Ala Leu Ala Glu Leu Ala Glu Arg Ser Phe Pro Lys
2345             2350             2355

Glu Glu Ala Pro Pro Ser Asp Ser Ala Ile Ser Leu Asp Ser Pro
2360             2365             2370

Ala Ala Asn Asp Pro Pro Ser Asp Cys Asp Gln Gly Ser Glu Ile
2375             2380             2385

Ser Phe Ser Ser Met Pro Pro Leu Glu Gly Glu Pro Gly Asp Pro
2390             2395             2400
```

```
Asp Leu Ser Asp Gly Ser Trp Ser Thr Val Ser Thr Arg Ser Asp
    2405                2410                2415

Val Ile Cys Cys Ser Met Ser Tyr Ser Trp Thr Gly Ala Leu Val
    2420                2425                2430

Thr Pro Ser Gly Pro Glu Glu Arg Leu Pro Ile Asn Ala Leu
    2435                2440                2445

Ser Asn Thr Met Leu Arg His Tyr Asn Met Val Tyr Ser Thr Thr
    2450                2455                2460

Ser Arg Ser Ala Ser Gln Arg Ala Lys Lys Val Thr Phe Asp Arg
    2465                2470                2475

Leu Gln Val Leu Asp Asp His Tyr Lys Arg Ala Leu Ala Asp Val
    2480                2485                2490

Lys Ala Asp Ala Ser Thr Val Lys Ala Gln Leu Leu Ser Val Glu
    2495                2500                2505

Glu Ala Ala Ala Leu Thr Pro Ala His Ser Ala Arg Ser Lys Phe
    2510                2515                2520

Gly Tyr Gly Ala Lys Glu Val Arg Ser Leu Ala Pro Lys Ala Met
    2525                2530                2535

Ser His Ile Lys Glu Val Trp Lys Asp Leu Leu Gln Asp Met Thr
    2540                2545                2550

Thr Pro Ile Pro Thr Thr Ile Met Ala Lys Asn Glu Val Phe Cys
    2555                2560                2565

Val Asn Pro Ala Lys Gly Gly Lys Lys Pro Ala Arg Leu Ile Val
    2570                2575                2580

Tyr Pro Asp Leu Gly Val Arg Val Cys Glu Lys Arg Ala Leu Tyr
    2585                2590                2595

Asp Ile Ala Gln Lys Leu Pro Lys Ala Ile Met Gly Gln Ala Tyr
    2600                2605                2610

Gly Phe Gln Tyr Ser Pro Ser Gln Arg Val Glu Tyr Leu Val Lys
    2615                2620                2625

Thr Trp Lys Ser Lys Arg Thr Pro Met Gly Phe Ser Tyr Asp Thr
    2630                2635                2640

Arg Cys Phe Asp Ser Thr Val Thr Glu Gln Asp Ile Arg Thr Glu
    2645                2650                2655

Ser Glu Ile Tyr Gln Cys Cys Asn Leu Asp Pro Glu Ala Arg Thr
    2660                2665                2670

Ile Ile Asn Ala Leu Thr Glu Arg Leu Tyr Val Gly Gly Pro Met
    2675                2680                2685

Phe Asn Ser Lys Gly Gln Arg Val Gly Tyr Arg Arg Cys Arg Ala
    2690                2695                2700

Ser Gly Val Phe Pro Thr Ser Met Gly Asn Thr Met Thr Cys Tyr
    2705                2710                2715

Ile Lys Ala Lys Ala Ala Ala Ala Ala Gly Leu Glu Ser Thr
    2720                2725                2730

Asp Phe Leu Val Cys Gly Asp Asp Leu Val Val Ile Cys Glu Ser
    2735                2740                2745

Lys Gly Val Glu Arg Asp Arg Ala Asp Leu Gln Ala Phe Ala Ala
    2750                2755                2760

Ala Met Thr Arg Tyr Ser Ala Pro Pro Gly Asp Met Pro Gln Pro
    2765                2770                2775

Ala Tyr Asp Leu Glu His Ile Asp Ser Cys Ser Ser Asn Val Ser
    2780                2785                2790

Val Ala Arg Asp Asn Ser Gly Lys Arg Val Tyr Tyr Leu Thr Arg
```

```
                              2795                2800                2805

Asp Pro Thr Asn Pro Leu Ser Arg Ala Ala Trp Glu Thr Ala Arg
    2810                2815                2820

His Ser Pro Val Asn Ser Trp Val Gly Asn Ile Ile Met Phe Ala
    2825                2830                2835

Pro Thr Ile Trp Val Arg Met Val Leu Met Thr His Phe Phe Ala
    2840                2845                2850

Leu Leu Leu Asn Glu Glu Arg Leu Asn Asp Pro Val Ser Phe Glu
    2855                2860                2865

Met Tyr Gly Ala Thr Tyr Val Cys Pro Thr Asp Leu Pro Asp
    2870                2875                2880

Ile Ile Gln Arg Leu His Gly Leu Arg Ala Phe Glu Leu His Thr
    2885                2890                2895

Tyr Ser Pro Ala Glu Leu Thr Arg Val Ala Ala Thr Leu Arg Lys
    2900                2905                2910

Leu Gly Val Pro Pro Leu Arg Thr Trp Arg Gln Arg Ala Arg Lys
    2915                2920                2925

Val Arg Ala Gly Leu Ile Gly Gln Gly Gly Arg Ala Arg Ile Cys
    2930                2935                2940

Gly Leu Tyr Leu Phe Asn Trp Ala Val Arg Thr Lys Ile Lys Leu
    2945                2950                2955

Thr Pro Leu Ala Gly Ala Gly Arg Leu Asp Leu Ser Ser Trp Phe
    2960                2965                2970

Ser Val Cys Ala Gly Glu Ala Asp Val Asp His Ser Thr Pro Arg
    2975                2980                2985

Ala His Pro Arg Pro Leu Leu Leu Cys Leu Leu Leu Ala Val
    2990                2995                3000

Gly Val Gly Ile Phe Leu Leu Pro Ala Arg
    3005                3010

<210> SEQ ID NO 22
<211> LENGTH: 3033
<212> TYPE: PRT
<213> ORGANISM: Hepatitis C virus

<400> SEQUENCE: 22

Met Ser Thr Asn Pro Lys Pro Gln Arg Lys Thr Lys Arg Asn Thr Asn
1               5                   10                  15

Arg Arg Pro Glu Asp Val Lys Phe Pro Gly Gly Gly Gln Ile Val Gly
                20                  25                  30

Gly Val Tyr Leu Leu Pro Arg Arg Gly Pro Arg Leu Gly Val Arg Thr
            35                  40                  45

Thr Arg Lys Thr Ser Glu Arg Ser Gln Pro Arg Gly Arg Arg Gln Pro
        50                  55                  60

Ile Pro Lys Asp Arg Arg Ser Thr Gly Lys Ala Trp Gly Lys Pro Gly
65                  70                  75                  80

Arg Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
                100                 105                 110

Arg His Arg Ser Arg Asn Val Gly Lys Val Ile Asp Thr Leu Thr Cys
            115                 120                 125

Gly Phe Ala Asp Leu Met Gly Tyr Ile Pro Val Val Gly Ala Pro Leu
        130                 135                 140

Ser Gly Ala Ala Arg Ala Val Ala His Gly Val Arg Val Leu Glu Asp
```

-continued

```
            145                 150                 155                 160
        Gly Val Asn Tyr Ala Thr Gly Asn Leu Pro Gly Phe Pro Phe Ser Ile
                        165                 170                 175

Phe Leu Leu Ala Leu Leu Ser Cys Ile Thr Val Pro Val Ser Ala Ala
                        180                 185                 190

Gln Val Lys Asn Thr Ser Ser Tyr Met Val Thr Asn Asp Cys Ser
                        195                 200                 205

Asn Asp Ser Ile Thr Trp Gln Leu Glu Ala Ala Val Leu His Val Pro
                        210                 215                 220

Gly Cys Val Pro Cys Glu Arg Val Gly Asn Thr Ser Arg Cys Trp Val
        225                 230                 235                 240

Pro Val Ser Pro Asn Met Ala Val Arg Gln Pro Gly Ala Leu Thr Gln
                        245                 250                 255

Gly Leu Arg Thr His Ile Asp Met Val Val Met Ser Ala Thr Phe Cys
                        260                 265                 270

Ser Ala Leu Tyr Val Gly Asp Leu Cys Gly Val Met Leu Ala Ala
                        275                 280                 285

Gln Val Phe Ile Val Ser Pro Gln Tyr His Trp Phe Val Gln Glu Cys
                        290                 295                 300

Asn Cys Ser Ile Tyr Pro Gly Thr Ile Thr Gly His Arg Met Ala Trp
        305                 310                 315                 320

Asp Met Met Met Asn Trp Ser Pro Thr Ala Thr Met Ile Leu Ala Tyr
                        325                 330                 335

Val Met Arg Val Pro Glu Val Ile Ile Asp Ile Val Ser Gly Ala His
                        340                 345                 350

Trp Gly Val Met Phe Gly Leu Ala Tyr Phe Ser Met Gln Gly Ala Trp
                        355                 360                 365

Ala Lys Val Ile Val Ile Leu Leu Leu Ala Ala Gly Val Asp Ala Gly
                        370                 375                 380

Thr Thr Thr Val Gly Gly Ala Val Ala Arg Ser Thr Asn Val Ile Ala
        385                 390                 395                 400

Gly Val Phe Ser His Gly Pro Gln Gln Asn Ile Gln Leu Ile Asn Thr
                        405                 410                 415

Asn Gly Ser Trp His Ile Asn Arg Thr Ala Leu Asn Cys Asn Asp Ser
                        420                 425                 430

Leu Asn Thr Gly Phe Leu Ala Ala Leu Phe Tyr Thr Asn Arg Phe Asn
                        435                 440                 445

Ser Ser Gly Cys Pro Gly Arg Leu Ser Ala Cys Arg Asn Ile Glu Ala
        450                 455                 460

Phe Arg Ile Gly Trp Gly Thr Leu Gln Tyr Glu Asp Asn Val Thr Asn
        465                 470                 475                 480

Pro Glu Asp Met Arg Pro Tyr Cys Trp His Tyr Pro Pro Lys Pro Cys
                        485                 490                 495

Gly Val Val Pro Ala Arg Ser Val Cys Gly Pro Val Tyr Cys Phe Thr
                        500                 505                 510

Pro Ser Pro Val Val Val Gly Thr Thr Asp Arg Arg Gly Val Pro Thr
                        515                 520                 525

Tyr Thr Trp Gly Glu Asn Glu Thr Asp Val Phe Leu Leu Asn Ser Thr
                        530                 535                 540

Arg Pro Pro Gln Gly Ser Trp Phe Gly Cys Thr Trp Met Asn Ser Thr
        545                 550                 555                 560

Gly Phe Thr Lys Thr Cys Gly Ala Pro Pro Cys Arg Thr Arg Ala Asp
                        565                 570                 575
```

-continued

```
Phe Asn Ala Ser Thr Asp Leu Leu Cys Pro Thr Asp Cys Phe Arg Lys
            580                 585                 590

His Pro Asp Ala Thr Tyr Ile Lys Cys Gly Ser Gly Pro Trp Leu Thr
            595                 600                 605

Pro Lys Cys Leu Val His Tyr Pro Tyr Arg Leu Trp His Tyr Pro Cys
610                 615                 620

Thr Val Asn Phe Thr Ile Phe Lys Ile Arg Met Tyr Val Gly Gly Val
625                 630                 635                 640

Glu His Arg Leu Thr Ala Ala Cys Asn Phe Thr Arg Gly Asp Arg Cys
                645                 650                 655

Asp Leu Glu Asp Arg Asp Arg Ser Gln Leu Ser Pro Leu Leu His Ser
            660                 665                 670

Thr Thr Glu Trp Ala Ile Leu Pro Cys Thr Tyr Ser Asp Leu Pro Ala
            675                 680                 685

Leu Ser Thr Gly Leu Leu His Leu His Gln Asn Ile Val Asp Val Gln
            690                 695                 700

Tyr Met Tyr Gly Leu Ser Pro Ala Ile Thr Lys Tyr Val Val Arg Trp
705                 710                 715                 720

Glu Trp Val Val Leu Leu Phe Leu Leu Ala Asp Ala Arg Val Cys
                725                 730                 735

Ala Cys Leu Trp Met Leu Ile Leu Leu Gly Gln Ala Glu Ala Ala Leu
            740                 745                 750

Glu Lys Leu Val Val Leu His Ala Ala Ser Ala Ala Asn Cys His Gly
            755                 760                 765

Leu Leu Tyr Phe Ala Ile Phe Phe Val Ala Ala Trp His Ile Arg Gly
            770                 775                 780

Arg Val Val Pro Leu Thr Thr Tyr Cys Leu Thr Gly Leu Trp Pro Phe
785                 790                 795                 800

Cys Leu Leu Leu Met Ala Leu Pro Arg Gln Ala Tyr Ala Tyr Asp Ala
                805                 810                 815

Pro Val His Gly Gln Ile Gly Val Gly Leu Leu Ile Leu Ile Thr Leu
            820                 825                 830

Phe Thr Leu Thr Pro Gly Tyr Lys Thr Leu Leu Gly Gln Cys Leu Trp
            835                 840                 845

Trp Leu Cys Tyr Leu Leu Thr Leu Gly Glu Ala Met Ile Gln Glu Trp
850                 855                 860

Val Pro Pro Met Gln Val Arg Gly Gly Arg Asp Gly Ile Ala Trp Ala
865                 870                 875                 880

Val Thr Ile Phe Cys Pro Gly Val Val Phe Asp Ile Thr Lys Trp Leu
                885                 890                 895

Leu Ala Leu Leu Gly Pro Ala Tyr Leu Leu Arg Ala Ala Leu Thr His
            900                 905                 910

Val Pro Tyr Phe Val Arg Ala His Ala Leu Ile Arg Val Cys Ala Leu
            915                 920                 925

Val Lys Gln Leu Ala Gly Gly Arg Tyr Val Gln Val Ala Leu Leu Ala
            930                 935                 940

Leu Gly Arg Trp Thr Gly Thr Tyr Ile Tyr Asp His Leu Thr Pro Met
945                 950                 955                 960

Ser Asp Trp Ala Ala Ser Gly Leu Arg Asp Leu Ala Val Ala Val Glu
                965                 970                 975

Pro Ile Ile Phe Ser Pro Met Glu Lys Lys Val Ile Val Trp Gly Ala
            980                 985                 990

Glu Thr Ala Ala Cys Gly Asp Ile  Leu His Gly Leu Pro  Val Ser Ala
            995                 1000                1005
```

-continued

Arg Leu Gly Gln Glu Ile Leu Leu Gly Pro Ala Asp Gly Tyr Thr
    1010            1015                1020

Ser Lys Gly Trp Lys Leu Leu Ala Pro Ile Thr Ala Tyr Ala Gln
    1025            1030                1035

Gln Thr Arg Gly Leu Leu Gly Ala Ile Val Val Ser Met Thr Gly
    1040            1045                1050

Arg Asp Arg Thr Glu Gln Ala Gly Glu Val Gln Ile Leu Ser Thr
    1055            1060                1065

Val Ser Gln Ser Phe Leu Gly Thr Thr Ile Ser Gly Val Leu Trp
    1070            1075                1080

Thr Val Tyr His Gly Ala Gly Asn Lys Thr Leu Ala Gly Leu Arg
    1085            1090                1095

Gly Pro Val Thr Gln Met Tyr Ser Ser Ala Glu Gly Asp Leu Val
    1100            1105                1110

Gly Trp Pro Ser Pro Pro Gly Thr Lys Ser Leu Glu Pro Cys Lys
    1115            1120                1125

Cys Gly Ala Val Asp Leu Tyr Leu Val Thr Arg Asn Ala Asp Val
    1130            1135                1140

Ile Pro Ala Arg Arg Gly Asp Lys Arg Gly Ala Leu Leu Ser
    1145            1150                1155

Pro Arg Pro Ile Ser Thr Leu Lys Gly Ser Ser Gly Gly Pro Val
    1160            1165                1170

Leu Cys Pro Arg Gly His Val Val Gly Leu Phe Arg Ala Ala Val
    1175            1180                1185

Cys Ser Arg Gly Val Ala Lys Ser Ile Asp Phe Ile Pro Val Glu
    1190            1195                1200

Thr Leu Asp Val Val Thr Arg Ser Pro Thr Phe Ser Asp Asn Ser
    1205            1210                1215

Thr Pro Pro Ala Val Pro Gln Thr Tyr Gln Val Gly Tyr Leu His
    1220            1225                1230

Ala Pro Thr Gly Ser Gly Lys Ser Thr Lys Val Pro Val Ala Tyr
    1235            1240                1245

Ala Ala Gln Gly Tyr Lys Val Leu Val Leu Asn Pro Ser Val Ala
    1250            1255                1260

Ala Thr Leu Gly Phe Gly Ala Tyr Leu Ser Lys Ala His Gly Ile
    1265            1270                1275

Asn Pro Asn Ile Arg Thr Gly Val Arg Thr Val Met Thr Gly Glu
    1280            1285                1290

Ala Ile Thr Tyr Ser Thr Tyr Gly Lys Phe Leu Ala Asp Gly Gly
    1295            1300                1305

Cys Ala Ser Gly Ala Tyr Asp Ile Ile Ile Cys Asp Glu Cys His
    1310            1315                1320

Ala Val Asp Ala Thr Ser Ile Leu Gly Ile Gly Thr Val Leu Asp
    1325            1330                1335

Gln Ala Glu Thr Ala Gly Val Arg Leu Thr Val Leu Ala Thr Ala
    1340            1345                1350

Thr Pro Pro Gly Ser Val Thr Thr Pro His Pro Asp Ile Glu Glu
    1355            1360                1365

Val Gly Leu Gly Arg Glu Gly Glu Ile Pro Phe Tyr Gly Arg Ala
    1370            1375                1380

Ile Pro Leu Ser Cys Ile Lys Gly Gly Arg His Leu Ile Phe Cys
    1385            1390                1395

His Ser Lys Lys Lys Cys Asp Glu Leu Ala Ala Ala Leu Arg Gly

-continued

```
                  1400                    1405                    1410
Met Gly Leu Asn Ala Val Ala Tyr Tyr Arg Gly Leu Asp Val Ser
    1415                    1420                    1425

Ile Ile Pro Ala Gln Gly Asp Val Val Val Ala Thr Asp Ala
    1430                    1435                    1440

Leu Met Thr Gly Tyr Thr Gly Asp Phe Asp Ser Val Ile Asp Cys
    1445                    1450                    1455

Asn Val Ala Val Thr Gln Ala Val Asp Phe Ser Leu Asp Pro Thr
    1460                    1465                    1470

Phe Thr Ile Thr Thr Gln Thr Val Pro Gln Asp Ala Val Ser Arg
    1475                    1480                    1485

Ser Gln Arg Arg Gly Arg Thr Gly Arg Gly Arg Gln Gly Thr Tyr
    1490                    1495                    1500

Arg Tyr Val Ser Thr Gly Glu Arg Ala Ser Gly Met Phe Asp Ser
    1505                    1510                    1515

Val Val Leu Cys Glu Cys Tyr Asp Ala Gly Ala Ala Trp Tyr Asp
    1520                    1525                    1530

Leu Thr Pro Ala Glu Thr Thr Val Arg Leu Arg Ala Tyr Phe Asn
    1535                    1540                    1545

Thr Pro Gly Leu Pro Val Cys Gln Asp His Leu Glu Phe Trp Glu
    1550                    1555                    1560

Ala Val Phe Thr Gly Leu Thr His Ile Asp Ala His Phe Leu Ser
    1565                    1570                    1575

Gln Thr Lys Gln Ala Gly Glu Asn Phe Ala Tyr Leu Val Ala Tyr
    1580                    1585                    1590

Gln Ala Thr Val Cys Ala Arg Ala Lys Ala Pro Pro Pro Ser Trp
    1595                    1600                    1605

Asp Ala Met Trp Lys Cys Leu Ala Arg Leu Lys Pro Thr Leu Ala
    1610                    1615                    1620

Gly Pro Thr Pro Leu Leu Tyr Arg Leu Gly Pro Ile Thr Asn Glu
    1625                    1630                    1635

Val Thr Leu Thr His Pro Gly Thr Lys Tyr Ile Ala Thr Cys Met
    1640                    1645                    1650

Gln Ala Asp Leu Glu Val Met Thr Ser Thr Trp Val Leu Ala Gly
    1655                    1660                    1665

Gly Val Leu Ala Ala Val Ala Ala Tyr Cys Leu Ala Thr Gly Cys
    1670                    1675                    1680

Val Ser Ile Ile Gly Arg Leu His Val Asn Gln Arg Val Val Val
    1685                    1690                    1695

Ala Pro Asp Lys Glu Val Leu Tyr Glu Ala Phe Asp Glu Met Glu
    1700                    1705                    1710

Glu Cys Ala Ser Arg Ala Ala Leu Ile Glu Glu Gly Gln Arg Ile
    1715                    1720                    1725

Ala Glu Met Leu Lys Ser Lys Ile Gln Gly Leu Leu Gln Gln Ala
    1730                    1735                    1740

Ser Lys Gln Ala Gln Asp Ile Gln Pro Ala Met Gln Ala Ser Trp
    1745                    1750                    1755

Pro Lys Val Glu Gln Phe Trp Ala Arg His Met Trp Asn Phe Ile
    1760                    1765                    1770

Ser Gly Ile Gln Tyr Leu Ala Gly Leu Ser Thr Leu Pro Gly Asn
    1775                    1780                    1785

Pro Ala Val Ala Ser Met Met Ala Phe Ser Ala Ala Leu Thr Ser
    1790                    1795                    1800
```

-continued

Pro Leu Ser Thr Ser Thr Thr Ile Leu Leu Asn Ile Met Gly Gly
1805                1810               1815

Trp Leu Ala Ser Gln Ile Ala Pro Pro Ala Gly Ala Thr Gly Phe
1820                1825               1830

Val Val Ser Gly Leu Val Gly Ala Ala Val Gly Ser Ile Gly Leu
1835                1840               1845

Gly Lys Val Leu Val Asp Ile Leu Ala Gly Tyr Gly Ala Gly Ile
1850                1855               1860

Ser Gly Ala Leu Val Ala Phe Lys Ile Met Ser Gly Glu Lys Pro
1865                1870               1875

Ser Met Glu Asp Val Ile Asn Leu Leu Pro Gly Ile Leu Ser Pro
1880                1885               1890

Gly Ala Leu Val Val Gly Val Ile Cys Ala Ala Ile Leu Arg Arg
1895                1900               1905

His Val Gly Pro Gly Glu Gly Ala Val Gln Trp Met Asn Arg Leu
1910                1915               1920

Ile Ala Phe Ala Ser Arg Gly Asn His Val Ala Pro Thr His Tyr
1925                1930               1935

Val Thr Glu Ser Asp Ala Ser Gln Arg Val Thr Gln Leu Leu Gly
1940                1945               1950

Ser Leu Thr Ile Thr Ser Leu Leu Arg Arg Leu His Asn Trp Ile
1955                1960               1965

Thr Glu Asp Cys Pro Ile Pro Cys Ser Gly Ser Trp Leu Arg Asp
1970                1975               1980

Val Trp Asp Trp Val Cys Thr Ile Leu Thr Asp Phe Lys Asn Trp
1985                1990               1995

Leu Thr Ser Lys Leu Phe Pro Lys Leu Pro Gly Leu Pro Phe Ile
2000                2005               2010

Ser Cys Gln Lys Gly Tyr Lys Gly Val Trp Ala Gly Thr Gly Ile
2015                2020               2025

Met Thr Thr Arg Cys Pro Cys Gly Ala Asn Ile Ser Gly Asn Val
2030                2035               2040

Arg Leu Gly Ser Met Arg Ile Thr Gly Pro Lys Thr Cys Met Asn
2045                2050               2055

Thr Trp Gln Gly Thr Phe Pro Ile Asn Cys Tyr Thr Glu Gly Gln
2060                2065               2070

Cys Ala Pro Lys Pro Pro Thr Asn Tyr Lys Thr Ala Ile Trp Arg
2075                2080               2085

Val Ala Ala Ser Glu Tyr Ala Glu Val Thr Gln His Gly Ser Tyr
2090                2095               2100

Ser Tyr Val Thr Gly Leu Thr Thr Asp Asn Leu Lys Ile Pro Cys
2105                2110               2115

Gln Leu Pro Ser Pro Glu Phe Phe Ser Trp Val Asp Gly Val Gln
2120                2125               2130

Ile His Arg Phe Ala Pro Thr Pro Lys Pro Phe Phe Arg Asp Glu
2135                2140               2145

Val Ser Phe Cys Val Gly Leu Asn Ser Tyr Ala Val Gly Ser Gln
2150                2155               2160

Leu Pro Cys Glu Pro Glu Pro Asp Ala Asp Val Leu Arg Ser Met
2165                2170               2175

Leu Thr Asp Pro Pro His Ile Thr Ala Glu Thr Ala Ala Arg Arg
2180                2185               2190

Leu Ala Arg Gly Ser Pro Pro Ser Glu Ala Ser Ser Ser Val Ser
2195                2200               2205

```
Gln Leu Ser Ala Pro Ser Leu Arg Ala Thr Cys Thr Thr His Ser
    2210                2215                2220

Asn Thr Tyr Asp Val Asp Met Val Asp Ala Asn Leu Leu Met Glu
    2225                2230                2235

Gly Gly Val Ala Gln Thr Glu Pro Glu Ser Arg Val Pro Val Leu
    2240                2245                2250

Asp Phe Leu Glu Pro Met Ala Glu Glu Ser Asp Leu Glu Pro
    2255                2260                2265

Ser Ile Pro Ser Glu Cys Met Leu Pro Arg Ser Gly Phe Pro Arg
    2270                2275                2280

Ala Leu Pro Ala Trp Ala Arg Pro Asp Tyr Asn Pro Pro Leu Val
    2285                2290                2295

Glu Ser Trp Arg Arg Pro Asp Tyr Gln Pro Pro Thr Val Ala Gly
    2300                2305                2310

Cys Ala Leu Pro Pro Lys Lys Ala Pro Thr Pro Pro Pro Arg
    2315                2320                2325

Arg Arg Arg Thr Val Gly Leu Ser Glu Ser Thr Ile Ser Glu Ala
    2330                2335                2340

Leu Gln Gln Leu Ala Ile Lys Thr Phe Gly Gln Pro Pro Ser Ser
    2345                2350                2355

Gly Asp Ala Gly Ser Ser Thr Gly Ala Gly Ala Ala Glu Ser Gly
    2360                2365                2370

Gly Pro Thr Ser Pro Gly Glu Pro Ala Pro Ser Glu Thr Gly Ser
    2375                2380                2385

Ala Ser Ser Met Pro Pro Leu Glu Gly Glu Pro Gly Asp Pro Asp
    2390                2395                2400

Leu Glu Ser Asp Gln Val Glu Leu Gln Pro Pro Gln Gly Gly
    2405                2410                2415

Gly Val Ala Pro Gly Ser Gly Ser Gly Ser Trp Ser Thr Cys Ser
    2420                2425                2430

Glu Glu Asp Asp Thr Thr Val Cys Cys Ser Met Ser Tyr Ser Trp
    2435                2440                2445

Thr Gly Ala Leu Ile Thr Pro Cys Ser Pro Glu Glu Glu Lys Leu
    2450                2455                2460

Pro Ile Asn Pro Leu Ser Asn Ser Leu Leu Arg Tyr His Asn Lys
    2465                2470                2475

Val Tyr Cys Thr Thr Ser Lys Ser Ala Ser Gln Arg Ala Lys Lys
    2480                2485                2490

Val Thr Phe Asp Arg Thr Gln Val Leu Asp Ala His Tyr Asp Ser
    2495                2500                2505

Val Leu Lys Asp Ile Lys Leu Ala Ala Ser Lys Val Ser Ala Arg
    2510                2515                2520

Leu Leu Thr Leu Glu Glu Ala Cys Gln Leu Thr Pro Pro His Ser
    2525                2530                2535

Ala Arg Ser Lys Tyr Gly Phe Gly Ala Lys Glu Val Arg Ser Leu
    2540                2545                2550

Ser Gly Arg Ala Val Asn His Ile Lys Ser Val Trp Lys Asp Leu
    2555                2560                2565

Leu Glu Asp Pro Gln Thr Pro Ile Pro Thr Thr Ile Met Ala Lys
    2570                2575                2580

Asn Glu Val Phe Cys Val Asp Pro Ala Lys Gly Gly Lys Lys Pro
    2585                2590                2595

Ala Arg Leu Ile Val Tyr Pro Asp Leu Gly Val Arg Val Cys Glu
```

```
                  2600              2605              2610
Lys Met Ala Leu Tyr Asp Ile Thr Gln Lys Leu Pro Gln Ala Val
    2615            2620            2625
Met Gly Ala Ser Tyr Gly Phe Gln Tyr Ser Pro Ala Gln Arg Val
    2630            2635            2640
Glu Tyr Leu Leu Lys Ala Trp Ala Glu Lys Lys Asp Pro Met Gly
    2645            2650            2655
Phe Ser Tyr Asp Thr Arg Cys Phe Asp Ser Thr Val Thr Glu Arg
    2660            2665            2670
Asp Ile Arg Thr Glu Glu Ser Ile Tyr Gln Ala Cys Ser Leu Pro
    2675            2680            2685
Glu Glu Ala Arg Thr Ala Ile His Ser Leu Thr Glu Arg Leu Tyr
    2690            2695            2700
Val Gly Gly Pro Met Phe Asn Ser Lys Gly Gln Thr Cys Gly Tyr
    2705            2710            2715
Arg Arg Cys Arg Ala Ser Gly Val Leu Thr Thr Ser Met Gly Asn
    2720            2725            2730
Thr Ile Thr Cys Tyr Val Lys Ala Leu Ala Ala Cys Lys Ala Ala
    2735            2740            2745
Gly Ile Val Ala Pro Thr Met Leu Val Cys Gly Asp Asp Leu Val
    2750            2755            2760
Val Ile Ser Glu Ser Gln Gly Thr Glu Glu Asp Glu Arg Asn Leu
    2765            2770            2775
Arg Ala Phe Thr Glu Ala Met Thr Arg Tyr Ser Ala Pro Pro Gly
    2780            2785            2790
Asp Pro Pro Arg Pro Glu Tyr Asp Leu Glu Leu Ile Thr Ser Cys
    2795            2800            2805
Ser Ser Asn Val Ser Val Ala Leu Gly Pro Arg Gly Arg Arg Arg
    2810            2815            2820
Tyr Tyr Leu Thr Arg Asp Pro Thr Thr Pro Leu Ala Arg Ala Ala
    2825            2830            2835
Trp Glu Thr Val Arg His Ser Pro Ile Asn Ser Trp Leu Gly Asn
    2840            2845            2850
Ile Ile Gln Tyr Ala Pro Thr Ile Trp Val Arg Met Val Leu Met
    2855            2860            2865
Thr His Phe Phe Ser Ile Leu Met Val Gln Asp Thr Leu Asp Gln
    2870            2875            2880
Asn Leu Asn Phe Glu Met Tyr Gly Ser Val Tyr Ser Val Asn Pro
    2885            2890            2895
Leu Asp Leu Pro Ala Ile Ile Glu Arg Leu His Gly Leu Asp Ala
    2900            2905            2910
Phe Ser Met His Thr Tyr Ser His His Glu Leu Thr Arg Val Ala
    2915            2920            2925
Ser Ala Leu Arg Lys Leu Gly Ala Pro Pro Leu Arg Val Trp Lys
    2930            2935            2940
Ser Arg Ala Arg Ala Val Arg Ala Ser Leu Ile Ser Arg Gly Gly
    2945            2950            2955
Lys Ala Ala Val Cys Gly Arg Tyr Leu Phe Asn Trp Ala Val Lys
    2960            2965            2970
Thr Lys Leu Lys Leu Thr Pro Leu Pro Glu Ala Arg Leu Leu Asp
    2975            2980            2985
Leu Ser Ser Trp Phe Thr Val Gly Ala Gly Gly Gly Asp Ile Phe
    2990            2995            3000
```

```
His Ser  Val Ser Arg Ala Arg  Pro Arg Ser Leu Leu  Phe Gly Leu
    3005             3010                 3015

Leu Leu  Leu Phe Val Gly Val  Gly Leu Phe Leu Leu  Pro Ala Arg
    3020             3025                 3030
```

<210> SEQ ID NO 23
<211> LENGTH: 9357
<212> TYPE: DNA
<213> ORGANISM: Hepatitis C virus

<400> SEQUENCE: 23

| | | | | | |
|---|---|---|---|---|---|
| gaatcactcc | cctgcgagga | accactgtcc | tcacgcagaa | agcgtctagc | catgacgtta | 60 |
| gtatgagtgt | cgtacagcct | ccaggacccc | cctcccggg | agagccatag | tggtctgcgg | 120 |
| aaccggtgag | tacaccggaa | ttgccgggaa | gactgggtcc | tttcttggat | caacccactc | 180 |
| tatgcccgga | gatttgggcg | tgcccccgcg | agactgctag | ccgagtagtg | ttgggtcgcg | 240 |
| aaaggccttg | tggtactgcc | tgatagggtg | cttgcgagtg | ccccgggagg | tctcgtagac | 300 |
| cgtgcaccat | gagcacgaat | cctaaacctc | aaagattaac | caaaagaaac | accgtccgtc | 360 |
| gcccacagaa | cgttaagttc | ccgggtggcg | ggcagatcgt | tggcggagtc | tacttgttgc | 420 |
| cgcgcagggg | ccctagattg | ggtgtgcgcg | gcactaggaa | gagttcggag | cgatcgcagc | 480 |
| ccaggggaag | acgccaacgt | atccccaaag | ctgcctcttc | acagggtaaa | gcctggggca | 540 |
| agcccgggta | cccttggccc | ctgtatggta | acgagggctg | tggctgggca | gggtggctcc | 600 |
| tgtcccccg | cggctctcga | cctacttggg | ccccacyga | ccccggcac | cgctcgcgaa | 660 |
| acctcggtaa | ggtgatcgac | accatgacct | gcgggtttgc | cgacctcatg | gggtacatcc | 720 |
| ctgtcctagg | cgcccccta | gggggcgttg | ccagggctct | ggcacatggt | gttagagttc | 780 |
| tggaggacgg | ggtcaactat | gcaacaggga | acttgcctgg | ttgctccttt | tctatcttcy | 840 |
| tactagccct | cctgtcatgt | ctaacagtcc | cggcatcggc | ttatgaagtc | cgcaactcca | 900 |
| gtggrgtcta | tcatctcacc | aatgactgcc | ccaacgctag | tatagtctat | gaaacagaca | 960 |
| acgccatcct | acacgagcct | gggtgcgtgc | cttgcgttcg | cgagggtaat | actagcaggt | 1020 |
| gttgggaacc | agtggccccc | actttggcgg | tccgctatcg | cggagcgctt | actgacgatt | 1080 |
| tgcggacgca | tattgaccta | gtggtggcgt | cagctaccct | gtgctccgcc | ttgtacgtgg | 1140 |
| gggacatttg | tggagccatc | ttcattgcca | gccaagctgt | tctctggaag | cccgggggg | 1200 |
| gtcggatagt | gcaagattgc | aattgttcga | tctacccggg | ccacgtcacc | ggccacagga | 1260 |
| tggcgtggga | catgatgcag | aactgggcgc | cggccttgtc | aatggttgcc | gcttacgctg | 1320 |
| tgagagtgcc | cggtgtcatc | attaccactg | tagcgggcgg | ccactggggt | gtgttatttg | 1380 |
| gcctcgctta | ctttgtatg | gcgggaaact | gggcaaaggt | aatactcatc | atgctactca | 1440 |
| tgtccggcgt | cgacgcggaa | accatggccg | tcggggctag | ggccgctcac | accactggcg | 1500 |
| cccttgtcag | cctgctcaat | ccagggccca | gtcagcgcct | gcagctgatc | aacaccaatg | 1560 |
| ggtcatggca | catcaaccgg | accgctttga | actgcaatga | ctctttgcag | acagggttca | 1620 |
| tagcggccct | cttctacaca | cataggttca | attctagtgg | ctgtcccgag | aggatggctt | 1680 |
| cttgtaaacc | tctcagtgac | tttgaccagg | ggtggggccc | gctgtggtac | aattcaacag | 1740 |
| aaagaccttc | ggaccagcga | ccctattgct | ggcactacgc | gccatcgccg | tgtggtattg | 1800 |
| tgccggctaa | ggatgtttgc | ggtccggtct | actgctttac | accaagcccg | ttgtggtgg | 1860 |
| gcaccacgga | tcgccggggg | gtgccacgt | atacttgggg | tgaaaatgag | tctgatgtct | 1920 |
| tcytgctcaa | cagcacaagg | ccgccgcaag | gcagttggtt | tgggtgctca | tggatgaaca | 1980 |

```
caacggggtt cacgaagacc tgcggaggtc ctccgtgcaa gatacgtccc cagggtgccc    2040
agagtaacac ctctctcact tgtcccacag actgcttcag gaaacatccg cgtgccacat    2100
actccgcttg cggatctggt ccgtggttga cacctagatg catggtccat taccccctata   2160 gactgtggca ctaccgtgt acagtcaact tcaccataca caaagtcagg ttatacatag     2220
ggggtgtaga acataggctc gatgcagcgt gcaattggac gcggggtgag cgatgcgacc    2280
tggaggaccg agacagggtg gacatgtccc ccctgctcca ttccactacg gagctcgcaa    2340
tacttccgtg ttcctttgtg ccgcttccgg ccttatctac gggactgatc cacctgcacc    2400
aaaacatcgt tgacgcccag tacctttatg gtctttctcc cgctataata agctgggcca    2460
tcagatggga gtgggtagtc ctcgttttcc tactcctggc ggacgcgcgg atctgcgcct    2520
gcctttggat gatgatgctt atggcccagg ctgaagccgc tctggagaac ttgatccacc    2580
tcaacgcggc cagccttgcg ggaacccatg gtatctggtg gctccttta gtcttttgtg     2640 cctcttggca tctacgaggc agggttgtcc ctctggtgac gtatgggata tgcgggatgt    2700
ggcccttctt cctcatgttg ctgagcctcc ccccacgagc gtatgctctg gacagggaag    2760
tgagcgcagc gttgggaacg ggcatgctcg ccatcatcct attagttacc ttgggaccgc    2820
actacaagag acttctagcc cttattctct ggtgggtcac atatttcctt acaaggtgtg    2880
aagcagcact ccaaacgtgg gtccctcctc tcaaccctcg ggggggcagg gacggtttca    2940
tcctgtgtgt gctgctgtgc tatccaggcc ttgtctttga catcacaaaa tggttgctgg    3000
tcatgatgtg ccctctctac ctcctccagt tgtgtttggt gaggactcca tactttgtga    3060
gggcccaggc cctcatcaga gtgtgttctc tcttcaaaac gctagctggg ggacggtacg    3120
tgcaggccgc gctgctcact attggccgct ggaccggcac ttatatttat aaccatctcg    3180
cccccctgga aacatgggcc gccggcggcc tacgggattt ggccgttgca gtcgagcccg    3240
tgatattctc ccccatggag aagaagatca tagtttgggg ggcggagacc actgcttgtg    3300
gcgacattct ttgtggcctg cctgtctcag ctcggctcgg cagggaagtc ctgctagggc    3360
ccgcggatga ctacaggtcc atgggatggc aactcctggc tccaatctca gcatacgcac    3420
agcagacccg cggtctcatc tctacccttg tcgtgagcct cactggccgt gataagaacg    3480
agactgccgg cgaggtgcag gtgttgtcca cctcaacgca gaccttcctg gggaccaatg    3540
tgggcggtgt catgtgggga ccttatcacg gagcgggcac gcggactgtg gccggccggg    3600
gtgggcctgt cctccagatg tacacgtcag tcagtgacga tctggtgggc tggcctgccc    3660
cgcctggctc caagtccctc gagccctgct cgtgcgggtc agcagacctt tacttggtga    3720
cgcgcaatgc tgacgtcctt cctcttagga ggaagggtga cggtacagcg tccctactgt    3780
ccccgcgccc tgtgtcctcc cttaaaggct cctcggagg gcctgtcttg tgcccccaaa    3840
gtcattgcgt tggcatcttc agagctgctg tctgcacccg cggtgtagcc aaagcagttc    3900
agtttgttcc catcgagaag atgcaggtgg cccagaggtc gccatcattc agtgacaata    3960
gcacccctcc agcggtgccc agcacctatc aagtaggcta tttacatgcc cccactggca    4020
gcggcaagag cactaaggtc cctgcggcgt atgccagcca gggctacaaa gtgctcgtgc    4080
ttaatccatc agtcgcggcc acccttgggt ttggtgccta catgtccaag gcttatggaa    4140
ttgatccaag tgtgcgcacc ggcgcgcgca cggtgaccac gggggctccc ataaacttact   4200 caacctatgg gaagttcctt gccgacgggg gttgttcagg tggtgcctat gatataatca    4260
tatgtgatga atgccatgcc atcgatgcta ccaccgtggt cggcataggc accgtgttgg    4320
accaggcaga gactagtggt gtccgacttg tggtgctagc tacggccacc ccccccggaa    4380
```

-continued

```
gcgttacggt gccccacccc aacatcgagg aggtcgccct tggcaacgat ggggaaattc    4440
ccttctatgg gaaagccatc ccctgcaac  acatcaaggg gggaaggcat ctcattttct    4500
gtcattccaa aaagaaatgt gatgagcttg ccgggaagct cacctcattg gggctgactg    4560
ccgttgctta ctatagggggg ttggatgttt cggtgatccc aacgtctggc gatgtagtcg   4620
tggtggctac tgatgccttg atgacgggct ttaccggaga cttcgactcc gtcatagact    4680
gcaacgtggc ggttacccag actgtagact tctccttgga ccccaccttc actattgaga    4740
ccaccacagt cccgcaagat tctgtctcgc gctctcagag acgtgggagg acaggtaggg    4800
gcaggcttgg catctacaga tacgtgtcca gtggcgagcg gccatccggt atgttcgaca    4860
ccagcgtgct ctgtgagtgc tatgacctgg ggtgctcgtg gtatgaacta acgcccagtg    4920
aaaccaccac gcgcctcaga gcctacctca attgccctgg tcttccagtg tgccaagacc    4980
atctggagtt ctgggagggc gtctttacgg gacttactca tattgatgca cacttcctgt    5040
cccagaccaa acaagagggc caaaattatg cgtacctgac tgcataccaa gctacagtgt    5100
gcgcccgggc gaaagccccc ccgccctcct gggacgtcca gtggaagtgt ctccaaagac    5160
taaagccact gttagtaggg cccacgcccct tgctatacag gctaggcagt gttaccaatg   5220
aagtcacatt cactcatccc atcaccaaat acattgccac gtgcatggct gccgacttgg    5280
aggtcactac gagcacctgg gtgatcgtag gtggcgtcct cgccgccgtg gccgcatatt    5340
gcatgtctac tggcagtgtt gttgtggttg gccgtgtggt ccttggatcc aacgtggtga    5400
cggcccccga cagagaggtt ttataccagc actttgatga gatggaagag tgctccaaag    5460
ctcctgaatt gctgaaacac gcccaaacca tcggcggaat gttcaaggac aaggccctcg    5520
ccgtcttgga tacgctcaag ccggccgccc aggctgctgt tcccattgtg gagaccaact    5580
tccaaaaggt ggagaagctg tggaatcagc atatgtggaa cttcataagc ggcattcaat    5640
acctagctgg gctatccaca ctgccaggta atccaactgt ggcctcactg atggccttca    5700
ccgcctcagt tactagcccc cttgctacat cgaccacact actagtcaac atcctgggtg    5760
ggtggttcgc aagccagtta gcgccgcccgt ctgctgccac gactttcgtg gtctcgggcc   5820
tcgcagggggg ggcagtgggt agtgttggct tgggcaaggt cttagttgat gtcctggccg   5880
gctatggcgc cggcatagct ggcgccctgg tggccttcaa aatcatgtct ggagaggtcc    5940
ctagcacaga ggatctggca aacctcttac ctgccatact ctcacctgga gctttagttg    6000
tgggagttgt ttgtgccgcg atcatcaaac ggcataccgg cactagtgag ggagtcacgc    6060
agtggatgaa ccgtctcatt gcgttcgcct cccgtggaaa tcacgtgtcg ccgacccact    6120
acatacagga tgatgatgcg tcaaaacgcg tcatggggat actcagctcc cttaccatca    6180
ccagcctcat aaaacgagta ctggcctggg cgcagactga ytattctgcg ccctgtgccg    6240
ggagctggct ccgggaggtg tgggactggg tttgcatggt cctatccgac tttgcatctt    6300
ggttgaaggc caaggtactt cccagccttc caggatccc  attcctatcc tgtcagaaag    6360
ggtataaagg tgagtggcgg aacgatggca tcatgaacac caagtgcccg tgtggggccc    6420
tgatagcagg gcacgtcaag aacggatcga tgcgcatcgt gggccccaag acctgccgaa    6480
acacctggtg gggaaccttc cctattaatt cccataccac gggaccaagt tctcctgtac    6540
cctcccaytg ttatcaaagg gccttgtgga gggtatctgc racgagtac  gtcgagatcc    6600
ttcgtcacaa tgaccagcat taygtggtgg gagtgacggc ggaggacctc aagtgcccgt    6660
gtcaggttcc ttcccccgaa ttcttcagct tgtggacgg  ggtgcggata cacagattcg    6720
cccctgaacc caagcccatg atccgggaag aagccgcttt cgtggtgggt ctgcactcat    6780
```

```
atgtggtggg gtctcagctc ccttgtgaac cggagccgga cgtccaaact gtctcgcagc    6840
tcctaaccga cccctcacac atcaccgcag aaaccgcggc tagaaggctc aggagaggtt    6900
ccccccatc caacgccagt tcttctgcta gtcaactctc agctccatct ctaaaagcca     6960
cccacacaac tctgccacaa catcctgacg cagaactgat agaggccaac ctcatgtggg    7020
aacataaggt tggtgccatc agaaggatgg agacagacac caaagtcatc atacttgact   7080
cctttgattc agcttcttcc gtygaggatg acatggaacc gtccaccgcc gcggagtgtc    7140
tgcgtacgcg taaggtcttc ccaccggcca tgcccatatg ggcgaggcca gactacaatc    7200
ctcctgttgt ggagaattgg aaggaccccg agtacgcacc tccccaggtg tctgggtgcg    7260
ctctaccacc tgcgcagacc cctcctgttc caccacccag gcggaagcgg gcggttatcc    7320
aactcacaga gtccgcggtt tccacggcac tggcggaact cgctgagagg tccttcccaa    7380
aggaggaggc accccccagc gactccgcca ttagtctgga ttcaccggcg gcaaatgacc   7440
ctccatctga ttgtgaccaa ggcagtgaga tctctttctc atccatgcca cccctagagg    7500
gggagccggg tgatccagac ttgtctgatg gctcttggtc aacagtcagc accagatctg    7560
acgtgatttg ctgttccatg tcctactcat ggacgggagc cttagtgacg ccctccggtc    7620
cggaggagga aaggctccca ataaatgccc tyagtaacac catgcttcgg cattataaca    7680
tggtttacag cacaacatca cgctcagctt cacaaagagc aaaaaaagtg acttttgaca    7740
gattgcaagt cctagacgac cactacaaaa gggcgctcgc cgacgtgaaa gcggatgctt    7800
ccacggttaa ggcgcagttg ctctcagtag aggaagctgc tgccctcacc cctgcccact    7860
cagccagatc taagtttggg tacggggcaa aggaagtcag atctcttgcg cccaaggcaa    7920
tgtctcacat caaagaggtc tggaaggact tgctacagga catgaccacc ccgataccga    7980
ccaccataat ggccaagaat gaagtcttct gcgtaaatcc tgccaagggc gggaaaaagc    8040
cagctagact gattgtttac cctgacctag gtgtgagggt atgcgagaag cgggctttgt    8100
acgacatagc tcaaaagctt ccgaaggcca taatggggca ggcgtacggg ttccaatatt    8160
caccatcgca gcgggtcgar tacytagtta agacgtggaa gtccaaacgg actcccatgg    8220
gcttctcata tgacacccgc tgctttgatt ccactgtcac agaacaagac atccgcactg    8280
agagcgagat ctatcagtgc tgcaacctcg accccgaggc tcgcaccatc attaacgccc    8340
ttaccgagag gttgtacgtg gggggaccca tgttcaactc taaaggtcag agggtcggtt    8400
atcgaaggtg cagagccagc ggagttttcc ccaccagcat gggaaacact atgacgtgct    8460
acatcaaagc caaagcggct gcagcagctg cagggctaga gagcactgat ttcctggtct    8520
gcggcgatga cttggtggtc atttgcgaga gcaagggagt cgaacgggat agggcggacc    8580
tgcaagcctt tgcagcggca atgaccaggt actccgctcc acccgggac atgccccagc     8640
ccgcttatga ccttgagcac attgactctt gctcatccaa tgtctcagtc gcccgggaca    8700
actcggggaa aagagtctac tacctcacta gagaccctac caacccacta tccagggcag    8760
cttgggagac cgcccgtcac tcacctgtaa actcctgggt gggcaacata atcatgtttg    8820
cccccaccat atgggtgagg atggttctca tgactcactt tttcgctctc ctcctcaatg    8880
aggagcgatt gaacgatcca gtgagttttg agatgtatgg tgcaacctac acggtctgcc    8940
caacagactt accagacatt atacaaagac tccatgggct ccgcgcattt gaactccata    9000
cttactctcc agcagaactg acgcgggtgg cagctaccct caggaagctt ggggtgccac    9060
ccctcaggac ctggagacaa cgggctcgca aggtccgcgc ggggctgata ggccagggg    9120
gcagggctcg catatgcggt ctctacctct tcaactgggc tgtcaggacc aagatcaaac    9180
```

-continued

```
tcactccact tgcaggcgct ggccggctcg atctttcgag ctggttcagc gtttgcgccg   9240
gcgaggcgga cgtggatcac agcacgccca gagcccatcc tcgcccatta ctcctgtgcc   9300
tactcctact tgccgtaggg gtaggcattt tcctcctacc cgctcggtaa gcgggta      9357
```

<210> SEQ ID NO 24
<211> LENGTH: 9678
<212> TYPE: DNA
<213> ORGANISM: Hepatitis C virus

<400> SEQUENCE: 24

```
acctgcccct aatagggggcg acactccgcc atgaatcact cccctgtgag gaactactgt     60
cttcacgcag aaagcgccta gccatggcgt tagtatgagt gtcgtacagc ctccaggccc    120 cccctcccg ggagagccat agtggtctgc ggaaccggtg agtacaccgg aattgccggg     180
aagactgggt cctttcttgg ataaacccac tctatgcccg gccatttggg cgtgcccccg    240
caagactgct agccgagtag cgttgggttg cgaaaggcct tgtggtactg cctgataggg    300
cgcttgcgag tgccccggga ggtctcgtag accgtgcacc atgagcacaa atcctaaacc    360
tcaaagaaaa accaaaagaa acaccaaccg tcgcccagaa gacgttaagt tcccgggcgg    420
cggccagatc gttggcggag tatacttgtt gccgcgcagg ggccccaggt tgggtgtgcg    480
cacgacaagg aaaacttcgg agcggtccca gccacgtggg agacgccagc ccatccccaa    540
agatcggcgc tccactggca aggcctgggg aaaaccaggt cgcccctggc ccctatatgg    600
gaatgaggga ctcggctggg caggatggct cctgtccccc cgaggctctc gcccctcctg    660
gggccccact gaccccccggc ataggtcgcg caacgtgggt aaagtcatcg acaccctaac    720
gtgtggcttt gccgacctca tggggtacat cccgtcgta ggcgcccgc ttagtggcgc    780 cgccagagct gtcgcgcacg gcgtgagagt cctggaggac ggggttaatt atgcaacagg    840
gaacctaccc ggtttcccct tttctatctt cttgctggcc ctgttgtcct gcatcaccgt    900
tccggtctct gctgccagg tgaagaatac cagtagcagc tacatggtga ccaatgactg    960
ctccaatgac agcatcactt ggcagctcga ggctgcggtt ctccacgtcc ccggtgcgt   1020 cccgtgcgag agagtgggga atacgtcacg gtgttgggtg ccagtctcgc caaacatggc   1080
tgtgcggcag cccggtgccc tcacgcaggg tctgcggacg cacatcgata tggttgtgat   1140
gtccgccacc ttctgctctg ctctctacgt gggggacctc tgtggcgggg tgatgctcgc   1200
ggcccaggtg ttcatcgtct cgccgcagta ccactggttt gtgcaagaat gcaattgctc   1260
catctaccct ggcaccatca ctggacaccg catggcatgg gacatgatga tgaactggtc   1320
gcccacggcc accatgatcc tggcgtacgt gatgcgcgtc cccgaggtca tcatagacat   1380
cgttagcggg gctcactggg gcgtcatgtt cggcttggcc tacttctcta tgcagggagc   1440
gtgggcgaag gtcattgtca tccttctgct ggccgctggg gtggacgcgg gcaccaccac   1500
cgttggaggc gctgttgcac gttccaccaa cgtgattgcc ggcgtgttca gccatggccc   1560
tcagcagaac attcagctca ttaacaccaa cggcagttgg cacatcaacc gtactgcctt   1620
gaattgcaat gactccttga acaccggctt tctcgcggcc ttgttctaca ccaaccgctt   1680
taactcgtca gggtgtccag ggcgcctgtc cgcctgccgc aacatcgagg ctttccggat   1740
agggtggggc acctacagt acgaggataa tgtcaccaat ccagaggata tgaggccgta   1800
ctgctggcac taccccccaa agccgtgtgg cgtagtcccc gcgaggtctg tgtgtggccc   1860
agtgtactgt ttcaccccca gccccgtagt agtgggcacg accgacagac gtggagtgcc   1920
cacctacaca tggggagaga atgagacaga tgtcttccta ctgaacagca cccgaccgcc   1980
```

-continued

```
gcagggctca tggttcggct gcacgtggat gaactccact ggtttcacca agacttgtgg    2040
cgcgccacct tgccgcacca gagctgactt caacgccagc acggacttgt tgtgccctac    2100
ggattgtttt aggaagcatc ctgatgccac ttatattaag tgtggttctg ggccctggct    2160
cacaccaaag tgcctggtcc actaccctta cagactctgg cattacccct gcacagtcaa    2220
ttttaccatc ttcaagataa gaatgtatgt agggggggtt gagcacaggc tcacggccgc    2280
atgcaacttc actcgtgggg atcgctgcga cttggaggac agggacagga gtcagctgtc    2340
tcctctgttg cactctacca cggaatgggc catcctgccc tgcacctact cagacttacc    2400
cgctttgtca actggtcttc tccaccttca ccagaacatc gtggacgtac aatacatgta    2460
tggcctctca cctgctatca caaaatacgt cgttcgatgg gagtgggtgg tactcttatt    2520
cctgctctta gcgacgcca gagtctgcgc ctgcttgtgg atgctcatct tgttgggcca    2580
ggccgaagca gcattggaga agttggtcgt cttgcacgct gcgagtgcgg ctaactgcca    2640
tggcctccta tattttgcca tcttcttcgt ggcagcttgg cacatcaggg gtcgggtggt    2700
ccccttgacc acctattgcc tcactggcct atggcccttc tgcctactgc tcatggcact    2760
gccccggcag gcttatgcct atgacgcacc tgtgcacgga cagataggcg tgggtttgtt    2820
gatattgatc accctcttca cactcacccc ggggtataag accctcctcg gccagtgtct    2880
gtggtggttg tgctatctcc tgaccctggg ggaagccatg attcaggagt gggtaccacc    2940
catgcaggtg cgcggcggcc gcgatggcat cgcgtgggcc gtcactatat tctgcccggg    3000
tgtggtgttt gacattacca aatggctttt ggcgttgctt gggcctgctt acctcttaag    3060
ggccgctttg acacatgtgc cgtacttcgt cagagctcac gctctgataa gggtatgcgc    3120
tttggtgaag cagctcgcgg ggggtaggta tgttcaggtg gcgctattgg cccttggcag    3180
gtggactggc acctacatct atgaccacct cacacctatg tcggactggg ccgctagcgg    3240
cctgcgcgac ttagcggtcg ccgtggaacc catcatcttc agtccgatgg agaagaaggt    3300
catcgtctgg ggagcggaga cggctgcatg tggggacatt ctacatggac ttcccgtgtc    3360
cgcccgactc ggccaggaga tcctcctcgg cccagctgat ggctacacct ccaaggggtg    3420
gaagctcctt gctcccatca ctgcttatgc ccagcaaaca cgaggcctcc tgggcgccat    3480
agtggtgagt atgacggggc gtgacaggac agaacaggcc ggggaagtcc aaatcctgtc    3540
cacagtctct cagtccttcc tcggaacaac catctcgggg gttttgtgga ctgtttacca    3600
cggagctggc aacaagactc tagccggctt acggggtccg gtcacgcaga tgtactcgag    3660
tgctgagggg gacttggtag gctggcccag ccccccctggg accaagtctt tggagccgtg    3720
caagtgtgga gccgtcgacc tatatctggt cacgcggaac gctgatgtca tcccggctcg    3780
gagacgcggg gacaagcggg gagcattgct ctccccgaga cccatttcga ccttgaaggg    3840
gtcctcgggg gggccggtgc tctgccctag gggccacgtc gttgggctct ccgagcagc    3900 tgtgtgctct cggggcgtgg ccaaatccat cgatttcatc cccgttgaga cactcgacgt    3960
tgttacaagg tctcccactt tcagtgacaa cagcacgcca ccggctgtgc cccagaccta    4020
tcaggtcggg tacttgcatg ctccaactgg cagtggaaag agcaccaagg tccctgtcgc    4080
gtatgccgcc caggggtaca agtactagt gcttaacccc tcggtagctg ccaccctggg    4140
gtttggggcg tacctatcca aggcacatgg catcaatccc aacattagga ctggagtcag    4200
gaccgtgatg accggggagg ccatcacgta ctccacatat ggcaaatttc tcgccgatgg    4260
gggctgcgct agcggcgcct atgacatcat catatgcgat gaatgccacg ctgtggatgc    4320
tacctccatt ctcggcatcg gaacggtcct tgatcaagca gagacagccg gggtcagact    4380
```

```
aactgtgctg gctacggcca caccccccgg gtcagtgaca accccccatc ccgatataga   4440
agaggtaggc ctcgggcggg agggtgagat ccccttctat gggagggcga ttccctatc    4500
ctgcatcaag ggagggagac acctgatttt ctgccactca agaaaaagt gtgacgagct    4560
cgcggcggcc cttcggggca tgggcttgaa tgccgtggca tactatagag ggttggacgt   4620
ctccataata ccagctcagg gagatgtggt ggtcgtcgcc accgacgccc tcatgacggg   4680
gtacactgga gactttgact ccgtgatcga ctgcaatgta gcggtcaccc aagctgtcga   4740
cttcagcctg gacccccacct tcactataac cacacagact gtcccacaag acgctgtctc   4800
acgcagtcag cgccgcgggc gcacaggtag aggaagacag ggcacttata ggtatgtttc    4860
cactggtgaa cgagcctcag gaatgtttga cagtgtagtg ctttgtgagt gctacgacgc    4920
aggggctgcg tggtacgatc tcacaccagc ggagaccacc gtcaggctta gagcgtattt    4980
caacacgccc ggcctacccg tgtgtcaaga ccatcttgaa ttttgggagg cagttttcac    5040
cggcctcaca cacatagacg cccacttcct ctcccaaaca aagcaagcgg gggagaactt    5100
cgcgtaccta gtagcctacc aagctacggt gtgcgccaga gccaaggccc ctccccgtc    5160
ctggacgcc atgtggaagt gcctggcccg actcaagcct acgcttgcgg gccccacacc    5220
tctcctgtac cgtttgggcc ctattaccaa tgaggtcacc ctcacacacc ctgggacgaa    5280
gtacatcgcc acatgcatgc aagctgacct tgaggtcatg accagcacgt gggtcctagc    5340
tggaggagtc ctggcagccg tcgccgcata ttgcctggcg actggatgcg tttccatcat    5400
cggccgcttg cacgtcaacc agcgagtcgt cgttgcgccg gataaggagg tcctgtatga    5460
ggcttttgat gagatggagg aatgcgcctc tagggcggct ctcatcgaag aggggcagcg    5520
gatagccgag atgttgaagt ccaagatcca aggcttgctg cagcaggcct ctaagcaggc    5580
ccaggacata caacccgcta tgcaggcttc atggcccaaa gtggaacaat ttgggccag    5640
acacatgtgg aacttcatta gcggcatcca atacctcgca ggattgtcaa cactgccagg    5700
gaaccccgcg gtggcttcca tgatggcatt cagtgccgcc ctcaccagtc cgttgtcgac    5760
cagtaccacc atccttctca acatcatggg aggctggtta gcgtcccaga tcgcaccacc    5820
cgcgggggcc accggctttg tcgtcagtgg cctggtgggg gctgccgtgg gcagcatagg    5880
cctgggtaag gtgctggtgg acatcctggc aggatatggt gcgggcattt cgggggccct    5940
cgtcgcattc aagatcatgt ctggcgagaa gccctctatg gaagatgtca tcaatctact    6000
gcctgggatc ctgtctccgg gagccctggt ggtgggggtc atctgcgcgg ccattctgcg    6060
ccgccacgtg ggaccggggg agggcgcggt ccaatgatg aacaggctta ttgcctttgc    6120
ttccagagga aaccacgtcg cccctactca ctacgtgacg gagtcggatg cgtcgcagcg    6180
tgtgaccca ctacttggct ctcttactat aaccagccta ctcagaagac tccacaattg    6240
gataactgag gactgcccca tcccatgctc cggatcctgg ctccgcgacg tgtgggactg    6300
ggtttgcacc atcttgacag acttcaaaaa ttggctgacc tctaaattgt tccccaagct    6360
gcccggcctc cccttcatct cttgtcaaaa ggggtacaag ggtgtgtggg ccggcactgg    6420
catcatgacc acgcgctgcc cttgcggcgc caacatctct ggcaatgtcc gcctgggctc    6480
tatgaggatc acagggccta aaacctgcat gaacacctgg caggggacct ttcctatcaa    6540
ttgctacacg gagggccagt gcgcgccgaa accccccacg aactacaaga ccgccatctg    6600
gagggtggcg gcctcggagt acgcggaggt gacgcagcat gggtcgtact cctatgtaac    6660
aggactgacc actgacaatc tgaaaattcc ttgccaacta ccttctccag agttttctc    6720
ctgggtggac ggtgtgcaga tccataggtt tgcacccaca ccaaagccgt ttttccggga    6780
```

```
tgaggtctcg ttctgcgttg ggcttaattc ctatgctgtc gggtcccagc ttccctgtga   6840
acctgagccc gacgcagacg tattgaggtc catgctaaca gatccgcccc acatcacggc   6900
ggagactgcg gcgcggcgct tggcacgggg atcacctcca tctgaggcga gctcctcagt   6960
gagccagcta tcagcaccgt cgctgcgggc cacctgcacc acccacagca acacctatga   7020
cgtggacatg gtcgatgcca acctgctcat ggagggcggt gtggctcaga cagagcctga   7080
gtccagggtg cccgttctgg actttctcga gccaatggcc gaggaagaga gcgaccttga   7140
gccctcaata ccatcggagt gcatgctccc caggagcggg tttccacggg ccttaccggc   7200
ttgggcacgg cctgactaca acccgccgct cgtggaatcg tggaggaggc cagattacca   7260
accgcccacc gttgctggtt gtgctctccc cccccccaag aaggcccga cgcctccccc    7320
aaggagacgc cggacagtgg gtctgagcga gagcaccata tcagaagccc tccagcaact   7380
ggccatcaag acctttggcc agccccctc gagcggtgat gcaggctcgt ccacgggggc    7440
gggcgccgcc gaatccggcg gtccgacgtc ccctggtgag ccggcccct cagagacagg    7500
ttccgcctcc tctatgcccc ccctcgaggg ggagcctgga gatccggacc tggagtctga   7560
tcaggtagag cttcaacctc cccccaggg ggggggggta gctcccggtt cgggctcggg     7620
gtcttggtct acttgctccg aggaggacga taccaccgtg tgctgctcca tgtcatactc   7680
ctggaccggg gctctaataa ctccctgtag ccccgaagag gaaaagttgc caatcaaccc   7740
tttgagtaac tcgctgttgc gataccataa caaggtgtac tgtacaacat caaagagcgc   7800
ctcacagagg gctaaaaagg taacttttga caggacgcaa gtgctcgacg cccattatga   7860
ctcagtctta aaggacatca agctagcggc ttccaaggtc agcgcaaggc tcctcacctt   7920
ggaggaggcg tgccagttga ctccaccca ttctgcaaga tccaagtatg gattcggggc    7980
caaggaggtc cgcagcttgt ccgggagggc cgttaaccac atcaagtccg tgtggaagga   8040
cctcctggaa gacccacaaa caccaattcc cacaaccatc atggccaaaa atgaggtgtt   8100
ctgcgtggac cccgccaagg ggggtaagaa accagctcgc ctcatcgttt accctgacct   8160
cggcgtccgg gtctgcgaga aaatggccct ctatgacatt acacaaaagc ttcctcaggc   8220
ggtaatggga gcttcctatg gcttccagta ctcccctgcc caacgggtgg agtatctctt   8280
gaaagcatgg gcggaaaaga aggaccccat gggttttttcg tatgatacccc gatgcttcga   8340
ctcaaccgtc actgagagag acatcaggac cgaggagtcc atataccagg cctgctccct   8400
gcccgaggag gcccgcactg ccatacactc gctgactgag agactttacg taggagggcc   8460
catgttcaac agcaagggtc aaacctgcgg ttacagacgt tgccgcgcca gcggggtgct   8520
aaccactagc atgggtaaca ccatcacatg ctatgtgaaa gccctagcgg cctgcaaggc   8580
tgcgggata gttgcgccca caatgctggt atgcggcgat gacctagtag tcatctcaga    8640
aagccagggg actgaggagg acgagcggaa cctgagagcc ttcacggagg ccatgaccag   8700
gtactctgcc cctcctggtg atccccccag accggaatat gacctggagc taataacatc   8760
ctgttcctca aatgtgtctg tggcgttggg cccgcggggc cgccgcagat actacctgac   8820
cagagaccca accactccac tcgcccgggc tgcctgggaa acagttagac actccctat    8880
caattcatgg ctgggaaaca tcatccagta tgctccaacc atatgggttc gcatggtcct   8940
aatgacacac ttcttctcca ttctcatggt ccaagacacc ctggaccaga acctcaactt   9000
tgagatgtat ggatcagtat actccgtgaa tcctttggac cttccagcca taattgagag   9060
gttacacggg cttgacgcct tttctatgca cacatactct caccacgaac tgacgcgggt   9120
ggcttcagcc ctcagaaaac ttggggcgcc acccctcagg gtgtggaaga gtcgggctcg   9180
```

```
cgcagtcagg gcgtccctca tctcccgtgg agggaaagcg gccgtttgcg gccgatatct    9240
cttcaattgg gcggtgaaga ccaagctcaa actcactcca ttgccggagg cgcgcctact    9300
ggacttatcc agttggttca ccgtcggcgc cggcgggggc gacattttc  acagcgtgtc    9360 gcgcgcccga ccccgctcat tactcttcgg cctactccta cttttcgtag gggtaggcct    9420
cttcctactc cccgctcggt agagcggcac acactaggta cactccatag ctaactgttc    9480
cttttttttt tttttttttt tttttttttt tttttttttt ttttctttt  ttttttttc    9540 cctctttctt cccttctcat cttattctac tttctttctt ggtggctcca tcttagccct    9600
agtcacggct agctgtgaaa ggtccgtgag ccgcatgact gcagagagtg ccgtaactgg    9660
tctctctgca gatcatgt                                                 9678
```

EFFICIENT CELL CULTURE SYSTEM FOR HEPATITIS C VIRUS GENOTYPE 7A

CROSS-REFERENCE TO RELATED APPLICATIONS

The present application is a National Stage application of International Patent Application No PCT/DK2009/050193, filed Jul. 31, 2009, which is incorporated herein by reference in its entirety and which claims the benefit of European Application No. EP 08162472.8, filed Aug. 15, 2008.

INCORPORATION OF SEQUENCE LISTING

A computer readable form of the Sequence Listing named "66146_94675_SEQ_LST.txt" and which is 277,780 bytes in size, is electronically filed herewith and herein incorporated by reference in its entirety. This Sequence Listing consists of SEQ ID NOs: 1-24

FIELD OF THE INVENTION

The present invention provides infectious recombinant hepatitis C genotype 7 viruses (HCV), and vectors, cells and animals comprising the same. The present invention provides methods of producing the infectious recombinant HCV genotype 7, and their use in identifying anti-HCV therapeutics including use in vaccines and diagnostics, as well as sequences of HCV associated with HCV pathogenesis.

BACKGROUND

Hepatitis C is one of the most widespread infectious diseases in the world. About 180 million people are infected with hepatitis C virus (HCV) worldwide with a yearly incidence of 3-4 million. While the acute phase of infection is mostly asymptomatic, the majority of acutely infected individuals develops chronic hepatitis and is at increased risk of developing liver cirrhosis and hepatocellular carcinoma. Thus, HCV infection is a major contributor to end-stage liver disease and in developed countries to liver transplantation.

HCV is a small, enveloped virus classified as a member of the Flaviviridae family. Its genome consists of a 9.6 kb single stranded RNA of positive polarity composed of 5' and 3' untranslated regions (UTR) and one long open reading frame (ORF) encoding a polyprotein, which is co- and post-translationally cleaved and thus yields the structural (Core, E1, E2), p7 and nonstructural (NS2, NS3, NS4A, NS4B, NS5A, NS5B) proteins.

HCV isolates from around the world exhibit significant genetic heterogeneity. At least 7 major HCV genotypes (genotypes 1-7) have been identified, which differ by 31-33% at the nucleotide level and deduced amino acid level. In addition, there are numerous subtypes (a, b, c, etc.), which differ by 20-25% on the nucleotide and deduced amino acid level.

While HCV genotypes 1-3 predominate in the Western World, genotypes 4-6 are more common in areas with high prevalence or even endemic levels of HCV infection. Genotype 6 is highly prevalent in Southeast Asia. Recently, a genotype 7a was discovered in Canadian and Belgian patients, who presumably were infected in Central Africa (Murphy et al., 2007). Thus, the knowledge about the natural history, susceptibility to treatment and neutralizing antibodies as well as receptor interactions of this new genotype is very limited.

While the only approved treatment for chronic HCV infection, combination therapy with interferon-α and ribavirin, leads to a sustained virologic response in most of genotype 2 or 3 patients, viral clearance is only obtained for about half of patients with genotype 1 or 4. There is nothing known about treatment responses of HCV genotype 7a infected patients. There is no vaccine against HCV.

Since its discovery in 1989, research on HCV has been hampered by the lack of appropriate cell culture systems allowing for research on the complete viral life cycle as well as new therapeutics and vaccines.

In 2001, a genotype 2a isolate (JFH1) was described (Kato et al., 2001), which yielded high RNA titers in the replicon system without adaptive mutations (Kato et al., 2003).

A major breakthrough occurred in 2005, when formation of infectious viral particles was reported after transfection of RNA transcripts from the JFH1 full-length consensus cDNA clone into Huh7 cells (Wakita et al., 2005) (Zhong et al., 2005).

At the same time, Lindenbach et al. demonstrated that the intragenotypic 2a/2a recombinant genome (J6/JFH1), in which the structural genes (Core, E1, E2), p7 and NS2 of JFH1 were replaced by the respective genes of clone J6CF, produced infectious viral particles in Huh7.5 cells (a cell line derived from bulk Huh7 cells) with an accelerated kinetic (Lindenbach et al., 2005). Cell culture derived J6/JFH viruses were apparently fully viable in vivo.

Despite the importance of the described cell culture systems they represent only a single subtype (genotype 2a) of HCV. It is important to develop cell culture systems for representative strains of other HCV genotypes, since neutralizing antibodies are not expected to cross-neutralize all genotypes and new specific antiviral compounds might have differential efficiencies against different genotypes. For the genotype specific study of the function of the structural proteins, p7 and NS2 as well as related therapeutics such as neutralizing antibodies, fusion inhibitors, ion-channel blockers and protease inhibitors, it would be sufficient to construct intergenotypic recombinant viruses in analogy to J6/JFH.

Pietschmann et al. 2006 disclose construction and characterization of infectious intragenotypic and intergenotypic hepatitis C virus recombinants. The authors created a series of recombinant genomes allowing production of infectious genotype 1a, 1b, 2a and 3a particles by constructing hybrid genomes between the JFH1 isolate and the HCV isolates: H77 (genotype 1a), Con1 (genotype 1b), J6 (genotype 2a) and 452 (genotype 3a) respectively. Thus, disclosing genotypes completely different from the genotype disclosed in the present application.

The infectious titers of the 1a, 1b and 3a genotypes disclosed in Pietschmann et al. 2006 are not at a level sufficiently high for practical utilization in functional analysis, drug and vaccine development or other applications. For such applications, including screening of potential drugs and development of potential vaccine candidates, the skilled person will know that infectivity titers below $10^3$ TCID50/mL contain insufficient amounts of infectious virus.

Accordingly, the study does not attempt cell culture adaptation of the genotype recombinants, e.g. by serial passage of cell culture derived viruses to naïve cells and it is not investigated whether adaptive mutations develop after transfection in cell culture. In fact, Pietschmann et al does not even provide any sequence data of the virus produced in the cell culture.

In D1 (WO 2006/096459), Rice et al. discloses intragentoypic and intergenotypic chimeric HCV genomes comprising Core, E1, E2, p7 and NS2 from a first HCV strain and 5'UTR, NS3, NS4A, NS4B, NS5A, NS5B and 3'UTR of a second HCV strain. As experimental work backing this claim is presented the following: 1) Generation and characterization of the intragenotypic recombinant J6/JFH1 (with Core-NS2 of genotype 2a strain J6 as well as 5'UTR, NS3-NS5B and 3'UTR of genotype 2a strain JFH1), 2) Generation and characterization of the intergenotypic recombinant H77/JFH1 (with Core-NS2 of genotype 1a strain H77 as well as 5'UTR, NS3-NS5B and 3'UTR of genotype 2a strain JFH1). Further, adaptive mutations are identified in H77/JFH1.

In D2, Gottwein et al. describe the generation and characterization of the intergenotypic HCV genome S52/JFH1 (with Core-NS2 of genotype 3a strain S52 as well as 5'UTR, NS3-NS5B and 3'UTR of genotype 2a strain JFH1). Adaptive mutations that are necessary for efficient growth in cell culture are identified and tested in reverse genetic studies. Optimally cell culture adapted S52/JFH1 genomes are constructed and characterized. Applicability of this genotype 3a/2a cell culture system is shown in receptor blocking studies (blocking of the putative HCV receptor CD81) and confocal microscopy studies, investigating co-localization of HCV Core with intracellular lipids.

In D3, Scheel et al. describe the generation and characterization of the intergenotypic HCV genome ED43/JFH1 (with Core-NS2 of genotype 4a strain ED43 as well as 5'UTR, NS3-NS5B and 3'UTR of genotype 2a strain JFH1). Adaptive mutations that are essential for viability in cell culture are identified and tested in reverse genetic studies. Optimally cell culture adapted ED43/JFH1 genomes are constructed and characterized. Applicability of this genotype 4a/2a cell culture system is shown in receptor blocking studies (blocking of the putative HCV receptor CD81) and neutralization studies.

SUMMARY OF INVENTION

In this study, the present inventors used the published sequence of the QC69 isolate (genotype 7a) to construct a viable, JFH1-based genome. The present inventors passaged QC69/JFH1 virus in cell culture and obtained both high infectivity titers, high HCV RNA titers and identified adaptive mutations aiding efficient growth.

The present inventors have developed robust cell culture systems for HCV genotype 7a. This is an important advance for the study of HCV, since it permits detailed molecular studies of this so far unknown HCV genotype and enhances the potential for developing broadly reactive reagents against HCV, including but not limited to small molecule drugs, antibodies and vaccines. Accordingly, the present invention may be used for individualised treatment of patients infected with one of the seven major genotypes.

In one aspect the present invention relates to a replicating RNA comprising the structural genes (Core, E1, E2), p7 and the non-structural gene NS2 of genotype 7a and the non-structural genes NS3, NS4A, NS4B, NS5A and NS5B from the JFH1 strain.

In another aspect the present invention pertains to an isolated nucleic acid molecule which encodes human hepatitis C virus of genotype 7a/JFH1, wherein said molecule is capable of expressing said virus when transfected into cells.

In yet another aspect the present invention pertains to a composition comprising a nucleic acid molecule according to the present invention, a cassette vector for cloning viral genomes, methods for producing a cell which replicates HCV 7a/JFH1 RNA and cells obtainable there from.

In another aspect the present invention pertains to methods for producing a hepatitis C virus particle, methods for in vitro producing a hepatitis C virus-infected cell.

In a further aspect the present invention pertains to methods for screening an anti-hepatitis C virus substance, hepatitis C vaccines comprising a hepatitis C virus particle, methods for producing a hepatitis C virus vaccine and antibodies against hepatitis C virus.

DETAILED DESCRIPTION OF THE DRAWINGS

FIG. 1 A, B. Viability of QC69/JFH1 recombinants with and without putative adaptive mutations after transfection of Huh7.5 cells. Huh7.5 cells were transfected in parallel with RNA transcripts from pS52/JFH1$_{I793S,K1404Q}$, pQC69/JFH1, QC69/JFH1$_{V157F,J414T}$, and QC69/JFH1$_{L882P,A2694V}$. (A) After immunostaining, the percentage of HCV NS5A positive cells was scored by fluorescence microscopy. (B) Infectivity titers of transfection supernatants were measured as TCID$_{50}$/mL. QC69/JFH1$_{V157F}$, QC69/JFH1$_{J414T}$, QC69/JFH1$_{L882P}$ and QC69/JFH1$_{A2694V}$ showed spread kinetics comparable to QC69/JFH1$_{V157F,J414T}$ and QC69/JFH1$_{L882P,A2694V}$ (data not shown).

FIG. 2 A, B. Importance of CD81 and SR-BI for entry of genotype 7a intergenotypic viruses. 6×10$^3$ Huh7.5 cells per well of a 96 well plate were treated for 1 hr with either anti-CD81 (A) or anti-SR-BI (B) at the indicated concentrations. ~150 FFU of the respective virus were added for 3 hrs. For J6/JFH1 reference virus, the virus stocks shown in Table 4 were used; QC69/JFH1 was derived from QC69/JFH1 exp.2 (Table 2). After 48 hrs, the number of FFU was evaluated following immunostaining for HCV NS5A. % inhibition was calculated by relating the number of FFU/well to the mean number of FFU/well of 3 untreated wells. Means of triplicates and standard errors of the mean are 30 shown. Control antibody preparations specified in Materials and Methods did not show any inhibitory effect at the equivalent concentrations. Stars, value <0. Data shown in B were generated in two different experiments (1st experiment: 1:10, 1:40 and 1:160 dilutions (1:160 not shown); 2nd experiment: 1:160 and 1:640 dilutions). The efficient blocking of infection of the different genotype recombinants with anti- SR-BI was confirmed in an independent experiment (data not shown).

DETAILED DESCRIPTION

The present invention advantageously provides hepatitis C virus (HCV) nucleotide sequences capable of replication, expression of functional HCV proteins, and infection in vivo and in vitro for development of antiviral therapeutics and diagnostics.

Nucleic Acid Molecules (cDNA Clones and RNA Transcripts)

In a broad aspect, the present invention is directed to a genetically engineered hepatitis C virus (HCV) encoded by nucleic acid sequences such as a complementary DNA (cDNA) sequence and replicating RNA (QC69/JFH1) comprising the structural genes (Core, E1, E2), p7 and the non-structural gene NS2 of genotype 7a (e.g. strain QC69, genbank accession number EF108306) and the non-structural genes NS3, NS4A, NS4B, NS5A and NS5B from the JFH1 strain (genotype 2a, genbank accession number AB047639).

Thus in one embodiment, the present invention relates to a replicating RNA comprising the structural genes (Core, E1, E2), p7 and the non-structural gene NS2 of genotype 7a and the non-structural genes NS3, NS4A, NS4B, NS5A and NS5B from the JFH1 strain.

In another embodiment the genotype 7a is of the strain QC69.

Soon after the discovery of HCV in 1989, the genetic heterogeneity of this virus became obvious. Therefore, it has been of great interest to achieve a consensus nomenclature system for classification of HCV isolates into genotypes and subtypes. Initially, different genotype classification systems were used, resulting in disagreement on the number of HCV genotypes. However, with the growing number of sequenced HCV isolates that could be studied, considerable consensus about classification systems was achieved. Already in 1994, HCV was classified into 6 genotypes by phylogenetic methods. In a consensus report published by Simmonds et al. 2005, this classification into 6 major HCV genotypes was reinforced, stating that genotypes differ by >30% on the nucleotide level. In addition, in this consensus report, guidelines for assignment of newly discovered HCV variants as new HCV genotypes were published. To assign a new variant to a new genotype, it needs to be demonstrated that there is no significant grouping within any of the existing genotypes. If a new variant fulfils these criteria, it is to be assigned with the next available genotype number. As already proposed in the consensus report by Simmonds et al. 2005, phylogenetic analysis of the open reading frame of the newly discovered QC69 HCV variant shows that it merits classification as a new HCV genotype: genotype 7. Thus, it is state of the art and commonly accepted, that all so far identified HCV variants can be grouped in genotype 1 to 7.

In the present context the term "genotype" is to be understood in accordance with Simmonds et al. 2005—i.e. the term "genotype" relate to the presently 7 identified major HCV genotypes.

In the present context the term "subtype" is to be understood in accordance with Simmonds et al. 2005—in relation to genotype 7, this means, the presently identified subtypes indicated by lower-case letters; e.g. 7a (Simmonds et al. 2005).

In the present context the term "isolate" is to be understood in accordance with Simmonds et al. 2005—in relation to subtype 7a this means for example QC69. Several different isolates/strains exist within the same subtype. The terms "isolate" and "strain" are used herein interchangeably.

The invention provides an isolated nucleic acid molecule encoding an infectious recombinant HCV genome, which nucleic acids comprise an intergenotypic HCV genome. In one embodiment, the intergenotypic HCV genome comprises sequences encoding structural genes (Core, E1, E2), p7 and nonstructural genes (NS2) from a first HCV strain, and sequences encoding the 5' untranslated region (UTR), nonstructural genes NS3, NS4A, NS4B, NS5A, NS5B, and the 3' UTR from a second HCV strain.

In one embodiment, the first HCV strain and the second HCV strain are from different genotypes.

In one embodiment, the first HCV strain is strain QC69, and in another embodiment, the second HCV strain is strain JFH1.

In one embodiment, the HCV nucleic acid molecule of the present invention comprises the nucleic acid sequence (cDNA) of QC69/JFH1, SEQ ID NO: 1. In another embodiment the nucleic acid molecule has at least a functional portion of a sequence as shown in SEQ ID NO: 1 which represents a specific embodiment of the present invention exemplified herein.

In yet an embodiment the nucleic acid molecule comprises the nucleic acid sequence with a sequence identity of at least 90% to that of SEQ ID NO: 1.

In another embodiment, the nucleic acid comprises a sequence sharing at least 90% identity with that set forth in SEQ ID NO: 1, such as 90% identity, 91% identity, 92% identity, 93% identity, 94% identity, 95% identity, 96% identity, 97% identity, 98% identity, or 99% identity.

As commonly defined "identity" is here defined as sequence identity between genes or proteins at the nucleotide or amino acid level, respectively. Thus, in the present context "sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned.

To determine the percent identity of two amino acid sequences or of two nucleic acids, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

One may manually align the sequences and count the number of identical amino acids. Alternatively, alignment of two sequences for the determination of percent identity may be accomplished using a mathematical algorithm. Such an algorithm is incorporated into the NBLAST and XBLAST programs of (Altschul et al. 1990). BLAST nucleotide searches may be performed with the NBLAST program, score=100, wordlength=12, to obtain nucleotide sequences homologous to a nucleic acid molecules of the invention. BLAST protein searches may be performed with the XBLAST program, score=50, wordlength=3 to obtain amino acid sequences homologous to a protein molecule of the invention. To obtain gapped alignments for comparison purposes, Gapped BLAST may be utilised. Alternatively, PSI-Blast may be used to perform an iterated search which detects distant relationships between molecules. When utilising the NBLAST, XBLAST, and Gapped BLAST programs, the default parameters of the respective programs may be used. See www.ncbi.nlm.nih.gov. Alternatively, sequence identity may be calculated after the sequences have been aligned e.g. by the BLAST program in the EMBL database (www.ncbi.nlm.gov/cgi-bin/BLAST). Generally, the default settings with respect to e.g. "scoring matrix" and "gap penalty" may be used for alignment. In the context of the present invention, the BLASTN and PSI BLAST default settings may be advantageous.

The percent identity between two sequences may be determined using techniques similar to those described above, with or without allowing gaps. In calculating percent identity, only exact matches are counted.

It should be noted that while SEQ ID NO: 1 is a DNA sequence, the present invention contemplates the corresponding RNA sequence, and DNA and RNA complementary sequences as well.

In a further embodiment, a region from an HCV isolate is substituted for a corresponding region, e.g., of an HCV nucleic acid having a sequence of SEQ ID NO: 1.

In another embodiment, the HCV nucleic acid is a DNA that codes on expression or after in vitro transcription for a replication-competent HCV RNA genome, or is itself a replication-competent HCV RNA genome.

In one embodiment, the HCV nucleic acid of the invention has a full-length sequence as depicted in or corresponding to SEQ ID NO: 1. Various modifications for example of the 5' and 3' UTR are also contemplated by the invention. In another embodiment, the nucleic acid further comprises a reporter gene, which, in one embodiment, is a gene encoding neomycin phosphotransferase, Renilla luciferase, secreted alkaline phosphatase (SEAP), Gaussia luciferase or the green fluorescent protein.

Naturally, as noted above, the HCV nucleic acid sequence of the invention is selected from the group consisting of double stranded DNA, positive-sense cDNA, or negative-sense cDNA, or positive-sense RNA or negative-sense RNA or double stranded RNA. Thus, where particular sequences of nucleic acids of the invention are set forth, both DNA and corresponding RNA are intended, including positive and negative strands thereof.

In a further embodiment, the nucleic acid sequence of SEQ ID NO: 1 or the said nucleic acid sequence with any mutation described in this document is obtained by any other means than what is described above.

In another embodiment, the complementary DNA (cDNA) provided by the present invention encodes human hepatitis C virus of genotype 7a/JFH1, wherein said molecule is capable of expressing said virus when transfected into cells and further capable of infectivity in vivo and wherein said molecule encodes the amino acid sequence of QC69/JFH1, SEQ ID NO: 2.

According to various aspects of the invention, HCV nucleic acid, including the polyprotein coding region, can be mutated or engineered to produce variants or derivatives with, e.g., silent mutations, conservative mutations, etc. In a further preferred aspect, silent nucleotide changes in the polyprotein coding regions (i.e., variations of the first, second or third base of a codon leading to a new codon that encodes the same amino acid) are incorporated as markers of specific HCV clones.

Thus, one aspect of the present invention relates to any of the amino acid sequences disclosed herein, such as but not limited to SEQ ID NO: 2.

In yet an embodiment the isolated nucleic acid molecule encodes the amino acid sequence with a sequence identity of at least 90% to that of SEQ ID NO: 2.

In another embodiment, the amino acid sequences comprises a sequence sharing at least 90% identity with that set forth in SEQ ID NO: 2, such as 90% identity, 91% identity, 92% identity, 93% identity, 94% identity, 95% identity, 96% identity, 97% identity, 98% identity, or 99% identity.

It is to be understood that a sequence identity of at least 90%, such as 90% identity, 91% identity, 92% identity, 93% identity, 94% identity, 95% identity, 96% identity, 97% identity, 98% identity, or 99% identity applies to all sequences disclosed in the present application.

In one embodiment of the present invention the invention pertains to an isolated nucleotide acid molecule which encodes a JFH-1 based intergenotypic HCV chimera, wherein said molecule is capable of expressing said virus when transfected into cells and wherein said molecule encodes the amino acid sequence of the Core, E1, E2, p7 and NS2 of SEQ ID NO: 21 and that of NS3, NS4A, NS4B, NS5A, NS5B of SEQ ID NO: 22 or an amino acid sequence with a sequence identity of at least 90% over the whole of each of said sequences.

In another embodiment, the amino acid sequence comprises a sequence sharing at least 90% identity with the Core-NS2 sequence set forth in SEQ ID NO: 21, such as 90% identity, 91% identity, 92% identity, 93% identity, 94% identity, 95% identity, 96% identity, 97% identity, 98% identity, or 99% identity.

In another embodiment, the amino acid sequence comprises a sequence sharing at least 90% identity with the NS3-NS5B sequence set forth in SEQ ID NO: 22, such as 90% identity, 91% identity, 92% identity, 93% identity, 94% identity, 95% identity, 96% identity, 97% identity, 98% identity, or 99% identity.

In one embodiment of the present invention the invention pertains to an isolated nucleic acid molecule which encodes a JFH-1 based intergenotypic HCV chimera, wherein said molecule is capable of expressing said virus when transfected into cells and wherein said molecule encodes the nucleic acid sequence of the Core, E1, E2, p7 and NS2 of SEQ ID NO: 23 and that of 5' UTR, NS3, NS4A, NS4B, NS5A, NS5B and 3' UTR of SEQ ID NO: 24 or a nucleic acid sequence with a sequence identity of at least 90% over the whole of each of said sequences.

In another embodiment, the nucleic acid sequence comprises a sequence sharing at least 90% identity with the Core-NS2 sequence set forth in SEQ ID NO: 23, such as 90% identity, 91% identity, 92% identity, 93% identity, 94% identity, 95% identity, 96% identity, 97% identity, 98% identity, or 99% identity.

In another embodiment, the nucleic acid sequence comprises a sequence sharing at least 90% identity with the 5'UTR, NS3-NS5B, and 3'UTR sequence set forth in SEQ ID NO: 24, such as 90% identity, 91% identity, 92% identity, 93% identity, 94% identity, 95% identity, 96% identity, 97% identity, 98% identity, or 99% identity.

In another embodiment the sequence identity is calculated on the sequence of the Core, E1, E2, p7 and NS2 from QC69.

In another embodiment the sequence identity is calculated on the sequence of the 5' UTR, NS3, NS4A, NS4B, NS5A, NS5B and 3' UTR from JFH1.

SEQ ID NO: 23 can also be found deposited in genbank with the accession number: EF108306. It contains the partial 5'UTR, complete ORF (Core, E1, E2, P7, NS2, NS3, NS4A, NS4B, NS5A, NS5B), and the partial 3'UTR of genotype 7a isolate QC69.

SEQ ID NO: 24 can also be found deposited in genbank with the accession number: AB047639. It contains the complete 5'UTR, complete ORF (Core, E1, E2, P7, NS2, NS3, NS4A, NS4B, NS5A, NS5B), and the complete 3'UTR of genotype 2a isolate JFH1.

Nucleic acid molecules according to the present invention may be inserted in a plasmid vector for translation of the corresponding HCV RNA. Thus, the HCV DNA may comprise a promoter 5' of the 5'-UTR on positive-sense DNA, whereby transcription of template DNA from the promoter produces replication-competent RNA. The promoter can be selected from the group consisting of a eukaryotic promoter, yeast promoter, plant promoter, bacterial promoter, or viral promoter.

In one embodiment the present invention provides a cassette vector for cloning viral genomes, comprising, inserted therein, the nucleic acid sequence according to the invention and having an active promoter upstream thereof.

Adaptive Mutations

Adapted mutants of a HCV-cDNA construct or HCV-RNA full-length genome with improved abilities to generate infectious viral particles in cell culture compared to the original HCV-cDNA construct or the original HCV-RNA full-length genome are characterized in that they are obtainable by a method in which the type and number of mutations in a cell culture adapted HCV-RNA genome are determined through sequence analysis and sequence comparison and these mutations are introduced into a HCV-cDNA construct, particularly a HCV-cDNA construct according to the present invention, or into an (isolated) HCV-RNA full-length genome, either by site-directed mutagenesis, or by exchange of DNA fragments containing the relevant mutations.

The present inventors here report adaptive mutations, which allow efficient formation and release of viral particles in cell culture, and thus the present invention relates to these adaptive mutations in the present use as well as use in other strains by changing equivalent positions of such genomes to the adapted nucleotide or amino acid described.

A group of preferred HCV-cDNA constructs, HCV-RNA full-length genomes with the ability to release viral particles in cell culture, which are consequently highly suitable for practical use, is characterized in that it contains one, several or all of the nucleic acid exchanges listed below and/or one or several or all of the following amino acid exchanges.

In four independent RNA transfections of Huh7.5 cells, QC69/JFH1 spread to >50% of the culture on day 3 (data not shown; FIGS. 1A, B). Passage of QC69/JFH1 yielded HCV RNA titers of ~$10^8$ IU/mL and infectivity titers of ~$10^{4.5}$ TCID$_{50}$/mL. In passaged virus recovered from all 4 transfections, no dominant coding mutations were observed. However, in 2 passages, positions with a 50/50 quasispecies of the original and a mutated sequence were observed, G809T (V157F) (Core) and T1581C (I414T) (E2), or T2985C (L882P) (NS2) and C8421T(A2694V) (NS5B), respectively (Table 2). In reverse genetic studies, QC69/JFH1 viruses containing G809T (V157F), T1581C (I414T), T2985C (L882P) and C8421T (A2694V), singly or in combinations had similar spread kinetics and infectivity titers as the 3a/JFH1 reference virus S52/JFH1$_{1793S,K1404Q}$, whereas kinetics of the original QC69/JFH1 were delayed (data not shown; FIGS. 1A, B). In analysis of passaged viruses, none of the recombinants had amino acid changes, but positions that had evidence of a minor change were observed for both experiments with the original QC69/JFH1 and for QC69/JFH1$_{V157F}$ (Table 2). Thus, all single adaptive mutations G809T (V157F), T1581C (I414T), T2985C (L882P) and C8421T (A2694V) as well as combination of G809T (V157F) with T1581C (I414T) and T2985C (L882P) with C8421T (A2694V) led to improvement of growth kinetics. The constructs with T1581C (I414T), T2985C (L882P) and C8421T (A2694V) single mutations as well as the ones with combination of G809T (V157F) with T1581C (I414T) and T2985C (L882P) with C8421T (A2694V) were genetically stable (Table 2). Thus these single mutations/combinations of mutations are important for efficient growth characteristics of QC69/JFH1.

In the 2 other transfection experiments, QC69/JFH1 acquired other amino acid changes as minor quasispecies: QC69/JFH1 acquired after transfection and passage as minor quasispecies A1623G (N428S) (E2) (exp. 3, Table 2) and A1511G (R391G) (E2) (exp. 4, Table 2). Further QC69/JFH1$_{V157F}$ acquired after transfection and passage as minor quasispecies A6648G (Y2103C) (NS5A).

One embodiment of the present invention relates to adaptive mutations, wherein the adaptive mutation is a mutation that can be observed by clonal or direct sequencing of recovered replicating genomes of SEQ ID NO: 1.

Thus in a further embodiment, the present invention relates to nucleic acid molecules according to the present invention, wherein said molecule comprises one or more adaptive mutations in Core, E2, NS2, NS5A and NS5B singly or in combination.

In the context of the present invention the term "adaptive mutation" is meant to cover mutations identified in passaged QC69/JFH1 viruses that provide the original QC69/JFH1 and any other HCV sequence the ability to grow efficiently in culture. Furthermore all introductions of mutations into the QC69/JFH1 sequences described, whether or not yielding better growth abilities, and the introduction of these mutations into any HCV sequence should be considered.

Thus the described mutations enable the HCV-RNA genome (e.g. derived from a HCV-cDNA clone) to form viral particles in and release these from suitable cell lines. In addition some of the described mutations might change the function of the concerned proteins in favourable ways, which might be exploited in other experimental systems employing these proteins. This also includes other HCV genomes with adaptive mutations, all of them, combinations of them or individual mutations that grow in culture. In this case the titers might be lower than those listed.

It should be understood that any feature and/or aspect discussed above in connection with the mutations according to the invention apply by analogy to both single mutations and any combination of the mutations.

To test various combinations of adaptive mutations, the following constructs were made, and found to efficiently spread and produce infectious viral particles in culture after transfection: pQC69/JFH1(G809T), pQC69/JFH1(T1581C), pQC69/JFH1(T2985C) and pQC69/JFH1(C8421T) (SEQ ID NOs: 3, 5, 7 and 9 with resulting amino acid sequences SEQ ID NOs: 4, 6, 8 and 10). Further, two constructs with combinations of these mutations were made and found to efficiently spread and produce infectious viral particles in culture after transfection: pQC69/JFH1(G809T;T1581C), pQC69/JFH1(T2985C;C8421T).

Figure 1B:
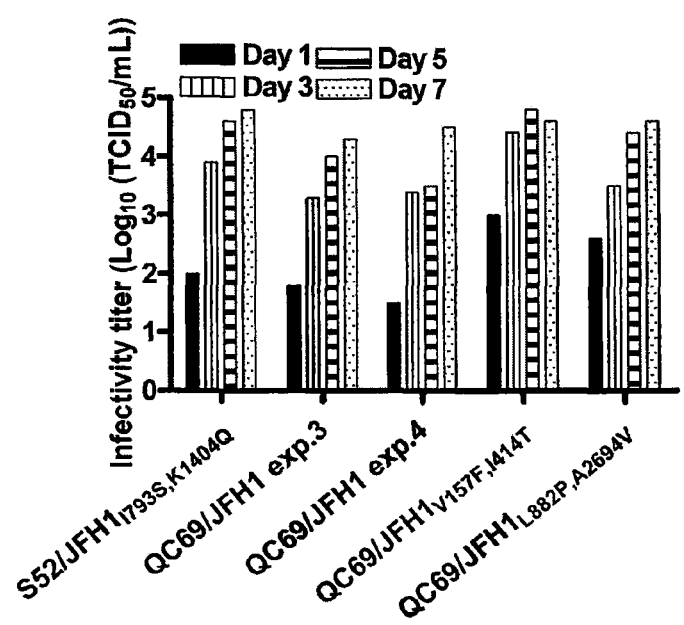

Surprisingly, QC69/JFH1 recombinants with combinations of 2 adaptive mutations, QC69/JFH1(G809T;T1581C) and QC69/JFH1(T2985C;C8421T) showed accelerated viral spread kinetics compared to QC69/JFH1 without adaptive mutations. When monitoring viral spread in transfected Huh7.5 cultures by immunostaining for HCV NS5A, QC69/JFH1(G809T;T1581C) and QC69/JFH1(T2985C;C8421T) spread to almost the complete culture on day 3 post transfection, while QC69/JFH1 infected most culture cells first on day 5 post transfection (FIG. 1A). Also QC69/JFH1(G809T; T1581C) and QC69/JFH1(T2985C;C8421T) yielded high infectivity titers earlier after transfection. Thus, infectivity titers >$10^4$TCID$_{50}$/ml were achieved on day 3 post transfection for QC69/JFH1(G809T;T1581C) and QC69/JFH1 (T2985C;C8421T). However, similar infectivity titers were first achieved on day 7 post transfection for QC69/JFH1 (FIG. 1B). Thus, adaptive mutations identified improved viral growth kinetics. Such improved growth kinetics are beneficial for further use, such as production of viral stocks for research experiments as testing of neutralizing antibodies and antivirals as well as for use in an whole virus inactivated vaccine.

When sequencing HCV genomes from the supernatant of QC69/JFH1 infected cell cultures, the following changes at the nucleotide level were observed at least once; G809T, A1511G, T1581C, A1623G, T2985C, A6648G and C8421T.

Thus, one embodiment the present invention relates to adaptive mutations, wherein said adaptive mutation is at least one of the replacements of the first said nucleotide at the said position of SEQ ID NO: 1 by the following said nucleotide selected from the group consisting of G809T, A1511G, T1581C, A1623G, T2985C, A6648G and C8421T.

In another embodiment the present invention relates to adaptive mutations, wherein said adaptive mutation is at least one of the replacements of the first said nucleotide at the said position of SEQ ID NO: 1 by the following said nucleotide selected from the group consisting of G809T, T1581C, T2985C and C8421T.

In another embodiment the present invention relates to adaptive mutations, wherein said adaptive mutation is at least one of the replacements of the first said nucleotide at the said position of SEQ ID NO: 1 by the following said nucleotide selected from the group consisting of G809T, T1581C.

In another embodiment the present invention relates to adaptive mutations, wherein said adaptive mutation is at least one of the replacements of the first said nucleotide at the said position of SEQ ID NO: 1 by the following said nucleotide selected from the group consisting of T2985C, C8421T.

In yet an embodiment the present invention relates to a nucleic acid molecule according to claim 1, wherein said molecule comprises the nucleic acid sequence with a sequence identity of at least 90% to that SEQ ID NO: 1, said nucleic acid sequence comprises at least one adaptive mutation, said adaptive mutation is at least one of the replacements of the first said nucleotide at the said position of SEQ ID NO: 1 by the following said nucleotide selected from the group consisting of G809T, A1511G, T1581C, A1623G, T2985C, A6648G and C8421T.

One embodiment of the present invention relates to adaptive mutations, wherein said adaptive mutation is a replacement of G in position 809 of SEQ ID NO: 1 with T.

One embodiment of the present invention relates to adaptive mutations, wherein said adaptive mutation is a replacement of A in position 1511 of SEQ ID NO: 1 with G.

One embodiment of the present invention relates to adaptive mutations, wherein said adaptive mutation is a replacement of T in position 1581 of SEQ ID NO: 1 with C.

One embodiment of the present invention relates to adaptive mutations, wherein said adaptive mutation is a replacement of A in position 1623 of SEQ ID NO: 1 with G.

One embodiment of the present invention relates to adaptive mutations, wherein said adaptive mutation is a replacement of T in position 2985 of SEQ ID NO: 1 with C.

One embodiment of the present invention relates to adaptive mutations, wherein said adaptive mutation is a replacement of A in position 6648 of SEQ ID NO: 1 with G.

One embodiment of the present invention relates to adaptive mutations, wherein said adaptive mutation is a replacement of C in position 8421 of SEQ ID NO: 1 with T.

In one embodiment the present invention pertains to n isolated nucleic acid molecule which encodes human hepatitis C virus of genotype 7a/JFH1, wherein said molecule:
(i) is capable of expressing said virus when transfected into cells,
(ii) is capable of infectivity in vivo,
(iii) comprises the nucleic acid sequence with a sequence identity of at least 90% to that of SEQ ID NO: 1, which
(iv) comprises at least one adaptive mutation in the nucleic acid sequence of Core, E2, NS2, NS5A and NS5B selected from the group consisting of G809T, A1511G, T1581C, A1623G, T2985C, A6648G, C8421T.

In another embodiment all the amino acid changes observed herein are provided by the present application. The skilled addressee can easily obtain the same amino acid change by mutating another base of the codon and hence all means of obtaining the given amino acid sequence is intended.

One embodiment of the present invention relates to adaptive mutations, wherein said adaptive mutation is at least one of the replacements of the first said amino acid at the said position of SEQ ID NO: 2 by the following said amino acid selected from the group consisting of V157F, R391G, I414T, N428S, L882P, Y2103C and A2694V.

In another embodiment the present invention relates to an isolated nucleic acid molecule which encodes human hepatitis C virus of genotype 7a/JFH1, wherein said molecule is capable of expressing said virus when transfected into cells and wherein said molecule encodes the amino acid sequence with a sequence identity of at least 90% to that of SEQ ID NO: 2 said amino acid sequence comprises at least one adaptive mutation, said adaptive mutation is at least one of the replacements of the first said amino acid at the said position of SEQ ID NO: 2 by the following said amino acid selected from the group consisting of V157F, R391G, I414T, N428S, L882P, Y2103C, and A2694V.

One embodiment of the present invention relates to adaptive mutations, wherein said adaptive mutation is at least one of the replacements of the first said amino acid at the said position of SEQ ID NO: 2 by the following said amino acid selected from the group consisting of V157F, I414T, L882P, and A2694V.

In another embodiment the present invention relates to adaptive mutations, wherein said adaptive mutation is at least one of the replacements of the first said amino acid at the said position of SEQ ID NO: 2 by the following said nucleotide selected from the group consisting of V157F, I414T.

In another embodiment the present invention relates to adaptive mutations, wherein said adaptive mutation is at least one of the replacements of the first said amino acid at the said position of SEQ ID NO: 2 by the following said nucleotide selected from the group consisting of L882P and A2694V.

Another embodiment of the present invention relates said adaptive mutation is a replacement of V in position 157 of SEQ ID NO: 2 with F.

Another embodiment of the present invention relates said adaptive mutation is a replacement of R in position 391 of SEQ ID NO: 2 with G.

Another embodiment of the present invention relates said adaptive mutation is a replacement of I in position 414 of SEQ ID NO: 2 with T.

Another embodiment of the present invention relates said adaptive mutation is a replacement of N in position 428 of SEQ ID NO: 2 with S.

Another embodiment of the present invention relates said adaptive mutation is a replacement of L in position 882 of SEQ ID NO: 2 with P.

Another embodiment of the present invention relates said adaptive mutation is a replacement of Y in position 2103 of SEQ ID NO: 2 with C.

Another embodiment of the present invention relates said adaptive mutation is a replacement of A in position 2694 of SEQ ID NO: 2 with V.

In one embodiment the present invention pertains to an isolated nucleic acid molecule which encodes human hepatitis C virus of genotype 7a/JFH1, wherein said molecule:
(i) is capable of expressing said virus when transfected into cells,
(ii) is capable of infectivity in vivo,
(iii) encodes the amino acid sequence with a sequence identity of at least 90% to that of SEQ ID NO: 2, which
(iv) comprises at least one adaptive mutation in the amino acid sequence of Core, E2, NS2, NS5A and NS5B selected from the group consisting of V157F, R391G, I414T, N428S, L882P, Y2103C and A2694V.

Titer

To determine the efficiency of the developed system, HCV RNA titers are determined in IU/ml (international units/ml) with Taq-Man Real-Time-PCR and infectious titers are determined with a 50% tissue culture infectious dose method. This titer shows the dilution of the examined viral stock, at which 50% of the replicate cell cultures used in the essay become infected and is given in $TCID_{50}$/ml. Alternatively the infectious titers are determined as FFU/ml (focus forming unites/ml) (Table 4); in this method, infectivity titers are determined by infection of cell culture replicates with serial dilutions of virus containing supernatants and, following immuno-stainings for HCV antigens, counting of HCV-antigen positive cell foci.

HCV RNA titers and infectivity titers can be determined extracellularly, in cell culture supernatant (given as IU and $TCID_{50}$ or FFU per ml, respectively) or intracellularly, in lysates of pelleted cells (given as IU and $TCID_{50}$ or FFU related to a the given cell number, which was lysed).

One embodiment of the present invention relates to a nucleic acid molecule of the present invention, wherein said molecule is capable of generating a HCV RNA titer of $10^4$ IU/ml or above following transfection and/or subsequent viral passage, such as a titer of at least $10^5$ IU/mL, such as a titer of at least $10^6$ IU/mL, such as a titer of at least $10^7$ IU/mL, such as a titer of at least $10^8$ IU/mL, such as a titer of at least $10^9$ IU/mL, such as a titer of at least $10^{10}$ IU/mL, such as a titer of at least $10^{11}$ IU/mL, or such as a titer of at least $10^{12}$ IU/mL.

In another embodiment, the present invention relates to a nucleic acid molecule according to the invention, wherein said molecule is capable of generating a HCV infectivity titer of at least $10^2$ $TCID_{50}$/ml or above following transfection and/or subsequent viral passage, such as a titer of at least $10^3$ TCID50/ml, such as a titer of at least $10^4$ $TCID_{50}$/ml, such as a titer of at least $10^5$ $TCID_{50}$/ml, such as a titer of at least $10^6$ $TCID_{50}$/ml, such as a titer of at least $10^7$ $TCID_{50}$/ml, such as a titer of at least $10^8$ $TCID_{50}$/ml, such as a titer of at least $10^9$ $TCID_{50}$/ml or such as a titer of at least $10^{10}$ $TCID_{50}$/ml.

It is of course evident to the skilled addressee that the titers described here are obtained using the assay described in this text. Any similar or equivalent titer determined by any method is thus evidently within the scope of the present invention.

Compositions

One embodiment of the present invention relates to a composition comprising a nucleic acid molecule according to the invention suspended in a suitable amount of a pharmaceutical acceptable diluent or excipient.

In another embodiment, this invention provides for compositions comprising an isolated nucleic acid, vector or cell of this invention, or an isolated nucleic acid obtained via the methods of this invention.

In one embodiment, the term "composition" refers to any such composition suitable for administration to a subject, and such compositions may comprise a pharmaceutically acceptable carrier or diluent, for any of the indications or modes of administration as described. The active materials in the compositions of this invention can be administered by any appropriate route, for example, orally, parenterally, intravenously, intradermally, subcutaneously, or topically, in liquid or solid form.

It is to be understood that any applicable drug delivery system may be used with the compositions and/or agents/vectors/cells/nucleic acids of this invention, for administration to a subject, and is to be considered as part of this invention.

The compositions of the invention can be administered as conventional HCV therapeutics. The compositions of the invention may include more than one active ingredient which interrupts or otherwise alters groove formation, or occupancy by RNA or other cellular host factors, in one embodiment, or replicase components, in another embodiment, or zinc incorporation, in another embodiment.

The precise formulations and modes of administration of the compositions of the invention will depend on the nature of the anti-HCV agent, the condition of the subject, and the judgment of the practitioner. Design of such administration and formulation is routine optimization generally carried out without difficulty by the practitioner.

It is to be understood that any of the methods of this invention, whereby a nucleic acid, vector or cell of this invention is used, may also employ a composition comprising the same as herein described, and is to be considered as part of this invention.

"Pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans.

The term "excipient" refers to a diluent, adjuvant, carrier, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The term "adjuvant" refers to a compound or mixture that enhances the immune response to an antigen. An adjuvant can serve as a tissue depot that slowly releases the antigen and also as a lymphoid system activator that non-specifically enhances the immune response. Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvmm*. Preferably, the adjuvant is pharmaceutically acceptable.

Cells

The nucleotides of the present invention may be used to provide a method for identifying additional cell lines that are permissive for infection with HCV, comprising contacting (e.g. transfecting) a cell line in tissue culture with an infectious amount of HCV RNA of the present invention, e.g., as produced from the plasmid clones, and detecting replication and formation and release of viral particles of HCV in cells of the cell line.

Naturally, the invention extends as well to a method for identifying an animal that is permissive for infection with HCV, comprising introducing an infectious amount of the HCV RNA, e.g., as produced by the plasmids, to the animal, and detecting replication and formation and release of viral particles of HCV in the animal. By providing infectious HCV, e.g. comprising a dominant selectable marker, the invention further provides a method for selecting for HCV with further adaptive mutations that permit higher levels of HCV replication in a permissive cell line or animal comprising contacting (e.g. transfecting) a cell line in culture, or introducing into an animal, an infectious amount of the HCV RNA, and detecting progressively increasing levels of HCV RNA and infectious HCV viral particles in the cell line or the animal.

In a specific embodiment, the adaptive mutation permits modification of HCV tropism. An immediate implication of this aspect of the invention is creation of new valid cell culture and animal models for HCV infection.

The permissive cell lines or animals that are identified using the nucleic acids of the invention are very useful, inter alia, for studying the natural history of HCV infection, isolating functional components of HCV, and for sensitive, fast diagnostic applications, in addition to producing authentic HCV virus or components thereof.

Because the HCV DNA, e.g., plasmid vectors, of the invention encode HCV components, expression of such vectors in a host cell line transfected, transformed, or transduced with the HCV DNA can be effected.

For example, a baculovirus or plant expression system can be used to express HCV virus particles or components thereof. Thus, a host cell line may be selected from the group consisting of a bacterial cell, a yeast cell, a plant cell, an insect cell, and a mammalian cell.

In one embodiment, the cell is a hepatocyte, or in another embodiment, the cell is the Huh-7 hepatoma cell line or a derived cell line such as Huh7.5, Huh7.5.1 cell line.

In one embodiment, the cell, or in another embodiment, cell systems of this invention comprise primary cultures or other, also non hepatic cell lines. "Primary cultures" refers, in one embodiment, to a culture of cells that is directly derived from cells or tissues from an individual, as well as cells derived by passage from these cells, or immortalized cells.

In one embodiment, "cell line" refers to a population of cells capable of continuous or prolonged growth and division in vitro. The term "cell lines" also includes immortalized cells. Often, cell lines are clonal populations derived from a single progenitor cell. Such cell lines are also termed "cell clones". It is further known in the art that spontaneous or induced changes can occur in karyotype during storage or transfer of such clonal populations. Therefore, cells derived from the cell clones referred to may not be precisely identical to the ancestral cells or cultures. According to the present invention, such cell clones may be capable of supporting replication of a vector, virus, viral particle, etc., of this invention, without a significant decrease in their growth properties, and are to be considered as part of this invention.

It is to be understood that any cell of any organism that is susceptible to infection by or propagation of an HCV construct, virus or viral particle of this invention is to be considered as part of this invention, and may be used in any method of this invention, such as for screening or other assays, as described herein.

Thus in one embodiment the present invention relates to a method for producing a cell which replicates HCV 7a/JFH1 RNA and produces a virus particle comprising introducing the said RNA according to the invention into a cell.

In another embodiment the present invention pertains to a method for producing a cell, which replicates an RNA comprising the structural genes (Core, E1, E2), p7 and the non-structural gene NS2 of genotype 7a strain, QC69, and the non-structural genes NS3, NS4A, NS4B, NS5A and NS5B from the JFH1 strain and produces a virus particle comprising introducing the said RNA into a cell wherein said RNA encodes an amino acid sequence comprising at least one adaptive mutation, said adaptive mutation is at least one of the replacements of the first said amino acid at the said position of SEQ ID NO: 2 by the following said amino acid selected from the group consisting of V157F, R391G, I414T, N428S, L882P, Y2103C and A2694V.

In a further embodiment the present invention relates to a method for producing a cell, which replicates HCV 7a/JFH1 and produces a virus particle comprising:
(i) introducing a nucleic acid molecule into a cell, wherein said nucleic acid molecule comprises at least 90% identity to that of SEQ ID NO: 1, which
(ii) comprises at least one adaptive mutation in the nucleic acid sequence of Core, E2, NS2, NS5A and NS5B.

In another embodiment the present invention relates to a method for producing a cell, which replicates HCV 7a/JFH1 and produces a virus particle comprising:
(i) introducing a nucleic acid molecule into a cell, wherein said nucleic acid molecule comprises at least 90% identity to that of SEQ ID NO: 1, which
(ii) comprises at least one adaptive mutation in the nucleic acid sequence of Core, E2, NS2, NS5A and NS5B selected from the group consisting of G809T, A1511G, T1581C, A1623G, T2985C, A6648G, C8421T.

In one embodiment the 7a strain is QC69.

Also, a method for in vitro producing a hepatitis C virus-infected cell comprising culturing the cell which produces virus particles of the present invention and infecting other cells with the produced virus particle in the culture.

Naturally, the invention extends to any cell obtainable by such methods, for example any in vitro cell line infected with HCV, wherein the HCV has a genomic RNA sequence as described herein such as a hepatitis C virus infected cell obtainable by any of the methods described.

In one embodiment, the cell line is a hepatocyte cell line such as Huh7 or derived cell lines e.g. Huh7.5 or Huh7.5.1.

In another embodiment the cell is Huh7.5.

In another embodiment the cell is any cell expressing the genes necessary for HCV infection and replication, such as but not limited to CD81, SR-BI, Claudin-1, -4, -6 or -9 and the low-density lipid receptor.

Importance of CD81 for HCV entry has in previous studies been shown for pseudoviral particles (HCVpp) of genotypes 1-6, and for cell culture derived HCV (HCVcc) of genotypes 1a (H77), 1b (Con-1), 3a (S52), 4a (ED43) and 5a (SA13). Blocking of SR-BI receptors was found to inhibit infection with HCVpp of genotypes 1-6. In the HCVcc system, genotypes 2a and 5a in previous studies depended on SR-BI. In comparative studies, the present investigators showed that entry of genotype 7a was efficiently inhibited when relative high doses of blocking antibodies against the respective HCV co-receptor were used (FIG. 2). Thus, CD81 and SR-BI play an important role for entry of prototype isolates of the seven major genotypes.

The invention further provides various methods for producing HCV virus particles, including by isolating HCV virus particles from the HCV-infected non-human animal of invention; culturing a cell line of the invention under conditions that permit HCV replication and virus particle formation; or culturing a host expression cell line transfected with HCV DNA under conditions that permit expression of HCV particle proteins; and isolating HCV particles or particle proteins from the cell culture. The present invention extends to an HCV virus particle comprising a replication-competent HCV genome RNA, or a replication-defective HCV genome RNA, corresponding to an HCV nucleic acid of the invention as well.

Virus Particle

The production of authentic virus proteins (antigens) may be used for the development and/or evaluation of diagnostics.

The cell culture system according to the invention also allows the expression of HCV antigens in cell cultures. In principle these antigens can be used as the basis for diagnostic detection methods.

The production of HCV viruses and virus-like particles, in particular for the development or production of therapeutics and vaccines as well as for diagnostic purposes is an embodiment of the present invention. Especially cell culture adapted complete HCV genomes, which could be produced by using the cell culture system according to the invention, are able to replicate and form viral particles in cell culture with high efficiency. These genomes have the complete functions of HCV and in consequence they are able to produce infectious viruses.

Thus in one embodiment the present invention relates to a method for producing a hepatitis C virus particle of the present invention or parts thereof, comprising culturing a cell or an animal to allow either to produce the virus.

In another embodiment the inventions provides a hepatitis C virus particle obtainable by the method described.

Because the invention provides, inter alia, infectious HCV RNA, the invention provides a method for infecting an animal with HCV which comprises administering an infectious dose of HCV RNA, such as the HCV RNA transcribed from the plasmids described above, to the animal. Naturally, the invention provides a non-human animal infected with HCV of the invention, which non-human animal can be prepared by the foregoing methods.

A further advantage of the present invention is that, by providing a complete functional HCV genome, authentic HCV viral particles or components thereof, which may be produced with native HCV proteins or RNA in a way that is not possible in subunit expression systems, can be prepared.

In addition, since each component of HCV of the invention is functional (thus yielding the authentic HCV), any specific HCV component is an authentic component, i.e., lacking any errors that may, at least in part, affect the clones of the prior art. Indeed, a further advantage of the invention is the ability to generate HCV virus particles or virus particle proteins that are structurally identical to or closely related to natural HCV virions or proteins. Thus, in a further embodiment, the invention provides a method for propagating HCV in vitro comprising culturing a cell line contacted with an infectious amount of HCV RNA of the invention, e.g., HCV RNA translated from the plasmids described above, under conditions that permit replication of the HCV RNA.

Further the viability of the developed viruses may be determined in vivo, either in SCID-uPA mice engrafted with human liver tissue or in chimpanzees as shown in Lindenbach et al. 2006.

In one embodiment, the method further comprises isolating infectious HCV. In another embodiment, the method further comprises freezing aliquots of said infectious HCV. According to this aspect of the invention, and in one embodiment, the HCV is infectious following thawing of said aliquots, and in another embodiment, the HCV is infectious following repeated freeze-thaw cycles of said aliquots.

Screening for anti-viral drugs and the determination of drug resistance.

It can be assumed that resistance to therapy occurs due to the high mutation rate of the HCV genome. This resistance, which is very important for the clinical approval of a substance, can be detected with the cell culture system according to the invention. Cell lines, in which the HCV-RNA construct or the HCV genome or subgenome replicates and produces infectious viral particles, are incubated with increasing concentrations of the relevant substance and the replication of the viral RNA is either determined by means of an introduced reporter gene or through the qualitative or quantitative detection of the viral nucleic acids or proteins. The release of viral particles is determined by measuring HCV RNA and infectivity titers in the cell culture supernatant. Resistance is given if no or a reduced inhibition of the replication and release of viral particles can be observed with the normal concentration of the active substance. The nucleotide and amino acid replacements responsible for the therapy resistance can be determined by recloning the HCV-RNA (for example by the means of RT-PCR) and sequence analysis. By cloning the relevant replacement(s) into the original construct its causality for the resistance to therapy can be proven.

While the replicon systems facilitated testing of drugs interfering with replication such as NS3/4A protease and polymerase inhibitors, the variant genomes obtained in the present invention may prove useful for different research topics. Genomes with the original QC69 Core could be applied to examine genotype 7a specific features of Core.

The systems developed in this invention are ideal candidates for genotype 7a specific testing of therapeutics in general and therapeutics targeting viral entry, assembly and release. Genomes with the QC69 sequences are valuable for testing of neutralizing antibodies and other drugs acting on entry level, such as fusion inhibitors.

The present inventors conducted cross-genotype neutralization studies in HCV cell culture systems recapitulating the entire viral life cycle using JFH1-based viruses with envelope sequences of all 7 major genotypes, and important subtypes 1b and 2b, which has previously not been possible. HCV E1/E2 assembled on HCV pseudo particles (HCVpp), used in previous neutralization studies could show an unphysiological confirmation, glycosylation pattern and/or lipoprotein association due to the nature of the HCVpp as well as the non-hepatic producer cell-lines used in such experiments.

In such studies the viral particles are incubated with the neutralizing substance, e.g. patient derived antibodies present in serum, prior to incubation with cells permissive and susceptible to viral infection. The neutralizing effect, i.e. the inhibitory effect on viral entry, is measured e.g. by relating the number of focus forming units (FFUs, defined as foci of adjacent infected cells) to the equivalent count in a control experiment done under same circumstances without the active inhibitor molecule.

The inventors of the present invention showed that JFH1-based viruses of the genotype 1a, 1b, 2b, 4a, 5a, 6a and 7a were efficiently neutralized by chronic phase H06 genotype 1a serum derived from reference Patient H (Table 3). The results in the cell culture systems compare well to neutralization experiments using Patient H serum from year 26 (H03) carried out in HCVpp systems with envelope proteins of the same prototype isolates of all 6 HCV genotypes as used in the present application, and heterogeneity between the genotypes is thus as previously reported by Meunier et al. 2005.

In addition the present inventors found that cross-genotype neutralization extended to a chronic phase genotype 4a serum (AA), which efficiently neutralized genotype 2b, 4a, 5a, 6a and 7a (Table 3). Also, the cross-genotype neutralization extended to a chronic phase genotype 5a serum (SA3), which efficiently neutralized genotype 2b, 4a, 5a, 6a and 7a (Table 3). Accordingly, the JFH1-based cell culture systems which have been developed for HCV genotype 1a, 1b, 2a, 2b, 3a, 4a, 5a, 6a and 7a provide a valuable tool for efficiently screening for and identifying new candidate HCV genotype 1a, 1b, 2a, 2b, 3a, 4a, 5a, 6a and 7a inhibitors e.g. of entry e.g. in serum derived from infected patients. Accordingly this invention, allows identification and raise of cross-neutralizing antibodies, which is important for the development of active and passive immunization strategies. Furthermore the availability of cell culture grown HCV particles bearing envelope proteins of the seven major genotypes and important subtypes enables the development of inactivated whole virus vaccines and comprehensive virus neutralization studies.

In one embodiment the present invention relates to a method for identifying neutralizing antibodies.

In another one embodiment the present invention relates to a method for identifying cross-genotype neutralizing antibodies.

In one embodiment the present invention relates to a method of raising neutralizing antibodies.

In another embodiment the present invention relates to a method of raising cross neutralizing antibodies.

In one embodiment the present invention related to a method for screening new HCV genotype 1a, 1b, 2a, 2b, 3a, 4a, 5a, 6a and/or 7a inhibitors or neutralizing antibodies, comprising
- a) culturing at least one selected from the group consisting of a cell according to the present invention, a hepatitis C virus infected cell according to the present invention and a hepatitis C virus particle obtainable by the present invention together with a hepatitis C virus permissive cell, and
- b) subjecting said virus or virus infected cell culture to a blood sample or derivatives thereof from a HCV genotype 1a, 1b, 2a, 2b, 3a, 4a, 5a, 6a and/or 7a infected patient
- c) detecting the amount of replicating RNA and/or the virus particles.

The p7 peptide features two transmembrane domains (TM1 and TM2), and p7 monomers multimerize to form a putative ion channel. Additionally p7 has been shown to contain genotype specific sequences required for genotype specific interactions between p7 and other HCV proteins. Hence, new compounds targeting the putative p7 ion-channel and autoprotease inhibitors interfering with NS2, and drugs targeting cellular proteins involved in the described processes can be tested.

Thus, one embodiment of the present invention relates to a method for screening an anti-hepatitis C virus substance, comprising
- a) culturing at least one selected from the group consisting of a cell according to the present invention, a hepatitis C virus infected cell according to the present invention and a hepatitis C virus particle obtainable by the present invention together with a hepatitis C virus permissive cell,
- b) subjecting said virus or virus infected cell culture to the anti-hepatitis C virus substance, and
- c) detecting the replicating RNA and/or the virus particles in the resulting culture.

In another embodiment, the inhibition of HCV replication and/or infection and/or pathogenesis includes inhibition of downstream effects of HCV. In one embodiment, downstream effects include neoplastic disease, including, in one embodiment, the development of hepatocellular carcinoma.

In one embodiment, the invention provides a method of screening for anti-HCV therapeutics, the method comprising contacting a cell with an isolated nucleic acid molecule encoding an infectious recombinant HCV genome, comprising a chimeric HCV genome and contacting the cell with a candidate molecule, independently contacting the cell with a placebo and determining the effects of the candidate molecule on HCV infection, replication, or cell-to-cell spread, versus the effects of the placebo, wherein a decrease in the level of HCV infection, replication, or cell-to-cell spread indicates the candidate molecule is an anti-HCV therapeutic.

In one embodiment, the method may be conducted be in vitro or in vivo. In one embodiment, the cells as described may be in an animal model, or a human subject, entered in a clinical trial to evaluate the efficacy of a candidate molecule. In one embodiment, the molecule is labelled for easier detection, including radio-labelled, antibody labelled for fluorescently labelled molecules, which may be detected by any means well known to one skilled in the art.

In one embodiment, the candidate molecule is an antibody.

In one embodiment, the term "antibody" refers to intact molecules as well as functional fragments thereof, such as Fab, F(ab')2, and Fv. In one embodiment, the term "Fab" refers to a fragment, which contains a monovalent antigen-binding fragment of an antibody molecule, and in one embodiment, can be produced by digestion of whole antibody with the enzyme papain to yield an intact light chain and a portion of one heavy chain, or in another embodiment can be obtained by treating whole antibody with pepsin, followed by reduction, to yield an intact light chain and a portion of the heavy chain. In one embodiment, the term "F(ab')2", refers to the fragment of the antibody that can be obtained by treating whole antibody with the enzyme pepsin without subsequent reduction, F(ab')2 is a dimer of two Fab' fragments held together by two disulfide bonds. In another embodiment, the term "Fv" refers to a genetically engineered fragment containing the variable region of the light chain and the variable region of the heavy chain expressed as two chains, and in another embodiment, the term "single chain antibody" or "SCA" refers to a genetically engineered molecule containing the variable region of the light chain and the variable region of the heavy chain, linked by a suitable polypeptide linker as a genetically fused single chain molecule.

Methods of producing these fragments are known in the art.

In another embodiment, the candidate molecule is a small molecule. In one embodiment, the phrase "small molecule" refers to, inter-alia, synthetic organic structures typical of pharmaceuticals, peptides, nucleic acids, peptide nucleic acids, carbohydrates, lipids, and others, as will be appreciated by one skilled in the art. In another embodiment, small molecules, may refer to chemically synthesized peptidomimetics of the 6-mer to 9-mer peptides of the invention.

In another embodiment, the candidate molecule is a nucleic acid. Numerous nucleic acid molecules can be envisioned for use in such applications, including antisense, siRNA, ribozymes, etc., as will be appreciated by one skilled in the art.

It is to be understood that the candidate molecule identified and/or evaluated by the methods of this invention, may be any compound, including, inter-alia, a crystal, protein, peptide or nucleic acid, and may comprise an HCV viral product or derivative thereof, of a cellular product or derivative thereof. The candidate molecule in other embodiments may be isolated, generated synthetically, obtained via translation of sequences subjected to any mutagenesis technique, or obtained via protein evolution techniques, well known to those skilled in the art, each of which represents an embodiment of this invention, and may be used in the methods of this invention, as well.

In one embodiment, the compound identified in the screening methods as described, may be identified by computer modeling techniques, and others, as described herein. Verification of the activity of these compounds may be accomplished by the methods described herein, where, in one embodiment, the test compound demonstrably affects HCV infection, replication and/or pathogenesis in an assay, as described. In one embodiment, the assay is a cell-based assay, which, in one embodiment, makes use of primary isolates, or in another embodiment, cell lines, etc. In one embodiment, the cell is within a homogenate, or in another embodiment, a tissue slice, or in another embodiment, an organ culture. In one embodiment, the cell or tissue is hepatic in origin, or is a derivative thereof. In another embodiment, the cell is a commonly used mammalian cell line, which has been engineered to express key molecules known to be, or in another embodiment, thought to be involved in HCV infection, replication and/or pathogenesis.

In another embodiment, protein, or in another embodiment, peptide or in another embodiment, other inhibitors of the present invention cause inhibition of infection, replication, or pathogenesis of HCV in vitro or, in another embodiment, in vivo when introduced into a host cell containing the virus, and may exhibit, in another embodiment, an IC50 in the range of from about 0.0001 nM to 100 μM in an in vitro assay for at least one step in infection, replication, or pathogenesis of HCV, more preferably from about 0.0001 nM to 75 μM, more preferably from about 0.0001 nM to 50 μM, more preferably from about 0.0001 nM to 25 μM, more preferably from about 0.0001 nM to 10 μM, and even more preferably from about 0.0001 nM to 1 μM.

In another embodiment, the inhibitors of HCV infection, or in another embodiment, replication, or in another embodiment, pathogenesis, may be used, in another embodiment, in ex vivo scenarios, such as, for example, in routine treatment of blood products wherein a possibility of HCV infection exists, when serology shows a lack of HCV infection.

In another embodiment, the anti-HCV therapeutic compounds identified via any of the methods of the present invention can be further characterized using secondary screens in cell cultures and/or susceptible animal models. In one embodiment, a small animal model may be used, such as, for example, a tree shrew Tupaia belangeri chinensis. In another embodiment, an animal model may make use of a chimpanzee. Test animals may be treated with the candidate compounds that produced the strongest inhibitory effects in any of the assays/methods of this invention. In another embodiment, the animal models provide a platform for pharmacokinetic and toxicology studies.

Vaccines

The construct according to the invention by itself can also be used for various purposes in all its embodiments. This includes the construction of hepatitis C viruses or HCV-like particles and their production in cell cultures as described.

These HCV or HCV-like particles can be used in particular as vaccine. Thus, one embodiment of the present invention relates to a hepatitis C vaccine comprising a hepatitis C virus particle according to the invention or a part thereof.

In another embodiment, the nucleic acids, vectors, viruses, or viral particles may be further engineered to express a heterologous protein, which, in another embodiment, is mammalian or a derivative thereof, which is useful in combating HCV infection or disease progression. Such proteins may comprise cytokines, growth factors, tumor suppressors, or in one embodiment, may following infection, be expressed predominantly or exclusively on an infected cell surface. According to this aspect of the invention, and in one embodiment, such molecules may include costimulatory molecules, which may serve to enhance immune response to infected cells, or preneoplastic cells, or neoplastic cells, which may have become preneoplastic or neoplastic as a result of HCV infection. In one embodiment, the heterologous sequence encoded in the nucleic acids, vectors, viruses, or viral particles of this invention may be involved in enhanced uptake of a nucleic acids, vectors, viruses, or viral particles, and may specifically target receptors thought to mediate HCV infection.

Further, the present invention relates to a method for producing a hepatitis C virus vaccine comprising using a hepatitis C virus particle according to the invention as an antigen, and naturally any antibody against such hepatitis C virus particle.

Uses

The genotype 7a cell culture system developed of the present invention will be a valuable tool to address different research topics. It will allow the genotype specific study of functions of the structural proteins (Core, E1, E2) as well as p7 and NS2 using reverse genetics. While the replicon systems facilitated testing of drugs interfering with replication such as NS3/4A protease and polymerase inhibitors, the system developed in this study is ideal for the genotype 7 specific testing of new drugs, such as drugs interfering with viral entry, such as fusion inhibitors, as well as assembly and release.

Accordingly the genotype 7a developed cell culture systems allows individual patient targeting. This means that when a new potential therapeutic candidate is discovered it is possible to test this particular candidate or combination of candidates on this genotype. Knowing which specific genotype the candidate is functioning towards, it allows an individual treatment of each patient dependent on which specific genotype the patient is infected with. Furthermore these cell culture systems allow the development of antibodies and vaccines targeting individual patients.

In addition new therapeutics targeting the putative p7 ion-channel and protease inhibitors targeting NS2 can be tested specifically for genotype 7 thus allowing individual patient targeting.

QC69/JFH1 recombinant viruses will be well suited for screenings for broadly reactive neutralizing antibodies, thus aiding vaccine development.

The replication level of a virus can be determined, in other embodiments, using techniques known in the art, and in other embodiments, as exemplified herein. For example, the genome level can be determined using RT-PCR. To determine the level of a viral protein, one can use techniques including ELISA, immunoprecipitation, immunofluorescence, EIA, RIA, and Western blotting analysis. To determine the replication rate of a virus, one can use the method described in, e.g., Billaud et al., Virology 266 (2000) 180-188.

In one embodiment, the invention provides a method of identifying sequences in HCV associated with HCV pathogenicity, comprising contacting cells with an isolated nucleic acid molecule encoding an infectious recombinant HCV genome, comprising a chimeric HCV genome, contacting cells with an isolated nucleic acid molecule comprising at least one mutation of the chimeric HCV genome, independently culturing the cells and determining HCV infection, replication, or cell-to-cell spread, in cells contacted with the mutant, versus the chimeric HCV, whereby changes in HCV infection, replication, or cell-to-cell spread in cells contacted with the mutant virus shows the mutation is in an HCV sequence associated with HCV pathogenicity.

In one embodiment, the invention provides a method of identifying HCV variants with improved growth in cell culture, the method comprising contacting cells with an isolated nucleic acid molecule encoding an infectious recombinant HCV genome, comprising a chimeric HCV genome contacting cells with an isolated nucleic acid molecule comprising at least one mutation of the chimeric HCV genome, independently culturing the cells and determining HCV infection, replication, or cell-to-cell spread, in cells contacted with the chimeric HCV or the mutated virus, whereby enhanced HCV infection, replication, or cell-to-cell spread in cells contacted with the mutated virus shows that the HCV variant has improved growth in cell culture. In some embodiments, HCV variants are selected for enhanced replication, over a long course of time, in vitro culture systems. According to this aspect of the invention, and in some embodiments, cells contacted with the variants are characterized by reduced infection, as compared to cells contacted with the chimeric HCV.

Kits

In a related aspect, the invention also provides a test kit for HCV comprising HCV virus components, and a diagnostic test kit for HCV comprising components derived from an HCV virus as described herein.

Furthermore the invention also provide test kits, for screening for new HCV genotype 7a inhibitors, neutralizing and cross neutralizing antibodies, comprising HCV virus components.

General

Reference to any prior art in this specification is not, and should not be taken as, an acknowledgment or any form of suggestion that this prior art forms part of the common general knowledge in any country.

All patent and non-patent references cited in the present application, are hereby incorporated by reference in their entirety.

As will be apparent, preferred features and characteristics of one aspect of the invention may be applicable to other aspects of the invention. The invention may be embodied in other specific forms without departing from the spirit or essential characteristics thereof. The foregoing embodiments are therefore to be considered in all respects illustrative rather than limiting on the invention described herein. Scope of the invention is thus showed be the appended claims rather than by the foregoing description, and all changes that come within the meaning and range of equivalency of the claims are intended to be embraced by reference therein.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In addition, singular reference does not exclude a plurality. Thus, references to "a", "an", "first", "second" etc. do not preclude a plurality.

The invention may be embodied in other specific forms without departing from the spirit or essential characteristics thereof. The foregoing embodiments are therefore to be considered in all respects illustrative rather than limiting on the invention described herein. Scope of the invention is thus showed be the appended claims rather than by the foregoing description, and all changes that come within the meaning and range of equivalency of the claims are intended to be embraced by reference therein.

The invention will hereinafter be described by way of the following non-limiting Figures and Examples.

Sequences

| SEQ ID NO | DNA/amino acid (AA) | Name |
|---|---|---|
| SEQ ID NO: 1 | DNA | QC69/JFH1-DNA |
| SEQ ID NO: 2 | AA | QC69/JFH1-AA |
| SEQ ID NO: 3 | DNA | QC69/JFH1(G809T)-DNA |
| SEQ ID NO: 4 | AA | QC69/JFH1(G809T)-AA |
| SEQ ID NO: 5 | DNA | QC69/JFH1(T1581C)-DNA |
| SEQ ID NO: 6 | AA | QC69/JFH1(T1581C)-AA |
| SEQ ID NO: 7 | DNA | QC69/JFH1(T2985C)-DNA |
| SEQ ID NO: 8 | AA | QC69/JFH1(T2985C)-AA |
| SEQ ID NO: 9 | DNA | QC69/JFH1(C8421T)-DNA |
| SEQ ID NO: 10 | AA | QC69/JFH1(C8421T)-AA |
| SEQ ID NO: 11 | DNA | -84S_HCV-MOD |
| SEQ ID NO: 12 | DNA | 7aR1519 |
| SEQ ID NO: 13 | DNA | 7aF1299 |
| SEQ ID NO: 14 | DNA | 7aR2320 |
| SEQ ID NO: 15 | DNA | 7aF2038 |
| SEQ ID NO: 16 | DNA | 7aR2984 |
| SEQ ID NO: 17 | DNA | 7aF2635 |
| SEQ ID NO: 18 | DNA | 7aR3819 |
| SEQ ID NO: 19 | DNA | 7aF3409 |
| SEQ ID NO: 20 | DNA | 4118R_JFH1 |
| SEQ ID NO: 21 | AA | QC69 |
| SEQ ID NO: 22 | AA | JFH1 |
| SEQ ID NO: 23 | DNA | QC69 |
| SEQ ID NO: 24 | DNA | JFH1 |

EXAMPLES

Materials and Methods

Construction of Intergenotypic Recombinants pQC69/JFH1 was constructed by insertion of the EcoRI-SpeI fragment of a synthetic sequence (Genscript) containing JFH1 5'UTR, QC69 Core-NS2 (accession number EF108306), and JFH1 NS3 into pFL-J6/JFH. For reverse genetic studies, mutations were introduced using mutated primers in fusion PCR with Pfu Polymerase (Stratagene) or with Quick Change II XL Site-Directed Mutagenesis Kit (Stratagene). Restriction enzymes for standard cloning procedures were purchased from New England Biolabs and ligations were performed using Rapid DNA ligation kit (Roche) according to the protocol. DNA preparations were carried out using QIAGEN QIAprep spin miniprep kit or QIAfilter plasmid maxi kit (both Qiagen).

In Vitro Transcription

For in vitro transcription 5 µg plasmid was XbaI-linearized (New England Biolabs). Transcription was carried out for 2 hrs with T7 RNA polymerase (Promega) according to protocol. RNA production was evaluated by gel electrophoresis.

Huh7.5 Cell Culture and Generation of Virus Stocks

The human hepatoma cell line Huh7.5 is an INF-α cured clone of the Huh7 hepatoma cell line, with increased HCV replication abilities. Cells were cultured in D-MEM+4500 mg/L Glucose+GlutaMAX-I+Pyruvate (Invitrogen) containing 10% heat inactivated fetal bovine serum (FBS) (Sigma), penicillin at 100 units/ml and streptomycin at 100 mg/ml (Invitrogen) at 5% CO2 and 37° C. Every 2-3 days cells were split after washing with PBS and trypsinizing (Trypsin/EDTA, Invitrogen). Supernatants were sterile filtered to exclude cells and debris and stored at −80° C.

For transfection of HCV RNA transcripts, naïve Huh7.5 cells were plated at $4 \times 10^5$/well in 6-well plates the day before transfection. Prior to transfection 2.5 µg of unpurified RNA transcripts were incubated with Lipofectamine2000 (Invitrogen) in 500 µL Opti-MEM (Invitrogen) for 20' at room temperature. RNA-Lipofectamine2000 transfection complexes were left on cells for 12-24 hrs before washing.

To prove the production of infectious viruses, sterile filtered supernatant from infected cultures was used to infect naïve Huh7.5 cells. Unless other is described, 1 mL supernatant was used for infection of Huh7.5 cells plated in 6-well plates at $4 \times 10^5$/well the day before. Supernatants were left on cells for 3-8 hrs as described in figure and table legends.

Negative controls in transfections were RNA transcripts from replication deficient JFH1-based genomes (with the GND motif); in the kinetic experiment, non-infected cells were used (data not shown).

Viral spread was monitored by HCV Core or NS5A immunostainings with mouse anti-HCV core protein monoclonal antibody (B2) (Anogen, Yes Biotech Laboratories) or anti-NS5A, 9E10, respectively, as described in the following section. Supernatant infectivity titers were determined as 50% tissue culture infectious dose ($TCID_{50}$)/mL or as focus forming units (FFU)/mL, as described in the following section. Supernatant HCV RNA titers were measured by a 5'UTR based Real Time RT-PCR as described below.

For generation of virus stocks, Huh7.5 cells were infected at a multiplicity of infection (MOI) of ~0.003. After viral spread to >80% of the culture (Core or NS5A immunostaining), supernatants were filtered, aliquoted and stored at −80° C. Size of each viral stock was ~100 mL, with exception of the QC69/JFH1 virus stocks, which were ~100 mL.

Immunostainings for HCV antigens and lipids; titration of infectivity For staining, cells grown over night on 4- or 8-well chamberslides (Nunc) were washed 2× with PBS and fixed for 5 minutes with acetone. After washing 2× with PBS and 1× with PBS/Tween-20 (0.1%), slides were incubated with 1° antibody (MAB Murine Anti-Human HCV, Core Protein, Clone B2 (Anogen) or anti-NS5A, 9E10 (gift from C. Rice, Rockefeller University) used at 1:200 in PBS containing 5% bovine serum albumine (BSA) for 20' at room temperature. After washing as above, 2° antibody (Alexa Fluor 594 goat anti-mouse IgG (H+L)) and Hoechst33342 (both Invitrogen) for cell nuclei counterstaining, used at 1:500 and 1:10000 dilutions, respectively in PBS/Tween, was added for 5 min. Lipids were stained with oil red 0 (Fisher scientific) as described previously. Finally, slides were washed with PBS, mounted with Fluoromount-G (Southern Biotech) and cover slipped. Staining was visualized using a Leica TCS SP5 confocal microscope. Percentage of infected cells was evaluated by assigning values of 0% (no cells infected), 1% (or below), 5%, 10-90% in steps of 10, 95% and 100% (all cells infected).

Viral infectivity titers were determined by the tissue culture infectious dose 50 ($TCID_{50}$) or focus forming unit method. $6 \times 10^3$/well naive Huh7.5 cells were plated out in a poly-D-lysine coated 96-well plate (Nunc) the day before infection. Cells were then incubated with 10-fold dilutions of cell culture supernatants. For $TCID_{50}$ determinations, 6 replicates per dilution were incubated for 2-3 days. For FFU determinations, wells were incubated for 48 rs. After incubation, cells were permeabilized for 5' with cold methanol. After washing 1× with PBS and 1× with PBS/Tween-20, blocking was carried out for 20' with sterile filtered 1% BSA/0.2% skim milk in PBS followed by a 5' blocking of endogenous peroxidase activity using 3% H2O2. Cells were washed as above and incubated with a 1:200 dilution of 1° Ab α-NS5A (9E10) in PBS/0.1% tween-20 over night at 4° C. After washing, a 1:300 dilution of 2° Ab HRP-goat anti-mouse IgG (H+L) (Amersham Biosciences) in PBS/0.1% tween-20 was added and incubated for 30' at room temperature. Staining was developed using DAB substrate kit (DAKO) for 30' after washing. In $TCID_{50}$ determinations, wells were scored positive if one or more cells were infected, and the $TCID_{50}$ was calculated according to the Reed and Muench method. $TCID_{50}$ values are derived from single or multiple determinations as indicated. FFU determinations are based on counts of wells with 5-100 FFU and three independent virus dilutions with one replicate each. However, FFU calculations for virus stocks (Table 4) were based on two independent virus dilutions with 6 replicates each.

Real-time PCR (TaqMan) assay for determination of HCV RNA titers.

Supernatant HCV RNA titers were measured by a 5' UTR based Real Time RT-PCR. RNA was purified from 200 µL of heat inactivated (56° C. for 30') cell culture supernatant and eluted in a final volume of 50 µL using the Total Nucleic Acid Isolation Kit (Roche) in combination with the Total NA Variable Elution Volume protocol on a MagNA Pure LC Instrument (Roche). As an internal control, Phocine Distemper Virus (PDV) was added to the lysis buffer in a concentration titrated to yield a Ct of ~32 upon real-time PCR analysis. In parallel to RNA purified from cell culture supernatants a quantitative HCV standard panel covering RNA concentrations of 0 to $5 \times 10^6$ IU/mL in one-log increments (OptiQuant HCV Panel, AcroMetrix) was analysed. Real-time PCR analyses of HCV and PDV RNA were carried out in two separate reactions using the TaqMan EZ RT-PCR Kit (Applied Biosystems). For HCV, primers and a FAM-labelled MGB-probe were directed against the 5' UTR and were previously shown to perform equivalently against a panel of the six major HCV genotypes in a different TaqMan assay (Engle et al. 2008). For PDV, a ready-to-use primer/probe mix was used (Dr. H. G. M. Niesters, Department of Virology, Erasmus Medical Centre, Rotterdam, The Netherlands). The PCR analysis was performed on a 7500 Real-Time PCR System (Applied Biosystems) using 50° C. for 2', 60° C. for 30' and 95° C. for 5' followed by 45 cycles of 94° C. for 20" and 62° C. for 1'. HCV RNA titers (IU/ml) were calculated using a standard curve created from the known concentrations of the standard panel and their corresponding Ct values. The reproducible detection limit of the assay was 500 IU/ml. In order to confirm successful purification, amplification and the absence of PCR inhibitors, the Ct value of the PDV reaction was compared to the expected Ct value (based on a mean of all previous runs; n>9) using the MedLab QC freeware programme. The results of samples with an actual Ct value within ±2 SD of the expected Ct value were accepted.

Treatment, Receptor Blocking and Neutralization

For treatment, interferon-α2b (Schering-Plough), ribavirin (Sigma) or amantadine (Sigma) was used; cell viability was monitored with CellTiter 96 AQueous One Solution Cell Proliferation Assay (Promega).

For blocking of CD81 and SR-BI and neutralization assays, Huh7.5 cells were plated 6×10³ per well of a poly-D-lysine-coated 96-well plate and incubated for 24 hrs. For blocking experiments, cells were incubated with anti-CD81 (JS-81; BD Biosciences Pharmingen, Franklin Lakes, N.J.) or isotype-matched control antibody (anti-human immunodeficiency virus, p24, clone Kal-1; DAKO) and rabbit polyclonal anti-SR-BI (GeneTex) or rabbit polyclonal control antibody (anti-human Retinoblastoma (Rb) Ab-6, Thermo Scientific), respectively, for 1 hr. Subsequently, cells were infected with ~150 FFU of the respective virus for 3 hrs followed by washing with PBS. After 48 hrs of incubation with normal growth medium, cells were stained for HCV NS5A to determine the number of focus forming units (FFU) per well. Experiments were performed in triplicates unless stated otherwise. Percent inhibition by anti-CD81 and anti-SR-BI was calculated by comparison to the FFU mean of at least 3 replicate wells incubated with virus only.

For neutralization, heat inactivated sera were pre-incubated with ~30-150 FFU for 1 hr at 37° C., preceding 3 hrs incubation on 6×10³ Huh7.5 cells. After 48 hrs incubation with normal growth medium, cultures were immunostained for NS5A, and the number of FFU was determined. Neutralization experiments were performed in triplicates and percent inhibition by patient sera was calculated by comparison to the FFU mean of at least 3 replicate wells incubated with virus only. Sera used for neutralization were derived for from persistently infected Patient H (2006, year 29 after infection, genotype 1a), an Egyptian Patient (AA, 1994, genotype 4a), and a South African hepatocellular carcinoma patient (SA3, genotype 5a).

Sequencing of Cell Culture Derived HCV

Direct sequencing of complete ORF was done to identify adaptive mutations. RNA was extracted from plasma and cell culture supernatant using the High Pure Viral Nucleic Acid Kit (Roche) according to the manufacturer's protocol. Reverse transcription-polymerase chain reactions (RT-PCR) were carried out using RNA extracted from 100 μL cell culture supernatant. Primers (TAG Copenhagen) were 1.25 μM and dNTPs (Invitrogen) were 0.5 mM in RT reactions. For denaturation, RNA was incubated for 2' at 65° C. together with primer and dNTPs and placed on ice. cDNA syntheses was done in a 20 μL volume with SuperScriptIII (Invitrogen). The final RT reaction was treated with 1-4 U RNase H (Invitrogen) and 1000 U RNase T1 (Ambion) for 20' at 37° C. to degrade RNA. 1st round PCR was performed in a 50 μL volume on 2.5 μL of the cDNA reaction using the Advantage 2 PCR Enzyme System (Clontech). Cycle parameters were 5 cycles of 35" at 99° C., 30" at 67° C. and 10' at 68° C., 10 cycles of 35" at 99° C., 30" at 67° C. and 11' at 68° C., 10 cycles of 35" at 99° C., 30" at 67° C. and 12' at 68° C. and 10 cycles of 35" at 99° C., 30" at 67° C. and 13' at 68° C. 12~1 kb products were synthesized in a nested PCR covering the entire ORF Table 1). PCR was set up as above using 2.5 μL of the 1st round PCR for each reaction. Initial denaturation was 35 sec at 99° C. followed by 35 cycles with 35 sec at 99° C., 30 sec at 67° C. and 6 min at 68° C. Genotype 7a specific primers used in 2$^{nd}$ round of the long RT-PCR procedure are given in Table 1. PCR products were agarose gel purified and directly sequenced in both directions.

Sequencing, Sequence Analysis and Databases

All sequence reactions was performed at Macrogen Inc., Seoul, South Korea. Sequence analysis was performed with Sequencher 4.7, Gene Codes Corporation and freeware BioEdit v. 7.0.5. HCV sequences used for alignments were retrieved from The European HCV database (euHCVdb; euhcvdb.ibcp.fr/euHCVdb/) and the American HCV database (LANL; hcv.lanl.gov/content/hcv-db/index).

Example 1

Cell Culture Adaptation of Intergenotypic 7a/2a Recombinant (QC69/JFH1)

In four independent RNA transfections of Huh7.5 cells, QC69/JFH1 spread to >50% of the culture on day 3 (data not shown; FIGS. 1A, B). Passage of QC69/JFH1 yielded HCV RNA titers of ~10⁸ IU/mL and infectivity titers of ~$10^{4.5}$ $TCID_{50}$/mL. In passaged virus recovered from all 4 transfections, no dominant coding mutations were observed. However, in 2 passages, positions with a 50/50 quasispecies of the original and a mutated sequence were observed, G809T (V157F) (Core) and T1581C(I414T) (E2), or T2985C (L882P) (NS2) and C8421T(A2694V) (NS5B), respectively (Table 2). In reverse genetic studies, QC69/JFH1 viruses containing G809T (V157F), T1581C(I414T), T2985C (L882P) and C8421T(A2694V), singly or in combinations had similar spread kinetics and infectivity titers as S52/JFH1$_{1793S,K1404Q}$, whereas kinetics of the original QC69/JFH1 were slightly delayed (data not shown; FIGS. 1A, B). In analysis of passaged viruses, none of the recombinants had amino acid changes, but positions that had evidence of a minor change were observed for both experiments with the original QC69/JFH1 and for QC69/JFH1$_{V157F}$ (Table 2).

Example 2

Titrated Stocks of Genotype 2a and 7a Viruses

The supernatant virus stocks of genotype 2a and 7a JFH1-based intergenotypic recombinants were characterized (Table 4). Infectivity titers were $10^{5.2}$ and $10^{4.5}$ $TCID_{50}$/mL and HCV RNA titers were $10^{7.6}$ to and $10^{7.9}$ IU/mL, respectively. Specific infectivities, defined as infectious titer relative to the HCV RNA titer were 1/251 and 1/2518 $TCID_{50}$/IU, respectively. There was a good correlation between the infectivity titers determined as $TCID_{50}$/mL and FFU/mL, respectively (Table 4).

Example 3

Importance of CD81 and SR-B1 for HCV Genotype 7a Infection

Infection with genotype 2a and 7a recombinants was blocked by anti-CD81 in a dose dependent manner (FIG. 2A); >90% inhibition was observed at 2.5 μg/mL anti-CD81, whereas at 0.02 μg/mL anti-CD81 <50% inhibition was found. In SR-BI blocking experiments, the present inventors showed for all genotype recombinants >90% infection inhibition with a 1:10 dilution of polyclonal anti-SR-BI (FIG. 2B). This inhibition was dose dependent, and at 1:160 and 1:640 dilution about 50% inhibition was found for genotype 7a recombinants.

Example 4

Cross-Genotype Neutralization with Chronic Phase HCV Patient Sera

Chronic phase sera from patients infected with genotypes 1a (H06), 4a (AA) and 5a (SA3) with relative high neutralization titers against the homologous genotype virus was identified previously. The cross-genotype neutralization potential of these sera against 1a, 2a, 3a, 4a, 5a and 6a viruses were tested previously (Table 3) (Scheel et al., 2008) (Jensen et al., 2008).

These sera also showed high 50% neutralization titers against the 7a virus (Table 3). Relative high neutralization titers were found against 1b and 2b viruses with the H06 sera, whereas the AA and SA3 sera showed limited neutralization of these viruses (Table 3).

TABLE 1

Primers used for QC69/JFH1 long RT-PCR procedure to generate amplicons for direct sequencing of the ORF*

| Amplification step and amplicon | Primer name | SEQ ID NO | Primer sequence |
|---|---|---|---|
| 2nd round PCR | | | |
| Amplicon 1 | −84S_HCV-MOD | SEQ ID NO: 11 | 5'-GTAGCGTTGGGTTGCGAAAGGCCTTGTGGTACTGCCTGAT-3' |
|  | 7aR1519 | SEQ ID NO: 12 | 5'-GACGGCCATGGTTTCCGCGTCGAC-3' |
| Amplicon 2 | 7aF1299 | SEQ ID NO: 13 | 5'-CCACAGGATGGCGTGGGACATGATG-3' |
|  | 7aR2320 | SEQ ID NO: 14 | 5'-CCCGCGTCCAATTGCACGCTG-3' |
| Amplicon 3 | 7aF2038 | SEQ ID NO: 15 | 5'-CGGGGTTCACGAAGACCTGCGGAG-3' |
|  | 7aR2984 | SEQ ID NO: 16 | 5'-CCCCCCGAGGGTTGAGAGGAGG-3' |
| Amplicon 4 | 7aF2635 | SEQ ID NO: 17 | 5'-CCTCAACGCGGCCAGCCTTGC-3' |
|  | 7aR3819 | SEQ ID NO: 18 | 5'-CCCGCGTCTCCGAGCCGGGATG-3' |
| Amplicon 5 | 7aF3409 | SEQ ID NO: 19 | 5'-GTCCTGCTAGGGCCCGCGGATG-3' |
|  | 4118R_JFH1 | SEQ ID NO: 20 | 5'-CGCCCGAGGCCTACCTCTTCTATATC-3' |

*Primers used for cDNA synthesis, $1^{st}$ round PCR and $2^{nd}$ round PCR amplicon 6 to 12 bind to the JFH1 portion of the recombinant and are given in Supplementary Material and Methods of Gottwein et al (2007).

TABLE 2

| HCV gene | | Core | E2 | E2 | E2 | NS2 | NS5A | NS5B |
|---|---|---|---|---|---|---|---|---|
| Nucleotide position † | | | | | | | | |
| QC69/JFH1 | | 809 | 1511 | 1581 | 1623 | 2985 | 6648 | 8421 |
| H77 abs ref | | 810 | 1512 | 1582 | 1624 | 2975 | 6637 | 8356 |
| pQC69/JFH1 | | G | A | T | A | T | A | C |
| Original construct | Passage (day) | | | | | | | |
| QC69/JFH1, exp. 1* | 1st (12) | G/T | • | T/C | • | • | • | • |
| QC69/JFH1, exp. 2 | 1st (12) | • | • | • | • | T/C | • | C/T |
| QC69/JFH1, exp. 3 | 1st (3) | • | • | • | A/g | • | • | • |
| QC69/JFH1, exp. 4 | 1st (3) | • | A/g | • | • | • | • | • |
| Mutated constructs | | | | | | | | |
| QC69/JFH1$_{V157F}$ | 1st (3) | T | • | • | • | • | A/g | • |
| QC69/JFH1$_{I414T}$ | 1st (3) | • | • | C | • | • | • | • |
| QC69/JFH1$_{L882P}$ | 1st (3) | • | • | • | • | C | • | • |
| QC69/JFH1$_{A2694V}$, exp. 1 | 1st (5) | • | • | • | • | • | • | T |
| QC69/JFH1$_{A2694V}$, exp. 2 | 1st (5) | • | • | • | • | • | • | T |
| QC69/JFH1$_{V157F, I414T}$ | 1st (3) | T | • | C | • | • | • | • |
| QC69/JFH1$_{L882P, A2694V}$ | 1st (3) | • | • | • | • | C | • | T |

TABLE 2-continued

| Amino acids position † | | | | | | | |
|---|---|---|---|---|---|---|---|
| QC69/JFH1 | 157 | 391 | 414 | 428 | 882 | 2103 | 2694 |
| H77 abs ref | 157 | 391 | 414 | 428 | 878 | 2099 | 2672 |
| Change | V→F | R→G | I→T | N→S | L→P | Y→C | A→V |

Coding nucleotide changes of original and adapted QC69/JFH1 recombinants in Huh7.5 cells.
†Positions are numbered according to the HCV sequence of pQC69/JFH1. Corresponding H77 (AF009606) absolute reference positions are given. Coding mutations are shown. Dots indicate identity with the original plasmid sequence. Positions with mixtures are written with the dominant sequence in capital and the minor sequence in lower case letters (a 50/50 quasispecies is shown as two capital letters). Highlighted positions are mutations engineered into QC69/JFH1. In addition, the following non-coding mutation was found: QC69/JFH1 (exp.2) 1st (12) T8593T/A.
*QC69/JFH1 (exp.1) 1st (12) is the virus stock also shown in Table 4.

TABLE 3

Cross-genotype neutralization potential of chronic phase genotype 1a, 4a and 5a serum against genotype 1-7 recombinant viruses.

| Core-NS2 | Reciprocal 50% serum neutralizing antibody titer | | |
|---|---|---|---|
| Genotype | 1a (H06) | 4a (AA) | 5a (SA3) |
| 1a | 1600 | <100* | <100 |
| 1b | 800 | <100* | <100* |
| 2a | <100* | <100** | <100 |
| 2b | 3200 | 400 | 200 |
| 3a | <100* | <100** | <100 |
| 4a | 12800 | 6400 | 200 |
| 5a | 25600 | 3200 | 6400 |
| 6a | 204800 | 25600 | 12800 |
| 7a | 25600 | 3200 | 1600 |

Neutralization of genotype 1a, 2a, 3a, 4a, 5a and 6a viruses with 1a (H06), 4a (AA) and 5a (SA3) chronic phase serum was described previously (Scheel et al., 2008. Jensen et al., 2008). Similarly, approximately 150 FFU of J4/JFH1$_{F886L,Q1496L}$, 80 or 150 FFU of J8/JFH1, and 30 FFU of QC69/JFH1 stock (Table 4) viruses were pre-incubated with 2-fold dilutions of sera in triplicates, before infection of 6×10$^3$ Huh7.5 cells for 3 hrs. After 48 hrs incubation, the number of FFUs was determined for each culture by anti-NS5A immunostaining. 50% neutralization titers indicate the serum dilution, which led to an at least 50% reduction of FFU compared to the mean of 6 non-serum treated cultures. * 50% neutralization observed at 1:50 serum dilution; ** less than 50% neutralization observed at 1:50 serum dilution.

TABLE 4

Titrated Stocks of JFH1-based Intergenotypic Recombinants of HCV Genotype 2a and 7a.

| Core-NS2 Genotype | Virus † | Viral Passage | HCV Infectivity titer * LOG$_{10}$ TCID$_{50}$/mL | HCV Infectivity titer * LOG$_{10}$ FFU/mL | HCV RNA titer # LOG$_{10}$ IU/mL | Specific infectivity ** TCID$_{50}$/IU |
|---|---|---|---|---|---|---|
| 2a | J6/JFH1 | 2nd | 5.2 ± 0.1 | 5.0 ± 0.2 | 7.6 ± 0.0 | 1/251 |
| 7a | QC69/JFH1 | 1st | 4.5 ± 0.1 | 4.4 ± 0.0 | 7.9 ± 0.2 | 1/2512 |

† HCV recombinant with engineered adaptive mutations given as subscript. HCV ORF sequences, including the presence of specific mutations, were verified by direct sequencing of stock genomes; a 50/50 quasispecies coding mutation was revealed for QC69/JFH1 (V157V/F, I414I/T).
* Measured as TCID$_{50}$/mL (mean of four determinations, each based on serial dilution with 6 replicates per dilution; ±SEM, standard error of the mean) and FFU/mL (mean of two determinations, each based on serial dilution with 6 replicates per dilution; ±SEM).
Measured as IU/mL (mean of two determinations, ±SEM) in a Real-Time RT-PCR assay.
** Determined as HCV RNA titer (IU/mL) related to HCV infectivity titer (TCID$_{50}$/mL).

REFERENCES

Billaud, J. N. et al. (2000). Replication rate of feline immunodeficiency virus in astrocytes is envelope dependent: implications for glutamate uptake. Virology 266, 180-188.

Engle, R. E. et al. (2008) TaqMan assay for the six major genotypes of hepatitis C virus: comparison with commercial assays. J Med Virol. 80, 72-79.

Gottwein, J. M. et al. (2007) Robust Hepatitis C Genotype 3a Cell Culture Releasing Adapted Intergenotypic 3a/2a (S52/JFH1) Viruses Gastroenterology 133, 1614-1626.

Jensen, T. B. et al. (2008). Highly efficient JFH1-based cell culture system of hepatitis C virus genotype 5a: failure to control infection with homologous neutralizing antibody treatment. J Inf Dis, in press.

Kato, T. et al. (2001). Sequence analysis of hepatitis C virus isolated from a fulminant hepatitis patient. J Med Virol. 64, 334-339

Kato, T. et al. (2003). Efficient replication of the genotype 2a hepatitis C virus subgenomic replicon. Gastroenterology. 125, 1808-1817.

Lindenbach, B. D. et al. (2005) Complete replication of hepatitis C virus in cell culture. Science. 309, 623-626.

Lindenbach, B. D. et al. (2006) Cell culture-grown hepatitis C virus is infectious in vivo and can be recultured in vitro. Proc Natl Acad Sci USA. 103(10), 3805-9. Epub 2006 Feb. 16

Meunier, J. C. et al. (2005) Evidence for Cross-Genotype Neutralization of Hepatitis C Virus Pseudo-Particles and Enhancement of Infectivity by Apolipoprotein C1 Proc Natl Acad Sci USA 102, 4560-4565.

Murphy, D. et al. (2007) A new genotype of hepatitis C virus orginating from central Africa. Hepatology 46, 623A Scheel, T. K., et al. (2008) Development of JFH1-based cell culture systems for hepatitis C virus genotype 4a and evidence for cross-genotype neutralization. Proc Natl Acad Sci USA 105, 997-1002.

Wakita, T. et al (2005). Production of infectious hepatitis C virus in tissue culture from a cloned viral genome. Nat. Med. 11, 791-796.

Zhong, J. et al. (2005). Robust hepatitis C virus infection in vitro. Proc. Natl. Acad. Sci. U.S.A. 102, 9294-9299.

The invention claimed is:

1. An isolated nucleic acid molecule encoding the amino acid sequence with at least 90% identity to SEQ ID NO:2 and comprising at least one adaptive mutation in the amino acid sequence of Core, E2, NS2, NS5A, or NS5B selected from the group consisting of V157F, R391G, I414T, N428S, L882P, Y2103C and A2694V, wherein said molecule is a genetically engineered human hepatitis C virus intergenotypic recombinant.

2. The nucleic acid molecule according to claim 1, wherein said molecule:
   (i) comprises the nucleic acid sequence with at least 90% identity to SEQ ID NO:1;
   (ii) comprises at least one adaptive mutation in the nucleic acid sequence of Core, E2, NS2, NS5A or NS5B selected from the group consisting of G809T, A1511G, T1581C, A1623G, T2985C, A6648G and C8421T; and
   (ii) is selected from the group consisting of double-stranded DNA, complementary DNA (cDNA), positive-sense cDNA, negative-sense cDNA, positive-sense RNA, negative-sense RNA, and double-stranded RNA.

3. The nucleic acid molecule according to claim 1, wherein the human hepatitis C virus is of genotype 7a/2a, wherein the genotype 7a is strain QC69 and wherein the genotype 2a is strain JFH1.

4. The nucleic acid molecule according to claim 1, wherein said molecule encodes the amino acid sequence with a sequence identity of at least 95% to that of SEQ ID NO 2.

5. An isolated cell comprising a nucleic acid molecule of claim 1.

6. The cell according to claim 5, wherein the cell is Huh7.5.

7. A method for producing a hepatitis C virus particle, comprising culturing the cell according to claim 5 to produce the genetically engineered human hepatitis C virus intergenotypic recombinant.

8. An isolated hepatitis C virus particle comprising a nucleic acid molecule according to claim 1.

9. The nucleic acid molecule according to claim 1, wherein said molecule comprises in the encoded amino acid sequence:
   i) the combination of adaptive mutations V157F with I414T; or ii) the combination of adaptive mutations L882P with A2694V.

10. The nucleic acid molecule according to claim 2, wherein said molecule comprises in the nucleic acid sequence: i) the combination of adaptive mutations G809T with T1581C; or ii) the combination of adaptive mutations T2985C with C8421T.

11. The nucleic acid molecule according to claim 1, wherein said molecule encodes the amino acid sequence with at least 98% identity to SEQ ID NO: 2.

12. The nucleic acid molecule according to claim 1, wherein said molecule encodes the amino acid sequence with at least 99% identity to SEQ ID NO: 2.

13. The nucleic acid molecule according to claim 2, wherein said molecule comprises the nucleic acid sequence with at least 95% identity to SEQ ID NO: 1.

14. The nucleic acid molecule according to claim 13, wherein said molecule comprises the nucleic acid sequence with at least 98% identity to SEQ ID NO: 1.

15. The nucleic acid molecule according to claim 13, wherein said molecule comprises the nucleic acid sequence with at least 99% identity to SEQ ID NO: 1.

* * * * *